US007442501B2

(12) United States Patent
Horvitz et al.

(10) Patent No.: US 7,442,501 B2
(45) Date of Patent: Oct. 28, 2008

(54) SQV NUCLEIC ACIDS AND POLYPEPTIDES

(75) Inventors: H. Robert Horvitz, Auburndale, MA (US); Ho Yon Hwang, Somerville, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 173 days.

(21) Appl. No.: 10/347,470

(22) Filed: Jan. 17, 2003

(65) Prior Publication Data
US 2004/0002054 A1 Jan. 1, 2004

Related U.S. Application Data

(60) Provisional application No. 60/390,930, filed on Jun. 24, 2002, provisional application No. 60/349,630, filed on Jan. 18, 2002.

(51) Int. Cl.
*C12Q 1/68* (2006.01)
*C07K 1/00* (2006.01)

(52) U.S. Cl. .......................................... 435/6; 530/350

(58) Field of Classification Search ..................... 435/6; 536/23.1; 530/350
See application file for complete search history.

(56) References Cited

OTHER PUBLICATIONS

Herman et al. sqv mutants of *Caenorhabditis elegans* are defective in vulval epithelail invagination. PNAS, vol. 96, pp. 968-973, 1999.*
Bulik et al. sqv-3, 7, and -8, a set of genes affecting morphogenesis in *Caenorhabditis elegans*, encode enzymes required for glycosaminoglycan biosynthesis. PNAS, vol. 97, No. 20, pp. 10838-10843, 2000.*
Sasamura et al. Effects of AT1 receptor antagonist on proteoglycan ene expression in hypertensive rats. Hypertens Res., vol. 24, pp. 165-172, 2001.*
Herman et al. sqv mutants of *Caenorhabditis elegans* are defective in vulval epithelial invagination. PNAS, vol. 96, pp. 968-973, 1999.*
International Preliminary Examination Report, mailed Aug. 7, 2007, for PCT/US03/01558.
International Search Report from PCT/US2003/001558, mailed Jun. 4, 2007.
Almeida et al., "Cloning and Expression of a Proteoglycan UDP-Galactose:β Xylose β1,4-Galactosyltransferase I," J. Biol. Chem. 274:26165-26171, (1999).
Bai et al., "Biosynthesis of the Linkage Region of Glycosaminoglycans," J. Biol. Chem. 276:48189-48195, (2001).
Berninsone et al., "SQV-7, A Protein Involved in *Caenorhabditis elegans* Epithelial Invagination and Early Embryogenesis, Transports UDP-glucuronic Acid, UDP-N-acetylgalactosamine, and UDP-galactose," Proc. Natl. Acad. Sci. 98:3738-3743, (2001).
Bdolah et al., "Uridine Diphosphate-D-Glucose Dehydrogenase of Hen Oviduct," Biochim. Biophys. Acta 159:176-178, (1968).
Bulik et al., "SQV-3, -7, and -8, A Set of Genes Affecting Morphogenesis in *Caenorhabditis elegans*, Encode Enzymes Required for Glycosaminoglycan Biosynthesis," Proc. Natl. Acad. Sci., 97:10838-10843, (2000).

Campbell et al., "Properties and Kinetic Analysis of UDP-glucose Dehydrogenase from Group A Streptococci," J. Biol. Chem. 272:3416-3422, (1997).
Duncan et al., "The Link Between Heparan Sulfate and Hereditary Bone Disease: Finding a Function for the EXT Family of Putative Tumor Suppressor Proteins," J. Clin. Invest. 108:511-516, (2001).
Esko et al., "Animal Cell Mutants Defective in Glycosaminoglycan Biosynthesis," Proc. Natl. Acad. Sci., 82:3197-3201; (1985).
Gotting et al., "Molecular Cloning and Expression of Human UDP-D-Xylose: Proteoglycan Core Protein β-D-Xylosyltransferase and its First Isoform XT-li," J. Mol. Biol. 304:517-528, (2000).
Hempel et al., "UDP-Glucose Dehydrogenase from Bovine Liver: Primary Structure and Relationship to Other Dehydrogenases," Protein Science 3:10/4-1080, (1994).
Herman et al, "sqv Mutants of *Caenorhabditis elegans* are Defective in Vulval Epithelial Invagination," Proc. Natl. Acad. Sci. 96:968-973 (1999).
Herman et al, "Three Proteins involved in *Caenorhabditis elegans* Vuval Invagination are Similar to Components of a Glycosylation Pathway," Proc. Natl. Acad. Sci. 96:974-979 (1999).
John et al, "UDP-glucuronate Carboxy-lyase in Cultured Chondrocytes," J. Biol. Chem. 252:6707-6710, (1977).
Kearns et al., "Topography of Glycosylation and UDP-Xylose Production," J. Biol. Chem. 268:11097-11104, (1993).
Kjellen et al., "Proteoglycans: Structures and Interactions," Annu. Rev. Biochem. 60:443-475, (1991).
Kitagawa et al., "Molecular Cloning and Expression of a Human Chondroitin Synthase," J. Biol. Chem. 276:38721-38726, (2001).
Lind et al., "The Putative Tumor Suppressors EXT1 and EXT2 are Glycosyltransferases Required for the Biosynthesis of Heparan Sulfate," J. Biol. Chem. 273:26265-26268, (1998).
Okajima et al, "Human Homolog of *Caenorhabditis elegens sqv-3* Gene is Galactosyltransferase I Involved in the Biosynthesis of the Glycosaminoglycan-Protein Linkage Region of Proteoglycans," J. Biol. Chem. 274:22915-22918, (1999).
Okajima et al, "Molecular Basis for the Progeroid Variant of Ehlers-Danlos Syndrome," J. Biol. Chem. 274:28841-28844, (1999).
Schiller et al., Partial Purification and Properties of UDPG Dehydrogenase from *Escherichia coli* Biochim. Biophys. Acta 293:1-10, (1973).
Singh et al., "Some Observations on Moulting in *Caenorhabditis elegans*," Nematologica 24:63-71, (1978).
Strominger et al., "Enzymatic Oxidation of Uridine Diphosphate Glucose to Uridine Diphosphate Glucuronic Acid," J. Amer. Chem. Soc. 76:6411-6412, (1954).
Varki, "Factors Controlling the Glycosylation Potential of Golgi Apparatus," Trends Cell Biol. 8:34-40, (1998).
Vertel et al., "Xylosylation is an Endoplasmic Reticulum to Golgi Event," J. Biol. Chem. 268:11105-11112, (1993).

* cited by examiner

*Primary Examiner*—Suryaprabha Chunduru
(74) *Attorney, Agent, or Firm*—Clark & Elbing LLP; Kristina Bieker-Brady

(57) ABSTRACT

The invention generally features sqv nucleic acid and polypeptide molecules associated with connective tissue diseases, progeroid disorders, and aging, and methods for isolating such molecules.

8 Claims, 99 Drawing Sheets

```
sqv-1 genomic sequence 3370       3380       3390       3400       3410       3420       3430       3440
TCAAATTTTC GTATTTTCTG CTGAACTTTT AATATTCATA GTCTCCAAGG CTATGTTAAT ATTCTTGGTT TAAGAGTTTG
d2096_1_80 AGTTTAAAAG CATAAAGAC GACTTGAAAA TTATAAGTAT CAGAGGTTCC GATACAATTA TAAGAACCAA ATTCTCAAAC 3450       3460       3470       3480       3490       3500       3510       3520
CTTTGTTGCT TTCTAAATAT ATTTTTTTTA CTTTCTCTTT GTAACTTTTT TAAATTTCAT ATTTGGAAGC GTAATACATT
d2096_1_80 GAAACAACGA AAGATTTATA TAAAAAAAAT GAAAGAGAAA CATTGAAAAA ATTTAAAGTA TAAACCTTCG CATTATGTAA 3530       3540       3550       3560       3570       3580       3590       3600
TTCCAAAACT TCAGGCATCT GCATGCAACC AATCAATAAT CAACGCGCAT GCTGAGCCCC AGACGTATCC GTAACAACTC
d2096_1_80 AAGGTTTTGA AGTCCGTAGA CGTACGTTGG TTAGTTATTA GTTGCGCGTA CGACTCGGGG TCTGCATAGG CATTGTTGAG 10         20         30         40         50         60
cDNA-> AGGCATCT GCATGCAACC AATCAATAAT CAACGCGCAT GCTGAGCCCC AGACGTATCC GTAACAACTC>
jmpl str +      ||||||||  |||||||||| |||||||||| |||||||||| |||||||||| |||||||||| ||||||||||
d2096_1_80      AGGCATCT GCATGCAACC AATCAATAAT CAACGCGCAT GCTGAGCCCC AGACGTATCC GTAACAACTC 3610       3620       3630       3640       3650       3660       3670       3680
GATTCGATG GCAACACGTG GAGCATGTGC TGTACTAATC ACATTTTTTC TCATATTTGG TTAGTGAAAA CAATTTTTAA
d2096_1_80 CTAAAGCTAC CGTTGTGCAC CTCGTACACG ACATGATTAG TGTAAAAAAG AGTATAAACC AATCACTTTT GTTAAAAATT 70         80         90         100        110        120        130
jmpl str + GATTCGATG GCAACACGTG GAGCATGTGC TGTACTAATC ACATTTTTTC TCATATTTGT GTTGATAAC>
           ||||||||| |||||||||| |||||||||| |||||||||  |||||||||| |||||||||   |  ||
d2096_1_80 GATTCGATG GCAACACGTG GAGCATGTGC TGTACTAATC ACATTTTTTC TCATATTTGG TTAGTGAAA 3690       3700       3710       3720       3730       3740       3750       3760
CAATACAATC AATTTTCATA AATATTCGTC AACTCCAATA ATTTTTGAC AAAAGTTTGT TTAATGATTA CGGTTTTCAG
d2096_1_80 GTTATGTTAG TTAAAGTAT TTATAAGCAG TTGAGGTTAT TAAAAACTG TTTCAAACA AATTACTAAT GCCAAAGTC
```

```
jmp1 str +                                                                                                      TTT CTCATATTTG>
                                                                                                                 ||  |||||||||||
d2096_1_80                                                                                                      TTA CGGTTTTTCAG
                 3770       3780       3790       3800       3810       3820       3830       3840
           TGTTGATAAC AAATACATCG AACAAATCAT TGTCGAGTGA CGTCATTGAA AAAAGCGAGC AAAAAATCAG TCAGATGGAG
           |||||||||| |||||||||| |||| ||||| |||||||||| |||||||||| |||||||||| |||||||||| ||||||||||
d2096_1_80 ACAACTATTG TTTATGTAGC TTGTTTAGTA ACAGCTCACT GCAGTAACTT TTTTCGCTCG TTTTTTAGTC AGTCTACCTC
                130        140        150        160        170        180        190        200 jmp1 str + TGTTGATAAC AAATACATCG AACAAATCAT TGTCGAGTGA CGTCATTGAA AAAAGCGAGC AAAAAATCAG TCAGATGGAG>
           |||||||||| |||||||||| |||||||||| |||||||||| |||||||||| |||||||||| |||||||||| ||||||||||
d2096_1_80 TGTTGATAAC AAATACATCG AACAAATCAT TGTCGAGTGA CGTCATTGAA AAAAGCGAGC AAAAAATCAG TCAGATGGAG
                3850       3860       3870       3880       3890       3900       3910       3920
           GAGGAAGGAC GATTGTCGAA TTTAATAAGT ATGGATTAAT TTTTTGAAAA ACATTTTTGC TTATCGTCTG
           |||||||||| |||| ||||| |||||||||| |||| |||||  |||||||||| |||||||||| ||||||||||
d2096_1_80 CTCCTTCCTG CTCCTCTATG CTAACAGCTT AAATTATTCA AAAAAACTTT TGTAAAAACG AATAGCAGAC
                210        220        230        240        250 jmp1 str + GAGGAAGGAC GATTGTCGAA TTTAATAAAA ACAATA>
           |||||||||| |||||||||| |||||||||| ||||||
d2096_1_80 GAGGAAGGAC GATTGTCGAA TTTAATAAGT ATGGAT
                3930       3940       3950       3960       3970       3980       3990       4000
           GTAGGGTTTT TCTTCACAGA AAAAATTGATT TTTCTCTAAT TTAGACTTTT TCAAAAAAT GATCAACACA TAGAAACAGA
           |||||||||| |||||||||| |||||||||| |||||||||| |||||||||| |||||||||| |||||||||| ||||||||||
d2096_1_80 CATCCCAAAA AGAAGTGTCT TTTTAACTAA AAAGAGATTA AATCTGAAAA AAGTTTTTTA CTAGTGTGT ATCTTTGTCT
                4010       4020       4030       4040       4050       4060       4070       4080
           AAAAAAATCT ATCAATTTAA AAATACCAAT TAAAGTTATC AACGTGAAGA TATGAAATGT ATATTTTTTC AGAAACAATA
           |||||||||| |||||||||| |||||||||| |||||||||| |||||||||| |||||||||| |||||||||| ||||||||||
d2096_1_80 TTTTTTTAGA TAGTTAAATT TTTATGGTTA ATTTCAATAG TTGCACTTCT ATACTTTACA TATAAAAAAG TCTTTGTTAT
                                                                                          240        250 jmp1 str +                                                                          T CGAATTTAAT AAAAACAATA>
                                                                                    |  |||||||||| ||||||||||
d2096_1_80                                                                          T ATATTTTTTC AGAAACAATA
```

Figure 1C cont.

```
d2096_1_80        4090       4100       4110       4120       4130       4140       4150       4160
           TTCCTGACGA CACTGTCTCA TCATTACTGG AAAGAATAAA ATTACTTGAA GACGAACTTT CGTCGATGAG AACTCGGATG
                      AAGGACTGCT GTGACAGAGT AGTAATGACC TTTCTTATTT TAATGAACTT CTGCTTGAAA GCAGCTACTC TTGAGCCTAC jmp1 str +        260        270        280        290        300        310        320        330
           TTCCTGACGA CACTGTCTCA TCATTACTGG AAAGAATAAA ATTACTTGAA GACGAACTTT CGTCGATGAG AACTCGGATG>
           |||||||||| |||||||||| |||||||||| |||||||||| |||||||||| |||||||||| |||||||||| ||||||||||
d2096_1_80 TTCCTGACGA CACTGTCTCA TCATTACTGG AAAGAATAAA ATTACTTGAA GACGAACTTT CGTCGATGAG AACTCGGATG 4170       4180       4190       4200       4210       4220       4230       4240
d2096_1_80 GATGATGCTG AAAATCGAGA AGGAAATGCT GCAAATGGAG ATGAAATTGT TGCACCTCTC CCGACAACGT AAGATATCCG
           CTACTACGAC TTTTAGCTCT TCCTTTACGA CGTTTACCTC TACTTTAACA ACGTGGAGAG GGCTGTTGCA TTCTATAGGC jmp1 str +        340        350        360        370        380        390        400        410
           GATGATGCTG AAAATCGAGA AGGAAATGCT GCAAATGGAG ATGAAATTGT TGCACCTCTC CCGACAACAA AGTCATTC>
           |||||||||| |||||||||| |||||||||| |||||||||| |||||||||| |||||||||| ||||||||   |   |||
d2096_1_80 GATGATGCTG AAAATCGAGA AGGAAATGCT GCAAATGGAG ATGAAATTGT TGCACCTCTC CCGACAACGT AAGATATC 4250       4260       4270       4280       4290       4300       4310       4320
d2096_1_80 AGTTTATCAA AATGCTTTAA AAAAAGATTT TCAGAAAGTC ATTCCCATCT GTTCGATATC GGAATGAGGA AACTCGAAAA
           TCAAATAGTT TTACGAAATT TTTTTCTAAA AGTCTTTCAG TAAGGGTAGA CAAGCTATGG CCTTACTCCT TTGAGCTTTT jmp1 str +                                           400        410        420        430        440
                                             CCGA CAACAAAGTC ATTCCCATCT GTTCGATACC GGAATGAGGA AACTCGAAAA>
                                             ||||  ||| ||||| |||||||||| |||||||| | |||||||||| ||||||||||
d2096_1_80                                    ATTT TCAGAAAGTC ATTCCCATCT GTTCGATATC GGAATGAGGA AACTCGAAAA 4330       4340       4350       4360       4370       4380       4390       4400
d2096_1_80 CGTATTCTGA TTACTGGAGG AGCTGGTTTT GTTGGATCAC CAACCTAGTG TAAACCATCT ATTTGGTAGA TAAGCTGATG TTAGACGGGC ATGAAGTCAT
           GCATAAGACT AATGACCTCC TCGACCAAAA CAACCTAGTG TAAACCATCT ATTTGGTAGA TAAACCATCT ATTCGACTAC AATCTGCCCG TACTTCAGTA jmp1 str +        450        460        470        480        490        500        510        520
           CGTATTCTGA TTACTGGAGG AGCTGGTTTT GTTGGATCAC AGCTGGTTTT GTTGGATCAC ATTTGGTAGA TAAGCTGATG TTAGACGGGC ATGAAGTCAT>
           |||||||||| |||||||||| |||||||||| |||||||||| |||||||||| |||||||||| |||||||||| |||||||||| |||||||||| ||||||||||
d2096_1_80 CGTATTCTGA TTACTGGAGG AGCTGGTTTT GTTGGATCAC AGCTGGTTTT GTTGGATCAC ATTTGGTAGA TAAGCTGATG TTAGACGGGC ATGAAGTCAT
```

Figure 1C cont.

```
d2096_1_80        ||||||||||||   ||||||||||   |||||||||||||   ||||||||||||||   ||||||||||   |||||||||||
                  CGTATTCTGA TTACTGGAGG AGCTGGTTTT GTTGGATCAC ATTTGGTAGA TAAGCTGATG TTAGACGGGC ATGAAGTCAT
                       4410      4420      4430      4440      4450      4460      4470      4480
d2096_1_80        CGCACTGGAT AATTATTTCA CTGGAAGAAA GAAAAATGTT GAGCATTGGA TTGGACATCC AAATTTCGAA ATGGTTCATC
                  GCGTGACCTA TTAATAAAGT GACCTTCTTT CTTTTTACAA CTCGTAACCT AACCTGTAGG TTTAAAGCTT TACCAAGTAG
                       530       540       550       560       570       580       590       600
jmp1 str +        CGCACTGGAT AATTATTTCA CTGGAAGAAA GAAAAATGTT GAGCATTGGA TTGGACATCC AAATTTCGAA ATGGTTCATC>
                  ||||||||||  |||||||||  ||||||||||  ||||||||||  ||||||||||  ||||||||||  ||||||||||  ||||||||||
d2096_1_80        CGCACTGGAT AATTATTTCA CTGGAAGAAA GAAAAATGTT GAGCATTGGA TTGGACATCC AAATTTCGAA ATGGTTCATC
                       4490      4500      4510      4520      4530      4540      4550      4560
d2096_1_80        ACGATGTTGT GAATCCATAT TTTGTGGAAG TTGATCAGAT TTATCACTTG GCTTCTCCTG CATCACCACC TCATTATATG
                  TGCTACAACA CTTAGGTATA AAACACCTTC AACTAGTCTA AATAGTGAAC CGAAGAGGAC GTAGTGGTGG AGTAATATAC
                       610       620       630       640       650       660       670       680
jmp1 str +        ACGATGTTGT GAATCCATAT TTTGTGGAAG TTGATCAGAT TTATCACTTG GCTTCTCCTG CATCACCACC TCATTATATG>
                  ||||||||||  ||||||||||  ||||||||||  ||||||||||  ||||||||||  ||||||||||  ||||||||||  |||||||||
d2096_1_80        ACGATGTTGT GAATCCATAT TTTGTGGAAG TTGATCAGAT TTATCACTTG GCTTCTCCTG CATCACCACC TCATTATATG
                       4570      4580      4590      4600      4610      4620      4630      4640
d2096_1_80        TATAATCCTG TCAAAACTAT CAAAACGAAC ACATTGGGGA CTATTAATAT GCTTGGATTG GCAAAGTTCG TTTTTTTTTT
                  ATATTAGGAC AGTTTTGATA GTTTTGCTTG TGTAACCCCT GATAATTATA CGAACCTAAC CGTTTCAAGC AAAAAAAAAA
                       690       700       710       720       730       740       750       760
jmp1 str +        TATAATCCTG TCAAAACTAT CAAAACGAAC ACATTGGGGA CTATTAATAT GCTTGGATTG GCAAAAACGCG TCAA>
                  ||||||||||  ||||||||||  ||||||||||  ||||||||||  ||||||||||  ||||||||||  |||||||||||  ||||
d2096_1_80        TATAATCCTG TCAAAACTAT CAAAACGAAC ACATTGGGGA CTATTAATAT GCTTGGATTG GCAAAGTTCG TTTT
                       4650      4660      4670      4680      4690      4700      4710      4720
d2096_1_80        CAAATATTCA ATTTTGTGAA ACTACTATAC TCATACTTAA ATCGAATGTT CTGTAATCCT TACTTTTCAG ACGCGTCAAA
                  GTTTATAAGT TAAAACACTT TGATGATATG AGTAGTAATT TAGCTTACAA GACATTAGGA ATGAAAAGTC TGCGCAGTTT
```

Figure 1C cont.

```
                                                     750            760
jmp1 str +                                  GATTGGCAAA ACGCGTCAAA>
                                            ||||||||||  ||||||||||
d2096_1_80                                  TACTTTTCAG ACGCGTCAAA 4730       4740       4750       4760       4770       4780       4790       4800
jmp1 str +  GCCACAGTTC TTCTTGCATC AACTTCAGAA GTTTACGGAG ATCCAGAAGT TCACCCACAG CCAGAAACTT ATTGGGGACA
            |||||||||| |||||||||| |||||||||| |||||||||| |||||||||| |||||||||| |||||||||| ||||||||||
d2096_1_80  CGGTGTCAAG AAGAACGTAG TTGAAGTCTT CAAATGCCTC TAGGTCTTCA AGTGGGTGTC GGTCTTTGAA TAACCCCTGT
                 770        780        790        800        810        820        830        840 jmp1 str +  GCCACAGTTC TTCTTGCATC AACTTCAGAA GTTTACGGAG ATCCAGAAGT TCACCCACAG CCAGAAACTT ATTGGGGACA>
            |||||||||| |||||||||| |||||||||| |||||||||| |||||||||| |||||||||| |||||||||| ||||||||||
d2096_1_80  GCCACAGTTC TTCTTGCATC AACTTCAGAA GTTTACGGAG ATCCAGAAGT TCACCCACAG CCAGAAACTT ATTGGGGACA 4810       4820       4830       4840       4850       4860       4870       4880
jmp1 str +  TGTTAATACA ATTGCACCAC GAGCATGTTA TGATGAGGGT AAACCAGTTG CCGAATCGCT TATGGTTGCT TACAATAAAC
            |||||||||| |||||||||| |||||||||| |||||||||| |||||||||| |||||||||| |||||||||| ||||||||||
d2096_1_80  ACAATTATGT TAACCTGGTG CTCGTACAAT ACTACTCCCA TTTGCTCAAC GGCTTAGCGA ATACCAACGA ATGTTATTTG
                 850        860        870        880        890        900        910        920 jmp1 str +  TGTTAATACA ATTGGACCAC GAGCATGTTA TGATGAGGGT AAACCAGTTG CCGAATCGCT TATGGTTGCT TACAATAAAC>
            |||||||||| |||||||||| |||||||||| |||||||||| |||||||||| |||||||||| |||||||||| ||||||||||
d2096_1_80  TGTTAATACA ATTGGACCAC GAGCATGTTA TGATGAGGGT AAACGAGTTG CCGAATCGCT TATGGTTGCT TACAATAAAC 4890       4900       4910       4920       4930       4940       4950       4960
jmp1 str +  AAGAAAATAT CAAGATTCGA ATTGCTCGAA TTTTCAACAA AAAAGTTGTG AGAATGCACA TGAATGATGG ACGAGTTGTT
            |||||||||| |||||||||| |||||||||| |||||||||| |||||||||| |||||||||| |||||||||| ||||||||||
d2096_1_80  TTCTTTTATA GTTCTAAGCT TAACGAGCTT AAAACCTGGT TCTTACGTGT AGAATGCACA TGAATGATGG ACGAGTTGTT
                 930        940        950        960        970        980        990        1000 jmp1 str +  AAGAAAATAT CAAGATTCGA ATTGCTCGAA TTTTCAACGA TTTTGGACCA AGAATGCACA TGAATGATGG ACGAGTTGTT>
            |||||||||| |||||||||| |||||||||| |||||||||| |||||||||| |||||||||| |||||||||| ||||||||||
d2096_1_80  AAGAAAATAT CAAGATTCGA ATTGCTCGAA TTTTCAACAC TTTTGGACCA AGAATGCACA TGAATGATGG ACGAGTTGTT 4970       4980       4990       5000       5010       5020       5030       5040
d2096_1_80  TCGAATTTTA TAATTCAGGC ACTTCAGGAT AAACCAATCA CGGTGAGCAA TAGCTTCTTA TACTTAATAT GAAAAAATTA
```

```
                   5290       5300       5310       5320       5330       5340       5350       5360
d2096_1_80   CCAGATATCC GGAGAGCTGC TGAACAAATA TCATGGGCTC CACAAGTTCA TATGAAAGAC GGACTCCTTA AAACTGTTGA
             |||||||||| |||||||||| |||||||||| |||||||||| |||||||||| |||||||||| |||||||||| ||||||||||
             GGTCTATAGG CCTCTCGACG ACTTGTTTAT AGTACCCGAG GTGTTCAAGT ATACTTTCTG CCTGAGGAAT TTTGACAACT
                   1270       1280       1290       1300       1310       1320       1330       1340
jmpl str +   CCAGATATCC GGAGAGCTGC TGAACAAATA TCATGGGCTC CACAAGTTCA TATGAAAGAC GGACTCCTTA AAACTGTTGA>
             |||||||||| |||||||||| |||||||||| |||||||||| |||||||||| |||||||||| |||||||||| ||||||||||
d2096_1_80   CCAGATATCC GGAGAGCTGC TGAACAAATA TCATGGGCTC CACAAGTTCA TATGAAAGAC GGACTCCTTA AAACTGTTGA 5370       5380       5390       5400       5410       5420       5430       5440
d2096_1_80   CTACTTTCGT GCTGAAATTG ACCGAAATAA ACGAGGAGGG AAACCTGTAC CGGAGCCTGT AAGGCTTGCA GGTCTTGAGA
             |||||||||| |||||||||| |||||||||| |||||||||| |||||||||| |||||||||| |||||||||| ||||||||||
             GATGAAAGCA CGACTTTAAC TGGCTTTATT TGCTCCTCCC TTTGGACATG GCCTCGGACA TTCCGAACGT CCAGAACTCT
                   1350       1360       1370       1380       1390       1400       1410       1420
jmpl str +   CTACTTTCGT GCTGAAATTG ACCGAAATAA ACGAGGAGGG AAACCTGTAC CGGAGCCTGT AAGGCTTGCA GGTCTTGAGA>
             |||||||||| |||||||||| |||||||||| |||||||||| |||||||||| |||||||||| |||||||||| ||||||||||
d2096_1_80   CTACTTTCGT GCTGAAATTG ACCGAAATAA ACGAGGAGGG AAACCTGTAC CGGAGCCTGT AAGGCTTGCA GGTCTTGAGA 5450       5460       5470       5480       5490       5500       5510       5520
d2096_1_80   GTCGACGATG AGAACGCAAC AAGCAAGGCT CGAACCGAAA CTTCCAATTT ATATCATTTC TTTTTTCAAA ATATTTCCTG
             |||||||||| |||||||||| |||||||||| |||||||||| |||||||||| |||||||||| |||||||||| ||||||||||
             CAGCTGCTAC TCTTGCGTTG TTCGTTCCGA GCTTGGCTTT GAAGGTTAAA TATAGTAAAG AAAAAAGTTT TATAAAGGAC
                   1430       1440       1450       1460       1470       1480       1490       1500
jmpl str +   GTCGACGATG AGAACGCAAC AAGCAAGGCT CGAACCGAAA CTTCCAATTT ATATCATTTC TTTTTTCAAA ATATTTCCTG>
             |||||||||| |||||||||| |||||||||| |||||||||| |||||||||| |||||||||| |||||||||| ||||||||||
d2096_1_80   GTCGACGATG AGAACGCAAC AAGCAAGGCT CGAACCGAAA CTTCCAATTT ATATCATTTC TTTTTTCAAA ATATTTCCTG 5530       5540       5550       5560       5570       5580       5590       5600
d2096_1_80   TCTTTTAAAT ACGGGTAATT TCCTTATTCT AGGCATTATT TTACATTCTT CCAATCCTGG TTTACATGTA AAAACGTGCT
             |||||||||| |||||||||| |||||||||| |||||||||| |||||||||| |||||||||| |||||||||| ||||||||||
             AGAAAATTTA TGCCCATTAA AGGAATAAGA TCCGTAATAA AATGTAAGAA GGTTAGGACC AAATGTACAT TTTTGCACGA
                   1510       1520       1530       1540       1550       1560       1570       1580
jmpl str +   TCTTTTAAAT ACGGGTAATT TCCTTATTCT AGGCATTATT TTACATTCTT CCAATCCTGG TTTACATGTA AAAACGTGCT>
             |||||||||| |||||||||| |||||||||| |||||||||| |||||||||| |||||||||| |||||||||| ||||||||||
d2096_1_80   TCTTTTAAAT ACGGGTAATT TCCTTATTCT AGGCATTATT TTACATTCTT CCAATCCTGG TTTACATGTA AAAACGTGCT
```

Figure 1C cont.

```
                      5610        5620        5630        5640        5650        5660        5670        5680
d2096_1_80    TCATTATCAG TGCGTTTTCT CCGGTATTTT TGCTTTTTCA AAATCGATAT CATCTTGATT TAAATACGCG GTTCACATTT
              AGTAATAGTC ACGCAAAAGA GGCCATAAAA ACGAAAAAGT TTTAGCTATA GTAGAACTAA ATTTATGCGC CAAGTGTAAA
                      1590        1600        1610        1620        1630        1640        1650        1660
jmp1 str +    TCATTATCAG TGCGTTTTCT CCGGTATTTT TGCTTTTTCA AAATCGATAT CATCTTGATT TAAATACGCG GTTCACATTT>
              ||||||||||  |||||||||| |||||||||| |||||||||| |||||||||| |||||||||| |||||||||| ||||||||||
d2096_1_80    TCATTATCAG TGCGTTTTCT CCGGTATTTT TGCTTTTTCA AAATCGATAT CATCTTGATT TAAATACGCG GTTCACATTT 5690        5700        5710        5720        5730        5740        5750        5760
d2096_1_80    TCCTCTAATT CACAGTCTAT TTTCCGCTTT CATGTTGTAT ATTTCAATTT TATAGAATTT TTAAATGCAC CCGTCTTTGA
              AGGAGATTAA GTGTCAGATA AAAGGCGAAA GTACAACATA TAAAGTTAAA ATATCTTAAA AATTTACGTG GGCAGAAACT
                      1670        1680        1690        1700        1710        1720        1730        1740
jmp1 str +    TCCTCTAATT CACAGTCTAT TTTCCGCTTT CATGTTGTAT ATTTCAATTT TATAGAATTT TTAAATGCAC CCGTCTTTGA>
              |||||||||| |||||||||| |||||||||| |||||||||| |||||||||| |||||||||| |||||||||| ||||||||||
d2096_1_80    TCCTCTAATT CACAGTCTAT TTTCCGCTTT CATGTTGTAT ATTTCAATTT TATAGAATTT TTAAATGCAC CCGTCTTTGA 5770        5780        5790        5800        5810        5820        5830        5840
d2096_1_80    TAAAAATTGA ACTTTCGTAC AAGTGCTCGA CTTTTTTTTG TGAAGTGATA GATGTTGGTT GTCGTGCCTG
              ATTTTTAACT TGAAAGCATG TTCACGAGCT GAAAAAAAAC ACTTCACTAT CTACAACCAA CAGCACGGAC
                      1750        1760        1770
jmp1 str +    TAAAAATTGA ACTTTCGTAC AA>
              |||||||||| |||||||||| ||
d2096_1_80    TAAAAATTGA ACTTTCGTAC AA 5850        5860        5870        5880        5890        5900        5910        5920
d2096_1_80    GTTTCATTAC ATAAAAAAGC TTTCTAATTC CATATTGCCG GAAAATTTCA AGAGACTTTG TATTTCAGGA ATGGCCGCTG
              CAAAGTAATG TATTTTTTCG AAAGATTAAG GTATAACGGC CTTTTAAAGT TCTCTGAAAC ATAAAGTCCT TACCGGCGAC 5930        5940        5950        5960        5970        5980        5990        6000
```

Figure 1C cont.

```
d2096_1_80   AGCCTATGGA AGAGGACGAT AGCTTCAATG ATCCACTACC TAGAGCTGTA CCTTTTCCTC GACATTCTGT AACTCGAGACT
             TCGGATACCT TCTCCTGCTA TCGAAGTTAC TAGGTGATGG ATCTCGACAT GGAAAAGGAG CTGTAAGACA TTGAGTCTGA
                  6010       6020       6030       6040       6050       6060       6070       6080
d2096_1_80   GCTGCTCCGC TTTCATCAAA ACCTGTAGAT TCTGATCCTG ATTCAGATGA TTCTTTTGAA ACTTTTGCAC CGAACACAAAC
             CGACGAGGCG AAAGTAGTTT TGGACATCTA AGACTAGGAC TAAGTCTACT AAGAAAACTT TGAAAACGTG GCTGTGTTTG
                  6090       6100       6110       6120       6130       6140       6150       6160
d2096_1_80   AACAACAGGA AATTCACTGA AAAGTTCAGC AAGCAGTACA CAATCTACGG AAGCTAGTAA TATTTTCGAG AATAATAATG
             TTGTTGTCCT TTAAGTGACT TTTCAAGTCG TTCGTCATGT GTTAGATGCC TTCGATCATT ATAAAAGCTC TTATTATTAC
                  6170       6180       6190       6200       6210       6220       6230       6240
d2096_1_80   AGAAATTAAT TTTTTTTTCG TTTTCAGAAC CACCTCCTGT GCAATTCCCA CCACCGTCCA AAAATCCTCC AAAACACGTA
             TCTTTAATTA AAAAAAAAGC AAAAGTCTTG GTGGAGGACA CGTTAAGGGT GGTGGCAGGT TTTTAGGAGG TTTTGTGCAT
                  6250       6260       6270       6280       6290       6300       6310       6320
d2096_1_80   CATCAACAAA ACGTTTCAAG TGAGAACAAC TAATATTGAT CTTAAGGCAA TCTTCTGAAT TACAGAATCC CCACTGATTC
             GTAGTTGTTT TGCAAAGTTC ACTCTTGTTG ATTATAACTA GAATTCCGTT AGAAGACTTA AGTCTTAGG GGTGACTAAG
                  6330       6340       6350       6360       6370       6380       6390       6400
d2096_1_80   CACAACTTCC GCGAAATCAA GTTCCGACTC GACCTCAAAT AAATACAGTT CAATCTGTAC AACAGAAACC ATCAGCGAGT
             GTGTTGAAGG CGCTTTAGTT CAAGGCTGAG CTGGAGTTTA TTTATGTCAA GTTAGACATG TTGTCTTTGG TAGTCGCTCA
                  6410       6420       6430       6440       6450       6460       6470       6480
d2096_1_80   GCCACTGGCA GAGTAGGAAT AGGTGTGCAT TCAGCAGTTG CGAATACCAG AAATGGTGTG ATGACAAAAA GTGCGGCAAA
             CGGTGACCGT CTCATCCCTA TCCACACGTA AGTCGTCAAC GCTTATGGTC TTTACCACAC TACTGTTTTT CACGCCGTTT
```

Figure 1C cont.

human *sqv-1* homolog/ortholog assembled cDNA sequence

TCCTACATCAGAATGGTAACAGGGCCCCCGCGCGGCAGGGCCCTGGACCCGC
GCGGCTCCCGGGG

ATGGTGAGCAAGGCGCTGCTGCGCCTCGTGTCTGCCGTCAACCGCAGGAGGA
TGAAGCTGCTGCTGGGCATCGCCTTGCTGGCCTACGTCGCCTCTGTTTGGGGC
AACTTCGTTAATATGAGGTCTATCCAGGAAAATGGTGAACTAAAAATTGAAA
GCAAGATTGAAGAGATGGTTGAACCACTAAGAGAGAAAATCAGAGATTTAG
AAAAAAGCTTTACCCAGAAATACCCACCAGTAAAGTTTTTATCAGAAAAGGA
TCGGAAAAGAATTTTGATAACAGGAGGCGCAGGGTTCGTGGGCTCCCATCTA
ACTGACAAACTCATGATGGACGGCCACGAGGTGACCGTGGTGGACAATTTCT
TCACGGGCAGGAAGAGAAACGTGGAGCACTGGATCGGACATGAGAACTTCG
AGTTGATTAACCACGACGTGGTGGAGCCCCTCTACATCGAGGTTGACCAGAT
ATACCATCTGGCATCTCCAGCCTCCCCTCCAAACTACATGTATAATCCTATCA
AGACATTAAAGACCAATACGATTGGGACATTAAACATGTTGGGGCTGGCAAA
ACGAGTCGGTGCCCGTCTGCTCCTGGCCTCCACATCGGAGGTGTATGGAGAT
CCTGAAGTCCACCCTCAAAGTGAGGATTACTGGGGCCACGTGAATCCAATAG
GACCTCGGGCCTGCTACGATGAAGGCAAACGTGTTGCAGAGACCATGTGCTA
TGCCTACATGAAGCAGGAAGGCGTGGAAGTGCGAGTGGCCAGAATCTTCAAC
ACCTTTGGGCCACGCATGCACATGAACGATGGGCGAGTAGTCAGCAACTTCA
TCCTGCAGGCGCTCCAGGGGGAGCCACTCACGGTATACGGATCCGGGTCTCA
GACAAGGGCGTTCCAGTACGTCAGCGATCTAGTGAATGGCCTCGTGGCTCTC
ATGAACAGCAACGTCAGCAGCCCGGTCAACCTGGGGAACCCAGAAGAACAC
ACAATCCTAGAATTTGCTCAGTTAATTAAAAACCTTGTTGGTAGCGGAAGTG
AAATTCAGTTTCTCTCCGAAGCCCAGGATGACCCACAGAAAAGAAAACCAGA
CATCAAAAAAGCAAAGCTGATGCTGGGGTGGGAGCCCGTGGTCCCGCTGGAG
GAAGGTTTAAACAAAGCAATTCACTACTTCCGTAAAGAACTCGAGTACCAGG
CAAATAATCAGTACATCCCCAAACCAAAGCCTGCCAGAATAAAGAAAGGAC
GGACTCGCCACAGCTGA

ACTCCTCACTTTTAGGACACAAGACTACCATTGTACACTTGATGGGATGTATT
TTTGGCTTTTTTTGTTGTCGTTTAAAGAAAGACTTTAACAGGTGTCATGAAG
AACAAACTGGAATTTCATTCTGAAGCTTGCTTTAATGAAATGGATGTGCCTAA
AAGCTCCCCTCAAAAAACTGCAGATTTTGCCTTGCACTTTTTGAATCTCTCTTT
TTATGTAAAATAGCGTAGATGCATCTCTGCGTATTTTCAAGTTTTTTTATCTTG
CTGTGAGAGCATATGTTGTGACTGTCGTTGACAGTTTTATTTACTGGTTTCTTT
GTGAAGCTGAAAAGGAACATTAAGCGGGACAAAAAATGCCGATTTTATTTAT
AAAAGTGGGTACTTAATAAATGAGTCGTTATACTATGCATAAAGAAAAATCC
TAGCAGTATTGTCAGGTGGTGGTGCGCCGGCATTGATTTTAGGGCAGATAAA
AGAATTCTGTGTGAGAGCTTTATGTTTCTCTTTTAATTCAGAGTTTTTCCAAGG
TCTACTTTTGAGTTGCAAACTTGACTTTGAAATATTCCTGTTGGTCATGATCA
AGGATATTTGAAATCACTACTGTGTTTTGCTGCGTATCTGGGGCGGGGGCAG
GTTGGGGGGCACAAAGTTAACATATTCTTGGTTAACCATGGTTAAATATGCTA

Figure 1D

TTTTAATAAAATATTGAAACTCAAAAAAAAAAAAAAAAAAAAAAAAAAAA
AAAAAAAAA

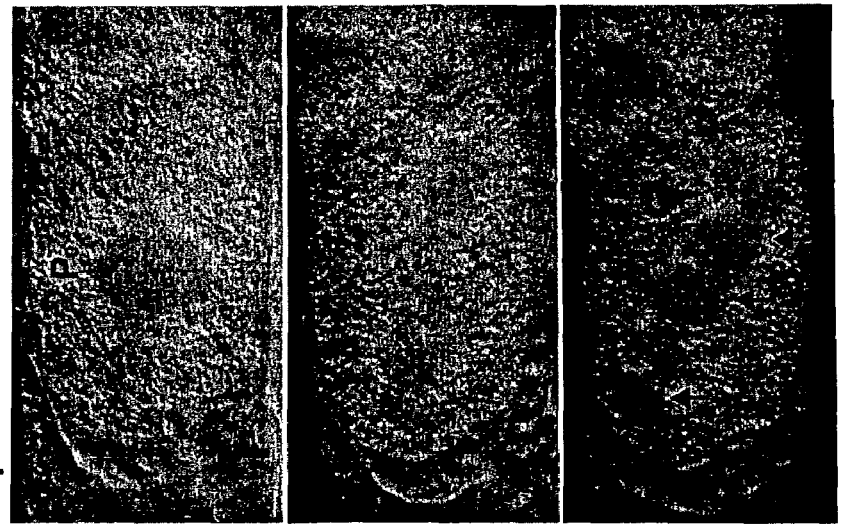
Figures 8A-F sqv-2 genomic sequence
Sequence Range: 1 to 5759

```
              10         20         30         40         50         60         70         80
Y110A2AL.1  GAATATAAAC ATGACAAGGT TCGGAGAAGT TTGAAATTTA TGTGGGTCTC TCGGCGAGCT GAGTTTAAAA ATTAAAAAAT
            CTTATATTTG TACTGTTCCA AGCCTCTTCA AACTTTAAAT ACACCCAGAG AGCCGCTCGA CTCAAATTTT TAATTTTTTA 90        100        110        120        130        140        150        160
Y110A2AL.1  TTAGAGAAAA AAAGAGTCCC AACGCGAAAA AATTCCAAAA ACTATGGGAT CTCGTGGCGG GTTTTTTCCA ATTTTTCACT
            AATCTCTTTT TTTCTCAGGG TTGCGCTTTT TTAAGGTTTT TGATACCCTA GAGCACCGCC CAAAAAAGGT TAAAAAGTGA 170        180        190        200        210        220        230        240
Y110A2AL.1  ACTGAAATGT TGTTTTTTTT TTCAGCCAAA TGCTGCCGGA ATGAGATTCT ACCGAACATA TTTGCTCGTA GCTGGCGCTT
            TGACTTTACA ACAAAAAAAA AAGTCGGTTT ACGACGGCCT TACTCTAAGA TGGCTTGTAT AAACGAGCAT CGACCGCGAA 10         20         30         40         50
jmp1 str +              CCAAA TGCTGCCGGA ATGAGATTCT ACCGAACATA TTTGCTCGTA GCTGGCGCTT>
                        ||||| |||||||||| |||||||||| |||||||||| |||||||||| ||||||||||
Y110A2AL.1              CCAAA TGCTGCCGGA ATGAGATTCT ACCGAACATA TTTGCTCGTA GCTGGCGCTT 250        260        270        280        290        300        310        320
Y110A2AL.1  TTTGCTCATT GTGCACACTT GCAGTAATAT TCAATTGTGG ATGGGATGAT TCACCGCCAG CAACACCTTC AGCCATCAAT
            |||||||||| |||||||||| |||||||||| |||||||||| |||||||||| |||||||||| |||||||||| ||||||||||
            TTTGCTCATT GTGCACACTT GCAGTAATAT TCAATTGTGG ATGGGATGAT TCACCGCCAG CAACACCTTC AGCCATCAAT 60         70         80         90        100        110        120        130
jmp1 str +  TTTGCTCATT GTGCACACTT GCAGTAATAT TCAATTGTGG ATGGGATGAT TCACCGCCAG CAACACCTTC AGCCATCAAT>
            |||||||||| |||||||||| |||||||||| |||||||||| |||||||||| |||||||||| |||||||||| ||||||||||
Y110A2AL.1  TTTGCTCATT GTGCACACTT GCAGTAATAT TCAATTGTGG ATGGGATGAT TCACCGCCAG CAACACCTTC AGCCATCAAT 330        340        350        360        370        380        390        400
Y110A2AL.1  GGTTCGGAGC AATTTTAAGC GGAAAAATTT GAAAAAATCC TCGAAATTTC GGAAAAAACT TTGAATTTTG AATTTTTAGC
            CCAAGCCTCG TTAAATTCG CCTTTTTAAA CTTTTTAAG AGCTTTAAAG CCTTTTTGA AACTTAAAAC TTAAAAATCG

```
jmp1 str +    GGCGGTGGC>
              ||
Y110A2AL.1    GGTTCGGAG 410        420        430        440        450        460        470        480
Y110A2AL.1    TCGAAAATTG CCATTTTTAG CCATTTTCGG AGATTTTGAC CCAAAAATTT GAATTTTTCC ATTAAAAAAC CCGAAATTCC
              AGCTTTTAAC GGTAAAAATC GGTAAAAGCC TCTAAAACTG CGTTTTTAAA CTTAAAAAGG TAATTTTTTG GGCTTTTAAGG 490        500        510        520        530        540        550        560
Y110A2AL.1    CGAGAATTAT CAGTAGAGCG CAGTTTCATT TTTCGAAAAA TTCAAATTTT TTGAATTTTC AAATAATGCG CCGGCGCTCTA
              GCTCTTAATA GTCATCTCGC GTCAAAGTAA AAAGCTTTTT AAGTTTAAAA AACTTAAAAG TTTATTACGC GGCGCGAGAT 570        580        590        600        610        620        630        640
Y110A2AL.1    CTGATATTTT TTCTAAAAAT TTCAAATTTT TTAGAAGCAG AGTGCACTTG CATTATTCGA AAATTTAGAA AAATATAAAA
              GACTATAAAA AAGATTTTTA AAGTTTAAAA AATCTTCGTC TCACGTGAAC GTAATAAGCT TTTAAATCTT TTTATATTTT 650        660        670        680        690        700        710        720
Y110A2AL.1    TTTTAGTTTT TGAAAAATGC AACCGTGCTC TACTGATAAT TTTTCTAAAA TTTTCGAATT TTGAGCTAAA TTGCATAAAT
              AAAATCAAAA ACTTTTTACG TTGGCACGAG ATGACTATTA AAAAGATTTT AAAAGCTTAA AACTCGATTT AACGTATTTA 730        740        750        760        770        780        790        800
Y110A2AL.1    TTCGTTCCGA GACCCATTTT TTCCACAAAA TTCCAATTTT TTAAAGGAAA ATTAACAGTA GAGTGCAGTT GCATTATTCG
              AAGCAAGGCT CTGGGTAAAA AAGGTGTTTT AAGGTTAAAA AATTCCTTT  TAATTGTCAT CTCACGTCAA CGTAATAAGC 810        820        830        840        850        860        870        880
Y110A2AL.1    GAAATTTAAA AAACATGAAA ATTGAATTTT TGAAGAATGC AACCGCGCTC TAATGATAAC TTTTCTAAAA ATTTCAAATT
              CTTTAAATTT TTTGTACTTT TAACTTAAAA ACTTCTTACG TTGGCGCGAG ATTACTATTG AAAAGATTTT TAAAGTTTAA 890        900        910        920        930        940        950        960
Y110A2AL.1    TTGGGCACAA AATTGTTTAA ATCTCGTTTC GAGACATCAA AATTTTAGAA AAATTGTCAG TAAAGCGAAT TTTGAATTTT
              AACCCGTGTT TTAACAAATT TAGAGCAAAG CTCTGTAGTT TTAAAATCTT TTTAACAGTC ATTTCGCTTA AAACTTAAAA
```

Figure 9C Cont.

```
                        970         980         990        1000        1010        1020        1030        1040
Y110A2AL.1   TGAAAAATGC AGCAACCGCG CTCTACTGAT AATTTTTCAA AATTTTGGAA ATTCGAGCTC AAAAATTGCA AAATTTTCGT
             ACTTTTTACG TCGTTGGCGC GAGATGACTA TTAAAAAGTT TTAAAACCTT TAAGCTCGAG TTTTTAACGT TTTAAAGCA 1050        1060        1070        1080        1090        1100        1110        1120
Y110A2AL.1   TTCGAGACTC ATTTCTCCGC AAAATTTTGA TTTTTGCTCC AAATGTCAGC AGCAACTGCG CCCTATTGAT
             AAGCTCTGAG TAAAGAGGCG TTTTAAAACT AAAAACGAGG TTTACAGTCG TCGTTGACGC GGGATAACTA 1130        1140        1150        1160        1170        1180        1190        1200
Y110A2AL.1   AATTTTGCGA AAAATTTCGA ATTTTGAGCT CAGAAATTGC TCAAATTTCG CTTCAAGACC CGATTTTTTC TCCAAATTTC
             TTAAAACGCT TTTTAAAGCT TAAAACTCGA GTCTTTAACG AGTTTAAAGC GAAGTTCTGG GCTAAAAAAG AGGTTTAAAG 1210        1220        1230        1240        1250        1260        1270        1280
Y110A2AL.1   CGATTTTTTT TCCAGAAAAA TCGATAATTT TCCCCAATTT TCAGGCGGTG GCTCCAATGC TCCTTTAATC TCCTCTCCAA
             GCTAAAAAAA AGGTCTTTTT AGCTATTAAA AGGGGTTAAA AGTCCGCCAC CGAGGTTACG AGGAAATTAG AGGAGAGGTT 130         140         150         160         170
jmp1 str +                               CCATC AATGGCGGTG GCTCCAATGC TCCTTTAATC TCCTCTCCAA>
                                         ||||| |||||||||| |||||||||| |||||||||| ||||||||||
Y110A2AL.1                               AATTT TCAGGCGGTG GCTCCAATGC TCCTTTAATC TCCTCTCCAA 1290        1300        1310        1320        1330        1340        1350        1360
Y110A2AL.1   CTAATCTTCC CGAAACATTT CTGTACATTT CAATTCTGAC GTCACCAAAC GAAACAGAAC GACGTCAAAA TGTCCGTGAC
             GATTAGAAGG GCTTTGTAAA GACATGTAAA GTTAAGACTG CAGTGGTTTG CAGTGGTTTT ACAGGCACTG 180         190         200         210         220         230         240         250
jmp1 str +   CTAATCTTCC CGAAACATTT CTGTACATTT CAATTCTGAC GTCACCAAAC GAAACAGAAC GACGTCAAAA TGTCCGTGAC>
             |||||||||| |||||||||| |||||||||| |||||||||| |||||||||| |||||||||| |||||||||| ||||||||||
Y110A2AL.1   CTAATCTTCC CGAAACATTT CTGTACATTT CAATTCTGAC GTCACCAAAC GAAACAGAAC GACGTCAAAA TGTCCGTGAC 1370        1380        1390        1400        1410        1420        1430        1440
```

Figure 9C Cont.

```
Y110A2AL.1       ACATGGTTCC GCCTATCAAC TAAAGGACCG TCCGTTTTTA TCGCAAAATT CGCCGTCGGA ACGATGGGCC TCGCGGCCGA
                 TGTACCAAGG CGGATAGTTG ATTTCCTGGC AGGCAAAAAT AGCGTTTTAA GCGGCAGCCT TGCTACCCGG AGCGCCGGCT
                     260        270        280        290        300        310        320        330
jmp1 str +       ACATGGTTCC GCCTATCAAC TAAAGGACCG TCCGTTTTTA TCGCAAAATT CGCCGTCGGA ACGATGGGCC TCGCGGCCGA>
                 |||||||||| |||||||||| |||||||||| |||||||||| |||||||||| |||||||||| |||||||||| ||||||||||
Y110A2AL.1       ACATGGTTCC GCCTATCAAC TAAAGGACCG TCCGTTTTTA TCGCAAAATT CGCCGTCGGA ACGATGGGCC TCGCGGCCGA
                    1450       1460       1470       1480       1490       1500       1510       1520
Y110A2AL.1       AGATCGTCGG TTGCTGGCCG AGGAAAATGA GAAATTCGGC GATTTGGCGC TTCTCGACCG CCATGAAGAG TCCTATGAGA
                 TCTAGCAGCC AACGACCGGC TCCTTTTACT CTTTAAGCCG CTAAACCGCG AAGAGCTGGC GGTACTTCTC AGGATACTCT
                     340        350        360        370        380        390        400        410
jmp1 str +       AGATCGTCGG TTGCTGGCCG AGGAAAATGA GAAATTCGGC GATTTGGCGC TTCTCGACCG CCATGAAGAG TCCTATGAGA>
                 |||||||||| |||||||||| |||||||||| |||||||||| |||||||||| |||||||||| |||||||||| ||||||||||
Y110A2AL.1       AGATCGTCGG TTGCTGGCCG AGGAAAATGA GAAATTCGGC GATTTGGCGC TTCTCGACCG CCATGAAGAG TCCTATGAGA
                    1530       1540       1550       1560       1570       1580       1590       1600
Y110A2AL.1       GGCTGGCAAA GAAGACTTTG GCCTGTTTTG TACACGCTTT TGCCAATTTT AAATTCAAAT TTTTCTTGAA GGTATACAAC
                 CCGACCGTTT CTTCTGAAAC CGGACAAAAC ATGTGCGAAA ACGGTTAAAA TTTAAGTTTA AAAAGAACTT CCATATGTTG
                     420        430        440        450        460        470        480        490
jmp1 str +       GGCTGGCAAA GAAGACTTTG GCCTGTTTTG TACACGCTTT TGCCAATTTT AAATTCAAAT TTTTCTTGAA GACCGACATC>
                 |||||||||| |||||||||| |||||||||| |||||||||| |||||||||| |||||||||| |||||||||| ||||
Y110A2AL.1       GGCTGGCAAA GAAGACTTTG GCCTGTTTTG TACACGCTTT TGCCAATTTT AAATTCAAAT TTTTCTTGAA GGTATACAAC
                    1610       1620       1630       1640       1650       1660       1670       1680
Y110A2AL.1       TGGAATTTGG CTGGAAATCC GCACTGCAAC TTTTTCCTGA CGAGGGACGA GGAAAAGTGG TTTCTAGGCC ATGGCCGAGG
                 ACCTTAAACC GACCTTTAGG CGTGACGTTG AAAAAGGACT GCTCCCTGCT CCTTTTCACC AAAGATCCGG TACCGGCTCC jmp1 str +       G>
Y110A2AL.1       T
```

Figure 9C Cont.

```
Y110A2AL.1      1690       1700       1710       1720       1730       1740       1750       1760
            GGCCGACAAG TTTCATCGGC CATTTATCTT GCTCTGTTTT CCGCCTGTTT TCTTTCGTTT TTCATCGATT TTTTTCGTTT
            CCGGCTGTTC AAAGTAGCCG GTAAATAGAA CGAGACAAAA GGCGGACAAA AGAAAGCAAA AAGTAGCTAA AAAAAGCAAA

Y110A2AL.1      1770       1780       1790       1800       1810       1820       1830       1840
            TTTCTTAATA AAACTGATAA ATAAATATTT TTTGCAGATG CTAAAACAAT TTCCGAGTAA AAAATTATGT ATTCAGTGGG
            AAAGAATTAT TTTGACTATT TATTTATAAA AACGTCTAC GATTTTGTTA AAGGCTCATT TTTTAATACA TAAGTCACCC

Y110A2AL.1      1850       1860       1870       1880       1890       1900       1910       1920
            CAAGCAGCGG TGAAAGTGGT CAATGTAAAA TGATGGATTA CGGGAATACA AAACCTAAAC TTTTTCTGAA ACATGATACA
            GTTCGTCGCC ACTTTCACCA GTTACATTTT ACTACCTAAT GCCCTTATGT TTTGGATTTG AAAAAGACTT TGTACTATGT

Y110A2AL.1      1930       1940       1950       1960       1970       1980       1990       2000
            TATGATGCTT AGATGTTGAA ATTACCTGAT TTTCATAACG AGACCGCTGA AAAAGTTTTG AGGTTTTCAA AATTCAAATT
            ATACTACGAA TCTACAACTT TAATGGACTA AAAGTATTGC TCTGGCGACT TTTTCAAAAC TCCAAAAGTT TTAAGTTTAA

Y110A2AL.1      2010       2020       2030       2040       2050       2060       2070       2080
            TTTTAGTGAA AAAGTCGAGA TTTTTCGCACA AAAAGTTTAA TTTTGAAAAT CTCAAAACTT TTTCAGCGGT CTCGTTATGA
            AAAATCACTT TTTCAGCTCT AAAAGCGTGT TTTTCAAATT AAAACTTTTA GAGTTTTGAA AAAGTCGCCA GAGCAATACT

Y110A2AL.1      2090       2100       2110       2120       2130       2140       2150       2160
            AAATCAGGTA ATTTCAGCAT CTAAGCATCA TATGTATCAT GTTTCAGAAA AAGTTTAGGT TTTGTATTCC CGTAATCCAT
            TTTAGTCCAT TAAAGTCGTA GATTCGTAGT ATACATAGTA CAAAGTCTTT TTCAAATCCA AAACATAAGG GCATTAGTA

Y110A2AL.1      2170       2180       2190       2200       2210       2220       2230       2240
            CATTTACAT TGACCACTTT CACCGCTGCT TGCCCACTGA ATACATAATT TTTACTCGG AAATTGTTTT AGCATCTGTG
            GTAAAATGTA ACTGGTGAAA GTGGCGACGA ACGGGTGACT TATGTATTAA AAAATGAGCC TTTAACAAAA TCGTAGACAC

Y110A2AL.1      2250       2260       2270       2280       2290       2300       2310       2320
            CAAAAAGTAT TTATTTATCA GTTTATTAA GAAAAACGA AAAAAAATCG ATGAAAAACG AAAGAAAACA GGCGAAAAC
```

Figure 9C Cont.

```
               GTTTTTCATA AATAAATAGT CAAAATAATT CTTTTTTGCT TTTTTTTAGC TACTTTTTGC TTTCTTTTGT CCGCCTTTTG
                     2330       2340       2350       2360       2370       2380       2390       2400
Y110A2AL.1  AAAGCAAGAT AAATGGCCGC TGAAACTTGT CGGCCCCTCG GCCATGGCCT AGAAACCACT TTTCCTCGTC CCTCGTGTGG
            TTTCGTTCTA TTTACCGGCG ACTTTGAACA GCCGGGGAGC CGGTACCGGA TCTTTGGTGA AAAGGAGCAG GGAGCACACC
                     2410       2420       2430       2440       2450       2460       2470       2480
Y110A2AL.1  AAAAAGTTGC AGTGATTTTG TAGATTTTCA CGGAAAAATT CATTATTCT TATAAAAAAA CTTGAAGTTT TAGTCTAACA
            TTTTTCAACG TCACTAAAAC ATCTAAAAGT GCCTTTTTAA GTAAATAAGA ATATTTTTTT GAACTTCAAA ATCAGATTGT
                     2490       2500       2510       2520       2530       2540       2550       2560
Y110A2AL.1  ATTAAGATTC TCGGTCAGTT TTAGAGATAA ATTACTCCAA AGTTGGGAGA TTTTTTGCGAA AAATCGTTAA AAATTATCAA
            TAATTCTAAG AGCCAGTCAA AATCTCTATT TAATGAGGTT TCAACCCTCT AAAAACGCTT TTTAGCAATT TTTAATAGTT
                     2570       2580       2590       2600       2610       2620       2630       2640
Y110A2AL.1  AAATGCCATA TTTTTGTCAGG AAAAATGTTT ATAATTTAAT AAACCCGAAA AATATCGAAA ATCGGCTAAA TTTTTTAGATT
            TTTACGGTAT AAAACAGTCC TTTTTACAAA TATTAAATTA TTTGGGCTTT TTATAGCTTT TAGCCGATTT AAAAATCTAA
                     2650       2660       2670       2680       2690       2700       2710       2720
Y110A2AL.1  TTTCAGCACA AAAAAATGAT GAGAAACTGT TGTGAAAAAC GGTTTTAATC CTCAAATTTT TTTTAAATCG GCAAAATGTG
            AAAGTCGTGT TTTTTTACTA CTCTTTGACA ACACTTTTTG CCAAAATTAG GAGTTTAAAA AAAATTTAGC CGTTTTACAC
                     2730       2740       2750       2760       2770       2780       2790       2800
Y110A2AL.1  AAATTTTGCC CAATTTTGTG CAAATTTTGA CTCAAAAAACC TCAATTTTCC TGTGGCAAAT GGATGTATCT ATTGAGTATT
            TTTAAAACGG GTTAAAACAC GTTTAAAACT GAGTTTTTGG AGTTAAAAGG ACACCGTTTA CCTACATAGA TAACTCATAA
                     2810       2820       2830       2840       2850       2860       2870       2880
Y110A2AL.1  GTGATGTGCA AAACCTCGTT AATTCGCCAA TAGAATTACG ATATTCTCAT CACAATTCCC GATGGGCTCC ATTTAGTCAC
            CACTACACGT TTTGGAGCAA TTAAGCGGGTT ATCTTAATGC TATAAGAGTA GTGTTAAGGG CTACCCGAGG TAAATCAGTG
```

Figure 9C Cont.

```
                   2890       2900       2910       2920       2930       2940       2950       2960
Y110A2AL.1   GTTTACGGGG AACCTCTGCC CAAATTTTCA TTTTTTGGCT AAAAACATTA AATTTTTCAA CAAAAAAAAA ACTCCGGTAG
             CAAATGCCCC TTGGAGACGG GTTTAAAAGT AAAAAACCGA TTTTTGTAAT TTAAAAAGTT GTTTTTTTTT TGAGGCCATC 2970       2980       2990       3000       3010       3020       3030       3040
Y110A2AL.1   AATTATTATT GTTATTATTT GCATTAAAAT TTTCCAATTT TTCACTCTAA AACCACCGCC GATTTTCCCC CAAAATCTCC
             TTAATAATAA CAATAATAAA CGTAATTTTA AAAGGTTAAA AAGTGAGATT TTGGTGGCGG CTAAAAGGGG GTTTTAGAGG jmp1 str +                                                                                        A>

C
Y110A2AL.1

3050       3060       3070       3080       3090       3100       3110       3120
Y110A2AL.1   CATTTTTTCA TCAGACCGAC ATCGACTCAT TCGTCCGAAT CACCCCACTA ATCATAAATC TCAAACAAAT TCAAGATCCA
             GTAAAAAAGT AGTCTGGCTG TAGCTGAGTA AGCAGGCTTA GTGGGGTGAT TAGTATTTAG AGTTTGTTTA AGTTCTAGGT 470        480        490        500        510        520        530        540
jmp1 str +   AATTTTTCTT GAAGACCGAC ATCGACTCAT TCGTCCGAAT CACCCCACTA ATCATAAATC TCAAACAAAT TCAAGATCCA>
             ||||||     |||||||||| |||||||||| |||||||||| |||||||||| |||||||||| |||||||||| ||||||||||
Y110A2AL.1   CATTTTTTCA TCAGACCGAC ATCGACTCAT TCGTCCGAAT CACCCCACTA ATCATAAATC TCAAACAAAT TCAAGATCCA 3130       3140       3150       3160       3170       3180       3190       3200
Y110A2AL.1   ATGCTCTACT GGGGATTCCT AGATGGTCGA GCTAAACCAT TCCGTAAAGG AAAATGGAAA GAACCCGAAT GGAATCTGTG
             TACGAGATGA CCCCTAAGGA TCTACCAGCT CGATTTGGTA AGGCATTTCC TTTTACCTTT CTTGGGCTTA CCTTAGACAC 550        560        570        580        590        600        610        620
jmp1 str +   ATGCTCTACT GGGGATTCCT AGATGGTCGA GCTAAACCAT TCCGTAAAGG AAAATGGAAA GAACCCGAAT GGAATCTGTG>
             |||||||||| |||||||||| |||||||||| |||||||||| |||||||||| |||||||||| |||||||||| ||||||||||
Y110A2AL.1   ATGCTCTACT GGGGATTCCT AGATGGTCGA GCTAAACCAT TCCGTAAAGG AAAATGGAAA GAACCCGAAT GGAATCTGTG 3210       3220       3230       3240       3250       3260       3270       3280
Y110A2AL.1   TGATCGTTAT CTTCCATATC AACTTGGCGG TGGTTATGTG CTCTCTTATG AGCTCATTCG ATTCTTGGCA ATCAATGCCC
             ACTAGCAATA GAAGGTATAG TTGAACCGCC ACCAATACAC GAGAGAATAC TCGAGTAAGC TAAGAACCGT TAGTTACGGG
```

Figure 9C Cont.

```
              630         640         650         660         670         680         690         700
jmp1 str +  TGATCGTTAT CTTCCATATC AACTTGGCGG TGGTTATGTG CTCTCTTATG AGCTCATTCG ATTCTTGGCA ATCAATGCCC>
            |||||||||| |||||||||| |||||||||| |||||||||| |||||||||| |||||||||| |||||||||| ||||||||||
Y110A2AL.1  TGATCGTTAT CTTCCATATC AACTTGGCGG TGGTTATGTG CTCTCTTATG AGCTCATTCG ATTCTTGGCA ATCAATGCCC 3290        3300        3310        3320        3330        3340        3350        3360
Y110A2AL.1  AACTCTTCCG ACACTATCGG AATGAAGATG TGTCGGTAGG CGCCTGGATA GGCGGCCTAG ATGTTAAATA TGTACATGAT
            |||||||||| |||||||||| |||||||||| |||||||||| |||||||||| |||||||||| |||||||||| ||||||||||
            TTGAGAAGGC TGTGATAGCC TTACTTCTAC ACAGCCATCC GCGACCTAT CCGCCGGATC TACAATTTAT ACATGTACTA 710         720         730         740         750         760         770         780
jmp1 str +  AACTCTTCCG ACACTATCGG AATGAAGATG TGTCGGTAGG CGCCTGGATA GGCGGCCTAG ATGTTAAATA TGTACATGAT>
            |||||||||| |||||||||| |||||||||| |||||||||| |||||||||| |||||||||| |||||||||| ||||||||||
Y110A2AL.1  AACTCTTCCG ACACTATCGG AATGAAGATG TGTCGGTAGG CGCCTGGATA GGCGGCCTAG ATGTTAAATA TGTACATGAT 3370        3380        3390        3400        3410        3420        3430        3440
Y110A2AL.1  CCGAGATTTG ATACCGAATG GAGATCCCGT GGATGTAATA ATGAGTATTT AATTACTCAT AAGCACACGG AGCAAGAGAT
            |||||||||| |||||||||| |||||||||| |||||||||| |||||||||| |||||||||| |||||||||| ||||||||||
            GGCTCTAAAC TATGGCTTAC CTCTAGGGCA CCTACATTAT TACTCATAAA TTAATGAGTA TTCGTGTGCC TCGTTCTCTA 790         800         810         820         830         840         850         860
jmp1 str +  CCGAGATTTG ATACCGAATG GAGATCCCGT GGATGTAATA ATGAGTATTT AATTACTCAT AAGCACACGG AGCAAGAGAT>
            |||||||||| |||||||||| |||||||||| |||||||||| |||||||||| |||||||||| |||||||||| ||||||||||
Y110A2AL.1  CCGAGATTTG ATACCGAATG GAGATCCCGT GGATGTAATA ATGAGTATTT AATTACTCAT AAGCACACGG AGCAAGAGAT 3450        3460        3470        3480        3490        3500        3510        3520
Y110A2AL.1  GCAAGAGATG TTTGAAAATT TGAAGAAAAC TGGAAAACTT TGTGCTAAAG AGTTCCAGTA AGTCAGCGGA AATGACGAA
            |||||||||| |||||||||| |||||||||| |||||||||| |||||||||| |||||||||| |||||||||| ||||||||||
            CGTTCTCTAC AAACTTTTAA ACTTCTTTTG ACCTTTTGAA ACACGATTTC TCAAGGTCAT TCAGTCGCCT TTACCTGCTT 870         880         890         900         910         920         930
jmp1 str +  GCAAGAGATG TTTGAAAATT TGAAGAAAAC TGGAAAACTT TGTGCTAAAG AGTTCCAAAA ACATC>
            |||||||||| |||||||||| |||||||||| |||||||||| |||||||||| |||||||| |
Y110A2AL.1  GCAAGAGATG TTTGAAAATT TGAAGAAAAC TGGAAAACTT TGTGCTAAAG AGTTCCAGTA AGTCA 3530        3540        3550        3560        3570        3580        3590        3600
```

Figure 9C Cont.

```
Y110A2AL.1    AAATCATCGC ATTTTTTGGG ATTTTTTGAAC CAATTTTCAA TAAAAATCAA TTTTTAGTGC TGAAAATTGA ATTTTCGCGC
              TTTAGTAGCG TAAAAAACCC TAAAAACTTG GTTAAAAGTT ATTTTTAGTT AAAAATCACG ACTTTTAACT TAAAAGCGCG
                    3610       3620       3630       3640       3650       3660       3670       3680
Y110A2AL.1    GAATTTTTAG GTTTTTACTG TGAAAATTGT GGGTGATTTA GAGCTTTTTT GGCCATTTTT CCGCGAAAAT GCCAGATTTT
              CTTAAAAATC CAAAAATGAC ACTTTTAACA CCCACTAAAT CTCGAAAAAA CCGGTAAAAA GGCGCTTTTA CGGTCTAAAA
                    3690       3700       3710       3720       3730       3740       3750       3760
Y110A2AL.1    AGGCTGAAAA ATGAAGAAAA ATCGATTAAA AACCCATTTT TCCGGGTAAA ATTAGAGAAA ATCGCATTTT TTTGGGATTT
              TCCGACTTTT TACTTCTTTT TAGCTAATTT TTGGGTAAAA AGGCCCATTT TAATCTCTTT TAGCGTAAAA AAACCCTAAA
                    3770       3780       3790       3800       3810       3820       3830       3840
Y110A2AL.1    TTGAGAACCA ATTTTTCATA ATAAAAAACA ATTTTTAGTG CTGAAAATCC GCATTTTGGG GGTTAAAAAT GTGAAAAATC
              AACTCTTGGT TAAAAAGTAT TATTTTTTGT TAAAAATCAC GACTTTTAGG CGTAAAACCC CCAAATTTTA CACTTTTTAG
                    3850       3860       3870       3880       3890       3900       3910       3920
Y110A2AL.1    CGGATTTTTC CGAGAAAAAT TTAGTATTTG AGCTAAACAG CCGAAAAACT TGCCATTTTC ATGAAAATTT CACTAATTTT
              GCCTAAAAAG GCTCTTTTTA AATCATAAAC TCGATTTGTC GGCTTTTTGA ACGGTAAAAG TACTTTTAAA GTGATTAAAA
                    3930       3940       3950       3960       3970       3980       3990       4000
Y110A2AL.1    CCGCTAAAAA TCAGAAAATT GGCAATTTTC GGGTAAAAAC TCTAAAAAAT CGTAATTTTT CGGGGTTTCA ACGGATTTT
              GGCGATTTTT AGTCTTTTAA CCGTTAAAAG CCCAATTTTG AGATTTTTTA GCATTAAAAA GCCCCAAAGT TGCGCTAAAA
                    4010       4020       4030       4040       4050       4060       4070       4080
Y110A2AL.1    TCAATTAAAA ATCGGTTTTT TGCGGAAAAT TTTGGAAATT TTTGGAATTT TTGGATTTTT AAAATTAAAA AAAAATTTT
              AGTTAATTTT TAGCCAAAAA ACGCCTTTTA ACCGGTTTTT AAACCTTTAA AACCTAAAAA TTTAATTTTT TTTTTAAAA
                    4090       4100       4110       4120       4130       4140       4150       4160
Y110A2AL.1    AAGATTTTTT AAAAATAATT TTGATTTTTT GGCCTAAAAA TCAAATTTTT GGCCTTAACA TTAAAGGATT TAGCCTTAAA
              TTCTAAAAAA TTTTTATTAA AACTAAAAAA CCGGATTTTT AGTTTTAAAA CCGGAATTGT AATTTCCTAA ATCGGAATTT
```

Figure 9C Cont.

| | 4170 | 4180 | 4190 | 4200 | 4210 | 4220 | 4230 | 4240 |
|---|---|---|---|---|---|---|---|---|
| Y110A2AL.1 | ATTTTGGATT | TTTTGAATTT | AAAAACAAAA | AAAAATTGAA | TTTTTGGTTT | AAAAATCGTC | AAAAATCGCC | GGAAAATTGG |
| | TAAAACCTAA | AAAACTTAAA | TTTTTGTTTT | TTTTTAACTT | AAAAACCAAA | TTTTTAGCAG | TTTTAGCGGG | CCTTTAACC |

| | 4250 | 4260 | 4270 | 4280 | 4290 | 4300 | 4310 | 4320 |
|---|---|---|---|---|---|---|---|---|
| Y110A2AL.1 | AAAAATTCACT | TTTTCCTAAG | AAAAATCGGA | AAAAATGGTC | CATTTTTCGA | AAAACTGAAT | TTTTTGACAA | AATTTTTACG |
| | TTTTAAGTGA | AAAAGGATTC | TTTTTAGCCT | TTTTTACCAG | GTAAAAAGCT | TTTTGACTTA | AAAAACTGTT | TTAAAAATGC |

| | 4330 | 4340 | 4350 | 4360 | 4370 | 4380 | 4390 | 4400 |
|---|---|---|---|---|---|---|---|---|
| Y110A2AL.1 | CCAAATTTTG | GATTTTTCCA | CCAAAAAAAA | CCCATGAAAT | CGCTCGAAAA | ATTAGAAAAA | TCGCCTTTTT | TTTCGGAAAT |
| | GGTTTAAAAC | CTAAAAAGGT | GGTTTTTTTT | GGGTACTTTA | GCGAGCTTTA | TAATCTTTTT | AGCGGAAAAA | AAAGCCTTTA |

| | 4410 | 4420 | 4430 | 4440 | 4450 | 4460 | 4470 | 4480 |
|---|---|---|---|---|---|---|---|---|
| Y110A2AL.1 | TTTTAAGCCG | ATTTTGTGAA | AAATGCGAAA | AAATTGCCCC | GGATTCGCTA | ATTTTTTGGG | TTTTTTTAGT | AAAAAAATCG |
| | AAAAATTCGGC | TAAAACACTT | TTTACGCTTT | TTTAACGGGG | CCTAAGCTTA | TAAAAAAACCC | AAAAAAATCA | TTTTTTAGC |

| | 4490 | 4500 | 4510 | 4520 | 4530 | 4540 | 4550 | 4560 |
|---|---|---|---|---|---|---|---|---|
| Y110A2AL.1 | TCAAAATCTC | CCGGAAAATT | GGACAAATCG | CAATTTTCAC | AATTTTTCAG | CCCAAAAAAC | CGAAATTTAG | CCTAAAACTG |
| | AGTTTTAGAG | GGCCTTTTAA | CCTGTTTAGC | GTTAAAAGTG | GTTAAAAGTC | GGGTTTTTTG | GCTTTAAATC | GGATTTTGAC |

| | 4570 | 4580 | 4590 | 4600 | 4610 | 4620 | 4630 | 4640 |
|---|---|---|---|---|---|---|---|---|
| Y110A2AL.1 | CCAAATCGCT | CGGATAATTA | GAAAATTCAC | AAGTTTCACC | AATTTTTTAA | AGCTATTTTC | TCAGATTTTT | GCCTAAAAAT |
| | GGTTTAGCGA | GCCTATTAAT | CTTTTAAGTG | TTCAAAGTGG | TTAAAAAATT | TCGATAAAAG | AGTCTAAAAA | CGGATTTTTA |

| | 4650 | 4660 | 4670 | 4680 | 4690 | 4700 | 4710 | 4720 |
|---|---|---|---|---|---|---|---|---|
| Y110A2AL.1 | TGCCAAAATC | TGCTGGACAA | ATTAGAAAAT | TCGCAATTTT | TACCCATTTT | TGGCCATTTT | CTGGGTTTTT | CCGCAAAAAA |
| | ACGGTTTTAG | ACGACCTGTT | TAATCTTTTA | AGCGTTAAAA | ATGGGTAAAA | ACCGGTAAAA | GACCCAAAAA | GGCGTTTTTT |

| | 4730 | 4740 | 4750 | 4760 | 4770 | 4780 | 4790 | 4800 |
|---|---|---|---|---|---|---|---|---|
| Y110A2AL.1 | ACCAGATTTT | TGTGTTAAAA | TCGGCCGGAA | AATTGGAAAA | ATCGGATAAA | AATGGTCGAT | TTTTACCGAA | AATCGTCCAA |

Figure 9C Cont.

```
                  TGGTCTAAAAA ACACAATTTT AGCCGGCCTT TTAACCTTTT TAGCCTATTT TTACCAGCTA AAAATGGCTT TTAGCAGGTT
                        4810       4820       4830       4840       4850       4860       4870       4880
Y110A2AL.1   TTTTCGACAT TCTTGTACAA AACCCCGAAA AATTCCAATT TTTTGCCAAT TTTTCCATTT TTCGACCAAA AAACTGATTT
             AAAAGCTGTA AGAACATGTT TTGGGGCTTT TTAAGGTTAA AAAACGGTTA AAAAGGTAAA AAGCTGGTTT TTTGACTAAA
                        4890       4900       4910       4920       4930       4940       4950       4960
Y110A2AL.1   TTCGTGCGAA AATTGCGCCA AATCACTCGA AAAATTGCAA AATTCGCATT TATAGGCCGA TTTTTTAGAA AGTCGGCGAA
             AAGCACGCTT TTAACGCGGT TTAGTGAGCT TTTTAACGTT TTAAGCGTAA ATATCCGGCT AAAAAATCTT TCAGCCGCTT
                        4970       4980       4990       5000       5010       5020       5030       5040
Y110A2AL.1   ACATTAAGCC ATTTTCGAAG TTTCTCGGGA AAAAACAGCG AAAAAAATCGA ATTTTCGCTT GTTTTTTGCT GGATTCGTAT
             TGTAATTCGG TAAAAGCTTC AAAGAGCCCT TTTTTGTCGC TTTTTTAGCT TAAAAGCGAA CAAAAAACGA CCTAAGCATA
                        5050       5060       5070       5080       5090       5100       5110       5120
Y110A2AL.1   TTAAAATGCA ATTTTCATCA ATTTTCCCAT CGAAAAACCG GAAATAACCT GCAAAAACCC CTTTTAATCG CCAAAATTAT
             AATTTTACGT TAAAAGTAGT TAAAAGGGTA GCTTTTTGGC CTTTATTGGA CGTTTTTGGG GAAAATTAGC GGTTTTAATA
                        5130       5140       5150       5160       5170       5180       5190       5200
Y110A2AL.1   GCGAAATTCG CGAAATTATT AATTCACCTC TTCTCCGAGA GGACTCCGTG GCCGCGACGA CCGATTCTCC ATAGAGCGCG
             CGCTTTAAGC GCTTTAATAA TTAAGTGGAG AAGAGGCTCT CCTGAGGCAC CGGCGCTGCT GGCTAAGAGG TATCTCGCGC
                        5210       5220       5230       5240       5250       5260       5270       5280
Y110A2AL.1   CTTGCCTAAA ATCGATTTCT CGGCCGCGTT AATCAATTTC CATCATTTTT TAACCAATTT CACCAATTTT CTTGCAGAAA
             GAACGGATTT TAGCTAAAGA GCCGGCGCAA TTAGTTAAAG GTAGTAAAAA GTGGTTAAAA ATTGGTTAAA GAACGTCTTT
                                                                                   920
jmpl str +                                                                    AG AGTTCCAAAA>
                                                                                   | ||
Y110A2AL.1                                                                    TT CTTGCAGAAA
```

Figure 9C Cont.

```
                     5290         5300         5310         5320         5330         5340         5350         5360
Y110A2AL.1   ACATCCATCC TACGTGTACG ATTTCTCGAA AGCACCCAGC GAATGTTGTA CAAGAGTCAA CGGATCGAAT ATTCCATAAT
             TGTAGGTAGG ATGCACATGC TAAAGAGCTT TCGTGGGTCG CTTACAACAT GTTCTCAGTT GCCTAGCTTA TAAGGTATTA
                     930          940          950          960          970          980          990         1000
jmp1 str   + ACATCCATCC TACGTGTACG ATTTCTCGAA AGCACCCAGC GAATGTTGTA CAAGAGTCAA CGGATCGAAT ATTCCATAAT>
             |||||||||| |||||||||| |||||||||| |||||||||| |||||||||| |||||||||| |||||||||| ||||||||||
Y110A2AL.1   ACATCCATCC TACGTGTACG ATTTCTCGAA AGCACCCAGC GAATGTTGTA CAAGAGTCAA CGGATCGAAT ATTCCATAAT 5370         5380         5390         5400         5410         5420         5430         5440
Y110A2AL.1   TTATTGCATT TTTTACTGAA TACGGGCCAA TTTTCCAGAT TTCTACGGTT TTCTACGGTT TTTCCGCGCA TAATAATTGT
             AATAACGTAA AAAATGACTT ATGCCCGGTT AAAAGGTCTA AAGATGCCAA AAGGCGCGT ATTATTAACA
                    1010         1020         1030         1040         1050         1060         1070         1080
jmp1 str   + TTATTGCATT TTTTACTGAA TACGGGCCAA TTTTCCAGAT TTCTACGGTT TTCTACGGTT TTTCCGCGCA TAATAATTGT>
             |||||||||| |||||||||| |||||||||| |||||||||| |||||||||| |||||||||| |||||||||| ||||||||||
Y110A2AL.1   TTATTGCATT TTTTACTGAA TACGGGCCAA TTTTCCAGAT TTCTACGGTT TTCTACGGTT TTTCCGCGCA TAATAATTGT 5450         5460         5470         5480         5490         5500         5510         5520
Y110A2AL.1   CTTTCTCGTA TAAATATTGC ATTTTTCCAC ATTTAAACCG ATTTTATTCA TTTTTCCCCC CGAAAAATCG TTGATTTTTC
             GAAAGAGCAT ATTTATAACG TAAAAAGGTG TAAATTTGGC TAAAATAAGT AAAAGGGGG GCTTTTTAGC AACTAAAAAG
                    1090         1100         1110         1120
jmp1 str   + CTTTCTCGTA TAAATATTGC ATTTTTCCAC ATTTAAA>
             |||||||||| |||||||||| |||||||||| |||||||
Y110A2AL.1   CTTTCTCGTA TAAATATTGC ATTTTTCCAC ATTTAAA 5530         5540         5550         5560         5570         5580         5590         5600
Y110A2AL.1   CCAGAAATAC CTATTTTTAC GCAAAATCCC CAGAAAAACC CATACATTCT CACAGATGTC CGATAATTCG CTGCCAGCCG
             GGTCTTTATG GATAAAAATG CGTTTTAGGG GTCTTTTTGG GTATGTAAGA GTGTCTACAG GCTATTAAGC GACGGTCGGC 5610         5620         5630         5640         5650         5660         5670         5680
Y110A2AL.1   GATGGGAAAA GCGTCAGAGC CGCTCGAATG GTTGGAAATT CGCGAAATTC TGCGAAATAA ATCGATAATT TTTCCAGATC
             CTACCCTTTT CGCAGTCTCG GCGAGCTTAC CAACCTTTAA GCGCTTTAAG ACGCTTTATT TAGCTATTAA AAAGGTCTAG
```

```
              5690       5700       5710       5720       5730       5740       5750
Y110A2AL.1    GCGTCTACTA CTTCAACACG GCCACCGGCC GCAGCCAATG GGAGCGCCCA GACGAGTCGG CGTTTGGAAA AGTGAGAAA
              CGCAGATGAT GAAGTTGTGC CGGTGGCCGG CGTCGGTTAC CCTCGCGGGT CTGCTCAGCC GCAAACCTTT TCACTCTTT
```

Figure 9C cont.

human sqv-2 homolog cDNA

ATAGCCACATCCCTGAATGTCACCTGTCCCTGGGTGAGAGCCATGCCTGACTT
GTCTTTCTTTCCTCTTCCTCTTCCGGCGCGGGCGCC

ATGAATCTGCTGCGGCGGGCGTGGCGGCGGCGGGCGGCGCTAGGCCTGGGC
ACGCTGGCGCTGTGCGGGGCGGCGCTGCTCTACCTGGCGCGCTGCGCGGCCG
AGCCCGGGGACCCCAGGGCGATGTCGGGCCGCAGCCCGCCTCCCCCCGCGCC
CGCGCGCGCCGCCGCCTTCCTGGCAGTGCTGGTGGCCAGCGCGCCCCGCGCC
GCCGAGCGCCGCAGCGTGATCCGCAGCACGTGGCTTGCGCGGCGCGGGGCCC
CGGGCGACGTGTGGGCGCGCTTTGCCGTGGGCACGGCCGGCCTGGGCGCCGA
GGAGCGGCGCGCCCTGGAGCGGGAGCAGGCGCGGCACGGGGACCTGCTGCT
GCTGCCCGCGCTGCGCGACGCCTACGAAAACCTCACGGCCAAGGTGCTGGCC
ATGCTGGCCTGGCTGGACGAGCACGTGGCCTTCGAGTTCGTGCTCAAGGCGG
ACGACGACTCCTTCGCGCGGCTGGACGCGCTGCTGGCCGAGCTGCGCGCCCG
CGAGCCCGCGCGCCGCCGCCGCCTCTACTGGGGCTTCTTCTCGGGCCGCGGC
CGAGTCAAGCCGGGGGGGCGCTGGCGCGAGGCCGCCTGGCAACTCTGCGACT
ACTACCTGCCCTACGCGCTGGGCGGCGGCTACGTGCTCTCGGCCGACCTGGT
GCACTACCTGCGCCTCAGCCGCGACTACCTGCGCGCCTGGCACAGCGAGGAC
GTGTCTCTGGGCGCCTGGCTGGCGCCGGTGGACGTCCAGCGGGAGCACGACC
CGCGCTTCGACACCGAATACCGGTCCCGCGGCTGCAGCAACCAGTACCTGGT
GACGCACAAGCAGAGCCTGGAGGACATGCTGGAGAAGCACGCGACGCTGGC
GCGCGAGGGCCGCCTGTGCAAGCGCGAGGTGCAGCTGCGCCTGTCCTACGTG
TACGACTGGTCCGCGCCGCCCTCGCAGTGCTGCCAGAGAAGGGAGGGCATCC
CCTGA

GCCGCCGCGGCCCGGCCCTCCGGGACACCTGCTTCACCCGGCGGCGCCTTGG
GGCAGGTGCCGAGCGGGCGCATACGCCCGGGCCCCAAGGCCCCCGTCCCGCA
GCCACGCTTGTGGTCGCTGCGTCCCGGTCTGCGTTTGGGAGACCCCTGGGGGT
TGCCGGGGCAGCGCGCCGTGTCCAGGTGGAGGTGCCCGTTCCTGGACCTCAG
CGAGCCTGAGCCGGGCCCGGCCGCACGCTGACCCCGTGCTGTCCCCGACCG
GCTCACGGGGCTGGGCTCCGATCTTCCGTGTCTCTTATCAGTGGCGTTTCTCA
CGTCTGCGTCTCAGATCTAACGTGGTTTCACATCAATCCGCTTTCATGGGATT
TTGGTCTCTGTCCAGTGACTTCGTGGTAAATGTAACTCAGTGTTTGCTTGCGA
CTTATTTATAAATATTGTAAGTTTGTGTCGATGAGTGTAAGTTGGCAGTGCGC
ACGTCTCGGTTTTTTACATGATTTAAGGAAAGACTTTTATGTCAGAACTTGG
TGCCTGTACCGTCAACCCCGCTGCTGCCCGTGTTTAAACGCAGGAGCACTTTA
AAACTGGCCATCTATCTTTTCAGTGTACAAGTCACTGAACCCATTGTTTCTTTC
TGAAGAGACTTTCCTTTCAAGGCTTCCCATGGGTCCGCGCCACACAGGGCCG
GTGCTGCTTTATTTCAGACTCTGCCCCAGGTTCCAGGAATCCGAACCCCGGAG
TGCTGACGCGGTTCCCCAACTTCCGCCTTAAGAAAACAGGACCAGCCGGCAC
CAGGCCCGTCTCTCACGTACTTAACACATCCTTGAAAGCCCCTCGTTTAATG
AGAAAA

```
sqv-6 genomic
          2010       2020       2030       2040       2050       2060       2070       2080
Untitled2 AGGCAACAAA ACATATTTT  TTCAATGTTT TTTCTACGGA AAACCAGCGA AAATGTTGAT TTTTGAAGGA AATTTTCATA
          TCCGTTGTTT TGTATAAAAA AAGTTACAAA AAAGATGCCT TTTGGTCGCT TTTACAACTA AAAACTTCCT TTAAAAGTAT 2090       2100       2110       2120       2130       2140       2150       2160
Untitled2 TTTTTAAAAC ATTTTCTATT TTTCTCTCGT CCAATAATTT AGTTTTCAAA AAAATAAACA TTAAATAGTA CTTTCGGCGG
          AAAAATTTTG TAAAAGATAA AAAGAGAGCA GGTTATTAAA TCAAAAGTTT TTTTATTTGT AATTTATTCAT GAAAGCCGCC 2170       2180       2190       2200       2210       2220       2230       2240
Untitled2 CCCCACATCT GTTTCGTGAT CCCAATAAAC ATTTTGAACG TTTAAACTCT CCGTTTTGCA AACATTTTGC ACTTTTTTCC
          GGGGTGTAGA CAAAGCACTA GGGTTATTTG TAAAACTTGC AAATTTGAGA GGCAAAACGT TTGTAAAACG TGAAAAAAGG 2250       2260       2270       2280       2290       2300       2310       2320
Untitled2 TCATTTTCTC AAGTTTTTAC AGGGCGTGCT CCTCATGTTA TTCAACGGGA CGACTAAATA TCGAGATTAT GCGATTGTGA
          AGTAAAAGAG TTCAAAAATG TCCCGCACGA GGAGTACAAT AAGTTGCCCT GCTGATTTAT AGCTCTAATA CGCTAACACT 10         20         30         40         50         60
jmp1 str + AGTTTTTAC  AGGGCGTGCT CCTCATGTTA TTCAACGGGA CGACTAAATA TCGAGATTAT GCGATTGTGA>
Untitled2  AGTTTTTAC  AGGGCGTGCT CCTCATGTTA TTCAACGGGA CGACTAAATA TCGAGATTAT GCGATTGTGA 2330       2340       2350       2360       2370       2380       2390       2400
```

Figure 11C

```
Untitled2      TATCATTATT CTTCCTGCTA AACGTCTATT TATTGTACAA TACGGCTCAA CACACGCAAG TCGGAAATTC GAAGCATATT
               ATAGTAATAA GAAGGACGAT TTGCAGATAA ATAACATGTT ATGCCGAGTT GTGTGCGTTC AGCCTTTAAG CTTCGTATAA
                    70         80         90         100        110        120        130        140
jmp1 str +     TATCATTATT CTTCCTGCTA AACGTCTATT TATTGTACAA TACGGCTCAA CACACGCAAG TCGGAAATTC GAAGCATATT>
               |||||||||| |||||||||| |||||||||| |||||||||| |||||||||| |||||||||| |||||||||| ||||||||||
Untitled2      TATCATTATT CTTCCTGCTA AACGTCTATT TATTGTACAA TACGGCTCAA CACACGCAAG TCGGAAATTC GAAGCATATT 2410       2420       2430       2440       2450       2460       2470       2480
Untitled2      TCGTCGGATA GCGGTGAAAA AGTTAGATTT TCTGGCTAAA AATTGAATTT TCTGCATATT CGGATGAATC CCGGCGCTTT
               AGCAGCCTAT CGCCACTTTT TCAATCTAAA AGACCGATTT TTAACTTAAA AGACGTATAA GCCTACTTAG GGCCGCGAAA 150        160        170
jmp1 str +     TCGTCGGATA GCGGGTGAAAA AACGTCG>
               |||||||||| ||||||||||| |||||||
Untitled2      TCGTCGGATA GCGGGTGAAAA AGTTAGA 2490       2500       2510       2520       2530       2540       2550       2560
Untitled2      TTTTGGCTTT TTCTTGCATA TTCATCTGAA TTATTTCATT TTTCGGTCAA GAACGCATTT TTTAGCGAAA AAACATTATT
               AAAACCGAAA AAGAACGTAT AAGTAGACTT AATAAAGTAA AAAGCCAGTT CTTGCGTAAA AAATCGCTTT TTTGTAATAA 2570       2580       2590       2600       2610       2620       2630       2640
Untitled2      AAAACTGTTT AAAATGTGTT TTATCAAAGA AAACGACAAA ATTCGCGCTA AAAATGAAGT AATTTTCATG AAAAAGCACT
               TTTTGACAAA TTTTACACAA AATAGTTTCT TTTGCTGTTT TAAGCGCGAT TTTTACTTCA TTAAAAGTAC TTTTTCGTGA 2650       2660       2670       2680       2690       2700       2710       2720
Untitled2      AAAAAATTCG ATTTTTTTTC GATTTCAGCA CGCCGAGCCT TCAACTAACT AGTTGATTGA TTTAAATACG AGGACTAAGG
               TTTTTTAAGC TAAAAAAAAG CTAAAGTCGT GCGGCTCGGA AGTTGATTGA TTTAAATACG AGGACTAAGG CTTTTAGCTA 2730       2740       2750       2760       2770       2780       2790       2800
Untitled2      ATGAAAAAAC TCAAAAAAT TTCCGTGATT TTATATAAAT TTTGAAAAT CAGGAAAATC CACTGGTTTG TTAAATTCAA
               TACTTTTTTG AGTTTTTTTA AAGGCACTAA AATATATTTA AAACTTTTA GTCCTTTTAG GTGACCAAAC AATTTAAGTT
```

Figure 11C cont.

```
          2810       2820       2830       2840       2850       2860       2870       2880
Untitled2 ACGATATCTT TTTGCCGCCC GATAACCGTG CCGAAGGTGT GGATTCCGA CGAGATTAAT ATTTTTCATT CAATTTTATT
          TGCTATAGAA AAACGGCGGG CTATTGGCAC GGCTTCCACA CCTAAAGGCT GCTCTAATTA TAAAAAGTAA GTTAAAATAA 2890       2900       2910       2920       2930       2940       2950       2960
Untitled2 TAATTTTCTT ACCGATTTTT TCGTTTTTCG TTGTTTTACA TTTAATTTCT TGTGATTTCC ATTAATTTAT GACTTTTTAA
          ATTAAAAGAA TGGCTAAAAA AGCAAAAAGC AACAAAAATGT AAATTAAAGA ACACTAAAGG TAATTAAATA CTGAAAAATT 2970       2980       2990       3000       3010       3020       3030       3040
Untitled2 CACTGAAAAT GAATAAAATT ACATGAAATA CCCTATTTTC ATGGAATTTT ATTTATTTTA ATTAAAGGTG GTGTAGTCGA
          GTGACTTTTA CTTATTTTAA TGTACTTTAT GGGATAAAAG TACCTTAAAA TAAATAAAAT TAATTCCAC CACATCAGCT 3050       3060       3070       3080       3090       3100       3110       3120
Untitled2 TTTTTTTAT TGCTTTATTA GACTCGAAAT TGTCTGAAAA CACCGATTTT TTAAAATGAAA CTTCTTGAAA ACTTTTCAGA
          AAAAAAAATA ACGAAATAAT CTGAGCTTTA ACAGACTTTT GTGGCTAAAA AATTTACTTT GAAGAACTTT TGAAAAGTCT 3130       3140       3150       3160       3170       3180       3190       3200
Untitled2 AAAAAGTTGT GACGACTCAA AAATGTCCTA AAATTAGTTA AAATTTGAAA TTTGACCGAC TTGTCAATGT CGCAGGGGCT
          TTTTTCAACA CTGCTGAGTT TTTACAGAT TTTAATCAAT TTTAAACTTT AAACTGGCTG AACAGTTACA GCGTCGCCGA 3210       3220       3230       3240       3250       3260       3270       3280
Untitled2 GGAAACAATT TTTTTTGAAG TCACTGTCAA ATTTTGAGTA TGCAATTCAA TTATCTTGCG TTTTAAACTT GATTAAGGTG
          CCTTTGTTAA AAAAAACTTC AGTGACAGTT TAAAACTCAT ACGTTAAGTT AATAGAACGC AAAATTTGAA CTAATTCCAC 3290       3300       3310       3320       3330       3340       3350       3360
Untitled2 TTTAAAGTC GATGGACGGC GAGAATTGAT TTTAAAAGAA TTAAAAATCT CGCCGTCCAT CGACTTTTAA ATACCTTAAT
          AAATTTTCAG CTACCTGCCG CTCTTAACTA AAATTTTCTT AATTTTTAGA GCGGCAGGTA GCTGAAAAATT TATGAATTA 3370       3380       3390       3400       3410       3420       3430       3440
Untitled2 CAAGTTTGAA ACGCAAGATA ATCGCACTGT ATACTCAAAA TTTGACGGTG ATTTCAAAAA AGTTAGTTTC CAGCCGCTGA
```

Figure 11C cont.

```
              3450       3460       3470       3480       3490       3500       3510       3520
Untitled2  CAAGTCAAAT TTCAAATTTT AACTGATTTT AGGCCATTTT TTGAGCGGTC ATAACTTTTT TTTGAGAAG TTTTCAAGAA
           GTTCAGTTTA AAGTTTTAAAA TTGACTAAAA TCCGGTAAAA AACTCGCCAG TATTGAAAAA AAACCTCTTC AAAAGTTCTT 3530       3540       3550       3560       3570       3580       3590       3600
Untitled2  GTTTCATTAT GAAATTCGGT GTTTTCAGAC AATTTTGAGT CCAGTAAAGC AATAAAAAAA TTCGACTACA CCATCTTTAT
           CAAAGTAATA CTTTAAGCCA CAAAAGTCTG TTAAAACTCA GGTCATTTCG TTATTTTTTT AAGCTGATGT GGTAGAAATA 3610       3620       3630       3640       3650       3660       3670       3680
Untitled2  AATTAAAAGG TACTTTTCCG ATTTCTGCCC CCCAAAATGT TTTTCAATCT TATTAAACTC TATTAAACTC AATATTTCAG TTTAAATTCA
           TTAATTTTCC ATGAAAAGGC TAAAGACGGG GGGTTTTACA AAAAGTTAGA ATAATTTGAG TTATAAAGTC AAATTTAAGT 3690       3700       3710       3720       3730       3740       3750       3760
Untitled2  CACATGAATG TTTATTTCAA TACTATTTCA ATTTTTAGGC TTAGAAACCA ACAATACTAA GCCTGAAATT TTCAAAAAAA
           GTGTACTTAC AAATAAAGTT ATGATAAAGT TAAAAATCCG AATCTTTGGT TGTTATGATT CGGACTTTAA AAGTTTTTTT 3770       3780       3790       3800       3810       3820       3830       3840
Untitled2  GTTCACGTTT CATTGATAAA AATATCGAAA ACACTTTGGG GGGGGGGGGC AGAAATCGGA AAAGTACCAA TTAAAAGTGA
           CAAGTGCAAA GTAACTATTT TTATAGCTTT TGTGAAACCC CCCCCCCCG TCTTTAGCCT TTTCATGGTT AATTTTCACT 3850       3860       3870       3880       3890       3900       3910       3920
Untitled2  CTTCAAAAAA ATTGTTTCCA GCCGCTGCGA CATTGACAAG TCGGTCAAAT TTCAAATTTT AACTAATTTT AGGACATTTT
           GAAGTTTTTT TAACAAAGGT CGGCGACGCT GTAACTGTTC AAGTTCTTCA AAGTTTAAAA TTGATTAAAA TCCTGTAAAA 3930       3940       3950       3960       3970       3980       3990       4000
Untitled2  TGAGTCGTCA CAACTTTTTT CTGAAAAGTT TTCAAGAAGT TTCATTTAAA AAATCGGTGT TTTCAAACAA TTTCGAGTCT
           ACTCAGCAGT GTTGAAAAAA GACTTTTCAA AAGTTCTTCA AAGTAAATTT TTTAGCCACA AAAGTTTGTT AAAGCTCAGA
```

Figure 11C cont.

```
Untitled2        4010       4020       4030       4040       4050       4060       4070       4080
          AATAAAGCAA TAAAAAAAT CGACTACACC ACCTTTAATT AAAATAAATA AAATTCCATG AAAATAGGGA TTTCATTTAA
          TTATTTCGTT ATTTTTTTA GCTGATGTGG TGGAAATTAA TTTTATTTAT TTTAAGGTAC TTTTATCCCT AAAGTAAATT Untitled2        4090       4100       4110       4120       4130       4140       4150       4160
          TTGAATTTTG TTTTCATTAA TAAAAGCAAT AAATTAATGA AAACCACAAT AAATGCAGTG TAAAACAACG AAAAATGAGA
          AACTTAAAAC AAAAGTAATT ATTTTCGTTA TTTAATTACT TTTGGTGTTA TTTACGTCAC ATTTTGTTGC TTTTTACTCT Untitled2        4170       4180       4190       4200       4210       4220       4230       4240
          GGAATTGGGA AAATCGGTAT GAAAATTTAA TAAAATTGAA TGAAAAATAT CCATCCGTA AATTCAACTT TATCGTTTGA
          CCTTAACCCT TTTAGCCATA CTTTTAAATT ATTTTAACTT ACTTTTTATA GGTAGAGCAT TTAAGTTGAA ATAGCAAACT Untitled2        4250       4260       4270       4280       4290       4300       4310       4320
          ATTTAAAGAA CCAATGGATT TTCCTAATAT TAAAAAATTA ATATAAAATA TCAGGGGCAT TTTTTTGAA TTTTTTCACA
          TAAATTTCTT GGTTACCTAA AAGGATTATA ATTTTTTAAT TATATTTTAT AGTCCCCGTA AAAAAACCTT AAAAAAGTGT Untitled2        4330       4340       4350       4360       4370       4380       4390       4400
          AGGGTATTCG GAATCAGGAG CATAAATAGA GTCTATCGTA AATTTTTTT TTTTTTGGTA AATTAAATAT TTTTTCAGACG
          TCCCATAAGC CTTAGTCCTC GTATTTATCT CAGATAGCAT TTAAAAAAA AAAAAACCAT TTAATTTATA AAAAGTCTGC jmp1 str +                                                                                 170
                                                                                   GG TGAAAAAACG>
                                                                                      |    |||
Untitled2                                                                          AT TTTTCAGACG Untitled2        4410       4420       4430       4440       4450       4460       4470       4480
          TCGAATCCTC TTCCATCATG CGAAATCACA GATGACCTGG CGAAAAGTGC AATTTCCCGT GCAATTACTC CATCCTGCAA
          AGCTTAGGAG AAGGTAGTAC GCTTTAGTGT CTACTGGACC GCTTTTCACG TTAAAGGGCA CGTTAATGAG GTAGGACGTT jmp1 str +       180        190        200        210        220        230        240        250
          TCGAATCCTC TTCCATCATG CGAAATCACA GATGACCTGG CGAAAAGTGC AATTTCCCGT GCAATTACTC CATCCTGCAA>
          ||||||||| ||||||||| ||||||||| ||||||||| ||||||||| ||||||||| ||||||||| |||||||||
Untitled2 TCGAATCCTC TTCCATCATG CGAAATCACA GATGACCTGG CGAAAAGTGC AATTTCCCGT GCAATTACTC CATCCTGCAA
```

Figure 11C cont.

```
Untitled2      4490       4500       4510       4520       4530       4540       4550       4560
           AGCAAAACTG CAGCTGGAAG CTTGTCAACT GAAAAATGGG ACTTTTACAA TAAATTTTCC GGAAAATCAA TGCCCGAACC
           TCGTTTTGAC GTCGACCTTC GAACAGTTGA CTTTTTACCC TGAAAATGTT ATTTAAAAGG CCTTTTAGTT ACGGGCTTGG
               260        270        280        290        300        310        320        330
jmp1 str + AGCAAAACTG CAGCTGGAAG CTTGTCAACT GAAAAATGGG ACTTTTACAA TAAATTTTCC GGAAAATCAA TGCCCGAACC>
           |||||||||| |||||||||| |||||||||| |||||||||| |||||||||| |||||||||| |||||||||| ||||||||||
Untitled2  AGCAAAACTG CAGCTGGAAG CTTGTCAACT GAAAAATGGG ACTTTTACAA TAAATTTTCC GGAAAATCAA TGCCCGAACC 4570       4580       4590       4600       4610       4620       4630       4640
Untitled2  ACGATAGCCG GCTTATCGAC CAACGAATCG GCTGTTTTTT GGACAAAAAA GAGGCTCGAG TGCTCACAGA GTTCGAGTAC
           TGCTATCGGC CGAATAGCTG GTTGCTTAGC CGACAAAAAA CCTGTTTTTT CTCCGAGCTC ACGAGTGTCT CAAGCTCATG
               340        350        360        370        380        390        400        410
jmp1 str + ACGATAGCCG GCTTATCGAC CAACGAATCG GCTGTTTTTT GGACAAAAAA GAGGCTCGAG TGCTCACAGA GTTCGAGTAC>
           |||||||||| |||||||||| |||||||||| |||||||||| |||||||||| |||||||||| |||||||||| ||||||||||
Untitled2  ACGATAGCCG GCTTATCGAC CAACGAATCG GCTGTTTTTT GGACAAAAAA GAGGCTCGAG TGCTCACAGA GTTCGAGTAC 4650       4660       4670       4680       4690       4700       4710       4720
Untitled2  AAACTTCCAA AGTCAAATGG GAAAGCGACG TGTCGAAAGC ACTGCTATAA AGCTGGTTTT TTGTATTTCG GACTTGAATT
           TTTGAAGGTT TCAGTTTACC CTTTCGCTGC ACAGCTTTCG TGACGATATT TCGACCAAAA AACATAAAGC CTGAACTTAA
               420        430        440        450        460        470        480        490
jmp1 str + AAACTTCCAA AGTCAAATGG GAAAGCGACG TGTCGAAAGC ACTGCTATAA AGCTGGTTTT TTGTATTTCG GACTTGAATT>
           |||||||||| |||||||||| |||||||||| |||||||||| |||||||||| |||||||||| |||||||||| ||||||||||
Untitled2  AAACTTCCAA AGTCAAATGG GAAAGCGACG TGTCGAAAGC ACTGCTATAA AGCTGGTTTT TTGTATTTCG GACTTGAATT 4730       4740       4750       4760       4770       4780       4790       4800
Untitled2  CGGACACGAA TGCTTCTGTG GGAATGATGT ATCAAATGCG ACGGCGGTTG ATGACGTGGA ATGTCGGGCG TATAAATGTC
           GCCTGTGCTT ACGAAGACAC CCTTACTACA TAGTTTACGC TGCCGCCAAC TACTGCACCT TACAGCCCGC ATATTTACAG
               500        510        520        530        540        550        560        570
jmp1 str + CGGACACGAA TGCTTCTGTG GGAATGATGT ATCAAATGCG ACGGCGGTTG ATGACGTGGA ATGTCGGGCG TATAAATGTC>
```

Figure 11C cont.

```
Untitled2    ||||||||||| ||||||||||| ||||||||||| ||||||||||| ||||||||||| ||||||||||| ||||||||||| |||||||||||
             CGGACACGAA TGCTTCTGTG GGAATGATGT ATCAAATGCG ACGGCGGTTG ATGACGTGGA ATGTCGGGCG TATAAATGTC
                 4810       4820       4830       4840       4850       4860       4870       4880
Untitled2    CGGGAAATGA GAACTCGGAG GAGTTCTGTG GTGGATTCAA TGCAGTCGAG ATTTTTAGGA CAGGATTTAG AAGTAATATT
             GCCCTTTACT CTTGAGCCTC CTCAAGACAC CACCTAAGTT ACGTCAGCTC TAAAAATCCT GTCCTAAATC TTCATTATAA
                 580        590        600        610        620        630        640        650
jmp1 str +   CGGGAAATGA GAACTCGGAG GAGTTCTGTG GTGGATTCAA TGCAGTCGAG ATTTTTAGGA CAGGATTTAG AAGCAAAGTG>
             ||||||||||| ||||||||||| ||||||||||| ||||||||||| ||||||||||| ||||||||||| ||||||||||| |||   
Untitled2    CGGGAAATGA GAACTCGGAG GAGTTCTGTG GTGGATTCAA TGCAGTCGAG ATTTTTAGGA CAGGATTTAG AAGTAATATT
                 4890       4900       4910       4920       4930       4940       4950       4960
Untitled2    AGGTCTCCAA ATAAGTTCCG GGTCAAAAAT CATAACTTTG TTCGCTGCGT ATCGATTTTT ATGAAATTGT GGGAATTTAT
             TCCAGAGGTT TATTCAAGGC CCAGTTTTTA GTATTGAAAC AAGCGACGCA TAGCTAAAAA TACTTTAACA CCCTTAAATA jmp1 str +   AAT>
             ---|
Untitled2    AGG
                 4970       4980       4990       5000       5010       5020       5030       5040
Untitled2    GTTATCAACC ATGATCTTTC ATTTGACAAT ACTCACAAAA TTTTTTTGCC GTCCGAAGTG CCCTAACTCG GAGCCAAATT
             CAATAGTTGG TACTAGAAAG TAAACTGTTA TGAGTGTTTT AAAAAAACGG CAGGCTTCAC GGGATTGAGC CTCGGTTTAA
                 5050       5060       5070       5080       5090       5100       5110       5120
Untitled2    TTTCAGGCAT TTTTCAGATC TCGCTTCTTT TACGCTTTGA TTTGAGGTTT GTGTGCGGAT TTAGCTTTGT TTAGTACATA
             AAAGTCCGTA AAAAGTCTAG AGCGAAGAAA ATGCGAAACT AAACTCCAAA CACACGCCTA AATCGAAACA AATCATGTAT
                 5130       5140       5150       5160       5170       5180       5190       5200
Untitled2    ATGTAAGAAA ACAAGAAAAG TTTGGAAAAA ATCCGTCCAA AAAAAAAATT TTTTTGTCGG TCGTCAAAAA ATGTTCAAAA
             TACATTCTTT TGTTCTTTTC AAACCTTTTT TAGGCAGGTT TTTTTTTAA AAAAACAGCC AGCAGTTTTT TACAAGTTTT
```

Figure 11C cont.

| | 5210 | 5220 | 5230 | 5240 | 5250 | 5260 | 5270 | 5280 |
|---|---|---|---|---|---|---|---|---|
| Untitled2 | AAATTTTGT | CGAAAATTCT | TGATTTTCA | TACAAAAATG | ATGTAACCAT | GTGCAAACTA | TTTGTTCACA | TACAAAACAT |
| | TTTAAAAACA | GCTTTTAAGA | ACTAAAAAGT | ATGTTTTTAC | TACATTGGTA | CACGTTTGAT | AACAAGTGT | ATGTTTTGTA |
| | 5290 | 5300 | 5310 | 5320 | 5330 | 5340 | 5350 | 5360 |
| Untitled2 | TTAAATTTAG | TGCGTCACAC | TAAAATAAAA | ACAGAAAACA | CACCTTTTTT | GAATTATTTT | CGAGTTTTTG | GAGTGTTTCT |
| | AATTTAAATC | ACGCAGTGTG | ATTTTATTTT | TGTCTTTTGT | GTGGAAAAAA | CTTAATAAAA | GCTCAAAAAC | CTCACAAAGA |
| | 5370 | 5380 | 5390 | 5400 | 5410 | 5420 | 5430 | 5440 |
| Untitled2 | CGAGATCCAA | ATTTCATACT | CAAATGTTTT | GTATGCGAAA | AAATAGTTTG | CACATGGTTA | CATCATTTTT | GTATAAAAAA |
| | GCTCTAGGTT | TAAAGTATGA | GTTTACAAAA | CATACGCTTT | TTTATCAAAC | GTGTACCAAT | GTAGTAAAAA | CATATTTTTT |
| | 5450 | 5460 | 5470 | 5480 | 5490 | 5500 | 5510 | 5520 |
| Untitled2 | TCAAGAATTT | TCGACAAAAA | CTTTTTTGAG | CATTTTTTAA | CGACCGACAA | AAAATTTTTT | TTTTTGGACG | GATTTTTTTC |
| | AGTTCTTAAA | AGCTGTTTTT | GAAAAAACTC | GTAAAAAATT | GCTGGCTGTT | TTTTAAAAAA | AAAAACCTGC | CTAAAAAAAG |
| | 5530 | 5540 | 5550 | 5560 | 5570 | 5580 | 5590 | 5600 |
| Untitled2 | TAAACTTTTC | TTGTTTTCTT | ACATTGTGTA | CTGAACAAAG | CTAAATCCGC | ACACAAACCT | CGAATCAAAG | CGTAAAAGAA |
| | ATTTGAAAAG | AACAAAAGAA | TGTAACACAT | GACTTGTTTC | GATTTAGGCG | TGTGTTTGGA | GCTTAGTTTC | GCATTTTCTT |
| | 5610 | 5620 | 5630 | 5640 | 5650 | 5660 | 5670 | 5680 |
| Untitled2 | GCGAGATCTG | AAAAAATTGG | CTCCGAATTA | GGGCACTTCG | GATGGCAAAA | AAATTTGTG | ACTATTGTCA | AATGAAAGAT |
| | CGCTCTAGAC | TTTTTTAACC | GAGGCTTAAT | CCCGTGAAGC | CTACCGTTTT | TTTAAACAC | TGATAACAGT | TTACTTTCTA |
| | 5690 | 5700 | 5710 | 5720 | 5730 | 5740 | 5750 | 5760 |
| Untitled2 | CACGGTTGAT | AACATAAATT | TCCACAGTTT | CATAAAAATC | GATACGCAGC | GAACAAGTT | ATGATTTTG | ACCCGGAACT |
| | GTGCCAACTA | TTGTATTTAA | AGGTGTCAAA | GTATTTTTAG | CTATGCGTCG | CTTGTTTCAA | TACTAAAAAC | TGGGCCTTGA |
| | 5770 | 5780 | 5790 | 5800 | 5810 | 5820 | 5830 | 5840 |
| Untitled2 | TATTTGGAGA | CCTAATATAT | TTTGAAATTT | TAGAAAATTT | GAAGAAAAAG | TTTACAAATG | TTTAAAAACC | AAAAAATTGT |

Figure 11C cont.

```
          ATAAACCTCT GGATTATATA AAACTTAAAA ATCTTTTAAA CTTCTTTTTC AAATGTTTAC AAATTTTTGG TTTTTTAACA
                5850       5860       5870       5880       5890       5900       5910       5920
Untitled2 TCATTTTGTT AGAAATGTCA TGTGTTTTTT TGTTTAAAAA ACGCCGATTT TCTCGGTTTT TCCCTGTAAT TTAGTCTGAA
          AGTAAAACAA TCTTTACAGT ACACAAAAAA ACAAATTTTT TGCGGCTAAA AGAGCCAAAA AGGGACATTA AATCAGACTT 5930       5940       5950       5960       5970       5980       5990       6000
Untitled2 ACACGTTTTT TTTTCTCGTT TTCGGGCACG AAATTAACGA CAAAACCCA AAAATCGTTT TTTTTTTTA ATTTTGCTT
          TGTGCAAAAA AAAAGAGCAA AAGCCCGTGC TTTAATTGCT GTTTTTGGGT TTTTAGCAAA AAAAAAAAT TAAAAACGAA 6010       6020       6030       6040       6050       6060       6070       6080
Untitled2 TAAAAATTGC TCGAATTTTC CAATTTTGGA AAACATTTTT ATTAAATTTT TATTAAAAAA TCACACATTC TTCTTAATTT
          ATTTTTAACG AGCTTAAAAG GTTAAAACCT TTTGTAAAAA TAATTTAAAA ATAATTTTTT AGTGTGTAAG AAGAATTAAA 6090       6100       6110       6120       6130       6140       6150       6160
Untitled2 TCGGGTATTT TTTTAATTCT TAGCTAGAAA ATTGAAATAA AATCAAAAAA CGTTGAAGAA AAAACCTTAA AATACCTGGA
          AGCCCATAAA AAAATTAAGA ATCGATCTTT TAACTTTATT TTAGTTTTTT GCAACTTCTT TTTTGGAATT TTATGGACCT 6170       6180       6190       6200       6210       6220       6230       6240
Untitled2 AATGTTGAAC AAAATGTAGT AAAAATCTCG GAGAAAGGTC TTTATATCTA CACTATTTTA TTTTAAAAAA AACATTGAAA
          TTACAACTTG TTTTACATCA TTTTTAGAGC CTCTTTCCAG AAATATAGAT GTGATAAAAT AAAATTTTTT TTGTAACTTT 6250       6260       6270       6280       6290       6300       6310       6320
Untitled2 ATTTAGGAAA AAAATGCAAA GAATCGGGGA ACCCCCTTAA GTTTTATTTT AAATTAAACA AAAAATTCCA AAAAACTTGC
          TAAATCCTTT TTTTACGTTT CTTAGCCCCT TGGGGGAATT CAAAATAAAA TTTAATTTGT TTTTTAAGGT TTTTGAACG 6330       6340       6350       6360       6370       6380       6390       6400
Untitled2 GAAATAAACT AAAATATTTT TGGAAAAGTT ACTCTTTTTA ATATATCGAA AATCCAAATT AAAAAATTCC AAATTTCGTT
          CTTTATTTGA TTTTATAAAA ACCTTTTCAA TGAGAAAAAT TATATAGCTT TTAGGTTTAA TTTTTTAAGG TTTAAAGCAA
```

Figure 11C cont.

```
Untitled2    6410       6420       6430       6440       6450       6460       6470       6480
         AAAATTTAAC CAAAAATTCT CCTAATAATC CAGAAGAATA ATCTGAAAAA TTTGAGGAAA TGAATCAAAA AATCTCACAA
         TTTTAAATTG GTTTTTAAGA GGATTATTAG GTCTTCTTAT TAGACTTTTT AAACTCCTTT ACTTAGTTTT TTAGAGTGTT Untitled2    6490       6500       6510       6520       6530       6540       6550       6560
         AATACCGAAA AATAGGTCTA AAAAGCATTG AAAGTTTTTG AAAAAAAAAT TAATTAAAC ATTTTGGAAA AGTAACGTTT
         TTATGGCTTT TTATCCAGAT TTTCGTAAC TTTCAAAACG TTTTTTTTA ATTAAATTG TAAAACCTTT TCATTGCAAA Untitled2    6570       6580       6590       6600       6610       6620       6630       6640
         TTTGAAAAAA TATTGGAAAT CTACAAAAAA AAAATTTTCG CAAATTTGAT ATTAAAAAAA TTGCGAAATA
         AAACTTTTTT ATAACCTTTA GATGTTTTTT TTTTAAAGC GTTTAAGTG GTTTAAACTA TAATTTTTT AACGCTTTAT Untitled2    6650       6660       6670       6680       6690       6700       6710       6720
         CTGAAAACTT TCTTGAAAAT TTGAAAAAAA AATCTTCAAA TTATCGTTCC CGAAATGCTC GACAAGCAAA CGCGCCCTGT
         GACTTTTGAA AGAACTTTTA AACTTTTTTT TTAGAAGTTT AATAGCAAGG GCTTTACGAG CTGTTCGTTT GCGCGGGACA Untitled2    6730       6740       6750       6760       6770       6780       6790       6800
         TGAACAACTT CTGCGCGCGC ATTCAAATTT AGTTTTTTTT TGCTTCCAAA TATTTTTATA CGGAAAAGTG ATAGTTTCAC
         ACTTGTTGAA GACGCGCGCG TAAGTTTAAA TCAAAAAAAA ACGAAGGTTT ATAAAAATAT GCCTTTTCAC TATCAAAGTG Untitled2    6810       6820       6830       6840       6850       6860       6870       6880
         ACTGAATTTG CAAATTTTAA AGAACATTTT TAACAAATTT TTTTTTAATG CCGCAAAATG AATAAAAAAT ATCCCAAAAA
         TGACTTAAAC GTTTAAAATT TCTTGTAAAA ATTGTTTAAA AAAAAATTAC GGCGTTTTAC TTATTTTTTA TAGGGTTTTT Untitled2    6890       6900       6910       6920       6930       6940       6950       6960
         ACCGAAAAAT TTCTTTTAAA AAACGAGAAT TCGATTATTT CCTAAATTTA TTATGCTGAA AATTTTTATA TGGAAAATAT
         TGGCTTTTTA AAGAAAATTT TTTGCTCTTA AGCTAGTTA GGATTTAAAT AATACGACTT TTAAAAATAT ACCTTTTATA Untitled2    6970       6980       6990       7000       7010       7020       7030       7040
         CGAAAAATCA TCTGAAAAAA TCTGAAAAAT GTCGATCAAT TAAAAAAAAA TGTACAAAAA CACTAAAAAT TGAACAAAAA
         GCTTTTTAGT AGACTTTTTT AGACTTTTTA CAGCTAGTTA ATTTTTTTT ACATGTTTT GTGATTTTTA ACTTGTTTT
```

Figure 11C cont.

```
Untitled2   7050       7060       7070       7080       7090       7100       7110       7120
            ATCGAAATAT CAGGTAAAAA CCCCTACAGT TTACGGATAA TTTTCAAAAA AAAACGGAAA TACTTTGATA ATTTTTAGAC
            TAGCTTTATA GTCCATTTTT GGGGATGTCA AATGCCTATT AAAAGTTTTT TTTTGCCTTT ATGAAACTAT TAAAAATCTG 7130       7140       7150       7160       7170       7180       7190       7200
Untitled2   AGAGTGAATC ACCAAAATTG AAAAAAAAAA TTGCAAAATA TTCGCCAAAA AACCGAAAAA TTTCTATAAA TATCCTTAAT
            TCTCACTTAG TGGTTTTAAC TTTTTTTTTT AACGTTTTAT AAGCGGTTTT TTGGCTTTTT AAAGATATTT ATAGGAATTA 7210       7220       7230       7240       7250       7260       7270       7280
Untitled2   TGAACAAAAA AAAAATTCTA GAAACAAGAT GTATTTCAAA AATTTTCCTG AAAATTCACA CTGAACCGCT AAAATTCAAA
            ACTTGTTTTT TTTTTAAGAT CTTTGTTCTA CATAAAGTTT TTAAAAGGAC TTTTAAGTGT GACTTGGCGA TTTTAAGTTT 7290       7300       7310       7320       7330       7340       7350       7360
Untitled2   TTCTAAAAAT TATCGAACAT CGACGATACC GTAAAATTAA AACAAAGAAT ATTCCGAAAA TTCGAGAAAA AAGCACCTTG
            AAGATTTTTA ATAGCTTGTA GCTGCTATGG CATTTTAATT TTGTTTCTTA TAAGGCTTTT AAGCTCTTTT TTCGTGGAAC 7370       7380       7390       7400       7410       7420       7430       7440
Untitled2   CAACTTACC  CTCACGAGGG ACGAGGAAAA GTGGTTTCTA GGCCATGGCC GAGTCCCCGA CAAGTTTCAG CGGCCATTTA
            GTTGAAATGG GAGTGCTCCC TGCTCCTTTT CACCAAAGAT CCGGTACCGG CTCAGGGGCT GTTCAAAGTC GCCGGTAAAT 7450       7460       7470       7480       7490       7500       7510       7520
Untitled2   TCTTGCTTTG TTTTCCGCCT GTTTTCTTTC GTTTTTCATC GATTTTTTTC GTTTTTTCTT AATAAAACTG ATAAATAAAT
            AGAACGAAAC AAAAGGCGGA CAAAAGAAAG CAAAAAGTAG CTAAAAAAAG CAAAAAAGAA TTATTTTGAC TATTTATTTA 7530       7540       7550       7560       7570       7580       7590       7600
Untitled2   ATTTTTTGCA GATGCTAAAA CAATTCCAA  GTAAAAAAAA TCATGTATTC AGTGGGCAAG CAGCGGTGAA AGTGGGCATT
            TAAAAAACGT CTACGATTTT GTTAAAGGTT CATTTTTTTT AGTACATAAG TCACCCGTTC GTCGCCACTT TCACCCGTAA 7610       7620       7630       7640       7650       7660       7670       7680
```

Figure 11C cont.

```
Untitled2    GTAATATGAT GGATTACGGG AATACAAAAC CTAAACTTTT TCTGAAACAT GATACATATG ATGCTTAGAT GCTGAAATTA
             CATTATACTA CCTAATGCCC TTATGTTTTG GATTTGAAAA AGACTTTGTA CTATGTATAC TACGAATCTA CGACTTTAAT
                  7690       7700       7710       7720       7730       7740       7750       7760

Untitled2    CCTGATTTTT ATAACGAGAC CGCTGAAAAA GTTTTGAGAT TTTCAAAATT CAACTTTTTT GGTGAAAAAG TCGTTACATT
             GGACTAAAAA TATTGCTCTG GCGACTTTTT CAAAACTCTA AAAGTTTTAA GTTGAAAAAA CCACTTTTTC AGCAATGTAA
                  7770       7780       7790       7800       7810       7820       7830       7840

Untitled2    GCCCACTTTC ACCGCTGCTT GCCCACTGAA TACATAATTT TTTTACTTGG AAATTGTTTT AGCATCTGCA AAAAATATTT
             CGGGTGAAAG TGGCGACGAA CGGGTGACTT ATGTATTAAA AAAATGAACC TTTAACAAAA TCGTAGACGT TTTTTATAAA
                  7850       7860       7870       7880       7890       7900       7910       7920

Untitled2    ATTTATCAGT TTTAATAAGA AAAAATCGGCA AAAATCGGCA AAAAACAAAA GAAAACAGGC GGAAAACAAA GCAAGATAAA
             TAAATAGTCA AAATTATTCT TTTTTGCCGT TTTTAGCCAC TTTTTGTTTT CTTTTGTCCG CCTTTTGTTT CGTTCTATTT
                  7930       7940       7950       7960       7970       7980       7990       8000

Untitled2    TGGCCGCTGA AACTTGTCGG CCCCTCGGCC ATGGCCTAGA AACCACTTTT CCTCGTCCCT CGTGAGGAAA AAGTTGCAGT
             ACCGGCGACT TTGAACAGCC GGGGAGCCGG TACCGGATCT TTGGTGAAAA GGAGCAGGGA GCACTCCTTT TTCAACGTCA
                  8010       8020       8030       8040       8050       8060       8070       8080

Untitled2    GAAACACTGA AAAATGCAAA AATTCAAATT TTCAGGCAAA GTGAATCACC GCAAGCCGAC ATATCTTCCA CCTAGCAGCG
             CTTTGTGACT TTTTACGTTT TTAAGTTTAA AAGTCCGTTT CACTTAGTGG CGTTCGGCTG TATAGAAGGT GGATCGTCGC
                  8090       8100       8110       8120       8130       8140       8150       8160
                                           640        650        660        670        680        690
jmp1 str +                         CAGGATT TAGAAGCAAA GTGAATCACC GCAAGCCGAC ATATCTTCCA CCTAGCAGCG>
                                   ||||||| ||||||||||  ||||||||| |||||||||| |||||||||| ||||||||||
Untitled2                          TCAAATT TTCAGGCAAA GTGAATCACC GCAAGCCGAC ATATCTTCCA CCTAGCAGCG Untitled2    ATTCTATCAA AAATCCCGTC AAAATTCTCT TCCTTCTTCA ATTAAATGGT AGAAATGAGC GTCAAGTGAA ACGATTTCTC
             TAAGATAGTT TTTAGGGCAG TTTTAAGAGA AGGAAGAAGT TAATTTACCA TCTTTACTCG CAGTTCACTT TGCTAAAGAG
                  8090       8100       8110       8120       8130       8140       8150       8160
```

Figure 11C cont.

```
jmp1 str +      700        710        720        730        740        750        760        770
           ATTCTATCAA AAATCCCGTC AAAATTCTCT TCCTTCTTCA ATTAAATGGT AGAAATGAGC GTCAAGTGAA ACGATTTCTC>
           |||||||||| |||||||||| |||||||||| |||||||||| |||||||||| |||||||||| |||||||||| ||||||||||
Untitled2  ATTCTATCAA AAATCCCGTC AAAATTCTCT TCCTTCTTCA ATTAAATGGT AGAAATGAGC GTCAAGTGAA ACGATTTCTC
                8170       8180       8190       8200       8210       8220       8230       8240

AAATCAATTT ATCTTCCACA TCATTATTAC TATATCCACG TGGATGCACG TCAGAATTAC ATGTTCTCAG AAATGCAAAA
Untitled2  |||||||||| |||||||||| |||||||||| |||||||||| |||||||||| |||||||||| |||||||||| ||||||||||
           TTTAGTTAAA TAGAAGGTGT AGTAATAATG ATATAGGTGC ACCTACGTGC AGTCTTAATG TACAAGAGTC TTTACGTTTT 780        790        800        810        820        830        840        850
jmp1 str + AAATCAATTT ATCTTCCACA TCATTATTAC TATATCCACG TGGATGCACG TCAGAATTAC ATGTTCTCAG AAATGCAAAA>
           |||||||     |||||||| |||||||||| |||||||     |||||||||| |||||||||| |||||||||| ||||||||||
Untitled2  AAATCAATTT ATCTTCCACA TCATTATTAC TATATCCACG TGGATGCACG TCAGAATTAC ATGTTCTCAG AAATGCAAAA
                8250       8260       8270       8280       8290       8300       8310       8320

AGTTGCTGAT TTTCTGGATA ATATTCATAT AACCGAACGG AGATTCAGCA CAATTGGGG  TGGAGCATCA CTTTTACAAG
Untitled2  |||||||||| |||||||||| |||||||||| |||||||||| |||||||||| |||||||||  |||||||||| ||||||||||
           TCAACGACTA AAAGACCTAT TATAAGTATA TTGGCTTGCC TCTAAGTCGT GTTAAACCCC ACCTCGTAGT GAAAATGTTT 860        870        880        890        900        910        920        930
jmp1 str + AGTTGCTGAT TTTCTGGATA ATATTCATAT AACCGAACGG AGATTCAGCA CAATTTGGGG TGGAGCATCA CTTTTACAAA>
           ||||||||   |||||||||| |||||||||| |||||||||| |||||||||| |||||||||| |||||||||| ||||||||||
Untitled2  AGTTGCTGAT TTTCTGGATA ATATTCATAT AACCGAACGG AGATTCAGCA CAATTTGGGG TGGAGCATCA CTTTTACAAA
                8330       8340       8350       8360       8370       8380       8390       8400

TGTTTCTGCA AGTGATTAGG GATTCGATGA AAATTGAGAA ATTCAAGGAT TGGGATTATA TTATTAATTT CTCGGAAAGT
Untitled2  |||||||||| |||||||||| |||||||||| |||||||||| |||||||||| |||||||||| |||||||||| ||||||||||
           ACAAAGACGT TCACTAATCC CTAAGCTACT TTTAACTCTT TAAGTTCCTA ACCCTAATAT AATAATTAAA GAGCCTTTCA 940        950        960        970        980        990        1000       1010
jmp1 str + TGTTTCTGCA AGTGATTAGG GATTCGATGA AAATTGAGAA ATTCAAGGAT TGGGATTATA TTATTAATTT CTCGGAAAGT>
           |||||||||| |||||||||| |||||||||| |||||||||| |||||||||| |||||||||| |||||||||| ||||||||||
Untitled2  TGTTTCTGCA AGTGATTAGG GATTCGATGA AAATTGAGAA ATTCAAGGAT TGGGATTATA TTATTAATTT CTCGGAAAGT
                8410       8420       8430       8440       8450       8460       8470       8480

Untitled2  GATTCCCGA TTCCGATTTT TCCGATTTT GAGAGACTTA TCACTGTGTA AGTTGGAGTG ATTTGAAACA TGTTTTAGGA
```

Figure 11C cont.

```
                  CTAAAGGGCT AAGATGGCTA AAGGCTAAAA CTCTCTGAAT AGTGACACAT TCAACCTCAC TAAACTTTGT ACAAATCCT
                        1020       1030       1040       1050       1060
jmp1 str +        GATTTCCCGA TTCTACCGAT TTCCGATTTT GAGAGACTTA TCACTGTAAA CAACGGA>
                  ||||||||| |||||||||| |||||||||| |||||||||| ||||||||||  |||
Untitled2         GATTTCCCGA TTCTACCGAT TTCCGATTTT GAGAGACTTA TCACTGTGTA AGTTGGA 8490       8500       8510       8520       8530       8540       8550       8560
Untitled2         TTAAACGAG  GGAAAAGTTG AAATTCAAAA ATCTGAATAT TCCACTGCAA CTTTTTCCTC ACGAGGGACG AGGAAAAGTG
                  AATTTGCTC  CCTTTTCAAC TTTAAGTTTT TAGACTTATA AGGTGACGTT GAAAAAGGAG TGCTCCCTGC TCCTTTTCAC 8570       8580       8590       8600       8610       8620       8630       8640
Untitled2         GCTTCTAGGC CACGGCCGAG GGGCCAGCAA GTTTCAGCGG CCATTTATCT TGCTTTGTTT TCCGCCTGTT TTCTTTCGTT
                  CGAAGATCCG GTGCCGGCTC CCCGGCTGTT CAAAGTCGCC GGTAAATAGA ACGAAACAA  AGGCGGACAA AAGAAAGCAA 8650       8660       8670       8680       8690       8700       8710       8720
Untitled2         TTTCATCGAT TTTTTTCGTT TTTTTCTTAA  AAAACTGATA AATAAATATT TTTTGCAGAT GCTAAAACAA TTTCCAAGTA
                  AAAGTAGCTA AAAAAAGCTA AAAAGAATTA TTTTGACTAT TTATTTATAA AAAACGTCTA CGATTTTGTT AAAGGTTCAT 8730       8740       8750       8760       8770       8780       8790       8800
Untitled2         AAAAAAATCA TGTATTCAGT GGGCAAGCAG CGGTGAAAGT GGGCATTGTA ATATGATGAA TTACGGGAAT ACAAAACCTA
                  TTTTTTAGT  ACATAAGTCA CCCGTTCGTC GCCACTTTCA CCCGTAACAT TATACTACCT AATGCCCTTA TGTTTTGGAT 8810       8820       8830       8840       8850       8860       8870       8880
Untitled2         AACTTTTCT  GAAACATGAT ACATATGATG CTTAGATGCT GAAATTACCT GATTTTCATA ACGAGACCGC TGAAAAAGTT
                  TTGAAAAAGA CTTTGTACTA TGTATACTAC GAATCTACGA CTTTAATGGA CTAAAAGTAT TGCTCTGGCG ACTTTTTCAA 8890       8900       8910       8920       8930       8940       8950       8960
Untitled2         TTGAGGTTTT CAAAATTCAA CTTTTTGTGC GAAAATCTCG ACTTTTTCAC CAAAAAAGTT GAATTTTGAA ATCCTCAAAA
                  AACTCCAAAA GTTTTAAGTT GAAAAACACG CTTTTAGAGC TGAAAAAGTG GTTTTTTCAA CTTAAAACTT TAGGAGTTTT
```

Figure 11C cont.

```
                 8970       8980       8990       9000       9010       9020       9030       9040
Untitled2   CTTTTTCAGC AGTCTCGTTA TGAAAATCAG GTAGTCTCAG CATTTAAGCA GCATATGTAT CATGTTTCAG AAAAAGTTTA
            GAAAAAGTCG TCAGAGCAAT ACTTTTAGTC CATCAGAGTC GTAAATTCGT CGTATACATA GTACAAAGTC TTTTTCAAAT 9050       9060       9070       9080       9090       9100       9110       9120
Untitled2   GGTTTGTAT TCCCGTAATC CATCATATTA CAATGACCAC TTTCACCGCT GCTGCCCAC TGAATACATG ATTTTTTAC
            CCAAAACATA AGGGCATTAG GTAGTATAAT GTTACTGGTG AAAGTGGCCA CGAACGGGTG ACTTATGTAC TAAAAAAATG 9130       9140       9150       9160       9170       9180       9190       9200
Untitled2   TTGGAAATTG TTTTAGCATC TGCAAAAAAT ATTTATTTAT CAGTTTTATT AAGAAAAAAC GAAAAAAATC GGTGAAAAAC
            AACCTTTAAC AAAATCGTAG ACGTTTTTTA TAAATAAATA GTCAAAATAA TTCTTTTTTG CTTTTTTTAG CCACTTTTTG 9210       9220       9230       9240       9250       9260       9270       9280
Untitled2   GAAAGAAAAC AGGCGAAAA CAAAGCAAGA TAAATGCCG ATGAAACTTG TCGGCCCCTC GGCCATGGCC TAGAAACCAC
            CTTTCTTTTG TCCGCCTTTT GTTTCGTTCT ATTTACCGGC TACTTTGAAC AGCCGGGGAG CCGGTACCGG ATCTTGGTG 9290       9300       9310       9320       9330       9340       9350       9360
Untitled2   TTTTCCTCGT CCCTCGTGAG GAAAAAGTTG CAGAGTATTC CAGAGAATTT ATGGAAATTT CAGATTTATA TTCCTAAAAA
            AAAAGGAGCA GGGAGCACTC CTTTTTCAAC GTCTCATAAG GTCTTAAAAA TACCTTTAAA GTCTAAATAT AAGGATTTTT 9370       9380       9390       9400       9410       9420       9430       9440
Untitled2   CTCACAAAAA AACAATTTTA TGGAAAAAA ATCGATTTTT TTTCACCGGA AAAATTAAAT TTTCAGAGAT TTTTAGATTA
            GAGTGTTTTT TTGTTAAAAT ACCTTTTTTT TAGCTAAAAA AAAGTGGCCT TTTAATTTA AAAGTCTCTA AAAATCTAAT 9450       9460       9470       9480       9490       9500       9510       9520
Untitled2   AAATAAGAAA AAATAGATTT TTTGGAGAAA TCCGCTTATT TTTTTGGAAA ATTCCGGAGA TTTTTCCGAA ATATGAAAAA
            TTTATTCTTT TTTATCTAAA AAACCTCTTT AGGCGAATAA AAAAACCTTT TAAGGCCTCT AAAAAGGCTT TATACTTTTT 9530       9540       9550       9560       9570       9580       9590       9600
Untitled2   AAAAACATTT TGGAATTCAA AAATCTGATT AATCCGGAAT TTTCATAAAA ATCGACGAAA ATCACCGAAA ATTTCAGATT
            TTTTTGTAAA ACCTTAAGTT TTTAGACTAA TTAGGCCTTA AAAGTATTTT TAGCTGCTTT TAGTGCTTT TAAAGTCTAA
```

Figure 11C cont.

```
Untitled2   9610       9620       9630       9640       9650       9660       9670       9680
            TTAATTTAGA AAAATCACAA AAAGAAAACA ATTTTATGGA AAAAAAATCG ATTTTTTCCG GAACAAAAAT CGAAACCGGA
            AATTAAATCT TTTTAGTGTT TTTCTTTTGT TAAAATACCT TTTTTTTAGC TAAAAAAGGC CTTGTTTTA  GCTTGGCCT Untitled2   9690       9700       9710       9720       9730       9740       9750       9760
            AAATCTGAAA TTTAACACAG AAATTTTTTG AAAGTGAGAG AAAATAAAAT GAAAAAAAAA TCGATTTTTC TTGAAAAAGT
            TTTAGACTTT AAATTGTGTC TTTAAAAAAC TTTCACTCTC TTTTATTTA  CTTTTTTTT  AGCTAAAAAG AACTTTTCA Untitled2   9770       9780       9790       9800       9810       9820       9830       9840
            TAATTTTCAG CGTTTTTTAA ATCGACCATT TGAAAACAAT TAAAATTTGA AAAAAAAAAC AATATTTTAC GACAATTTAC
            ATTAAAAGTC GCAAAAAATT TAGCTGGTAA ACTTTTGTTA ATTTTAAACT TTTTTTTTG  TTATAAAATG CTGTTAAATG Untitled2   9850       9860       9870       9880       9890       9900       9910       9920
            TCGGAATTTC AAAATTTTCA TTTTAAAAAA TCAAAAAATT TTGCTTTTTT CTAGACAAAA TTGATTTTCA GCGAATTTTC
            AGCCTTAAAG TTTTAAAAGT AAAATTTTTT AGTTTTTTTT AACGAAAAAA GATCTGTTTT AACTAAAAGT CGCTTAAAAG Untitled2   9930       9940       9950       9960       9970       9980       9990       10000
            CTGAAAAAAA TTTAGAACGG ATTTTTATCC GACAATATCG GAAGTTAACA TTTTTAATGA AAAAAAAACA CTTTTTCCA
            GACTTTTTTT AAATCTTGCC TAAAAATAGG CTGTTATAGC CTTCAATTGT AAAAATTACT TTTTTTTGT  GAAAAAAGGT Untitled2   10010      10020      10030      10040      10050      10060      10070      10080
            AAAAAAAAAA AAATAGAATT TTCGCAAAAA GTAAATTCGA AAAAAAATTT AACAACCTAT CGAATTCTAA ATTTTTTCAG
            TTTTTTTTTT TTTATCTTAA AAGCGTTTTT CATTTAAGCT TTTTTTAAA  TTGTTGGATA GCTTAAGATT TAAAAAGTC Untitled2   10090      10100      10110      10120      10130      10140      10150      10160
            ATTAAAATCG ATTTTTTTTG TAGAATTTTT GAAGATTTCA TCTAGTTTTT TTTTTGTTGA TAAGTTGCAA AAAATTATTT
            TAATTTTAGC TAAAAAAAAC ATCTTAAAAG CTTCTAAAGT AGATCAAAAA AAAAACAACT ATTCAACGTT TTTTAATAAA 10170      10180      10190      10200      10210      10220      10230      10240
```

Figure 11C cont.

```
Untitled2    TTTTTGATTT AAAAAAGTGC TAAAATATAT ATAAGAAAAA TATGAACATA AAGTAACTTT TAGAAATCGA AAAAAAAAAA
             AAAAACTAAA TTTTTTCACG ATTTATATA TATTCTTTTT ATACTTGTAT TTCATTGAAA ATCTTTAGCT TTTTTTTTTT 10250      10260      10270      10280      10290      10300      10310      10320
Untitled2    TTTTTTTTA AATTATTTCG AATTTCCAAT TTTCCAGAAA CAACGGAAAA TCATTCCTGG CCTCACACGG CTACAACACT
             AAAAAAAAT TTAATAAAGC TTAAGGTTA AAAGGTCTTT GTTGCCTTTT AGTAAGGACC GGAGTGTGCC GATGTTGTGA 1050       1060       1070       1080       1090       1100
jmp1 str +                                              TA TCACTGTAAA CAACGGAAAA TCATTCCTGG CCTCACACGG CTACAACACT>
                                                        || |||||||||| |||||||||| |||||||||| |||||||||| ||||||||||
Untitled2                                               AT TTTCCAGAAA CAACGGAAAA TCATTCCTGG CCTCACACGG CTACAACACT 10330      10340      10350      10360      10370      10380      10390      10400
Untitled2    GGAAAATTCA TTCAAAAACA AGGATTCGAA TACGTGTTCT CCGAATGCGA TAATCGAATG TTCCGTATCG GAAAACGCGA
             CCTTTTAAGT AAGTTTTTGT TCCTAAGCTT ATGCACAAGA GGCTTACGCT ATTAGCTTAC AAGGCATAGC CTTTTGCGCT 1110       1120       1130       1140       1150       1160       1170       1180
jmp1 str +   GGAAAATTCA TTCAAAAACA AGGATTCGAA TACGTGTTCT CCGAATGCGA TAATCGAATG TTCCGTATCG GAAAACGCGA>
             |||||||||| |||||||||| |||||||||| |||||||||| |||||||||| |||||||||| |||||||||| ||||||||||
Untitled2    GGAAAATTCA TTCAAAAACA AGGATTCGAA TACGTGTTCT CCGAATGCGA TAATCGAATG TTCCGTATCG GAAAACGCGA 10410      10420      10430      10440      10450      10460      10470      10480
Untitled2    ATTTCCACAA AATCTACGAA TTGACGGCGG ATCCGATTGG GTTGGAATTC ATCGAAATCT CGCCGAATTT TCGATTTCCG
             TAAAGGTGTT TTAGATGCTT AACTGCCGCC TAGGCTAACC CAACCTTAAG TAGCTTTAGA GCGGCTTAAA AGCTAAAGGC 1190       1200       1210       1220       1230       1240       1250       1260
jmp1 str +   ATTTCCACAA AATCTACGAA TTGACGGCGG ATCCGATTGG GTTGGAATTC ATCGAAATCT CGCCGAATTT TCGATTTCCG>
             |||||||||| |||||||||| |||||||||| |||||||||| |||||||||| |||||||||| |||||||||| ||||||||||
Untitled2    ATTTCCACAA AATCTACGAA TTGACGGCGG ATCCGATTGG GTTGGAATTC ATCGAAATCT CGCCGAATTT TCGATTTCCG 10490      10500      10510      10520      10530      10540      10550      10560
Untitled2    ACGAGGAATT GCCTCGAAAA TTGCGAAAAA CGTATGAAAG TATACTTCTA CCACTGGAAT CATTCTATCA TACTCTTGCG
             TGCTCCTTAA CGGAGCTTTT AACGCTTTTT GCATACTTTC ATATGAAGAT GGTGACCTTA GTAAGATAGT ATGAGAACGC
```

Figure 11C cont.

```
                  1270       1280       1290       1300       1310       1320       1330       1340
jmpl str +   ACGAGGAATT GCCTCGAAAA TTGCGAAAAA CGTATGAAAG TATACTTCTA CCACTGGAAT CATTCTATCA TACTCTTGCG>
             |||||||||| |||||||||| |||||||||| |||||||||| |||||||||| |||||||||| |||||||||| ||||||||||
Untitled2    ACGAGGAATT GCCTCGAAAA TTGCGAAAAA CGTATGAAAG TATACTTCTA CCACTGGAAT CATTCTATCA TACTCTTGCG
                  10570      10580      10590      10600      10610      10620      10630      10640
Untitled2    TTCAATTCCG AATTCTGTGA TGATCTACTG ATGAGCAATT TGCGGCTTAC GAATTGGTAC AGGAAACAGG GATGTCGGTG
                                   |||||||||| |||||||||| |||||||||| |||||||||| |||||||||| ||||||||||
             AAGTTAAGGC TTAAGACACT ACTAGATGAC TACTCGTTAA ACGCCGAATG CTTAACCATG TCCTTTGTCC CTACAGCCAC
                  1350       1360       1370       1380       1390       1400       1410       1420
jmpl str +   TTCAATTCCG AATTCTGTGA TGATCTACTG ATGAGCAATT TGCGGCTTAC GAATTGGTAC AGGAAACAGG GATGTCGGTG>
             |||||||||| |||||||||| |||||||||| |||||||||| |||||||||| |||||||||| |||||||||| ||||||||||
Untitled2    TTCAATTCCG AATTCTGTGA TGATCTACTG ATGAGCAATT TGCGGCTTAC GAATTGGTAC AGGAAACAGG GATGTCGGTG
                  10650      10660      10670      10680      10690      10700      10710      10720
Untitled2    TGCTTCATTG AAGCCTATTG TTGATTGGTG TGGATGTTCG CCGCTGGTTT TTCGTGAAGA AACTATGAAG AAATTTGAGC
                                   |||||||||| |||||||||| |||||||||| |||||||||| |||||||||| ||||||||||
             ACGAAGTAAC TTCGGATAAC AACTAACCAC GGCGACCAAA AAGCACTTCT TTGATACTTC TTTAAACTCG
                  1430       1440       1450       1460       1470       1480       1490       1500
jmpl str +   TGCTTCATTG AAGCCTATTG TTGATTGGTG TGGATGTTCG CCGCTGGTTT TTCGTGAAGA AACTATGAAG AAATTTGAGC>
             |||||||||| |||||||||| |||||||||| |||||||||| |||||||||| |||||||||| |||||||||| ||||||||||
Untitled2    TGCTTCATTG AAGCCTATTG TTGATTGGTG TGGATGTTCG CCGCTGGTTT TTCGTGAAGA AACTATGAAG AAATTTGAGC
                  10730      10740      10750      10760      10770      10780      10790      10800
Untitled2    TTCAAGTATG GCCAATTTTG GTTGTGGAGC TGAAAATTTC TGAAATTTTG GTCTTAAAAA AATCAAAAAA ATTCAAATTT
             AAGTTCATAC CGGTTAAAAC CAACACCTCG ACTTTTTAAG CAGAATTTTT TTAGTTTTTT TAAGTTTAAA
                  1510
jmpl str +   TTCAAAAAGC CA>
             |||||| ||
Untitled2    TTCAAGTATG GC
                  10810      10820      10830      10840      10850      10860      10870      10880
Untitled2    CTGTTTGAAT TTTCAAAGCA TTATTTACAT GAAAACCATA ATTTTCGTTT ATTTTTTTGC GATTTTTTGA AAAAAAAAGC
```

Figure 11C cont.

```
          GACAAACTTA AAAGTTTCGT AATAAATGTA CTTTTGGTAT TAAAAGCAAA TAAAAAAACG CTAAAAAACT TTTTTTTCG
               10890      10900      10910      10920      10930      10940      10950      10960
Untitled2 CGAACATTTT CGTTTTTTTT TTCAATTTTT TTCTGAAAAA AATCTTTAAA AATTGAAGTT TTTTCGTGTT TCTTTTCTC
          GCTTGTAAAA GCAAAAAAAA AAGTTAAAAA AAGACTTTTT TTAGAAATTT TTAACTTCAA AAAAGCACAA AGAAAAAGAG
               10970      10980      10990      11000      11010      11020      11030      11040
Untitled2 TGAAAAAAAC CGTTAAAATC AATTTTTTTT TTCGATTTTT TTTTGAAAAA ATGTTTTCAA AAAAACCTTT ATCCGAAAAA
          ACTTTTTTTG GCAATTTTAG TTAAAAAAAA AAGCTAAAAA AAAACTTTTT TACAAAAGTT TTTTTGGAAA TAGGCTTTTT
               11050      11060      11070      11080      11090      11100      11110      11120
Untitled2 GCGATAATTT TGGTTTTCTT TCGATCTTCT CAGAAAAAAC CGTAAAAATC AATAATTTAA TAGTTTTTGT TTCATTTTTG
          CGCTATTAAA ACCAAAAGAA AGCTAGAAGA GTCTTTTTTG GCATTTTTAG TTATTAAATT ATCAAAAACA AAGTAAAAAC
               11130      11140      11150      11160      11170      11180      11190      11200
Untitled2 CTGAAAAAAA AAACTTTAAA AAATGGAAGC TTTTCGTTTT TCAGCGATTT TCTCCAGAAA AAACTTTAAA AAATCAATAA
          GACTTTTTTT TTTGGAAATT TTTACCTTCG AAAAGCAAAA AGTCGCTAAA AGAGTCTTTT TTTGAAATTT TTTAGTTATT
               11210      11220      11230      11240      11250      11260      11270      11280
Untitled2 TTTTTGAAAA ACGCTGAAAA TTTTTCGGTT TTAGCGATTA TCTCATGAAA AAAACCGTAA TCGTCGTAGG CTTAAGCTTA
          AAAAACTTTT TGCGACTTTT AAAAGCCAAA AATCGCTAAT AGAGTACTTT TTTTGGCATT AGCAGCATCC GAATTCGAAT
               11290      11300      11310      11320      11330      11340      11350      11360
Untitled2 GGCTTGGGCG TAGGCTTAGG ATTTGGATTA AGCCTAGGGA CAATCCCAAC TTTCCGAAGGA TTTCCAGAAA AAAGAAAAAA
          CCGAACCCGC ATCCGAATCC TAAACCTAAT TCGGATCCCT GTTAGGGTTG AAGGCTTCCT AAAGGTCTTT TTTCTTTTT
               11370      11380      11390      11400      11410      11420      11430      11440
Untitled2 TATTATAAGT AAAAATCCAA AAAATACAAA AAAACCTTA TAAAATCGTC AAAAAATTAT TCAAAAAATT AGTAATTAAA
          ATAATATTCA TTTTTAGGTT TTTTATGTTT ATTTAGCAG ATTTTAAATA AGTTTTTTAA TCATTAATTT
```

Figure 11C cont.

```
Untitled2       11450      11460      11470      11480      11490      11500      11510      11520
         AAAAAATAAT TTTTCAAATT TCCAGAAAGC CATCTGAATA TAACTTTAAA AATCTGAACT GTCCGTTTTG TAGTGATTTT
         TTTTTATTA AAAAGTTTAA AGGTCTTTCG GTAGACTTAT ATTGAAATTT TTAGACTTGA CAGGCAAAAC ATCACTAAAA Untitled2       11530      11540      11550      11560      11570      11580      11590      11600
         CTCAGAAAAA AAAAACAAAA ACCCAAAAAA AACCCCAAAA AACTTACAAA AACCGGAAAA AAAAATTAAA TTTAAAGTTT
         GAGTCTTTTT TTTTTGTTTT TGGGTTTTTT TTGGGGTTTT TTGAATGTTT TTGGCCTTTT TTTTTAATTT AAATTTCAAA Untitled2       11610      11620      11630      11640      11650      11660      11670      11680
         CTAAATTTCC AGAAATCCAT CGCTTAAGCT GAGGCTTGGG CTTACTATTA GGCTTAGGCT CCCATAGTTT TAGGCTTAGG
         GATTTAAAGG TCTTTAGGTA GCGAATTCGA CTCCGAACCC GAATGATAAT CCGAATCCGA GGGTATCAAA ATCCGAATCC Untitled2       11690      11700      11710      11720      11730      11740      11750      11760
         GACAATCCCA ACTTACAAAG GATTTCCAGA AAAAATATAT TTTATAAGTA AAAATCCCAA AATCCTAAAA AATCCTAAAA
         CTGTTAGGGT TGAATGTTTC CTAAAGGTCT TTTTTATATA AAATATTCAT TTTTAGGGTT TTAGGATTTT TTAGGATTTT Untitled2       11770      11780      11790      11800      11810      11820      11830      11840
         ACCCCAAAAA TATACCAAAA ACCTTGTAGA ATCGAAAATA AATTAATTTT CTAAATTTCC AGAAAGCCAT CGCTTAAGCT
         TGGGTTTTT ATATGTTTT TGGAACATCT TAGCTTTTAT TTAATTAAAA GATTTAAAGG TCTTTCGGTA GCGAATTCGA Untitled2       11850      11860      11870      11880      11890      11900      11910      11920
         GAGGCTTGGG CTTACTACTA GGCTTTGTCT TAGGCTCAGG CTTAGAAAATA GTTTTAGGCT TAAGGAAAAT CCCAACTTCC
         CTCCGAACCC GAATGATGAT CCGAAACAGA ATCCGAGTCC GAATCTTTAT CAAAATCCGA ATTCCTTTA GGGTTGAAGG Untitled2       11930      11940      11950      11960      11970      11980      11990      12000
         AAAGGATTTC TAGAAAAAAA AAATTATAAG TAAAAAATCC CAAAATCCTA AAAACTCCAA AAATATAACA AAAACCGGGA
         TTTCCTAAAG ATCTTTTTT TTTAATATTC ATTTTTTAGG GTTTTAGGAT TTTTGAGGTT TTTATATTGT TTTTGCCCCT Untitled2       12010      12020      12030      12040      12050      12060      12070      12080
         AAAAAAAAAT TAAATTTTAA TTTTCTAAAT TTCCAGAAAG CCATCTCCAA ACCAACCTAC TTTGCCCGAA AATTCGATAG
         TTTTTTTTA ATTTAAAATT AAAAGATTTA AAGGTCTTTC GGTAGAGGTT TGGTTGGATG AAACGGGCTT TTAAGCTATC
```

Figure 11C cont.

```
                             1500       1510       1520       1530       1540
jmp1 str +                   TTTGAG CTTCAAAAAG CCATCTCCAA ACCAACCTAC TTTGCCCGAA AATTCGATAG>
                                  |    ||  |||  ||||||||||  ||||||||||  ||||||||||  ||||||||||
Untitled2               CTAAAT TTCCAGAAAG CCATCTCCAA ACCAACCTAC TTTGCCCGAA AATTCGATAG 12090      12100       12110       12120       12130       12140       12150       12160
Untitled2   TATGGTAGAT ATCGATTCAA TTGAAGCCGC CGAAATGCAA TCAATTTCAC CTGAAAAACT TCAATTAAAT CATCCAACCT
            ||||||||||  ||||||||||  ||||||||||  ||||||||||  ||||||||||  ||||||||||  ||||||||||  ||||||||||
            ATACCATCTA TAGCTAAGTT AACTTCGGCG GCTTTACGTT AGTTAAAGTG GACTTTTTGA AGTTAATTTA GTAGGTTGGA 1550       1560       1570       1580       1590       1600       1610       1620
jmp1 str +  TATGGTAGAT ATCGATTCAA TTGAAGCCGC CGAAATGCAA TCAATTTCAC CTGAAAAACT TCAATTAAAT CATCCAACCT>
            ||||||||||  ||||||||||  ||||||||||  ||||||||||  ||||||||||  ||||||||||  ||||||||||  ||||||||||
Untitled2   TATGGTAGAT ATCGATTCAA TTGAAGCCGC CGAAATGCAA TCAATTTCAC CTGAAAAACT TCAATTAAAT CATCCAACCT 12170      12180       12190       12200       12210       12220       12230       12240
Untitled2   ATCATTTCGC TTTTTGCAAAT ATTTTCAAAA CTGGAATCGA CGAGCAGAAG CTTCATTTCG AAAGTTTGGC GAATTTCGCG
            ||||||||||  ||||||||||  ||||||||||  ||||||||||  ||||||||||  ||||||||||  ||||||||||  ||||||||||
            TAGTAAAGCG AAAACGTTTA TAAAAGTTTT GACCTTAGCT GCTCGTCTTC GAAGTAAAGC TTTCAAACCG CTTAAAGCGC 1630       1640       1650       1660       1670       1680       1690       1700
jmp1 str +  ATCATTTCGC TTTTTGCAAAT ATTTTCAAAA CTGGAATCGA CGAGCAGAAG CTTCATTTCG AAAGTTTGGC GAATTTCGCG>
            ||||||||||  ||||||||||  ||||||||||  ||||||||||  ||||||||||  ||||||||||  ||||||||||  ||||||||||
Untitled2   ATCATTTCGC TTTTTGCAAAT ATTTTCAAAA CTGGAATCGA CGAGCAGAAG CTTCATTTCG AAAGTTTGGC GAATTTCGCG 1660       1650       1640
jmp1 str -      <ATTCCAG TTTTTGAAAAT ATTTGCAAAA GC
                 |||    ||  |||  |||||||||  ||
Untitled2       ATTTCGC TTTTTGCAAAT ATTTTCAAAA CT 12250      12260       12270       12280       12290       12300       12310       12320
Untitled2   CTGAAATCCA CCGAAACTCG GGCAAAATTC CGAAAAGTTT TGCGAATCGA TGCTCTTCGA GCTCATCATA ATGCTCTCAT
            ||||||||||  ||||||||||  ||||||||||  ||||||||||  ||||||||||  ||||||||||  ||||||||||  ||||||||||
            GACTTTAGGT GGCTTTGAGC CCGTTTTAAG GCTTTTCAAA ACGCTTAGCT ACGAGAAGCT CGAGTAGTAT TACGAGAGTA 1710       1720       1730       1740       1750       1760       1770       1780
jmp1 str +  CTGAAATCCA CCGAAACTCG GGCAAAATTC CGAAAAGTTT TGCGAATCGA TGCTCTTCGA GCTCATCATA ATGCTCTCAT>
```

Figure 11C cont.

```
Untitled2       |||||||||||  |||||||||||   ||||||||||  ||||||||||   ||||||||||  ||||||||||
                CTGAAATCCA  CCGAAACTCG   GGCAAAAATTC  CGAAAAGTTT   TGCGAATCGA  TGCTCTCTGA  GCTCATCATA  ATGCTCTCAT
                    12330       12340        12350        12360        12370       12380       12390       12400
Untitled2       CGAGATTGTC  ATGAAAATCG   AAACGACGGA   CGGCGCGACG   TTTGAATTTT  TGATTCATAG  ACTGTCCCAT  GTGAATTTGA
                GCTCTAACAG  TACTTTTAGC   TTTGCTGCCT   GCCGCGCTGC   AAACTTAAAA  ACTAAGTATC  TGACAGGGTA  CACTTAAACT
                  1790         1800         1810         1820         1830        1840        1850        1860
jmp1 str +      CGAGATTGTC  ATGAAAATCG   AAACGACGGA   CGGCGCGACG   TTTGAATTTT  TGATTCATAG  ACTGTCCCAT  GTGAATTTGA>
                ||||||||||  ||||||||||   ||||||||||   ||||||||||   ||||||||||  ||||||||||  ||||||||||  ||||||||||
Untitled2       CGAGATTGTC  ATGAAAATCG   AAACGACGGA   CGGCGCGACG   TTTGAATTTT  TGATTCATAG  ACTGTCCCAT  GTGAATTTGA
                    12410       12420        12430        12440        12450       12460       12470       12480
Untitled2       CGGAAAATGA  GGAGAAGCTT   GTGGAGCACG   GATATCTATT   GAGAGCTGTA  TCGTTTGGAA  CAAAATTTGA  ATGGAAAGAG
                GCCTTTTACT  CCTCTTCGAA   CACCTCGTGC   CTATAGATAA   CTCTCGACAT  AGCAAACCTT  GTTTAAACT   TACCTTTCTC
                  1870         1880         1890         1900         1910        1920        1930        1940
jmp1 str +      CGGAAAATGA  GGAGAAGCTT   GTGGAGCACG   GATATCTATT   GAGAGCTGTA  TCGTTTGGAA  CAAAATTTGA  ATGGAAAGAG>
                ||||||||||  ||||||||||   ||||||||||   ||||||||||   ||||||||||  ||||||||||  ||||||||||  ||||||||||
Untitled2       CGGAAAATGA  GGAGAAGCTT   GTGGAGCACG   GATATCTATT   GAGAGCTGTA  TCGTTTGGAA  CAAAATTTGA  ATGGAAAGAG
                    12490       12500        12510        12520        12530       12540       12550       12560
Untitled2       GAGCTTTGCA  GGGAATATAT   GGGATTTGTC   ACTGATGTTC   GTTGGTTTTT  TCGGCGGAAA  ATTTTGAAGA  AAATATTTTG
                CTCGAAACGT  CCCTTATATA   CCCTAAACAG   TGACTACAAG   CAACCAAAAA  AGCCGCCTTT  TAAAACTTCT  TTTATAAAAC
                  1950         1960         1970         1980         1990
jmp1 str +      GAGCTTTGCA  GGGAATATAT   GGGATTTGTC   ACTGATAACG   AC>
                ||||||||||  ||||||||||   ||||||||||   |||||
Untitled2       GAGCTTTGCA  GGGAATATAT   GGGATTTGTC   ACTGATGTTC   GT
                    12570       12580        12590        12600        12610       12620       12630       12640
Untitled2       GTCTTTTTTC  TACGAAAAAT   GAAAAAAAAA   AAAACAAAAA   TTATTGATTT  TTGAGGTTTT  TTTTTCAGA   AAAAAACTGT
                CAGAAAAAAG  ATGCTTTTTA   CTTTTTTTT    TTTGTTTTT    AATAACTAAA  AACTCCAAAA  AAAAAGTCT   TTTTTTGACA
```

Figure 11C cont.

| | 12650 | 12660 | 12670 | 12680 | 12690 | 12700 | 12710 | 12720 |
|---|---|---|---|---|---|---|---|---|
| Untitled2 | TTAAAAAAC | GGATTTTTT | TGATTATTTT | GGTATTTTCC | TGAAAAAATC | GAAAAATGAA | CATTTTCGGT | TTTTAAAAGT |
| | AATTTTTTG | CCTAAAAAAA | ACTAATAAAA | CCATAAAAGG | ACTTTTTTAG | CTTTTTACTT | GTAAAAGCCA | AAAATTTTCA |

| | 12730 | 12740 | 12750 | 12760 | 12770 | 12780 | 12790 | 12800 |
|---|---|---|---|---|---|---|---|---|
| Untitled2 | TTTTTGACAA | AAATTTTTTA | TTAGAAAATC | TAGACAATGA | AGAACTAAAA | ATTAAAAAAA | AACTTAAATT | ATCGATTTTT |
| | AAAAACTGTT | TTTAAAAAAT | AATCTTTTAG | ATCTGTTACT | TCTTGATTTT | TAATTTTTTT | TTGAATTTAA | TAGCTAAAAA |

| | 12810 | 12820 | 12830 | 12840 | 12850 | 12860 | 12870 | 12880 |
|---|---|---|---|---|---|---|---|---|
| Untitled2 | CCAGATTTTT | TCAGAAAAAA | CACTCAAATT | ACTGAAAATT | TCTTGGAGTT | TTTTTTTCAG | AAAATTGACA | AACCGAAAAA |
| | GGTCTAAAAA | AGTCTTTTTT | GTGAGTTTAA | TGACTTTTAA | AGAACCTCAA | AAAAAAAGTC | TTTTAACTGT | TTGGCTTTTT |

| | 12890 | 12900 | 12910 | 12920 | 12930 | 12940 | 12950 | 12960 |
|---|---|---|---|---|---|---|---|---|
| Untitled2 | GTCCGATTTG | TGGGGTTTTT | TTTTCGGAGA | AAAAATATTT | TAAAAACGAA | AAAAATCGAA | AAACTTTTTT | TTTTCACAAA |
| | CAGGCTAAAC | ACCCCAAAAA | AAAAGCCTCT | TTTTTATAAA | ATTTTTGCTT | TTTTTAGCTT | TTTGAAAAAA | AAAAGTGTTT |

| | 12970 | 12980 | 12990 | 13000 | 13010 | 13020 | 13030 | 13040 |
|---|---|---|---|---|---|---|---|---|
| Untitled2 | AAATTGGGAA | AAACTCAAAA | ATTTAGATTT | TTTTTATTTA | GAAAATTCG | AAGAATAAAC | AAAAATTACC | AAAAAATTTC |
| | TTTAACCCTT | TTTGAGTTTT | TAAATCTAAA | AAAAATAAAT | CTTTTTAAGC | TTCTTATTTG | TTTTTAATGG | TTTTTTAAAG |

| | 13050 | 13060 | 13070 | 13080 | 13090 | 13100 | 13110 | 13120 |
|---|---|---|---|---|---|---|---|---|
| Untitled2 | CGCGGTTTTT | TCAAAAAATC | GAAAAAAAA | CAAAAAATTT | CGATTTTTCA | GATATTTTTT | CAGAAAAATA | ATAATAATAA |
| | GCGCCAAAAA | AGTTTTTTAG | CTTTTTTTTT | GTTTTTTAAA | GCTAAAAAGT | CTATAAAAAA | GTCTTTTTAT | TATTATTATT |

| | 13130 | 13140 | 13150 | 13160 | 13170 | 13180 | 13190 | 13200 |
|---|---|---|---|---|---|---|---|---|
| Untitled2 | CAAAGTATT | CGATTTTTTT | TTTCGGAGA | AAATCGAAAA | ATTGAAAATT | CTCGTCAGAA | TTGATTAAAA | AACCGGTTTT |
| | GTTTTCATAA | GCTAAAAAAA | AAAAGCCTCT | TTTAGCTTTT | TAACTTTTAA | GAGCAGTCTT | AACTAATTTT | TTGGCCAAAA |

| | 13210 | 13220 | 13230 | 13240 | 13250 | 13260 | 13270 | 13280 |
|---|---|---|---|---|---|---|---|---|
| Untitled2 | TTTTGTTGA | AAAAGGGCTA | ATTAAAAACT | ATAATAATAA | TATTAACAC | GATTAATTTT | TTGCCGATTC | ACTGCAACTT |

Figure 11C cont.

```
                    AAAAACAACT TTTTCCCGAT TAATTTTTGA TATTATTATT ATAAATTGTG CTAATTAAAA AACGGCTAAG TGACGTTGAA
                               13290      13300      13310      13320      13330      13340      13350      13360
Untitled2  TTTCCTCACG AGGGACGAGG AAAAGTGGTT TCTAGGCCAT GGCCGAGGGA CCGACAAGTT TCAGCGGCCA TTTATCTTGC
           AAAGGAGTGC TCCCTGCTCC TTTTCACCAA AGATCCGGTA CCGGCTCCCT GGCTGTTCAA AGTCGCCGGT AAATAGAACG
                      13370      13380      13390      13400      13410      13420      13430      13440
Untitled2  TTTGTTTTCC GCCTGTTTTC TTTCGTTTTT CATCGATTTT TTTCGTTTTT TCTTAATAAA ACTGATAAAT AAATATTTTT
           AACAAAAGG  CGGACAAAAG AAAGCAAAAA GTAGCTAAAA AAAGCAAAAA AGAATTATTT TGACTATTTA TTTATAAAAA
                      13450      13460      13470      13480      13490      13500      13510      13520
Untitled2  TGCAGATGCT AAAACAATTT CCAAGTAAAA AAATTATGTA TTCAGTGGGC AAGCAGCGGT GAAAGTGGGC AATGTAACGA
           ACGTCTACGA TTTTGTTAAA GGTTCATTTT TTTAATACAT AAGTCACCCG TTCGTCGCCA CTTTCACCCG TTACATTGCT
                      13530      13540      13550      13560      13570      13580      13590      13600
Untitled2  CTTTTTCACC AAAAAAGTTG AATTTTGAAA ACCTCAAAAC TTTTTCAGCG GTCTCGTTAT GAAAATCAGG TAATTTCAGC
           GAAAAAGTGG TTTTTTCAAC TTAAAACTTT TGGAGTTTTG AAAAAGTCGC CAGAGCAATA CTTTTAGTCC ATTAAAGTCG
                      13610      13620      13630      13640      13650      13660      13670      13680
Untitled2  ATCTAAGCAT CATATGTATC ATGTTTCAGA AAAAGTTTAG GTTTTGTATT CCCGTAATCC ATCATATTAC AATGCCCACT
           TAGATTCGTA GTATACATAG TACAAAGTCT TTTTCAAATC CAAAACATAA GGGCATTAGG TAGTATAATG TTACGGGTGA
                      13690      13700      13710      13720      13730      13740      13750      13760
Untitled2  TTCACCGCTG CTTGCCCACT GAATACATGA TTTTTTTTAC TTGGAAATTG TTTTAGCATC TGCAAAAAAT ATTTATTTAT
           AAGTGGCGAC GAACGGGTGA CTTATGTACT AAAAAAAATG AACCTTTAAC AAAATCGTAG ACGTTTTTTA TAAATAAATA
                      13770      13780      13790      13800      13810      13820      13830      13840
Untitled2  CAGTTTTATT AGGAAAAAAC GAAAAAAATC GATGAAAAAC GAAAGAAAAC AGGCGGAAAA CAAAGCAAGA TAAATGGCCG
           GTCAAAATAA TCCTTTTTTG CTTTTTTTAG CTACTTTTTG CTTTCTTTTG TCCGCCTTTT GTTTCGTTCT ATTTACCGGC
```

Figure 11C cont.

```
Untitled2       ATGAAACTTG TCGGCCCCTC GGCCGTGGCC TAGAAGCCAC TTTTCCTCGT CCCTCGTGAG GAAAAAGTTG CAGTGGGATT
                TACTTTGAAC AGCCGGGGAG CCGGCACCGG ATCTTCGGTG AAAAGGAGCA GGGAGCACTC CTTTTTCAAC GTCACGCTAA
                    13850      13860      13870      13880      13890      13900      13910      13920

Untitled2       TTTATAAAAG TTATTTTTTT TAAAAATTTT ATTTCCAGAA CGACACTCTT CACACCCGCT TGCAATGGCA TCCGACAGAA
                AAATATTTTC AATAAAAAAA ATTTTTAAAA TAAAGGTCTT GCTGTGAGAA GTGTGGGCGA ACGTTACCGT AGGCTGTCTT
                    13930      13940      13950      13960      13970      13980      13990      14000 jmp1 str +                                          TCACTGATAA CGACACTCTT TGCAATGGCA TCCGACAGAA>
                                                    ||||||||   |||||||||| |||||||||| ||||||||||
Untitled2                                           ATTTCCAGAA CGACACTCTT TGCAATGGCA TCCGACAGAA
                                                      1980       1990       2000       2010       2020

Untitled2       CATGTGAAAA AAGTTGGAGA CAAGACGAGT CCCGAAATGA TATTCAAATA TCGAAAAGGC GATGAGCTCA TTGAGCAAAC
                GTACACTTTT TTCAACCTCT GTTCTGCTCA GGGCTTTACT ATAAGTTTAT AGCTTTTCCG CTACTCGAGT AACTCGTTTG
                    14010      14020      14030      14040      14050      14060      14070      14080 jmp1 str +      CATGTGAAAA AAGTTGGAGA CAAGACGAGT CCCGAAATGA TATTCAAATA TCGAAAAGGC GATGAGCTCA TTGAGCAAAC>
                |||||||||| |||||||||| |||||||||| |||||||||| |||||||||| |||||||||| |||||||||| ||||||||||
Untitled2       CATGTGAAAA AAGTTGGAGA CAAGACGAGT CCCGAAATGA TATTCAAATA TCGAAAAGGC GATGAGCTCA TTGAGCAAAC
                  2030       2040       2050       2060       2070       2080       2090       2100

Untitled2       TGTTGTAAAG CCGTACGATT CAGTGTTTGG AGGACAATTT GATAGTTGGA ATGTTGGGAA AAAGTTCGTG TTCTACTAGA
                ACAACATTTC GGCATGCTAA GTCACAAACC TCCTGTTAAA CTATCAACCT TACAACCCTT TTTCAAGCAC AAGATGATCT
                    14090      14100      14110      14120      14130      14140      14150      14160 jmp1 str +      TGTTGTAAAG CCGTACGATT CAGTGTTTGG AGGACAATTT GATAGTTGGA ATGTTGGGAA AAAACTCTCC AA>
                |||||||||| |||||||||| |||||||||| |||||||||| |||||||||| |||||||||  |||  ||  ||
Untitled2       TGTTGTAAAG CCGTACGATT CAGTGTTTGG AGGACAATTT GATAGTTGGA ATGTTGGGAA AAAGTTCGTG TT
                  2110       2120       2130       2140       2150       2160       2170

Untitled2       AATTGGATGG TCCCCCGAA AATTAAAAA TACCACAAAA AGAAAAAGGA AAAAACTCGG GAAAGTTTC GTAAAAAAAA
                TTAACCTACC AGGGGGCTT TTAAATTTTT ATGGTGTTTT TCTTTTTCCT TTTTTGAGCC CTTTTCAAAG CAATTTTTTT
                    14170      14180      14190      14200      14210      14220      14230      14240
```

Figure 11C cont.

```
           14250      14260      14270      14280      14290      14300      14310      14320
Untitled2  TGTTTTTGT  TGAAAATCCC TTTTTTATAA TTGAAATATG TTGAATTTTC GCAACATAGG TTTGAGACAA CAAAAAAATA
           ACAAAAAACA ACTTTTAGGG AAAAAATATT ATAATTTTAC AACTTAAAAG CGTTGTATCC AAACTCTGTT GTTTTTTTAT 14330      14340      14350      14360      14370      14380      14390      14400
Untitled2  ATTAAAAATC CAACTTATAA AAACATATTT TGAAGTTTTT TGCAAAGTTA TCTCCAAAAC GAGAACTACG ACTAATCAGC
           TAATTTTTAG GTTGAATATT TTTGTATAAA ACTTCAAAAA ACGTTTCAAT AGAGGTTTTG CTCTTGATGC TGATTAGTCG 14410      14420      14430      14440      14450      14460      14470      14480
Untitled2  GACTTGCCCC GCCCACACTT TTGAACCAAT CAGCGTCTTC CGAAGCCTGA TTGGTTCAAA AGAAGTGATC GTGGTTCTT
           CTGAACGGGG CGGGTGTGAA AACTTGGTTA GTCGCAGAAG GCTTCGGACT AACCAAGTTT TCTTCACTAG CACCAAAGAA 14490      14500      14510      14520      14530      14540      14550      14560
Untitled2  ATTTAGAACG GATTACGGAA AAATCGGGTT TTTCGATATT TTCTTACGTT TTTTGGGGGT CGGGCGTAAA AATGTGCTAG
           TAAATCTTGC CTAATGCCTT TTTAGCCCAA AAAGCTATAA AAGAATGCAA AAAACCCCCA GCCCGCATTT TTACACGATC 14570      14580      14590      14600      14610      14620      14630      14640
Untitled2  CGAATTAAAA AAAAAAACGC CGAAAAATTT AGTTTTTTCG TTTTTCTCTG CAAAAAAGCC CAAAAAAAAT CGGAAAAAAA
           GCTTAATTTT TTTTTTTGCG GCTTTTTAAA TCAAAAAAGC AAAAAGAGAC GTTTTTTTTA GCCTTTTTT 14650      14660      14670      14680      14690      14700      14710      14720
Untitled2  CAAAAAAAAC GAAAATTTCG TAATTCTGAA AAAAAAACCC AAAAAATCCA AATTCGTAGT TTTTTTCGA TTTTCTGAAA
           GTTTTTTTG CTTTAAAGC ATTAAGACTT CTTTTTGGG TTTTTAGGT TTAAGCATCA AAAAAAAGCT AAAAGACTTT 14730      14740      14750      14760      14770      14780      14790      14800
Untitled2  TTTTATTTA AATCGAAAAA AAAACGAAAA CATTAGTTAA TTTTTCTATT TTTTTTCGA TTAGGAAAAC ATCCCGAAAA
           AAAAATAAAT TTAGCTTTTT TTTTGCTTTT GTAATCAATT AAAAAGAAGCT AAAAAGATAA AATCCTTTTG TAGGGCTTTT 14810      14820      14830      14840      14850      14860      14870      14880
```

Figure 11C cont.

```
Untitled2   ATCTAAATTT GTAGTTTTTT TTTCGATTTT CTCAAAAAAA AAACCTAAAA AATCAATTTT TTCGATTTTT CGAAATTCTT
            TAGATTTAAA CATCAAAAAA AAAGCTAAAA GAGTTTTTTT TTTGGATTTT TTAGTTAAAA AAGCTAAAAA GCTTTAAGAA 14890      14900      14910      14920      14930      14940      14950      14960
Untitled2   TTTAAAAAAA GATTCAAAAA AATCAAACAA ATTTAAAATG TTTGCCGAAA ATCGGGGAA  CAACGAAAAA AAAAACGAAC
            AAATTTTTTT CTAAGTTTTT TTAGTTTGTT TAAATTTTAC AAACGGCTTT TAGCCCCCTT GTTGCTTTTT TTTTTGCTTG 14970      14980      14990      15000      15010      15020      15030      15040
Untitled2   ATTTTTTTC GATTTTCTCA GAAAAACAAA CTTTTTAAGT CAATAATTTT TTTTTAGTTT TCTCGATTTT TCGATTTTCT
            TAAAAAAAAG CTAAAAGAGT CTTTTTGTTT GAAAAATTCA GTTATTAAAA AAAAATCAAA AGAGCTAAAA AGCTAAAAGA 15050      15060      15070      15080      15090      15100      15110      15120
Untitled2   GAAAAATTC  CAAAAAAAGC AATAATTTTA AATTTTTTAA ACTTAATTTT TAATTTTTAA CTGTAAATTT TCGGTTTTAA
            CTTTTTTAAG GTTTTTTTCG TTATTAAAAT TTAAAAAAAT TGAATTAAAA ATTAAAAATT GACATTTAAA AGCCAAAATT 15130      15140      15150      15160      15170      15180      15190      15200
Untitled2   CAACAAAAA  AAATTTTTT  TTTTCGTTTT TTTTCCAATT CAAAAATTTC CAGACTCTCC AACCTGACGA CCTGTTCCAA
            GTTGTTTTTT TTTAAAAAAA AAAAGCAAAA AAAAGGTTAA GTTTTTAAAG GTCTGAGAGG TTGGACTGCT GGACAAGGTT 2170       2180       2190
jmp1 str +                                              GGGAA AAAACTCTCC AACCTGACGA CCTGTTCCAA>
                                                              |||||||||| |||||||||| ||||||||||
Untitled2                                               ATTTC CAGACTCTCC AACCTGACGA CCTGTTCCAA 15210      15220      15230      15240      15250      15260      15270      15280
Untitled2   TTTCTTCGTC GACATCATCT CCCCATCGTC ACCCGATGAT GCTCCACCGC TCGCCACACT ACATTTTCCC GTTTACACTG
            AAAGAAGCAG CTGTAGTAGA GGGGTAGCAG TGGGCTACTA CGAGGTGGCG AGCGGTGTGA TGTAAAGGG  CAAATGTGAC 2200       2210       2220       2230       2240       2250       2260       2270
jmp1 str +  TTTCTTCGTC GACATCATCT CCCCATCGTC ACCCGATGAT GCTCCACCGC TCGCCACACT ACATTTTCCC GTTTACACTG>
            |||||||||| |||||||||| |||||||||| |||||||||| |||||||||| |||||||||| |||||||||| ||||||||||
Untitled2   TTTCTTCGTC GACATCATCT CCCCATCGTC ACCCGATGAT GCTCCACCGC TCGCCACACT ACATTTTCCC GTTTACACTG
```

Figure 11C cont.

```
              15290      15300      15310      15320      15330      15340      15350      15360
Untitled2  ATCAAACGC GCATTGCCAC GTGGATTACC TACGCCAGTT CTTCAAAATT GCCGATTTTT GCACTTCCGG CGACGCTTGC
           TAGTTTTGCG CGTAACGGTG CACCTAATGG ATGCGGTCAA GAAGTTTTAA CGGCTAAAAA CGTGAAGGCC GCTGCGAACG 2280       2290       2300       2310       2320       2330       2340       2350
jmp1 str + ATCAAACGC GCATTGCCAC GTGGATTACC TACGCCAGTT CTTCAAAATT GCCGATTTTT GCACTTCCGG CGACGCTTGC>
           ||||||||| |||||||||| |||||||||| |||||||||| |||||||||| |||||||||| |||||||||| ||||||||||
Untitled2  ATCAAACGC GCATTGCCAC GTGGATTACC TACGCCAGTT CTTCAAAATT GCCGATTTTT GCACTTCCGG CGACGCTTGC 15370      15380      15390      15400      15410      15420      15430      15440
Untitled2  AAGGAAAAGA TCTGGAGTAC GAGCTATCCC GATCCGAAAT CAGATATTTT TGTCGGATAC GATGAGGATA CGCAGACCTT
           TTCCTTTTCT AGACCTCATG CTCGATAGGG CTAGGCTTTA GTCTATAAAA ACAGCCTATG CTACTCCTAT GCGTCTGGAA 2360       2370       2380       2390       2400       2410       2420       2430
jmp1 str + AAGGAAAAGA TCTGGAGTAC GAGCTATCCC GATCCGAAAT CAGATATTTT TGTCGGATAC GATGAGGATA CGCAGACCTT>
           |||||||||| |||||||||| |||||||||| |||||||||| |||||||||| |||||||||| |||||||||| ||||||||||
Untitled2  AAGGAAAAGA TCTGGAGTAC GAGCTATCCC GATCCGAAAT CAGATATTTT TGTCGGATAC GATGAGGATA CGCAGACCTT 15450      15460      15470      15480      15490      15500      15510      15520
Untitled2  GATTAGAAC ACATTTTTT GTTTGTAGAA ATTTCTGATT TTTTTTCTTC AAATTTTAAT TGTTTTATAG TGCTCAACGA
           CTAAATCTTG TGTAAAAAAA CAAACATCTT TAAAGACTAA AAAAAGAAG TTTAAAATTA ACAAATATC ACGAGTTGCT 2440
jmp1 str + GATTTAG>
           |||||||
Untitled2  GATTTAG 15530      15540      15550      15560      15570      15580      15590      15600
Untitled2  TTGGCTTTG CAATGTGTTA TTTTCAGCGA AAACCCCCTG AAAAAACAGT TTTTCTGGCA AAAAGCCGCA AAAAACGGTT
           AACCGAAAAC GTTACACAAT AAAAGTCGCT TTTGGGGGAC TTTTTTGTCA AAAAGACCGT TTTTCGGCGT TTTTTGCCAA 15610      15620      15630      15640      15650      15660      15670      15680
Untitled2  TTTTAAGCT TAAAACCCAA AAAAAAAAGG GGTTTTTTTT TTTGCTGAAA AACGCGAAAA AATAGGCAAT TCTGCTATTT
```

Figure 11C cont.

```
            AAAAATTCGA ATTTGGGTT TTTTTTTCC CCAAAAAAAA AAACGACTTT TTGCGCTTTT TTATCCGTTA AGACGATAAA
                 15690      15700      15710      15720      15730      15740      15750      15760
Untitled2   TTCAACACAA AAATGTCAAA TTTATGGCCT TTTCTGTAAA TTTACTCCTT TTTGGCAAC ATTTCAGAAA CAAATTCTTT
            AAGTTGTGTT TTTACAGTTT AAATACCGGA AAAGACATTT AAATGAGGAA AAACCCGTTG TAAAGTCTTT GTTTAAGAAA
                 15770      15780      15790      15800      15810      15820      15830      15840
Untitled2   TTTTTTTTTT TTTTTTGGAA AAATACGATT AAAATCCAGA AATTCACGTG TTTTTTTCAC GAAAAATACG AAAAACCAAA
            AAAAAAAAAA AAAAAACCTT TTTATGCTAA TTTTAGGTCT TTAAGTGCAC AAAAAAAGTG CTTTTTATGC TTTTTGGTTT
                 15850      15860      15870      15880      15890      15900      15910      15920
Untitled2   AATTCACCGT ACCTACATGT AGCAAAAGCC AATTTAAATA AAAACTGGAG CACCGGAATC TGGGAAATAT GTTTAAATTT
            TTAAGTGGCA TGGATGTACA TCGTTTTCGG TTAAATTTAT TTTTGACCTC GTGGCCTTAG ACCCTTTATA CAAATTTAAA
                 15930      15940      15950      15960      15970      15980      15990      16000
Untitled2   TTCCCCGAC TCCAAATTTT CCCCTGATTC CGAAAATCTA TGCAAAAAAA ATGCATTTAA AAAATTCCCA GATTTTATAT
            AAGGGGGCTG AGGTTTAAAA GGGGACTAAG GCTTTTAGAT ACGTTTTTTT TACGTAAATT TTTTAAGGGT CTAAATATA
```

```
sqv-4 genomic sequence
Sequence Range: 1 to 2000

10         20         30         40         50         60         70         80
Untitled1    TTGTGCATAT TCTGCATTGT ACGAGTTGAT TTTCTGTAGG GCGGCAATTC AAATGTAAAA GTTTTTTTT TCATTTTCAT
             AACACGTATA AGACGTAACA TGCTCAACTA AAAGACATCC CGCCGTTAAG TTTACATTTT CAAAAAAAAA AGTAAAAGTA 90        100        110        120        130        140        150        160
Untitled1    GTCTTGACGC CTTTCGAGTT GTTAAAAATC GTGTTCCTTT TGAAAGCTTT TCTTTATCGC TTACTAATTT TACTTTTCAT
             CAGAACTGCG GAAAGCTCAA CAATTTTTAG CACAAGGAAA ACTTTCGAAA AGAAATAGCG AATGATTAAA ATGAAAAGTA 170        180        190        200        210        220        230        240
Untitled1    TTTAAATATT TTCAAATTTC AGTAATGACT GATCAAGTCT TCGGAAAGGT GTCGAAAGTC GTTTGCGTCG GAGCTGGATA
             AAATTTATAA AAGTTTAAAG TCATTACTGA CTAGTTCAGA AGCCTTTCCA CAGCTTTCAG CAAACGCAGC CTCGACCTAT 10         20         30         40         50
jmp1 str +                        ATGACT GATCAAGTCT TCGGAAAGGT GTCGAAAGTC GTTTGCGTCG GAGCTGGATA
                    SNP →                ||||||     |||||||||| |||||||||| |||||||||| ||||||||||
Untitled1                         ATGACT GATCAAGTCT TCGGAAAGGT GTCGAAAGTC GTTTGCGTCG GAGCTGGATA 250        260        270        280        290        300        310        320
Untitled1    CGTTGGTGGA CCAACATGTG CAATGATTGC GCACAAGTGT CCACACATTA CAGTAACTGT CGTGGACATG AACACCGCTA
             GCAACCACCT GGTTGTACAC GTTACTAACG CGTGTTCACA GGTGTGTAAT GTCATTGACA GCACCTGTAC TTGTGGCGAT 60         70         80         90        100        110        120        130
jmp1 str +   CGTTGGTGGA CCAACATGTG CAATGATTGC GCACAAGTGT CCACACATTA CAGTAACTGT CGTGGACATG AACACCGCTA
             |||||||||| |||||||||| |||||||||| |||||||||| |||||||||| |||||||||| |||||||||| ||||||||||
Untitled1    CGTTGGTGGA CCAACATGTG CAATGATTGC GCACAAGTGT CCACACATTA CAGTAACTGT CGTGGACATG AACACCGCTA 330        340        350        360        370        380        390        400
Untitled1    AGATTGCCGA GTGGAACTCT GATAAATTGC CAATATACGA GGTGAGCTAT ATTTTTTTAA ATTTTCTCT AATAAACATA
             TCTAACGGCT CACCTTGAGA CTATTTAACG GTTATATGCT CCACTCGATA TAAAAAAATT TAAAAGAGA TTATTTGTAT 140        150        160        170        180
```

```
                      1210        1220        1230        1240        1250        1260        1270        1280
Untitled1       AAGGAGTGAT TAATATTAAC AACTGGCAAC GAAGACGTTT CGCAGACAAG ATTATTGCGG AGTTGTTTAA CACGGTGACT
                |||||||||| |||||||||| |||||||||| |||||||||| |||||||||| |||||||||| |||||||||| ||||||||||
                TTCCTCACTA ATTATAATTG TTGACCGTTG CTTCTGCAAA GCGTCTGTTC TAATAACGCC TCAACAAATT GTGCCACTGA 930         940         950         960         970         980         990        1000
jmp1 str +      AAGGAGTGAT TAATATTAAC AACTGGCAAC GAAGACGTTT CGCAGACAAG ATTATTGCGG AGTTGTTTAA CACGGTGACT>
                |||||||||| |||||||||| |||||||||| |||||||||| |||||||||| |||||||||| |||||||||| ||||||||||
Untitled1       AAGGAGTGAT TAATATTAAC AACTGGCAAC GAAGACGTTT CGCAGACAAG ATTATTGCGG AGTTGTTTAA CACGGTGACT 1290        1300        1310        1320        1330        1340        1350        1360
Untitled1       GATAAGAAAA TTGCAATCTT CGGATTCGCT TTCAAGAAGA ACACAGGTGA GTATAAGCGC AAAAAGCTGT TCAACATTAA
                |||||||||| |||||||||| |||||||||| |||||||||| |||||||||| |||||||||| |||||||||| ||||||||||
                CTATTCTTTT AACGTTAGAA GCCTAAGCGA AAGTTCTTCT TGTGTCCACT CATATTCGCG TTTTTCGACA AGTTGTAATT 1010        1020        1030        1040        1050
jmp1 str +      GATAAGAAAA TTGCAATCTT CGGATTCGCT TTCAAGAAGA ACACAGGTGA CACACG>
                |||||||||| |||||||||| |||||||||| |||||||||| ||||||||||
Untitled1       GATAAGAAAA TTGCAATCTT CGGATTCGCT TTCAAGAAGA ACACAGGTGA GTATAA 1370        1380        1390        1400        1410        1420        1430        1440
Untitled1       TCTAAAAATA CACCGAGAAT ATACATACGT TACATGCTTG TTTTACAATT TACAGGTATT TTAAAGCTAT GCATATTGCC
                |||||||||| |||||||||| |||||||||| |||||||||| |||||||||| |||||||||| |||||||||| ||||||||||
                AGATTTTTAT GTGGCTCTTA TATGTATGCA ATGTACGAAC AAAATGTTAA ATGTCCATAA AATTTCGATA CGTATAACGG 1450        1460        1470        1480        1490        1500        1510        1520
Untitled1       ATATTGTCAA GAAAATGAAT ATTATTACAA GTTTGGTTTT TCAGGTGACA CACGCGAATC ATCAGCCATT CACGTAATCA
                |||||||||| |||||||||| |||||||||| |||||||||| |||||||||| |||||||||| |||||||||| ||||||||||
                TATAACAGTT CTTTTACTTA TAATAATGTT CAAACCAAAA AGTCCACTGT GTGCGCTTAG TAGTCGGTAA GTGCATTAGT 1040        1050        1060        1070        1080
jmp1 str +                     AAGAAC ACAGGTGACA CACGCGAATC ATCAGCCATT CACGTAATCA>
                                |||||| |||||||||| |||||||||| |||||||||| ||||||||||
Untitled1                      GGTTTT TCAGGTGACA CACGCGAATC ATCAGCCATT CACGTAATCA 1530        1540        1550        1560        1570        1580        1590        1600
Untitled1       AACACTTGAT GGAGGAGCAT GCAAAATTAT CAGTCTACGA TCCAAAAGTG CAGAAATCGC AAATGCTCAA CGATCTGGCT
```

```
              1850       1860       1870       1880       1890       1900       1910       1920
Untitled1   CCAGATCAAG CTTATAATCT ATTCGGAACA GCTGGTTATT AATCGTGTCT TGGAAAATCT CCAATTCTCA CTATTGACTT
            GGTCTAGTTC GAATATTAGA TAAGCCTTGT CGACCAATAA TTAGCACAGA ACCTTTTAGA GGTTAAGAGT GATAACTGAA 1410       1420       1430       1440
jmpl str +  CCAGATCAAG CTTATAATCT ATTCGGAACA GCTGGTTATT AA>
            |||||||||| |||||||||| |||||||||| ||||||||||  ||
Untitled1   CCAGATCAAG CTTATAATCT ATTCGGAACA GCTGGTTATT AA 1930       1940       1950       1960       1970       1980       1990       2000
Untitled1   CAAAATTATT TATCTGCATG CTTCTTCTTT TTACTCATAA TTTATTGCAT TTTATGATAT CTAACTGCCT TAATAGTAAA
            GTTTTAATAA ATAGACGTAC GAAGAAGAAA AATGAGTATT AAATAACGTA AAATACTATA GATTGACGGA ATTATCATTI
```

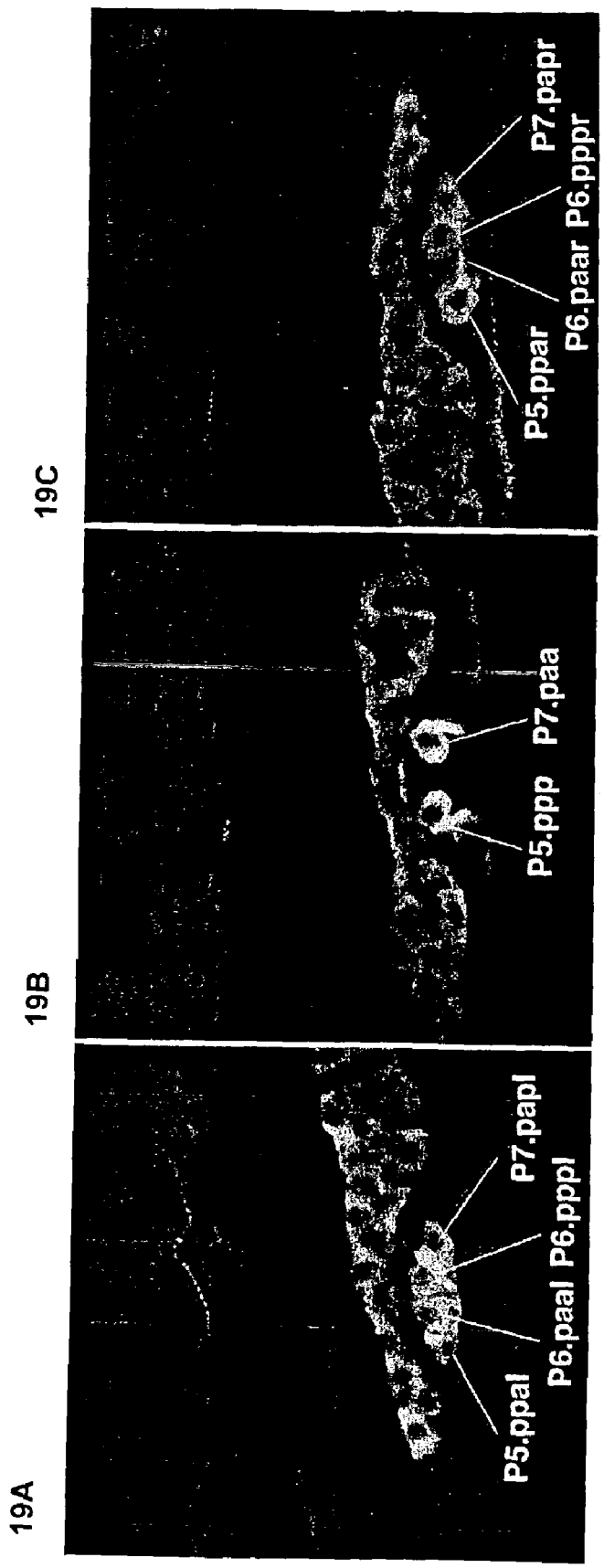
Figures 19A-C

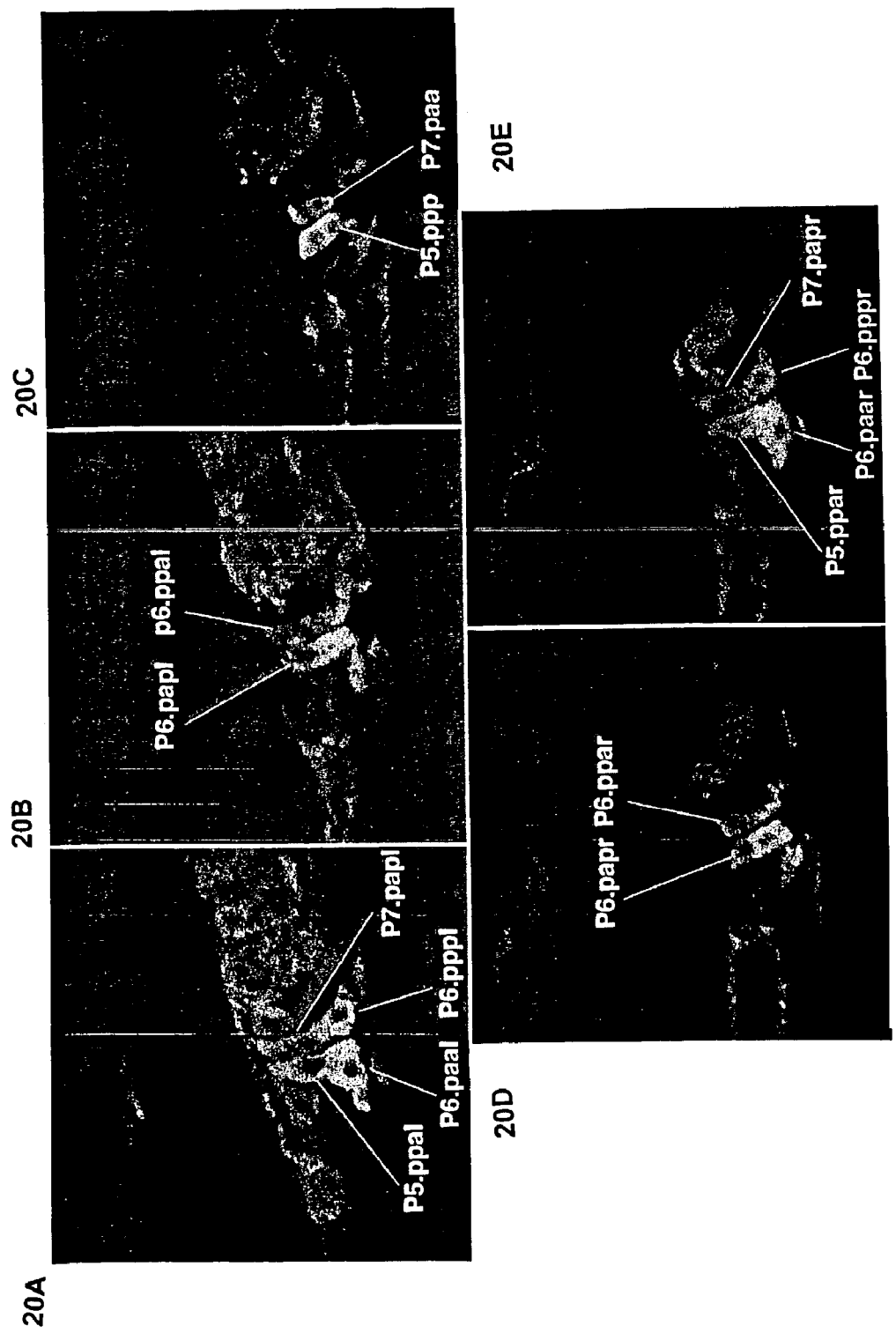
Figures 20A-E

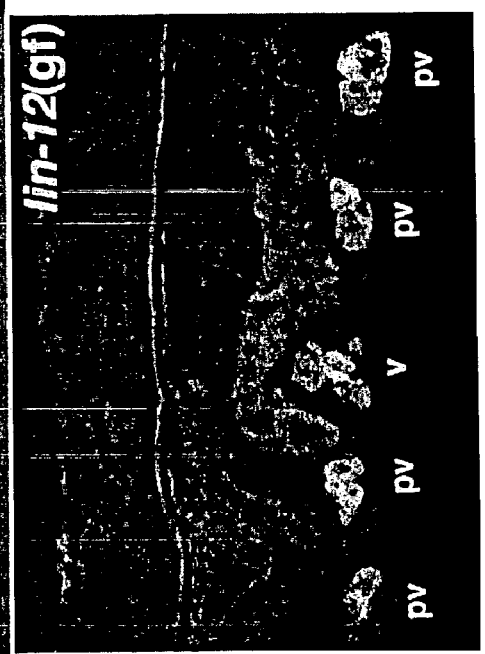
Figures 21A-B

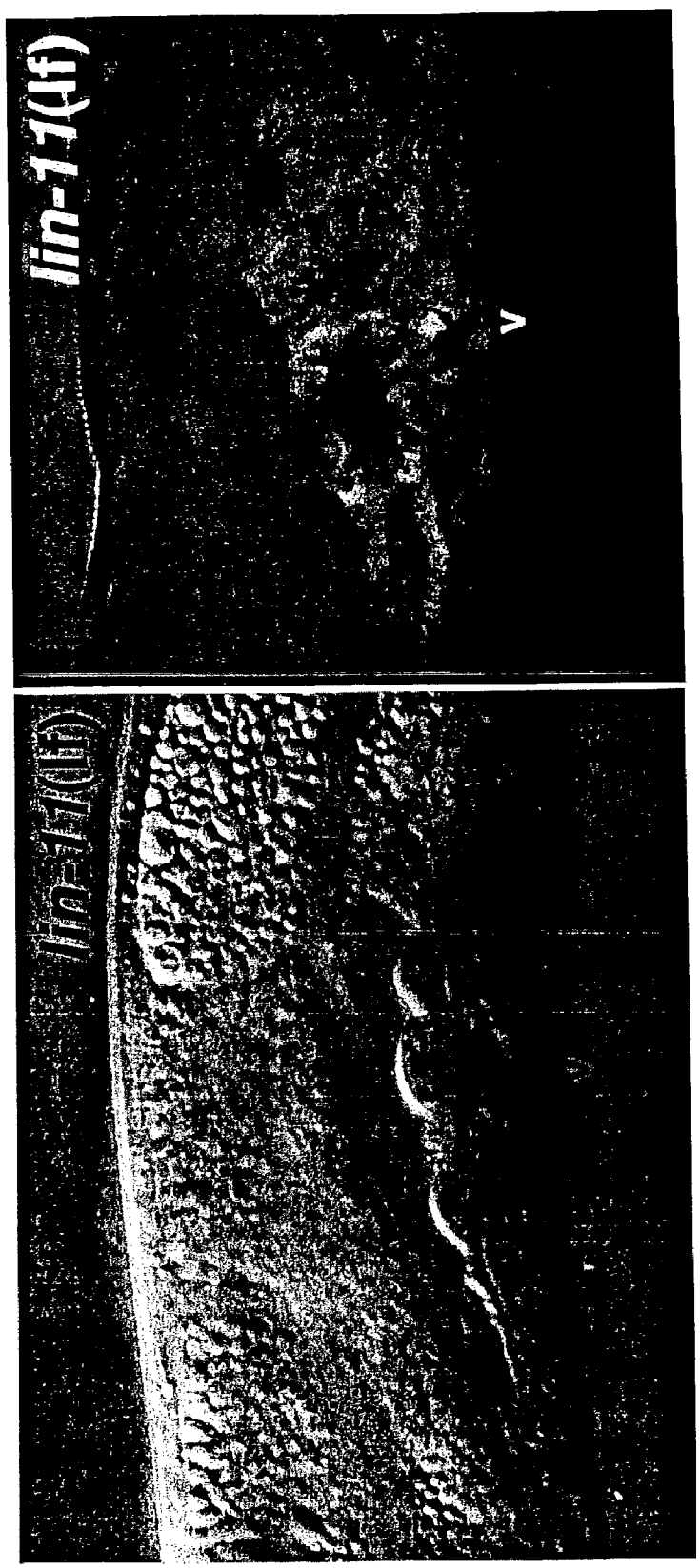
Figures 22A-B

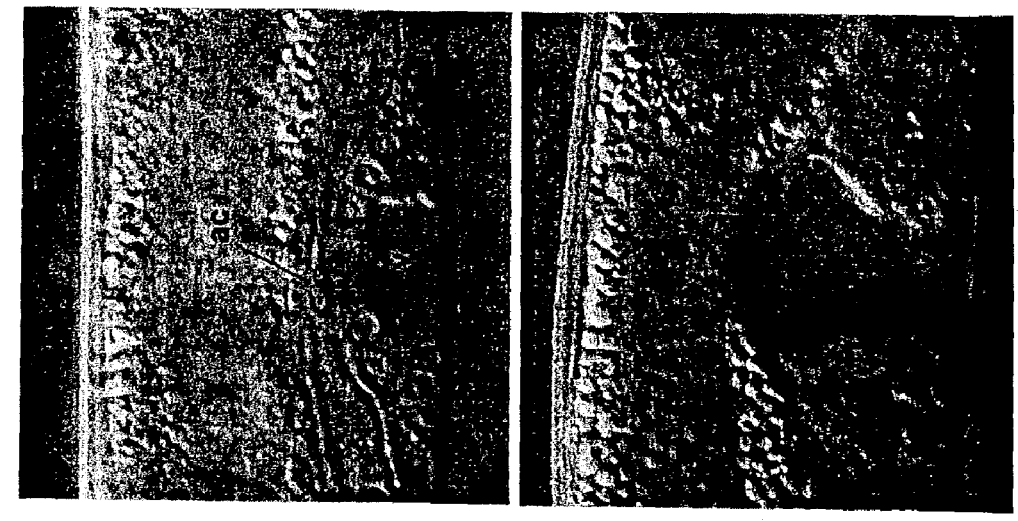
Figures 23A-D

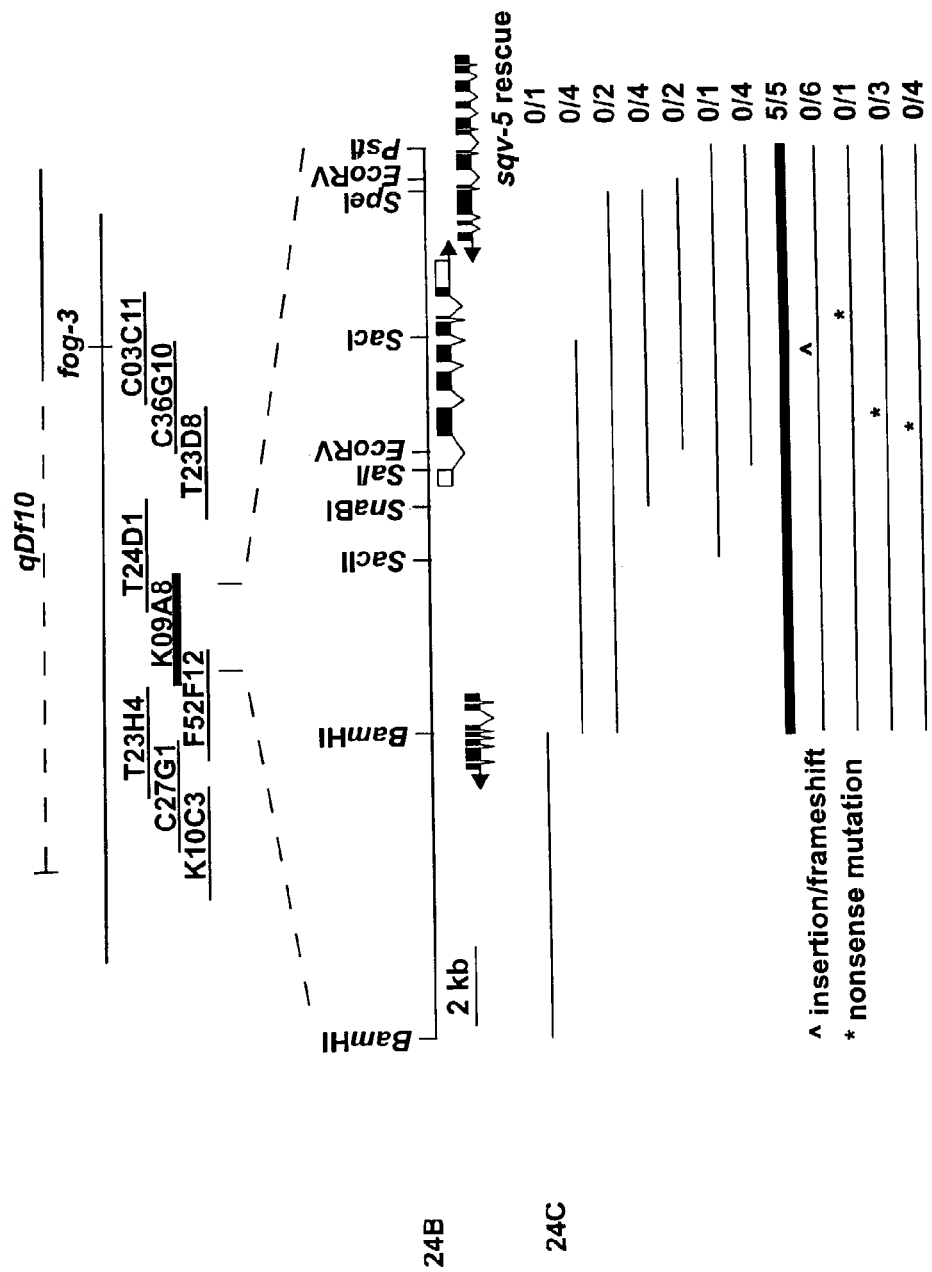
Figures 24A-C

Figure 25

```
acggatccaa gagttcctct tccaatcagc ctgaaaaaat aatttttta aaataaattt   60
cttttgtaaa tttatcttac tttcccaagc tataacgcct cggtatactt ggcaattttt  120
cggaatatct gcttgcttga ctcggcaatc cgtacgatcg accagccaat gttcctgcgt  180
aactttgtcg atcaaggtca ttctgtaaga tgaacaaaaa ttataataac tttatttttc  240
catttctcg aaaaaaatg caacgatttg ttcacaaaaa aagcctttaa aagtaatttt  300
aaaaagtttg ttcaatgttt tgaaaaccgt agccgaaaaa tattcaaatc gagtgatggg  360
tctcgccacg aaatgatttt tgtgcgcctt taactgaaaa ctacggttct cttttgttt  420
caacggattt tgttcttcat ttttgagatc ttttcttgct ttttcttcg agtttacttt  480
ttaaatgata ttttcatttt ctatttagat aagaaaattc taaattacat tttcaatagc  540
tattttatac ttacggtatt cggcaaactg tccattagcg ctttcataac gatattaggc  600
tcaggttcta tttcatcagg ttctgaaacc gttattatat ttcctgtttt cactcgaact  660
gtgtcctctt catattttg caacacaaat tccaccacta gtttctttcc attgtgctga  720
aatcttacta attagctttt ctgtcaatcg tctctctttt ttctttaaa attactttaa  780
ttgcctcgtc tagcgttttc tgtccatcta tgaccatttc gtactttccc atctcgtaca  840
aaatacggaa catgtccaga tttgtcgtct tccggcattt atcgacaagt tgctcgtaat  900
tattacatgc tctcgccaaa acttccactt ttttcctcag cttctgtttt tcgttcattg  960
atgagaccgc cattcgaatt taatgacgac ggtaaccgat gactcttcgt tttcgtctgc 1020
ttctgattct tccgaataac cattacatta cgggcgaagt ggattgagag tggagtagcc 1080
ggcagaagaa aaaagtggac aagtttgag gtgaaggcac ctggaaaata gaagaatggc 1140
catgtgtggg cacacaccga gacgagaaaa aagagtttg gctgagagaa aaaagaaaag 1200
agtgaggacc aatcgaagtg aattcgtgtg cacgctctcg tccaacagaa gccgcttaac 1260
atcgcccgca gtgagagcag tgctgagtaa acgaaaccat gaggggttca cgagaaaagc 1320
gcccgtcgct caataactga cgttttgtg gtgcgtgcaa atgttagaac cccttgtca 1380
taaaaatgtc tgattgaggc aatcttatca taacgctttc cgcgtttga tgatgattat 1440
gactttctct ggtgttagct tgattgcagt ggcgtcactg tccagaatta tcagtggcat 1500
ggaattgggg aattaaagag agcaaaagta cgcggaaaca atccgatttt aatttaatgt 1560
gagattgctt aacatctacg atgattccaa tgctgcaatg ccctatcctt tgcgataaac 1620
ttaattcgat tagttgcttt tacagggttt agctctaatt tcgacgttta cagaagcgtc 1680
tatgccgcgt gttagaacag caaggttatt ttaagaattg attcttcatt ggaaaatgat 1740
tgtgtacttt tggccaaatt gtcatgtgcg aactattgag catttgtgtt ttagaattga 1800
cacgttctca tattaccatc tcgatgatca aagtactact gatcactacg caagcttatc 1860
caaagaatct atacaagaac agcgaaggtg acaggctcat cactatttga acttgcctga 1920
acttgtttga actacgaccg ccaagtttgc acccttgta ctacagctgc aactatttca 1980
acgtgtccga ttcaatttc gtgttctcca gatgtttgcc gtttccgaaa ttcccgctat 2040
gcttgttctt ttttttgctg gcatgttgaa agaaagagcg actacttgaa tcgtcgagaa 2100
tacaccttat caatcgtcgc acctgagaga tgtctcgcgc ccaaatgcga tccggtgtat 2160
atgaataaga gaatgcgtct gatttcgaaa aaaagaaca caatcgaaaa acaccaatca 2220
ttctcgtttt ggcattaact atatcctcct cctcattctc ttctcactca tccacgacgt 2280
catcaattgt cgtagttgtc tcctttcgtg gaatgattac gccagaagac attcccatcg 2340
tttgtgatgc cacaactttg tgtccggcaa tctcatcgtt ggcaattccg ttcgtttcgt 2400
ttgcaaatca acttgactcg ctgtccactt cttgatttca ttcattttc ctattctacc 2460
tctttctttt cttcatgttc gtttaggatt cgaggacgtg tcggttttgg tattggtgtg 2520
tgtcagtgtg tgtgtacatg cccagtttgg taatcaaatg agatttctat gttaggccta 2580
gctaaagtgc acccgtacga cgagacaagg atatgtttcg ttctccgttc gtgtccgacc 2640
ttgatgtcta caggcctcca cgcttttgc cacgtcttct tgtgttactc aaaaaggaa 2700
agaacgacat cgcacaactt cctgccgtcg ctttcgtttt actttcaaag tggattgaga 2760
gcgaaattta cagctggtca cagatcttaa gttgaattct agatttatct ctatgaccaa 2820
catgacttac gaaaaaaaaa tttgtgtgct ttagaaatat caaaaatcaa aatttctgt 2880
acatttcaac atcttcaacc tcctttttca aatttggga ctccataaat ttttgttga 2940
gaaatttca aagtgaaata cgcttttaaa aaaattttt tatgaatctt tcaaagcgat 3000
caaaaagtt tgctattcca gttttttg tacaccacga aaattcaata tatctccaga 3060
gccttatctc aattgttttc atgattcact gatatacgtc acgaaatgct gaatcagtgt 3120
tcatcatttt acacgcaccg atcatttctg aaggccgcaa aaacttgaat gcgctcttga 3180
aagtactttc ttcttgggca ctatgccaga attttcccta attgaagtgg aaatcaaaga 3240
tctctatata atcttggtct agattttaca aaattgtagt ttgctgcacc acaagtaggt 3300
```

Figure 26

```
tcagagttcg gcatggtaaa acttgaggaa ctataaaaag ctatttgcac aacatttccg 3360
cttttaaaag ttgaacgcga tgcttcacaa ttatctttgt tctggattta tcatttggat 3420
tattttagat taagttctac tgattattca ttgaaattct ctcctagaaa aggaaattct 3480
cgtgccctca actttaaaaa atgtaattac tgggacgaat agttcaaaaa atttctttga 3540
agtgttggag tgctctatcg ttgcgtcaca aacgttgcac atctggcaca taacatgaat 3600
gtccctcttt tttacaattg ggaaaaaacg cacagccgaa tctaaatgat atggtattaa 3660
ttctatcacc tgctgcacac aattcaatta aaattccacc ctcattcgct tcttcagtca 3720
tatcttggta ttacgcagga ggtacgcaca cagatgttgc gcagttcagt gtcgcatttc 3780
tcattcctcc tcctttcctt ccacaacgca atcatctctt ctccggtcga ctgcggccag 3840
tggaggttga gccgcgtgta tgtgttggcc ctccaaacca tttacaatag attgccgtct 3900
cctcctcttg tattctttta tcccattcca atcataattt cttttggaat tgcaagtgag 3960
catcgcacag acaaaacggt cattgtctgt caaagtcggt ctcttgtctt cgtctacttg 4020
acgtcacctc ttatccttca tattgtttct cttaccgggt catcttgttc ttcacatcta 4080
ttttcttaca tctaaccatt taatgcagt ttatctaaat atacactttc tgccctcgtg 4140
aaaaaatcat gcgaaatga taataaaata gaaacaaga aatctttat catatcgagg 4200
cgcatagttt cattttgaaa caagtctttg atctatttac attctttgac tagcctgctg 4260
actgagaatg tagtttcgaa aaatataaag ctatgaccaa tagaagaaa agtgtgaatg 4320
ataatgatgg ttttttaggc ttgcagtcga attttctgta aaattgccaa atctttggta 4380
aataccaaaa ttttgtgaaa tccctaattt tttggtaaat tgcaaactt tttcataagt 4440
tgccaaattt ttggtaaatt tcaattttg taaaatcctt aatttttttt tggtaaatt 4500
accacatttt tcatggtaaa ttgctaattt tcgctaagtt gctaattt tgtaaaattg 4560
ctaattttt cggtaaatta caattttttt tgtaaattgc caaatgtgtc ataaataggc 4620
aatttttttt tggtagattg tcaaattttt tggtaaattg ccaaattgtc gagaaatgaa 4680
aattttctag tactttgag cattgctgca accctcagc ttagatacta caattgtaa 4740
cgagattaaa gtatattact caataaaaac caataaaaaa tgtagttgta tattccgtgg 4800
gtttaaaggt tattagtgaa atccctgtt tgtatgatca gctgtatcta gtaccaggtt 4860
caaccatatc agttttgat acaaaccga tttcctatat ggtatagttt gaaagtgtac 4920
tcatactcta acaaagatc agtcagtcgt tctcaattta aatctaggcc aactttagtt 4980
tctcattatc cgaaacgaaa cgctcacagt ttcatctcga tcttctcatt ttttttctac 5040
tctaataaca cctttgctgg tgttctcgga ttccttgaaa aacgccccca cacacacact 5100
ttctacttct tccgaaaata aaaataaaag tcaacgaacg actgtttgga tacgctgacc 5160
gcaaacactt ttggaactcc gccgactcgc cctggcttaa ctctttttc ttttcagttt 5220
gcgcccagat gtttcaagtt tcaattgata catatcatct ggctttctga aataaatgaa 5280
tggagagccg agtgtcggag atgaagctat gttgaaaaaa tattgtacag agcggcgaat 5340
ggttttccat gtctccagta ctgttgtgca ctcaatttgt ctctcttcat ctcctccact 5400
cgtgtgaatc tgtttgaaca gtggcgccgc ggctcgtttc tctccttctc tctctctctc 5460
tttgggccct ttggggtaaa atcaacgaag atgaagaaga agcgtgtcgt tttgtcggta 5520
gctatgctgc cagttcatcg gcaaataagc atgcttgtcc tacattatgt tctcatggat 5580
gacaatcctt ttttgtccct catttataat ttttattta tttttattgt catggaagta 5640
gacatagtag ttgtttctc cgaaggtttt cacgaattga atgtacaagt atcggaatga 5700
gaatgaacgt atttaggttc ctcataacaa tttgtgcata tatcaggtga cataaatcgt 5760
tatgtcgtaa aattatctag atttaatttc aaatttatcc ctcctcgtcc cactaacatt 5820
gtcacatgaa agggttattc agtagtagag aagtagcatc atccgacctc aactgtgatg 5880
cttatctctg ccgcatttc atcgacctct ctagtaggca gtaggcgaat atgcgtgaag 5940
aaaagatctc attctcaccc ggttttttg tctttctacc tcaacctatt catctagaaa 6000
ctgaacataa gttcacttt tcttgtattt ttcacccta tcatcaccac atccttcttt 6060
attttgaata ggccatgttc ttacgtggaa tcactgtcca ttcactcaaa aaatgttgcg 6120
aaaattactt ttttaatagc ttttccattc ggttcaacag atgacgatca gaaattcctg 6180
gtttgaacga taaagtgctt gcttcttctt tctaccacat ttagacccac catgggctta 6240
tctgtgggtg atctaggatt atatgagagt tgttaagacg cagagtgaaa gtgttgaggt 6300
cagatatagc caaaagtcg gttgagttat attatcagat tatctttcg ccgatatcaa 6360
gactatttag ttatgttgcc gactatatag ccagctcttg tcatatcgac ttccatttt 6420
ctattttcag tactgtttag agatattttt cggatttgtc gcatttttc ttagttggaa 6480
aaaaagtaa accgcacata tataatgaaa ccctcattcc ggggttttc taatttttt 6540
gtataaagaa tgaaataatt ttcgattccg tcctttgcta gagatcagta ccatcagaat 6600
attctctttt ttctcgccca cgactcatgc ttttgaaaca gagatgttaa atgaatgtgt 6660
```

```
atttataata taaattatta taacattcat cggcgtagtc aatcggcgtc tcacacattc 6720
ccattcttct caccatcttc aatttcaatc ggtcattacc acaccaacac taccaaaagc 6780
cgatggaaat tcgacgattt gtttataagt gacatgtgtg tctaagtctc gaactctctc 6840
cttctgactt ccaccaagtt gctccaatca ctttctgctg caccagtcta cgtaccactt 6900
gccactattt catttctttt ttccaatctc tgatctatct gcgtctctat ttctctacct 6960
ctactaatct tgttccacaa ttgtttgata gttgaaagtg caaaaaacgt ctcgtataac 7020
ggaccgcgaa aagtcgtcga gtgttcatat acttctttt tctcctcatt tttctcgtag 7080
taatgtgcta taattgttgt tgctgtgacc gttttcacat gactaccgtg atgctctaaa 7140
tgacctttc gttctgtccg caattagtac gaacactgcc gagataattg caagttgaga 7200
gggataccaa aaaaacgaa taagtgatag attggaatgg tcatggcgcg tagcagtttg 7260
aatgttgaga aaggtcatcg aagagcattt atttgcacat agaaggtgca aaattagtga 7320
tgttcaggta ctttatgagc tagttctcaa caagtcggcg gttttctta agatgatcaa 7380
caaatgttcg atctccttgt tcttttgtc tgatcaaaga tttatatttt cgaaaaaaat 7440
gcaaaaaaag tgtttaatgc gttattttg aatttatt ttggaattaa aaaattccaa 7500
tatttcaatg gctaactgat aatttaattt accaaaaaaa ttgacgaaat cagtgaaatt 7560
ttcccaagga cgaatgagaa aatacactat ttttaattta gatttgtagt ctcttcaaat 7620
atcttttttt taactgaaat gatttcaatt tttcgttgta tttattggta acaaaacaat 7680
tatatttctt tcctgtcaaa cataaaatag gcaaacaatt attatttgaa ccatatttac 7740
ttttatgttt actctctaga aagtaaactt tggtagtact tccatgcttg agttattctt 7800
ttcacaatgt aaaaatcaac gaaaaaaagg acaataagaa aacatttagt gtactttttt 7860
agtgaatcgt cgagaatata aaggtcacac ctgtttctca gctgtctttt cactcatttt 7920
gtgtcttcca tcatcatcca aaattcatta aattcggttc tgcaataata gcagatcgag 7980
aatgtttttt tacagccgtg ctaattttta accgaaaaat gtgtccggta aataaaaaat 8040
cgtcatacgg ctaattaaaa aagtgaaagc attccgttcg tctttgggtt tagataggta 8100
tctctttta tttttaaatt tagtttaatg aatcacgagg tggatggtaa tatagttacc 8160
gccatccaac atttttgag tcatttaggt caattgcagg tgactttgtt caaagaatt 8220
cacttattat caagtaccac ccctccagcc gaatgcttat cactcatgca tttgatctag 8280
tattgttaac acagttttcg tcatcgtttg tcaagaaaat gaaagaagac gttatgtagt 8340
tgtcgacaac ttcttgtcaa tcgctgtggt tgcaacattt tgctttctc tttctgattc 8400
gctttcctct tactctccgt ttttctcga tcaagagagg aggtcggaca ctattatttt 8460
ctgtgatttt cctttgattc tttcttttg tgtctcggtt atcattgatt catgttgtat 8520
ctccttaata tcaatccgaa ccatttttat tcgaattcca tttgattcct cggatttcgt 8580
ttatcaggag gtatagcaca caaatcaagg attgacgact aaaacatcga aatctcttc 8640
acattatttt tttgaaaaaa gtggtattaa aatattttta attttttga aattaattt 8700
tatgttattg aaatattgca aaaattcttt ccggattttt cgtttcgaat gttaaaaatc 8760
ccaaattaaa cccttctgta ggagctgcta agagtaattt ccaattaaat cctaacatgc 8820
gacaccttaa aattcagaag gttatttgt tttaatagtt tggaacaaag tatccaaaac 8880
tataaattct ggagaatttt atatagatat cggtcactca agataacctg ctaagaaaga 8940
gttcatcctg acaccttccg acacattttt ttttcacaa aatcatatgt tcaatcact 9000
ctcactctct ctctctcaat accttttcct ttatccattc agtataccac ccaagtgttg 9060
gattttatgg gctgatgaga aagtgagaac gtgtcaaagt ttcacacatg ttttgcggtt 9120
cgaaaagtta tcaactatcc ctctctctct ctctactctc taatatatat ctacccattt 9180
ttatgtgtgt ttttgttatt tttcagtcaa gatttgatag atagctattg agtatgtgtt 9240
gttagtgggt acattctccc accttgtgat caccttttgt tccgcctatt ttcacgctct 9300
catcttgaag tatctacatc agtatcgaac attttggcgg cgagtgaaac tgaaaacagt 9360
agttttgtt tcgacccctc gaaaatttt tgtgttgcca actttctatt ttaagaggcc 9420
atcggttgct aacctattaa ccagtttaaa tttcagacaa aatgtcttaa gagggtttgg 9480
acaaatttat ataataggtg gcgcgcgatt gtccggcttg aactttttt tctgtgtgaa 9540
aaagttgaac tttcactatt actccaaaaa taagtctagt ttcatcttgg cttactgaaa 9600
aaatccaatt ttctctttga tttatcgaaa aaaaagaac aaactaggtg aaaattatga 9660
atttatcaag aaaagatgta tattttgatt atcaacattt ctaacagag aaattatggg 9720
aaatttgaat ttttaccgaa aaatcgaaaa aatcgtaaaa atcctggttt acaaactaa 9780
ggttttgaaa ttagctctaa ctaatttcct cattttcgtg tttcttttct taatcaaatc 9840
attatcggct gtccacaaga taccataatt ttagttaata tgcaattcca aagaatgctt 9900
cgcttttta tgttagaaac cattaaaatc gaatatttcc ataaattctc aagaaaatcg 9960
```

Figure 26 cont.

```
gccaatttc  ttgcctttct  cttcatcgga  aatgtcgcaa  tcattcataa  tcgaaagggg  10020
ctgtctttcc  catccgttac  tagccttatt  ttcattcctt  tgtttcgctg  attccgtttc  10200
tgcaaaaatg  aaagaaaaaa  aaacatttc   acatagacta  ggtggctgcg  atctgttttt  10260
ttcttgctcc  ttgctctttg  tgtgttttct  catgccaacc  gttgtattgt  ttttcatatc  10320
gtcttggtct  atgttttgtc  gatattcact  ttaaaaactc  agatattatt  ggattttttt  10380
tttcaaaagt  tgagttttg   atttagacaa  aatttaaaa   aatctgaaat  tcttataata  10440
tcaatttac   aacaaaaaaa  ttctgaagaa  attttttttt  cgaattaaat  tttctaaaaa  10500
tttgaataaa  ttgacaagat  gttttataat  ttgatagaca  tattgaaatt  aaattttttt  10560
ttctagaatt  ctcttcgtat  acttcttcat  atatatttat  tatttttaat  tttcatgtgt  10620
attttttgca  gctttctgct  caaagttcca  acacgaggag  cggcggtgcg  gtgcgattcg  10680
cgacgaaaat  caatgaatca  gagtgccatc  tgacgtgcaa  ttatatgtcg  ccacctgctc  10740
atcttctcag  tgttaatcat  cttcatcaaa  tccacgagaa  gttcatcaca  atcatctcac  10800
tacgaccacc  aacatcatca  gcaacaacaa  aacacctgac  gaacacacca  cactatccag  10860
tgcaaacgtt  cagcagaaaa  aacacagaaa  ataacaaaaa  taacagtgag  aaccatcatc  10920
agtcgatttt  ggatcggagg  aggagagaag  gcggcggacg  aggagacgca  gacactcttg  10980
ctcgacgact  catccggtaa  tcgagaagac  acggaagaga  gtatgcgagt  ggtgagtcat  11040
ttttgatat   aattctaaaa  tcaaagaaa   tatgattcat  ttatgcataa  cggggtcagc  11100
agatgaatga  caccagtttc  ttcataatga  acaaatttg   gtcaacaata  ggcctgagtt  11160
tacgtgattg  tcgaaaaatt  aaaataaaag  cctgttttt   cttctataaa  aattcccaga  11220
tctgaaaatt  cgtcattttt  gttccaagaa  atacggtacc  cggtttcgaa  gcgaccgatt  11280
ttctcaaatg  taaaagagtg  tgctccttta  aggagtactg  tagtctccag  tttttttaaa  11340
actgttcaat  ttttctgttt  ttctagagct  aatcgaaaaa  ttgtaaattt  ctgcttaaaa  11400
tttttaaat   tgaaatccag  ttttgatta   ttcggaaaat  cgaaaaaaaa  ttttaaaata  11460
ataaaacat   ttcaattttt  aacaaaaat   aatttgatac  gaggaaaaaa  gcccaaaatt  11520
tgaagtgatt  ttttcgaaa   actcgtaaaa  tttaaaatcc  aaaaatagtg  tgcgctttaa  11580
aggagtactg  tagttcccaa  ctgctcgaaa  aaactttctt  tgatgtctca  taagtttcac  11640
cctccaaatt  ttcttctttt  ttttcaaca   attaataaaa  catcgaagaa  aattccgcag  11700
tgagaagatg  agaactacag  tactctttaa  aggcgcaaac  tttttttaa   accgaaaata  11760
gagtgtttta  ggtttttttt  ttgttacaga  aaaaataaa   attcctaaaa  tctctgaaat  11820
ttctgggaaa  attttttatt  tcagatttga  ataaactaaa  agtttataa   aaattaaaat  11880
gctcacattg  tttaatctat  tgtcagtttc  agcggagcac  atgcagaatg  ccggtctccc  11940
gagccaccgt  cacaatccta  ctcggaatcc  tgtttggttt  ctcaatcact  tactatctga  12000
cggctctcaa  atctctgaca  aatccaataa  tctgtggccc  agaacaacaa  attggcggtt  12060
tcgattatct  cgatgtgata  agtcaacgtg  ctgatgctga  tgttttcaca  agatcccaaa  12120
gtcttcccgg  tcatcgaagg  ggtctgattc  ttgtggctat  tatgactgct  gcaaaatacg  12180
ttgatacacg  tgcttataat  gtttggaaaa  catgggctca  acacattccc  ggacgagttt  12240
taatatttgt  tgccgaagga  actgaatcag  tgcatgagga  tatgccatta  attcgtctga  12300
aaggagttga  tgatacttat  ccaccacaga  agaaagttt   cgcaatggta  aatggttgg   12360
cagagaatat  ggctgatgaa  tatgattggt  tcttgcgagc  agacgacgac  ctctacatta  12420
gaggagaaga  gctcgcttta  ttcctaagat  ctgtcgattc  atccaaagct  catatcatcg  12480
gacaggctgg  acttggtaac  agtgcggaat  atggtcttct  agctcttgga  tctaccgata  12540
attattgtat  gggaggacct  ggaattgtta  tgagcaggga  caccttattg  tacgttgttt  12600
ttaagagaat  ttgtgggggt  tttgtcaaaa  taactgaaac  tgacttctca  acaaatttcc  12660
aaatttgct   aaaatctaaa  atttcgtcat  ttttccttgt  tgcagctgct  gaaatacagt  12720
tttattaaat  tatcactctt  tcattgagta  atttggtagt  ttatctcgca  ctaattcgac  12780
gatttagtca  caaatcgaat  ttatagttaa  aatatgcaag  aaaaaaagat  ttttgataac  12840
aactatattt  cagcttctac  aacagggaca  aattgatgaa  atttaagatt  tgagcaaaat  12900
ttggaaattt  tttgagaatt  ctcactatga  aattcgactg  tttcggggca  gttttaatct  12960
atttgatgaa  aaactcaaac  ctttttctctc tttcagtgat  aacaattata  atattatata  13020
tttttcagaa  aagtatctcc  tcatctcgaa  tcatgcctcc  aacacatgct  gacttctcac  13080
gaggacgtcg  aactcgggcg  gtgtattcga  aaacatgtcg  gtgtagcttg  cacgtggaat  13140
tatgaaatgc  aaaagttgtt  ccataataat  caaagtgcaa  tcaaggagtc  atatgcaaaa  13200
aatatgaaag  aattgaaaga  tgcaattact  cttcatccga  ttaaagatcc  agctgtaatg  13260
aggaaggttc  atcttcgaaa  tcgagaaatt  aaacttcgtg  aagcacgagc  taaacgaagt  13320
ctttgagtt   cggagctcag  tactgcaaaa  gcacagacat  tggtacgaat  gacaccgaat  13380
agaacgaatg  atttgacacc  atgggaatat  attaataaca  ataaaattct  gttttgtgcg  13440
```

```
gatcgggtca attgtcctcg gcatactgta gatttgagta ttcggacgga aatggccgac 13500
actatcacac aggtttgttc aaaattcaga tcaagtattg aaatttttaa atgctttttt 13560
cgaattttcg gaaaatcgga aactcaaaaa ttttcgtatg tctatttcca aattttctgg 13620
atgctacagt acttcttaaa ggcgcacact cttttacgct ataaaatcgg ccgtgtcgag 13680
actgagttcc gtattttaa agcaaaattc gcaaaaacat tcgagtaaat aattttcca 13740
aaaaactatc ccattttcag ttattcgacg agttcaacac aaatgctcgc caaagaggtc 13800
gtgttcttca atttcaaagt cttcaatatg gatacatgcg tgttgaacct acaaaaggag 13860
tcgattatgt tcttgacatg ttactttggt tcaaaaagtt ccgtccacca aacagaacaa 13920
caatttccgt tcgaagacac gcgtatgttc aacaaacatt cggaaaactt cgaagtctct 13980
ctgaaggagt gttccgatca aatatgagag caaactctac acttattgaa gatccaacat 14040
tgcatatgat tatgccatta agaggaagag ctgccatatt tgcaagattt gctcaacatt 14100
tgaagagtat ttgtgcgaga ggaggagatg atttagctgt ttcattgaca attgtattat 14160
actcgagtga agatgaaatg gagaataggt aagttttgga aattttaaaa tctacctatt 14220
tcggaatgaa aatccaattt ataaatcaaa aatgaatgtg tttacaaata tcgaacaaaa 14280
tttaattgat tcgaaagaaa gaataatttt tggtctaatt ggatctcaaa aactttgagc 14340
tctagaagaa attttaaaa cccaattggg atatttata atttacagag aaacgattga 14400
aatgctccgt gcaagcttca tcccagtaac agtaatcgaa atgggtgatg tttcattctc 14460
acgtggtgtt gctcttatgc gtggagctga aactcttcca gccaatgctc ttctattctt 14520
tactgatgtt gatatgctat tcacatgtga tgcattgaaa cgtataaaat cgaatacaat 14580
tctcaacgca caaatctact tcccgatcgt tttttctgaa ttctcacatg agagttggtc 14640
tgaaaatgac aagttattgg ctgacgcctt ccattatgga cgtggacgtg gatattttag 14700
acattttggt tatggtctcg cagcgatgta caaggtaaga tattttgaga aaatattttt 14760
tcttcaataa atttttaatt tcaggcggat ttgatggatg tcggagggtt tgacacaaag 14820
atcgaaggat ggggaaagga agatgttgac ttgtttgaga aggtaataca caagaccagg 14880
aatgcaaatt caaaaaatcg caaacatcca cttttcagtg tgtctaaaga atgatctgta 14940
aaacctacaa aaatcttttt ttatgtttag aataaatttg aagcttctct gaaatatctc 15000
ttttagaaat attttctgcg acttcatttt gacaaaataa aaactgggag tttgtagttt 15060
tttaaaattt tttccatttt tttcgaaaaa ttttccatgc agaattaaat acgcatgtta 15120
cagaaattca actttcttct ttttgcaaaa ccccaaaaat agttttaaa gttttttga 15180
tttattttg agtcaatgca aaaaaccggc aggccccgag ggataatcca taaaacctac 15240
aaaattcaat tttctgaata ttcctaattt agagcgtctc cgaagttgaa gaagttttga 15300
gtatttttg taattttttt tgatttctta cctgtacaca acattgtatt ttcttaacaa 15360
actccaaatt tttcaggcaa tcaaaaacgg tcgtctccga gtgattcgag tcctgaacc 15420
tggacttgtt cacatctatc acccaattca ttgcgatgaa aatatgccaa ctgctcaaaa 15480
ggatatgtgc catggttcaa aagcagcaag tcttgcttca attgatacac ttgtcgagca 15540
gattgcccag tacacatgat agccttgccg gttttccacc tctatcttcc cgttttttct 15600
ttctcaattt tcgaattctt tccgttttta tgaatacggt tgtccctcag ttttcatccg 15660
ggtaattatt gtttctttga tttgtttat ccacttctca cactcacttt tccccaaaa 15720
ttcctttatt gcatccattt gattaatcac gattattata tatttctat tccccggttg 15780
agttttacca ttttccatca taatttccta acattgccat tttcacaaga agcacacgga 15840
gcttgccccc atttgaagtt caaatttcaa attaattaat tcagttcatg tcaaataata 15900
taatagttca gttaatgacc tattttgaaa cgagtaattg tcccatgctc ccctataaag 15960
ctcagccttt cattgttcaa atgtttattt cacttaaaac attattgatt gttcttcgct 16020
ttaaattcct taattcaatt gttttcttc atattaatat gagatttcca tcaaatcttt 16080
gattgtttct agctttacac aattgtctca ccatcatcat tttgtccatt ctgttgccat 16140
ttctcttccc ccaactacaa caagcatcgg tgttctgtgc ttactcgaaa taaattaatt 16200
gattgcagag tgtagtaatg aacaattgtg gaatcaatac tttacaagtt gtcatgtaag 16260
acatcaattt gacaaaaaag taagtataat ttaaataacc acatgataac gcacacaact 16320
ataaaatata agaatgaatg agaatcttgg tacaatatgg gaggaataac cgaaattaag 16380
atcaattgtt tgggagactc gaagtagaag gcaaagatga atcggatgaa gtgtttgctg 16440
atgttatacc ggctttcttc acattttct gaattgttgt catcatcaga acaccggcac 16500
gaccagtcca aggagcacga caaagtggac atgatgatcc ttccattgaa cctttacggg 16560
ctgcatacca acgacgaaca caactgaaaa tagtcaaatt agggttttcc ttgaattttc 16620
gtaaatgaga ttacgacgtt ttttaaacg taattcagag aaaaatgatg atttagtgag 16680
aacttgggtc cactggaact agcgattctt ttcagctact ctcaaatggt tttgaatttt 16740
```

Figure 26 cont.

```
tctgattttt cggagttttt tatcttttaa aattgaggaa aagattaatt taagatctct 16800
gaagatcacc atttaataat ataaaaactc actctgtaca tccaaggaat tgtaggcact 16860
ttttgcatcc ttgtggtttt attggtggat tggaacacat tgtacaatct ccccacgtgg 16920
aatctctgaa atgttttat ttttatcaag tattctggaa gcttacgggg ttattcatgt 16980
gctgtcgaaa attacaaaaa aaaaatttt gtatatttg acggcacatg aataagccca 17040
ttatgaagaa agacttacgg ttcaactagt tttcctccag ctgacactgg ttttgcagct 17100
ggaacgatat attcttcttc atcatgatac aattctagtt catgattgta catgacacga 17160
tcttcgtcga atatcggttg tcttatgtga tttctatcgg catgaactgc tccccttcca 17220
ccaataatca gaacatcatc atcatcactt agatcaataa ctgatgaacc atttgattga 17280
gcttcatcat catcagaatc tgcgtctaca ttctcaggat cactttcatc ttcattattc 17340
aatccagaac ggtaaagtgg atctcttcgt ggattatcag gatatatacg ggaatgaagt 17400
agatcacgta tataatctgc actgatgttg tgttggccac ttccacgata tcttccaggt 17460
gttatcactc taccacggcc tcctggacct cttccgcttc ttgcatatga tcctcttgga 17520
ttaaatgcac gtggcatgtc tctttcttca tgatcagatt cagcctcaga gtctgcatca 17580
gattcagatg atgagattgt aatcgtcgca tttcgttctt cttcttcttc attgtcgctc 17640
tgcgtataat cactgtcatc gtcgtcatct gggaaatagg tttccgccct ggaaattatt 17700
attttttaa ataattcaat ttagatattg atgtattcta ctaacgttat atcacgtatt 17760
tcatctccct ggcgtacttg aacacgatct ccttcaaatt gcatttgagg gtctgcaaaa 17820
aataatcaaa tttgtaagaa tgttatctat atgatagttt tcgaaaatat ttcaaaattt 17880
tcgtaaaaat actatttttt tctgctatta taggctcaaa atatgtccaa ataaacgaac 17940
aatttctcac taatatttaa tggggattca cagtttggaa aaaatattat ttccagctta 18000
aatctccaat tttgccaact tttccgtgtc gcagaaacag gaaattaatt tttatttaaa 18060
aatcgtcgta tttggcatat tttttatagc ttaagctaat atgtcaaata cgacaattat 18120
caaataaaaa ttaatttcct gctactatat ttcgtacgga atttgaatat tcaaaaataa 18180
tttagctttc ttgcactcac taggatttct tgtctggcgt gtcgaacgac gccggttcgg 18240
actctcggat atttgctgat ttgcacgtgt tcgattcatc gtcgttcac caccccttgc 18300
cgatcctctt ccacgtcttg cagacgttgt tcctctggtg cctcgacctc tgactgagct 18360
ggatgaagat ggtccagcat ctgacgttcc tgcggtgctt cttatccgtg aacgtgaata 18420
tggacttgct ctttctcgtg ctgcag                                     18446
```

Figure 26 cont.

```
agctttctgc tcaaagttcc aacacgagga gcggcggtgc ggtgcgattc gcgacgaaaa  60
tcaatgaatc agagtgccat ctgacgtgca attatatgtc gccacctgct catcttctca  120
gtgttaatca tcttcatcaa atccacgaga agttcatcac aatcatctca ctacgaccac  180
caacatcatc agcaacaaca aaacacctga cgaacacacc acactatcca gtgcaaacgt  240
tcagcagaaa aaacacagaa aataacaaaa ataacagtga gaaccatcat cagtcgattt  300
tggatcggag gaggagagaa ggcggcggac gaggagacgc agacactctt gctcgacgac  360
tcatccggta atcgagaaga cacggaagag agtatgcgag tgcggagcac atgcagaatg  420
ccggtctccc gagccaccgt cacaatccta ctcggaatcc tgtttggttt ctcaatcact  480
tactatctga cggctctcaa atctctgaca aatccaataa tctgtggccc agaacaacaa  540
attggcggtt tcgattatct cgatgtgata agtcaacgtg ctgatgctga tgttttcaca  600
agatcccaaa gtcttcccgg tcatcgaagg ggtctgattc ttgtggctat tatgactgct  660
gcaaaatacg ttgatacacg tgcttataat gtttggaaaa catgggctca acacattccc  720
ggacgagttt taatatttgt tgccgaagga actgaatcag tgcatgagga tatgccatta  780
attcgtctga aaggagttga tgatacttat ccaccacaga agaaaagttt cgcaatggta  840
aaatggttgg cagagaatat ggctgatgaa tatgattggt tcttgcgagc agacgacgac  900
ctctacatta gaggagaaga gctcgcttta ttcctaagat ctgtcgattc atccaaagct  960
catatcatcg gacaggctgg acttggtaac agtgcggaat atggtcttct agctcttgga  1020
tctaccgata attattgtat gggaggacct ggaattgtta tgagcaggga caccttatta  1080
aaagtatctc ctcatctcga atcatgcctc caacacatgc tgacttctca cgaggacgtc  1140
gaactcgggc ggtgtattcg aaaacatgtc ggtgtagctt gcacgtggaa ttatgaaatg  1200
caaaagttgt tccataataa tcaaagtgca atcaaggagt catatgcaaa aaatatgaaa  1260
gaattgaaag atgcaattac tcttcatccg attaaagatc cagctgtaat gaggaaggtt  1320
catcttcgaa atcgagaaat taaacttcgt gaagcacgag ctaaacgaag tcttttgagt  1380
tcggagctca gtactgcaaa agcacagaca ttggtacgaa tgacaccgaa tagaacgaat  1440
gatttgacac catgggaata tattaataac aataaaattc tgttttgtgc ggatcgggtc  1500
aattgtcctc ggcatactgt agatttgagt attcggacgg aaatggccga cactatcaca  1560
cagttattcg acgagttcaa cacaaatgct cgccaaagag gtcgtgttct tcaatttcaa  1620
agtcttcaat atggatacat gcgtgttgaa cctacaaaag gagtcgatta tgttcttgac  1680
atgttacttt ggttcaaaaa gttccgtcca ccaaacagaa caacaatttc cgttcgaaga  1740
cacgcgtatg ttcaacaaac attcggaaaa cttcgaagtc tctctgaagg agtgttccga  1800
tcaaatatga gagcaaactc tacacttatt gaagatccaa cattgcatat gattatgcca  1860
ttaagaggaa gagctgccat atttgcaaga tttgctcaac atttgaagag tatttgtgcg  1920
agaggaggag atgatttagc tgtttcattg acaattgtat tatactcgag tgaagatgaa  1980
atggagaata gagaaacgat tgaaatgctc cgtgcaagct tcatcccagt aacagtaatc  2040
gaaatgggtg atgtttcatt ctcacgtggt gttgctctta tgcgtggagc tgaaactctt  2100
ccagccaatg ctcttctatt ctttactgat gttgatatgc tattcacatg tgatgcattg  2160
aaacgtataa aatcgaatac aattctcaac gcacaaatct acttcccgat cgttttttct  2220
gaattctcac atgagagttg gtctgaaaat gacaagttat tggctgacgc cttccattat  2280
ggacgtggac gtggatattt tagacatttt ggttatggtc tcgcagcgat gtacaaggcg  2340
gatttgatgg atgtcggagg gtttgacaca aagatcgaag gatggggaaa ggaagatgtt  2400
gacttgtttg agaaggcaat caaaacggt cgtctccgag tgattcgagt ccctgaacct  2460
ggacttgttc acatcatca cccaattcat tgcgatgaaa atatgccaac tgctcaaaag  2520
gatatgtgcc atggttcaaa agcagcaagt cttgcttcaa ttgatacact tgtcgagcag  2580
attgcccagt acacatgata gccttgccgg ttttccacct ctatcttccc gttttttctt  2640
tctcaatttt cgaattcttt ccgtttttat gaatacggtt gtccctcagt tttcatccgg  2700
gtaattattg tttctttgat ttgttttatc cacttctcac actcactttt ccccgaaaat  2760
tcctttattg catccatttg attaatcacg attattatat attttctatt ccccggttga  2820
gttttaccat tttccatcat aatttcctaa cattgccatt tcacaagaag cacacggag  2880
cttgccccca tttgaagttc aaatttcaaa ttaattaatt cagttcatgt caaataatat  2940
aatagttcag ttaatgacct attttgaaac gagtaattgt cccatgctcc cctataaagc  3000
tcagcctttc attgttcaaa tgtttatttc acttaaaaca ttattgattg ttcttcgctt  3060
taaattcctt aattcaattg ttttctttca tattaatatg agatttccat caaatctttg  3120
attgtttcta gctttacaca attgtctcac catcatcatt ttgtccattc tgttgccatt  3180
tctcttcccc caactacaac aagcatcggt gttctgtgct tactcgaaat aaattaattg  3240
attgcagagt gt                                                      3252
```

Figure 27

```
ggcgagctaa gccggaggat gtgcagctgc ggcggcggcg ccggctacga agaggacggg   60
gacaggcgcc gtgcgaaccg agcccagcca gccggaggac gcgggcaggg cgggacggga  120
gcccggactc gtctgccgcc gccgtcgtcg ccgtcgtgcc ggccccgcgt ccccgcgcgc  180
gagcgggagg agccgccgcc acctcgcgcc cgagccgccg ctagcgcgcg ccgggcatgg  240
tcccctctta aaggcgcagg ccgcggcggc ggggcgggc gtgcggaaca aagcgccggc  300
gcggggcctg cgggcggctc ggggccgcg atgggcgcgg cgggcccgcg gcggcggcgg  360
cgctgcccgg gccgggcctc gcggcgctag ggcgggctgg cctccgcggg cggggcagc  420
gggctgaggg cgcgcggagc ctgcggcggc ggccggcgg gcggagcggc gcgggcatgg  480
ccgcgcgcgg ccggcgcgcc tggctcagcg tgctgctcgg gctcgtcctg ggcttcgtgc  540
tggcctcgcg gctcgtcctg ccccgggctt ccagctgaa gcgagcgggc ccacggcgcc  600
gcgccagccc cgagggctgc cggtccgggc aggcggcggc ttcccaggcc ggcggggcgc  660
gcggcgatgc gcgcggggcg cagctctggc cgcccggctc ggacccagat ggcggcccgc  720
gcgacaggaa ctttctcttc gtgggagtca tgaccgccca gaaatacctg cagactcggg  780
ccgtggccgc ctacagaaca tggtccaaga caattcctgg gaaagttcag ttcttctcaa  840
gtgagggttc tgacacatct gtaccaattc cagtagtgcc actacgggt gtggacgact  900
cctacccgcc ccagaagaag tccttcatga tgctcaagta catgcacgac cactacttgg  960
acaagtatga atggtttatg agagcagatg atgacgtgta catcaaagga accgtctgg 1020
agaacttcct gaggagtttg aacagcagcg agccctctt tcttgggcag acaggcctgg 1080
gcaccacgga agaaatggga aaactggccc tggagcctgg tgagaacttc tgcatggggg 1140
ggcctggcgt gatcatgagc cgggaggtgc ttcggagaat ggtgccgcac attggcaagt 1200
gtctccggga gatgtacacc acccatgagg acgtggaggt gggaaggtgt gtccggaggt 1260
ttgcagggggt gcagtgtgtc tggtcttatg agatgcagca gctttttat gagaattacg 1320
agcagaacaa aaggggtac attagagatc tccataacag taaaattcac caagctatca 1380
cattacaccc caacaaaaac ccaccctacc agtacaggct ccacagctac atgctgagcc 1440
gcaagatatc cgagctccgc catcgcacaa tacagctgca ccgcgaaatt gtcctgatga 1500
gcaaatacag caacacagaa attcataaag aggacctcca gctgggaatc cctccctcct 1560
tcatgaggtt tcagccccgc cagcgagagg agattctgga atgggagttt ctgactggaa 1620
aatacttgta ttcggcagtt gacggccagc cccctcgaag aggaatggac tccgcccaga 1680
gggaagcctt ggacgacatt gtcatgcagg tcatggagat gatcaatgcc aacgccaaga 1740
ccagagggcg catcattgac ttcaaagaga tccagtacgg ctaccgccgg gtgaacccca 1800
tgtatggggc tgagtacatc ctggacctgc tgcttctgta caaaaagcac aaagggaaga 1860
aaatgacggt ccctgtgagg aggcacgcgt atttacagca gactttcagc aaaatccagt 1920
ttgtggagca tgaggagctg gatgcacaag agttggccaa gagaatcaat caggaatctg 1980
gatccttgtc ctttctctca aactccctga agaagctcgt ccccttcag ctccctggg 2040
cgaagagtga gcacaaagaa cccaaagata aaaagataaa catactgatt cctttgtctg 2100
ggcgtttcga catgtttgtg agatttatgg gaaactttga gaagacgtgt cttatcccca 2160
atcagaacgt caagctcgtg gttctgcttt tcaattctga ctccaaccct gacaaggcca 2220
aacaagttga actgatgaga gattaccgca ttaagtaccc taaagccgac atgcagattt 2280
tgcctgtgtc tggagagttt tcaagagccc tggccctgga agtaggatcc tccagtttta 2340
acaatgaatc tttgctcttc ttctgcgacg tcgacctcgt gtttactaca gaattccttc 2400
agcgatgtcg agcaaataca gttctgggcc aacaaatata ttttccaatc atcttcagcc 2460
agtatgaccc aaagattgtt tatagtggga agttcccag tgacaaccat tttgcccttta 2520
ctcagaaaac tggcttctgg agaaactatg ggtttggcat cacgtgtatt tataagggag 2580
atcttgtccg agtgggtggc tttgatgttt ccatccaagg ctgggggctg gaggatgtgg 2640
accttttcaa caaggttgtc caggcaggtt tgaagacgtt taggagccag gaagtaggag 2700
tagtccacgt ccaccatcct gtctttgtg atcccaatct tgaccccaaa cagtacaaaa 2760
tgtgcttggg gtccaaagca tcgacctatg ggtccaccca gcagctggct gagatgtggc 2820
tggaaaaaaa tgatccaagt tacagtaaaa gcagcaataa taatggctca gtgaggacag 2880
cctaatgtcc agctttgctg gaaaagacgt ttttaattat ctaatttatt tttcaaaaat 2940
tttttgtatg atcagttttt gaagtccgta tacaaggata tattttacaa gtggttttct 3000
tacataggac tcctttaaga ttgagctttc tgaacaagaa ggtgatcagt gtttgccttt 3060
```

Figure 28

```
gaacacatct tcttgctgaa cattatgtag cagacctgct taactttgac ttgaaatgta 3120
cctgatgaac aaaactttt  taaaaaaatg ttttcttttg agaccctttg ctccagtcct 3180
atggcagaaa acgtgaacat tcctgcaaag tattattgta acaaaacact gtaactctgg 3240
taaatgttct gttgtgattg ttaacattcc acagattcta ccttttgtgt tttgttttt  3300
ttttttacaa ttgttttaaa gccatttcat gttccagttg taagataagg aaatgtgata 3360
atagctgttt catcattgtc ttcaggagag ctttccagag ttgatcattt cctctcatgg 3420
tactctgctc agcatggcca cgtaggtttt ttgtttgttt tgttttgttc tttttttgag 3480
acggagtctc actctgttac ccaggctgga atgcagtggc gcaatcttgg ctcactttaa 3540
cctccacttc cctggttcaa gcaattcccc tgcctttgcc tcccgagtag ctgggattac 3600
aggcacacac caccacgccc agctagtttt tttgtatttt tagtagagac ggggtttcac 3660
catgcaagcc cagctggcca cgtaggtttt aaagcaaggg gcgtgaagaa ggcacagtga 3720
ggtatgtggc tgttctcgtg gtagttcatt cggcctaaat agacctggca ttaaatttca 3780
agaaggattt ggcattttct cttcttgacc cttctcttta aagggtaaaa tattaatgtt 3840
tagaatgaca aagatgaatt attacaataa atctgatgta cacagactga aacatacaca 3900
catacaccct aatcaaaacg ttggggaaaa atgtatttgg ttttgttcct ttcatcctgt 3960
ctgtgttatg tgggtggaga tggttttcat tctttcatta ctgttttgtt ttatcctttg 4020
tatctgaaat acctttaatt tatttaatat ctgttgttca gagctctgcc atttcttgag 4080
tacctgttag ttagtattat ttatgtgtat cgggagtgtg tttagtctgt tttatttgca 4140
gtaaaccgat ctccaaagat ttcctttgg  aaacgctttt tccctcctt  aatttttata 4200
ttccttactg ttttactaaa tattaagtgt tctttgacaa ttttggtgct catgtgtttt 4260
ggggacaaaa gtgaaatgaa tctgtcatta taccagaaag ttaaattctc agatcaaatg 4320
tgccttaata aatttgtttt catttagatt tcaaacagtg atagacttgc cattttaata 4380
cacgtcattg gagggctgcg tatttgtaaa tagcctgatg ctcatttgga aaaataaacc 4440
agtgaacaat attttctat  tgtacttttc gaaccatttt gtctcattat tcctgttta  4500
gctgaagaat tgtattacat ttggagagta aaaacttaa  acacg                 4545
```

SQV NUCLEIC ACIDS AND POLYPEPTIDES

PRIORITY CLAIMS

This application claims benefit from copending U.S. Provisional Application Nos. 60/349,630, filed Jan. 18, 2002, and 60/390,930, filed Jun. 24, 2002, each of which is incorporated by reference.

STATEMENT AS TO FEDERALLY SPONSORED RESEARCH

This application was supported in part by NIH grant GM24663. The government may have certain rights to this invention.

BACKGROUND OF THE INVENTION

The invention is in the field of nucleic acid and polypeptide molecules associated with connective tissue diseases, progeroid disorders, and aging; methods for isolating such molecules; and the use of such molecules in human and veterinary practice.

Recently, recognition of the importance of glycosaminoglycans in animal development and human health has grown. Mutations in a human glycosaminoglycan (GAG) biosynthetic enzyme, galactosyltransferase I, may cause a progeroid variant of the connective-tissue disorder Ehlers-Danlos syndrome (EDS), a group of heritable disorders characterized by hyperelasticity of the skin and hypermobile joints.

Another GAG biosynthetic enzyme, murine EXT1, is a glycosyltransferase required for polymerization of the repeating disaccharides of heparan sulfate. Mutations in the human EXT tumor suppressor gene family are associated with a hereditary disorder, hereditary multiple exostoses (HME) that is characterized by multiple cartilaginous tumors that can be transformed to chondrosarcomas or osteosarcomas. The identification of additional mammalian genes that encode proteins that function in GAG synthesis will benefit our understanding of the role that GAG's play in human health and disease. In addition, therapeutic agents are required to modulate GAG biosynthetic pathways for the treatment of connective tissue diseases and disorders.

SUMMARY OF THE INVENTION

We have identified and characterized a number of nucleic acid molecules and polypeptides that function in eukaryotic glycosaminoglycan (GAG) biosynthetic pathways. Given the functional and structural similarities to human proteins, C. elegans wild-type and mutant worms will be useful in screening for compounds that modulate eukaryotic GAG biosynthetic pathways. The invention provides a number of targets that are useful for the development of drugs that specifically enhance or inhibit a eukaryotic GAG biosynthetic pathway. In addition, the methods of the invention provide a facile means to identify compounds that are safe for use in eukaryotic organisms (i.e., compounds which do not adversely affect the normal development and physiology of the organism), and efficacious in modulating a GAG biosynthetic pathway (i.e., by enhancing or inhibiting the activity of a SQV polypeptide). In addition, the methods of the invention provide a route for analyzing virtually any number of compounds for an effect on a eukaryotic GAG pathway with high-volume throughput, high sensitivity, and low complexity. The methods are also relatively inexpensive to perform and enable the analysis of small quantities of active substances found in either purified or crude extract form. Drugs that target a eukaryotic glycosaminoglycan biosynthetic pathway are useful in the treatment or prevention of connective tissue diseases and disorders. Moreover, insights into the C. elegans GAG biosynthetic pathway will benefit our understanding of the role of GAGs in human health and disease.

In a first aspect, the invention generally features a method of identifying a compound that modulates a glycosaminoglycan biosynthetic biological activity, the method involves (a) providing a cell containing a sqv nucleic acid molecule; (b) contacting the cell with a candidate compound; and (c) detecting an alteration in a glycosaminoglycan biosynthetic biological activity of the cell, where the alteration identifies the compound as modulating a glycosaminoglycan biosynthetic biological activity. In some embodiments, the cell is a mammalian cell or a nematode cell. In a preferred embodiment, the nematode cell is in a nematode and the alteration is of a vulval phenotype. In other embodiments the detecting is of an enzymatic activity or an immunological assay. In still other embodiments, the sqv nucleic acid molecule is selected from the group consisting of a sqv-1, sqv-2, sqv-4, sqv-5, and sqv-6.

In another aspect, the invention features a screening method for identifying a compound that modulates the expression of a sqv nucleic acid molecule that encodes a polypeptide that has a glycosaminoglycan biosynthetic biological activity, the method involves (a) providing a cell containing a sqv nucleic acid molecule; (b) contacting the cell with a compound; and (c) detecting the level of nucleic acid molecule expression in the presence of the compound with the level of nucleic acid molecule expression in the absence of the compound; where an alteration in nucleic acid molecule expression indicates that the compound modulates the expression of a sqv nucleic acid molecule that encodes a polypeptide that has a glycosaminoglycan biosynthetic biological activity. In some embodiments, the sqv nucleic acid molecule is selected from the group consisting of a sqv-1, sqv-2, sqv-4, sqv-5, and sqv-6. In other embodiments, the cell is a C. elegans cell. In preferred embodiments, the cell is a mammalian cell.

In another aspect, the invention features a screening method for identifying a compound that modulates the glycosaminoglycan biosynthetic biological activity of a SQV polypeptide, or fragment thereof, the method involves (a) providing a SQV polypeptide, or fragment thereof, where the polypeptide has a glycosaminoglycan biosynthetic biological activity; (b) contacting the polypeptide with a compound; and (c) detecting the level of biological activity of the polypeptide contacted with the compound with the level of biological activity in a polypeptide not contacted with the compound; where an alteration in the biological activity indicates that the compound modulates the glycosaminoglycan biosynthetic biological activity of a SQV polypeptide. In some embodiments, the polypeptide is in a mammalian cell. In other embodiments, the polypeptide is in a nematode cell. In preferred embodiments, the nematode cell is in a nematode and the detecting is of a vulval phenotype. In other preferred embodiments, the detecting is of an enzymatic activity. In preferred embodiments, the sqv nucleic acid molecule is selected from the group consisting of a sqv-1, sqv-2, sqv-4, sqv-5, and sqv-6.

In another aspect, the invention features a screening method for identifying a compound that modulates the glycosaminoglycan biosynthetic biological activity of a SQV polypeptide, or fragment thereof, the method involves detecting binding of a candidate compound to a SQV polypeptide, where the detecting identifies the compound as a compound that modulates the glycosaminoglycan biosynthetic biological activity of a SQV polypeptide. In some embodiments, the sqv polypeptide is selected from the group consisting of SQV-1, SQV-2, SQV-4, SQV-5, and SQV-6.

In another aspect, the invention features a method of treating an organism having a connective tissue disease, progeroid disorder, or cellular damage related to aging the method involves (a) contacting the organism with a therapeutically effective amount of a nucleic acid encoding a SQV polypeptide, or the complement of the nucleic acid; and (b) detecting the expression of the nucleic acid; where the contacting modulates the level of expression of a SQV polypeptide. In preferred embodiments, the nucleic acid is a cDNA, and the contacting leads to an increase in expression of the polypeptide encoded by sqv nucleic acid molecule.

In another aspect, the invention features a method for diagnosing a connective tissue disease or progeroid disorder, or the propensity to develop the disease or disorder, the method involves detecting SQV polypeptide expression or activity in a sample derived from an organism relative to a sample derived from a control organism not having a connective tissue disease or progeroid disorder, where an alteration in the expression or activity of the SQV polypeptide in the organism is indicative of the organism's having or having a propensity to develop a connective tissue disease or progeroid disorder. In preferred embodiments, the SQV polypeptide is selected from the group consisting of SQV-1, SQV-2, SQV-4, SQV-5, and SQV-6.

In another aspect, the invention features a method for diagnosing a connective tissue disease or progeroid disorder or the propensity to develop the disease or disorder in an organism, where the method involves detecting the sequence of a sqv nucleic acid molecule in a sample derived from the organism relative to a wild-type nucleic acid sequence, where an alteration in the sequence of the organism is indicative of the organism having or having a propensity to develop a connective tissue disease or progeroid disorder. In some embodiments, the SQV nucleic acid molecule is selected from the group consisting of sqv-1, sqv-2, sqv-4, sqv-5, and sqv-6.

In another aspect, the invention features a method for identifying a candidate compound for the treatment of a connective tissue disease, progeroid disorder, or the tissue damage associated with aging the method involves (a) contacting a SQV polypeptide with a candidate compound; and (b) detecting an alteration in the biological activity of the polypeptide. In some embodiments, the SQV polypeptide is selected from the group consisting of SQV-1, SQV-2, SQV-4, SQV-5, and SQV-6.

In another aspect, the invention features a pharmaceutical composition including a pharmaceutical excipient and a sqv nucleic acid molecule, or portion thereof, selected from the group consisting of sqv-1, sqv-2, sqv-4, sqv-5, and sqv-6.

In another aspect, the invention features a pharmaceutical composition containing a pharmaceutical excipient and an RNA sqv nucleic acid inhibitor containing at least a portion of a sqv nucleic acid molecule of an organism, or its complement, selected from the group consisting of sqv-1, sqv-2, sqv-4, sqv-5, and sqv-6.

In another aspect, the invention features a transgenic organism containing a sqv nucleic acid molecule, or complement thereof, that alters the function of a glycosaminoglycan biosynthetic biological activity in the organism. In preferred embodiments, the nucleic acid molecule is selected from the group consisting of sqv-1, sqv-2, sqv-4, sqv-5, and sqv-6.

In another aspect, the invention features an isolated SQV-1 polypeptide, or fragment thereof, containing an amino acid sequence having at least 50%, 60%, 70%, 80%, 90%, 95%, or 100% amino acid sequence identity to SEQ ID NO:4, where the polypeptide has a glycosaminoglycan biosynthetic biological activity. In some embodiments, the polypeptide contains the amino acid sequence of SEQ ID NO:4. In other embodiments, the polypeptide consists essentially of the amino acid sequence of SEQ ID NO:4, or a fragment thereof.

In another aspect, the invention features an isolated polypeptide fragment of SEQ ID NO:4, where the fragment has a glycosaminoglycan biosynthetic biological activity.

In another aspect, the invention features an isolated SQV-1 polypeptide, or fragment thereof, containing an amino acid sequence having at least 50%, 60%, 70%, 80%, 90%, 95%, or 100% amino acid sequence identity to SEQ ID NO:4, containing a mutation that inhibits the biological activity of the polypeptide. In some embodiments, the mutation corresponds to a mutation selected from the group consisting of n2820, n2824, n2828, n2848, ku246, and n2819. In some embodiments, the polypeptide contains the amino acid sequence of human SQV-1 (SEQ ID NO:5). In other embodiments, the polypeptide consists essentially of the amino acid sequence of human SQV-1 (SEQ ID NO:5), or a fragment thereof. In still other embodiments, the polypeptide contains the amino acid sequence of *Drosophila* SQV-1 (SEQ ID NO:6). In still other embodiments, polypeptide consists essentially of the amino acid sequence of *Drosophila* SQV-1 (SEQ ID NO:6), or a fragment thereof.

In another aspect, the invention features an isolated sqv-1nucleic acid molecule, or fragment thereof, that encodes a polypeptide sequence having 50%, 60%, 70%, 80%, 90%, 95%, or 100% amino acid sequence identity to SEQ ID NO:4, where the polypeptide has a glycosaminoglycan biosynthetic biological activity. In other embodiments, nucleic acid molecule contains the nucleotide sequence of SEQ ID NO:2, or a complement thereof. In still other embodiments, nucleic acid molecule consists essentially of the nucleotide sequence of SEQ ID NO:2, or a fragment thereof. In still other embodiments, nucleic acid molecule encodes the amino acid sequence of human SQV-1 (SEQ ID NO:5). In still other embodiments, nucleic acid molecule consists essentially of the nucleic acid sequence of human SQV-1 (SEQ ID NO:3), or a fragment thereof. In still other embodiments, the nucleic acid contains a mutation that corresponds to a mutation selected from the group consisting of n2820, n2824, n2828, n2848, ku246, and n2819.

In another aspect, the invention features an isolated nucleic acid molecule that hybridizes under high stringency conditions to SEQ ID NO:2.

In another aspect, the invention features an isolated nucleic acid molecule that hybridizes under high stringency conditions to SEQ ID NO:5.

In another aspect, the invention features an isolated sqv-1 nucleic acid, regardless of length, complementary to at least a portion of SEQ ID NO:5, capable of decreasing the expression of a SQV-1 polypeptide. In other embodiments, the nucleic acid is a dsRNA, antisense RNA, or siRNA.

In another aspect, the invention features an isolated SQV-2 polypeptide, or fragment thereof, containing an amino acid sequence having at least 25%, 30%, 40%, 50%, 60%, 70%, 80%, 90%, or 95% amino acid sequence identity to SEQ ID NO:10, where the polypeptide has a glycosaminoglycan biosynthetic biological activity. In other embodiments, polypeptide contains the amino acid sequence SEQ ID NO:10. In other embodiments, polypeptide consists essentially of the amino acid sequence SEQ ID NO:10, or a fragment thereof.

In another aspect, the invention features an isolated polypeptide fragment of SEQ ID NO:10, where expression of the fragment has a glycosaminoglycan biosynthetic biological activity.

In another aspect, the invention features an isolated SQV-2 polypeptide, or fragment thereof, containing an amino acid sequence having at least 25%, 30%, 40%, 50%, 60%, 70%, 80%, 90%, or 95% amino acid sequence identity to SEQ ID NO:10, and containing a mutation that inhibits the biological activity of the polypeptide. In some embodiments, the mutation corresponds to the mutation in n3037 or n3038. In other embodiments, polypeptide contains the amino acid sequence of human SQV-2 (SEQ ID NO:12). In yet other embodiments, polypeptide consists essentially of the amino acid sequence of human SQV-2 (SEQ ID NO:12), or a fragment thereof. In some embodiments, the polypeptide contains the amino acid sequence of *Drosophila* SQV-2 (SEQ ID NO:11). In other embodiments, polypeptide consists essentially of the amino acid sequence of *Drosophila* SQV-2 (SEQ ID NO:11), or a fragment thereof.

In another aspect, the invention features an isolated sqv-2 nucleic acid molecule, or fragment thereof, that encodes a polypeptide sequence having 25%, 28%, 30%, 40%, 50%, 60%, 70%, 80%, 90%, or 95% amino acid sequence identity to SEQ ID NO:10, where expression of the nucleic acid molecule has a glycosaminoglycan biosynthetic biological activity. In some embodiments, the isolated nucleic acid molecule contains the nucleotide sequence of SEQ ID NO:8, or a complement thereof. In some embodiments, the isolated nucleic acid molecule consists essentially of the nucleotide sequence of SEQ ID NO:8, or a fragment thereof. In other embodiments, the nucleic acid molecule encodes the amino acid sequence of human SQV-2 (SEQ ID NO:12). In other embodiments, the nucleic acid molecule consists essentially of the nucleic acid sequence of human SQV-2 (SEQ ID NO:9), or a fragment thereof. In some embodiments, the sqv-2 nucleic acid molecule further contains a mutation corresponding to the mutation in sqv-2 allele n3037 or n3038 that inhibits the biological activity of the polypeptide.

In another aspect, the invention features an isolated nucleic acid molecule that hybridizes under high stringency conditions to SEQ ID NO:8.

In another aspect, the invention features an isolated nucleic acid molecule that hybridizes under high stringency conditions to SEQ ID NO:9.

In another aspect, the invention features an isolated sqv-2 nucleic acid, regardless of length, complementary to at least a portion of the nucleic acid sequence capable of decreasing the expression of a SQV-2 polypeptide. In some embodiments, the nucleic acid is a dsRNA, antisense RNA, or siRNA.

In another aspect, the invention features an isolated SQV-5 polypeptide, or fragment thereof, containing an amino acid sequence having at least 25%, 35%, 40%, 50%, 60%, 70%, 80%, 90%, or 95% amino acid sequence identity to SEQ ID NO:24, where the polypeptide has a glycosaminoglycan biosynthetic biological activity. In some embodiments, the polypeptide contains the amino acid sequence SEQ ID NO:24. In other embodiments, the polypeptide consists essentially of the amino acid sequence SEQ ID NO:24, or a fragment thereof In another aspect, the invention features an isolated polypeptide fragment of SEQ ID NO:24, where the fragment has a glycosaminoglycan biosynthetic biological activity.

In another aspect, the invention features an isolated SQV-5 polypeptide, or fragment thereof, containing an amino acid sequence having at least 35%, 40%, 50%, 60%, 70%, 80%, 90%, or 95% amino acid sequence identity to SEQ ID NO:24, and further contains a mutation that inhibits the biological activity of the polypeptide. In some embodiments, the polypeptide further contains a mutation that corresponds to sqv-5 (n3039) and inhibits the biological activity of the polypeptide. In other embodiments, the polypeptide contains the amino acid sequence of human SQV-5 (SEQ ID NO:25). In some embodiments, the polypeptide consists essentially of the amino acid sequence of human SQV-5 (SEQ ID NO:25), or a fragment thereof. In other embodiments, the substantially pure polypeptide is substantially identical to the *Drosophila* amino acid sequence of SEQ ID NO:26.

In another aspect, the invention features a substantially pure polypeptide that contains the *Drosophila* amino acid sequence of SEQ ID NO:26. In some embodiments, the isolated sqv-5 nucleic acid molecule, or fragment thereof, that encodes a polypeptide sequence having 38%, 40%, 50%, 60%, 70%, 80%, 90%, or 95% amino acid sequence identity to SEQ ID NO:24, where the nucleic acid molecule has a glycosaminoglycan biosynthetic biological activity. In other embodiments, the isolated nucleic acid molecule contains the nucleotide sequence of SEQ ID NO:28 or a complement thereof. In other embodiments, the isolated nucleic acid molecule consists essentially of the nucleotide sequence of SEQ ID NO:28 or a fragment thereof. In some embodiments, the isolated nucleic acid molecule further contains a mutation that corresponds to the mutation identified in sqv-5 (n3039) or n3611.

In another aspect, the invention features an isolated nucleic acid molecule that hybridizes under high stringency conditions to SEQ ID NO:8.

In another aspect, the invention features an isolated nucleic acid molecule that hybridizes under high stringency conditions to SEQ ID NO:9.

In another aspect, the invention features a sqv-5 nucleic acid, regardless of length, that contains the nucleic acid sequence, or a complement thereof, and decreases the expression of a SQV-5 polypeptide. In some embodiments, the nucleic acid is a dsRNA, antisense RNA, or siRNA.

In another aspect, the invention features an isolated SQV-4 polypeptide, or fragment thereof, containing an amino acid sequence having at least 65%, 70%, 80%, 90%, or 95% amino acid sequence identity to SEQ ID NO:20, where the polypeptide has a glycosaminoglycan biosynthetic biological activity. In some embodiments, the polypeptide contains the amino acid sequence SEQ ID NO:20. In other embodiments, the polypeptide consists essentially of the amino acid sequence SEQ ID NO:20, or a fragment thereof.

In another aspect, the invention features an isolated SQV-4 polypeptide, or fragment thereof, containing an amino acid sequence having at least 65%, 70%, 80%, 90%, or 95% amino acid sequence identity to SEQ ID NO:20, where the polypeptide has a glycosaminoglycan biosynthetic biological activity.

In another aspect, the invention features an isolated SQV-4 polypeptide, or fragment thereof, containing an amino acid sequence having at least 65%, 70%, 80%, 90%, or 95% amino acid sequence identity to SEQ ID NO:20, where the polypeptide further contains a mutation that inhibits the biological activity of the polypeptide. In some embodiments, the mutation corresponds to the mutation identified in sqv-4 (n2827) or (n2840).

In another aspect, the invention features an isolated sqv-4 nucleic acid molecule, or fragment thereof, that encodes a polypeptide sequence having at least 65%, 70%, 80%, 90%, or 95% amino acid sequence identity to SEQ ID NO:20, where the nucleic acid molecule has a glycosaminoglycan biosynthetic biological activity. In some embodiments, the isolated nucleic acid molecule contains the nucleotide sequence of SEQ ID NO:18, or a complement thereof. In some embodiments, the isolated nucleic acid molecule consists essentially of the nucleotide sequence of SEQ ID NO:18, or a fragment thereof.

In another aspect, the invention features an isolated sqv-4 nucleic acid molecule, or fragment thereof, that encodes a polypeptide sequence having at least 65%, 70%, 80%, 90%, or 95% amino acid sequence identity to SEQ ID NO:20, where the nucleic acid molecule contains a mutation that inhibits the biological activity of an encoded polypeptide. In some embodiments, the mutation corresponds to the mutation identified in sqv-4 allele n2827 or n2840.

In another aspect, the invention features an isolated SQV-6 polypeptide, or fragment thereof, containing an amino acid sequence having at least 30%, 40%, 50%, 60%, 70%, 80%, 90%, or 95% amino acid sequence identity to SEQ ID NO:15, where the polypeptide has a glycosaminoglycan biosynthetic biological activity. In some embodiments, the polypeptide contains the amino acid sequence SEQ ID NO:15. In other embodiments, the polypeptide consists essentially of the amino acid sequence SEQ ID NO:15, or a fragment thereof.

In another aspect, the invention features an isolated polypeptide fragment of SEQ ID NO:15, where the fragment has a glycosaminoglycan biosynthetic biological activity.

In another aspect, the invention features an isolated SQV-6 polypeptide, or fragment thereof, containing an amino acid sequence having at least 30% amino acid sequence identity to SEQ ID NO:15, where the polypeptide further contains a mutation that inhibits the biological activity of the polypeptide. In some embodiments, the mutation corresponds to the mutation identified in sqv-6 (n2845).

In another aspect, the invention features an isolated sqv-6 nucleic acid molecule, or fragment thereof, that encodes a polypeptide sequence having at least 25%, 30%, 40%, 50%, 60%, 70%, 80%, 90%, or 95% amino acid sequence identity to SEQ ID NO:15, where the nucleic acid molecule has a glycosaminoglycan biosynthetic biological activity. In some embodiments, the isolated nucleic acid molecule contains the nucleotide sequence of SEQ ID NO:14, or a complement thereof. In some embodiments, the isolated nucleic acid molecule consists essentially of the nucleotide sequence of SEQ ID NO:14, or a fragment thereof.

In another aspect, the invention features an isolated sqv-6 nucleic acid molecule, or fragment thereof, that encodes a polypeptide sequence having at least 30% amino acid sequence identity to SEQ ID NO:15, where the nucleic acid molecule contains a mutation that corresponds to the mutation identified in sqv-6 allele n2845 that inhibits the biological activity of an encoded polypeptide.

In another aspect, the invention features a sqv-6 nucleic acid molecule, regardless of length, that contains the nucleic acid sequence of SEQ ID NO:13, or a complement thereof, and decreases the expression of a SQV-6 polypeptide. In some embodiments, the nucleic acid molecule is a dsRNA, antisense RNA, or siRNA.

By "antisense" is meant a nucleic acid sequence, regardless of length or particular backbone chemistry, that is complementary to the coding strand or mRNA of a gene. Preferably, the antisense nucleic acid is capable of decreasing mRNA levels of a mammalian or C. elegans sqv gene and/or altering a GAG pathway. Preferably the alteration is at least 10%, relative to a control, more preferably 25%, 30%, 40%, or 50%, and most preferably 60%, 70%, 80%, 90%, or more. Preferably, a sqv antisense nucleic acid molecule includes 8, 10, 15, 20, 25, or 30 nucleotides. A sqv antisense nucleic acid molecule may also contain at least 40, 60, 85, 120, or more consecutive nucleotides that are complementary to a sqv mRNA or cDNA, and may be as long as a full-length sqv gene or mRNA. The antisense nucleic acid may contain a modified backbone, for example, phosphorothioate, phosphorodithioate, or other modified backbones known in the art, or may contain non-natural internucleoside linkages.

By "biological activity" is meant any naturally occurring activity of a nucleic acid molecule or polypeptide in the organism from which it is derived. For example, by a SQV biological activity is meant any activity that contributes to the production of a glycosaminoglycan, including any activity of a SQV nucleic acid or polypeptide of the invention (e.g., a UDP-glucuronic acid decarboxylase, GAG galactosyltransferase II, UDP-glucose dehydrogenase, chondroitin synthase, or GAG xylosyltransferase activity).

By "derived from" is meant isolated from or having the sequence of a naturally-occurring sequence (e.g., a cDNA, genomic DNA, synthetic, or combination thereof).

By "high stringency conditions" is meant conditions that allow hybridization comparable with the hybridization that occurs using a DNA probe of at least 300, 400, or 500 nucleotides in length, in a buffer containing 0.5 M $NaHPO_4$, pH 7.2, 7% SDS, 1 mM EDTA, and 1% BSA (fraction V), at a temperature of 65° C., or a buffer containing 48% formamide, 4.8×SSC, 0.2 M Tris-Cl, pH 7.6, 1×Denhardt's solution, 10% dextran sulfate, and 0.1% SDS, at a temperature of 42° C. (These are typical conditions for high stringency northern or Southern hybridizations.) High stringency hybridization is also relied upon for the success of numerous techniques routinely performed by molecular biologists, such as high stringency PCR, DNA sequencing, single strand conformational polymorphism analysis, and in situ hybridization. In contrast to Northern and Southern hybridizations, these techniques are usually performed with relatively short probes (e.g., usually 16 nucleotides or longer for PCR or sequencing, and 40 nucleotides or longer for in situ hybridization). The high stringency conditions used in these techniques are well known to those skilled in the art of molecular biology, and examples of them can be found, for example, in Ausubel et al., *Current Protocols in Molecular Biology*, Wiley Interscience, New York, 2000, which is hereby incorporated by reference.

By "inhibits" is meant to decrease. For example, a nucleic acid molecule, compound, polypeptide or other agent that inhibits the expression or activity of a composition of the invention, decreases the activity or expression by at least 10%, 20%, 30%, 40%, 50%, 60%, 70%, 80%, 90%, or 100%.

By "enhance" is meant increase. For example, a nucleic acid molecule, compound, polypeptide or other agent that enhances the expression or activity of a composition of the invention, increases the activity or expression by at least 10%, 20%, 30%, 40%, 50%, 60%, 70%, 80%, 90%, or 100%.

By "fragment" is meant at least a portion of the full length nucleic acid or polypeptide molecule that has 25%, 30%, 40%, 50%, 60%, 70%, 80%, 90%, or even 100% sequence identity to a reference nucleic acid molecule or polypeptide; that binds an antibody that specifically binds to the polypeptide from which the fragment is derived; or that includes a conserved domain required for biological activity. Domains required for biological activity typically share a high degree of sequence identity (e.g., 70%, 80%, 90%, 95%, or 100% within a particular domain) with a reference nucleic acid or polypeptide. In addition, domains required for biological activity may be identified by the presence of a mutation that inhibits the biological activity of the reference polypeptide. The presence of such mutations in a particular protein domain or region identifies that domain or region as functionally important. Fragments may have as few as 10, 20, 30, 40, 50, 60, 70, 80, 90, or 100 amino acids or nucleotides. Fragments may have as many as 150, 200, 300, 400, 500, 600, 700, 800, 900, or 1000 amino acids or nucleotides.

By "isolated nucleic acid molecule" is meant a nucleic acid (e.g., a DNA) that is free of the genes which, in the naturally-occurring genome of the organism from which the nucleic acid molecule of the invention is derived, flank the gene. The term therefore includes, for example, a recombinant DNA that is incorporated into a vector; into an autonomously replicating plasmid or virus; or into the genomic DNA of a prokaryote or eukaryote; or that exists as a separate molecule (for example, a cDNA or a genomic or cDNA fragment produced by PCR or restriction endonuclease digestion) independent of other sequences. In addition, the term includes an RNA molecule which is transcribed from a DNA molecule, as well as a recombinant DNA which is part of a hybrid gene encoding additional polypeptide sequence.

By "isolated polypeptide" is meant a polypeptide of the invention that has been separated from components which naturally accompany it. Typically, the polypeptide is substantially pure when it is at least 60%, by weight, free from the proteins and naturally-occurring organic molecules with which it is naturally associated. Preferably, the preparation is at least 75%, more preferably at least 90%, and most preferably at least 99%, by weight, a polypeptide of the invention. An isolated polypeptide of the invention may be obtained, for example, by extraction from a natural source (for example, a cell or cell extract); by expression of a recombinant nucleic acid encoding such a polypeptide; or by chemically synthesizing the protein. Purity can be measured by any appropriate method, for example, column chromatography, polyacrylamide gel electrophoresis, or by HPLC analysis.

By "polypeptide" is meant any chain of amino acids, regardless of length or post-translational modification (for example, glycosylation or phosphorylation). By "positioned for expression" is meant that the DNA molecule is positioned adjacent to a DNA sequence which directs transcription and translation of the sequence (i.e., facilitates the production of, for example, a recombinant polypeptide of the invention, or an RNA molecule).

By "purified antibody" is meant an antibody which is at least 60%, by weight, free from proteins and naturally-occurring organic molecules with which it is naturally associated. Preferably, the preparation is at least 75%, more preferably 90%, and most preferably at least 99%, by weight, antibody. A purified antibody of the invention may be obtained, for example, by affinity chromatography using a recombinantly-produced polypeptide of the invention and standard techniques.

By "specifically binds" is meant a compound or antibody which recognizes and binds a polypeptide of the invention, but which does not substantially recognize and bind other molecules in a sample, for example, a biological sample, which naturally includes a polypeptide of the invention.

By "substantially identical" is meant a polypeptide or nucleic acid molecule exhibiting at least 30% identity to a reference amino acid sequence (e.g., a polypeptide encoded by sqv-1, sqv-2, sqv-4, sqv-5, or sqv-6) or nucleic acid sequence. Preferably, such a sequence is at least 30%, 40%, 50%, 60%, 70%, more preferably 80% or 85%, and most preferably 90% or even 95% identical at the amino acid or nucleic acid level to the reference sequence used for comparison.

Sequence identity is typically measured using sequence analysis software (for example, Sequence Analysis Software Package of the Genetics Computer Group, University of Wisconsin Biotechnology Center, 1710 University Avenue, Madison, Wis. 53705, BLAST, BESTFIT, GAP, or PILEUP/ PRETTYBOX programs). Such software matches identical or similar sequences by assigning degrees of homology to various substitutions, deletions, and/or other modifications. Conservative substitutions typically include substitutions within the following groups: glycine, alanine; valine, isoleucine, leucine; aspartic acid, glutamic acid, asparagine, glutamine; serine, threonine; lysine, arginine; and phenylalanine, tyrosine. In an exemplary approach to determining the degree of identity, a BLAST program may be used, with a probability score between $e^{-3}$ and $e^{-100}$ indicating a closely related sequence.

By "transformed cell" is meant a cell into which (or into an ancestor of which) has been introduced, by means of recombinant DNA techniques, a DNA molecule encoding (as used herein) a polypeptide of the invention.

By "sample" is meant a tissue biopsy, amniotic fluid, cell, blood, serum, urine, stool, or other specimen obtained from a patient or a test subject. The sample can be analyzed to detect a mutation in a sqv-1, sqv-2, sqv-4, sqv-5, or sqv-6 nucleic acid sequence using methods that are known in the art. For example, methods such as sequencing, single-strand conformational polymorphism (SSCP) analysis, or restriction fragment length polymorphism (RFLP) analysis of PCR products derived from a patient sample can be used to detect a mutation in a sqv-1, sqv-2, sqv-4, sqv-5, or sqv-6 nucleic acid molecule.

By a "SQV polypeptide" is meant a SQV amino acid molecule, or fragment thereof, substantially identical to, and having the biological activity of a SQV polypeptide of the invention, for example, the activity of SQV-1, SQV-2, SQV-4, SQV-5, or SQV-6 polypeptide, or a polypeptide that functions in a pathway. Specifically excluded by this definition is the biological activity of a SQV-3, SQV-7, or SQV-8 polypeptide.

By "sqv gene" is meant a sqv nucleic acid sequence that encodes a SQV polypeptide, for example, a polypeptide, or fragment thereof, substantially identical to the SQV amino acid sequence provided in FIG. 2, 10, 12A, 14, or 25. Specifically excluded by this definition are sqv-3, sqv-7, or sqv-8.

By "SQV-1 biological activity" is meant any activity of a SQV-1 polypeptide of FIG. 2, such as an enzymatic activity (e.g., that of a GAG biosynthetic enzyme or that of a UDP-glucuronic acid decarboxylase). Such an activity can be assayed, for example, by an assay for decarboxylase activity as described at page 20.

By "SQV-1 polypeptide" is meant a polypeptide or fragment thereof, having SQV-1 biological activity and substantially identical to a SQV-1 polypeptide sequence, for example, a polypeptide that is at least 50%, 60%, 70%, 80%, 85%, 90%, 95%, or even 99% identical to a human, *Drosophila*, or nematode SQV-1 amino acid sequence provided in FIG. 2.

By "sqv-1" is meant a sqv-1 nucleic acid sequence that encodes a SQV-1 polypeptide, for example, a polypeptide, or fragment thereof, substantially identical to a SQV-1 amino acid sequence provided in FIG. 2.

By "SQV-2 biological activity is, meant any activity of a SQV-2 polypeptide of FIG. 10, such as an enzymatic activity (e.g., that of a GAG biosynthetic enzyme or GAG galactosyltransferase II). Such an activity can be assayed, for example, in a GAG galactosyltransferase II assay, as described by Bai et al. (*J. Biol. Chem.* 276:189-95, 2001).

By "SQV-2 polypeptide" is meant a polypeptide, or fragment thereof, substantially identical to and having the biological activity of SQV-2 polypeptide, for example, a polypeptide that is at least 40%, 45%, 50%, 60%, 70%, 80%, 85%, 90%, 95% or even 99% identical to a human, *Drosophila*, or nematode to SQV-2 amino acid sequence provided in FIG. 10.

By "sqv-2" is meant a sqv-2 nucleic acid sequence that encodes a SQV-2 polypeptide, for example, a polypeptide substantially identical to a SQV-2 amino acid sequence provided in FIG. 10.

By "sqv-4" is meant a sqv-4 nucleic acid sequence that encodes a SQV-4 polypeptide, for example, a polypeptide substantially identical to a SQV-4 amino acid sequence provided in FIG. 14.

By "SQV-4 biological activity" is meant any activity of the SQV-4 polypeptide of FIG. 14, such as an enzymatic activity (e.g., that of a GAG biosynthetic enzyme or UDP-glucose dehydrogenase). Such an activity may be assayed, for example, in an assay for a UDP-glucose dehydrogenase activity (Strominger et al., *J. Amer. Chem. Soc.* 76:6411-6412, 1954; Hempel et al., *Protein Science* 3:1074-1080, 1994).

By "SQV-4 polypeptide" is meant a polypeptide, or fragment thereof, having SQV-4 biological activity and substantially identical to a SQV-4 amino acid sequence, for example, a polypeptide that is at least 75%, 80%, 85%, 90%, or 95% identical to a human, *Drosophila, Arabidopsis*, or nematode SQV-4 amino acid sequence provided in FIG. 14.

By "sqv-5" is meant a sqv-5 nucleic acid sequence that encodes a SQV-5 polypeptide, for example, a polypeptide substantially identical to a SQV-5 amino acid sequence provided in FIG. 25.

By "SQV-5 biological activity" is meant any activity of a SQV-5 nematode, *Drosophila* or human polypeptide of FIG. 25, for example, an enzymatic activity (e.g., that of GAG biosynthetic enzyme or chondroitin synthase). Such an activity may be assayed, for example, as described by DeAngelis et al. (*J. Biol. Chem.* 27:24124-24129, 2000).

By "SQV-5 polypeptide" is meant a polypeptide having SQV-5 biological activity and substantially identical to a SQV-5 amino acid sequence of FIG. 25, for example, a polypeptide that is at least 35%, 38%, 40%, 50%, 60%, 70%, 80%, 90%, or 95% identical to a human, *Drosophila*, or nematode SQV-5 amino acid sequence provided in FIG. 25.

By "sqv-6" is meant a sqv-6 nucleic acid sequence that encodes a SQV-6 polypeptide, for example, a polypeptide substantially identical to a human or nematode SQV-6 amino acid sequence provided in FIG. 12A.

By "SQV-6 biological activity" is meant any activity of a SQV-6 polypeptide of FIG. 12A, such as an enzymatic activity (e.g., that of GAG biosynthetic enzyme or a GAG xylosyltransferase). Such an activity may be assayed, for example, in a GAG xylosyltransferase activity assay, as described by Esko et al. (*Proc. Natl. Acad. Sci.* 82:3197-201).

By "SQV-6 polypeptide" is meant a polypeptide that has SQV-6 biological activity or is substantially identical to a SQV-6 polypeptide sequence, for example, a polypeptide that is at least 50%, 60%, 75%, 80%, 85%, 90%, or 95% identical to the SQV-6 amino acid sequence provided in FIG. 12A.

BRIEF DESCRIPTION OF THE DRAWINGS

FIG. 1C shows the *C. elegans* sqv-1 genomic sequence (D2096.1) (SEQ ID NO:1) aligned with the sqv-1 cDNA (SEQ ID NO:2). The start and stop codons are indicated in bold.

FIG. 1D shows the nucleic acid sequence of human sqv-1 (SEQ ID NOS:3 and 82-84).

FIG. 2 shows an amino acid sequence alignment of *C. elegans* SQV-1 (SEQ ID NOS:4 and 85-87), SQV-1 Human (SEQ ID NOS:5 and 93-97), and *Drosophila* (SEQ ID NOS:6 and 88-92) homologs. The numbers on the right indicate amino acid positions. Identities shared by at least two polypeptides are shaded in black. The missense mutations for the sqv-1 mutant alleles are indicated. The putative transmembrane domains are underlined.

Seam cells line the length of the worm from head to tail. The distal tip cell is located at the end of the migrating gonad, which is to the left of the DTC in this image.

Figures 5A, 5B, 5C, 5D, 5E:
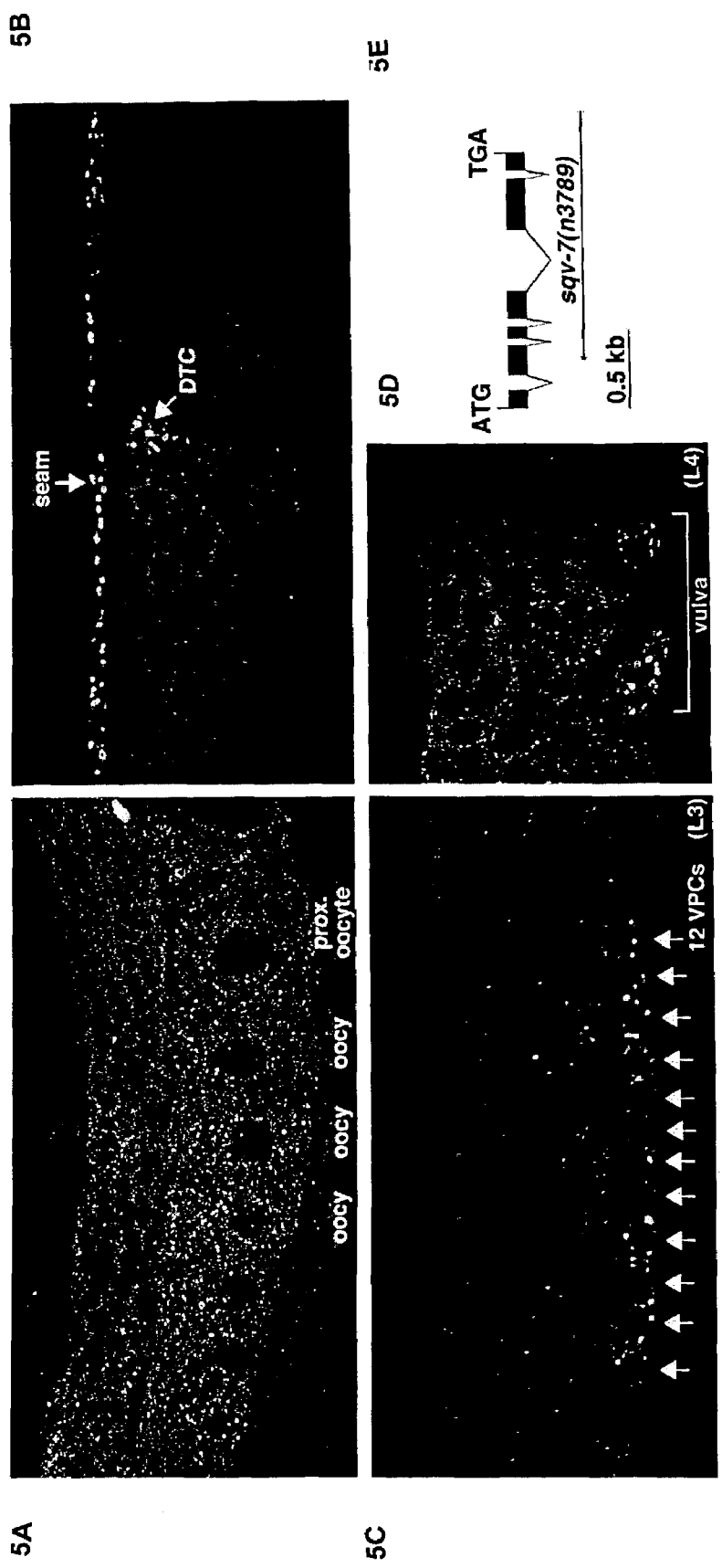
FIG. 5A is a photomicrograph showing SQV-7 staining in oocytes. The four most mature oocytes (oocy), including the most proximal oocyte (prox oocy), are indicated. The oocytes were prepared in whole-mount staining of wild-type nematodes using anti-SQV-7 peptide antibodies. SQV-7 antibodies localized to punctate cytoplasmic foci.
FIG. 5B is a photomicrograph showing SQV-7 staining in seam cells (seam) and the distal tip cell (DTC) in an L4 larva.

FIG. 5C is a photomicrograph showing SQV-7 staining in the vulval precursor cells (VPCs) in an L3 larva. Twelve VPCs are indicated by arrows. Ten of the twelve VPCs will divide once more to generate the twenty-two vulval cells that form the vulva.

FIG. 5D is a photomicrograph showing SQV-7 staining in vulval cells (v) during vulval morphogenesis in an L4 larva. A subset of the twenty-two vulval cells is visible in this focal plane.

FIG. 5E is a diagram showing the structure of the sqv-7 gene using solid boxes to indicate exons. The initiation and termination codons are indicated. The sqv-7(n3789) deletion allele is shown using a thin solid line to depict the extent of the deletion.

Figures 6A, 6B, 6C:
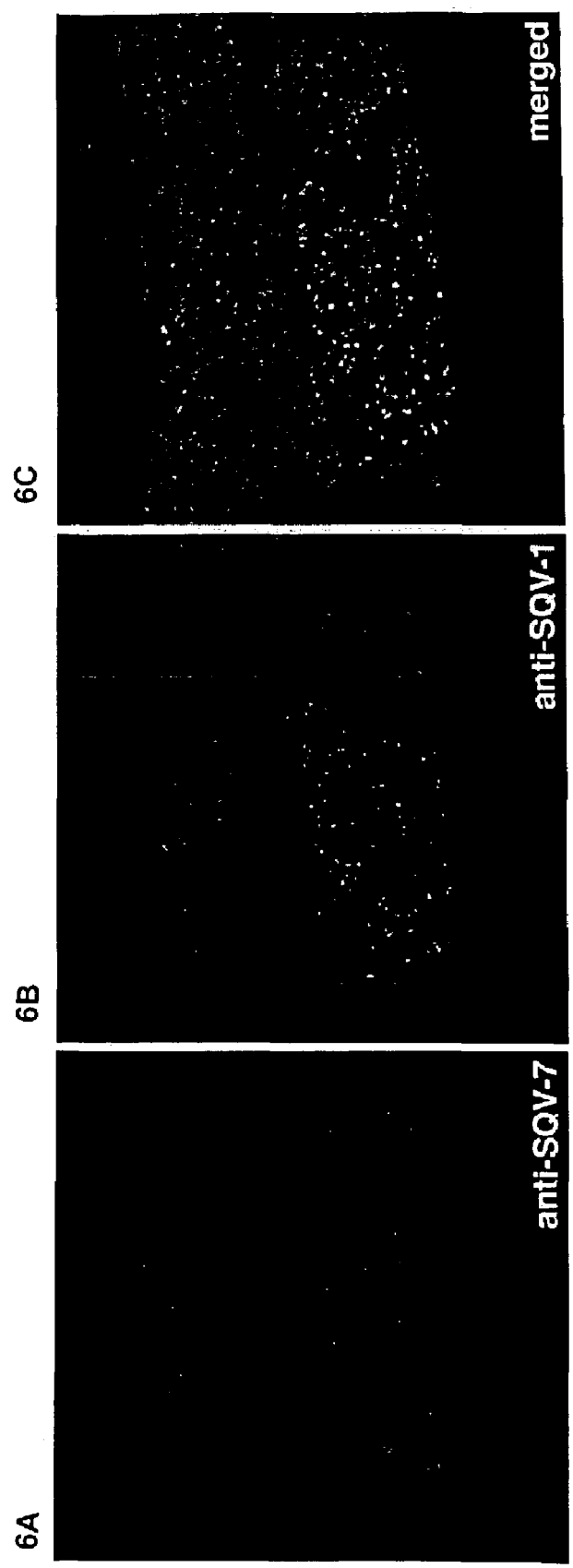

FIG. 6A is a photomicrograph showing SQV-7 staining of oocytes. Anti-SQV-7 rabbit peptide antibody staining was visualized using Texas Red-conjugated secondary antibodies.

FIG. 6B is a photomicrograph showing SQV-1 staining of the same oocytes shown in FIG. 6A. SQV-1-MBP rat antibody staining was visualized by FITC-conjugated secondary antibodies.

FIG. 6C is a photomicrograph showing a merged image of FIGS. 6A and 6B. SQV-1 and SQV-7 colocalized in oocytes.

Figures 7A, 7B, 7C, 7D, 7E, 7F:
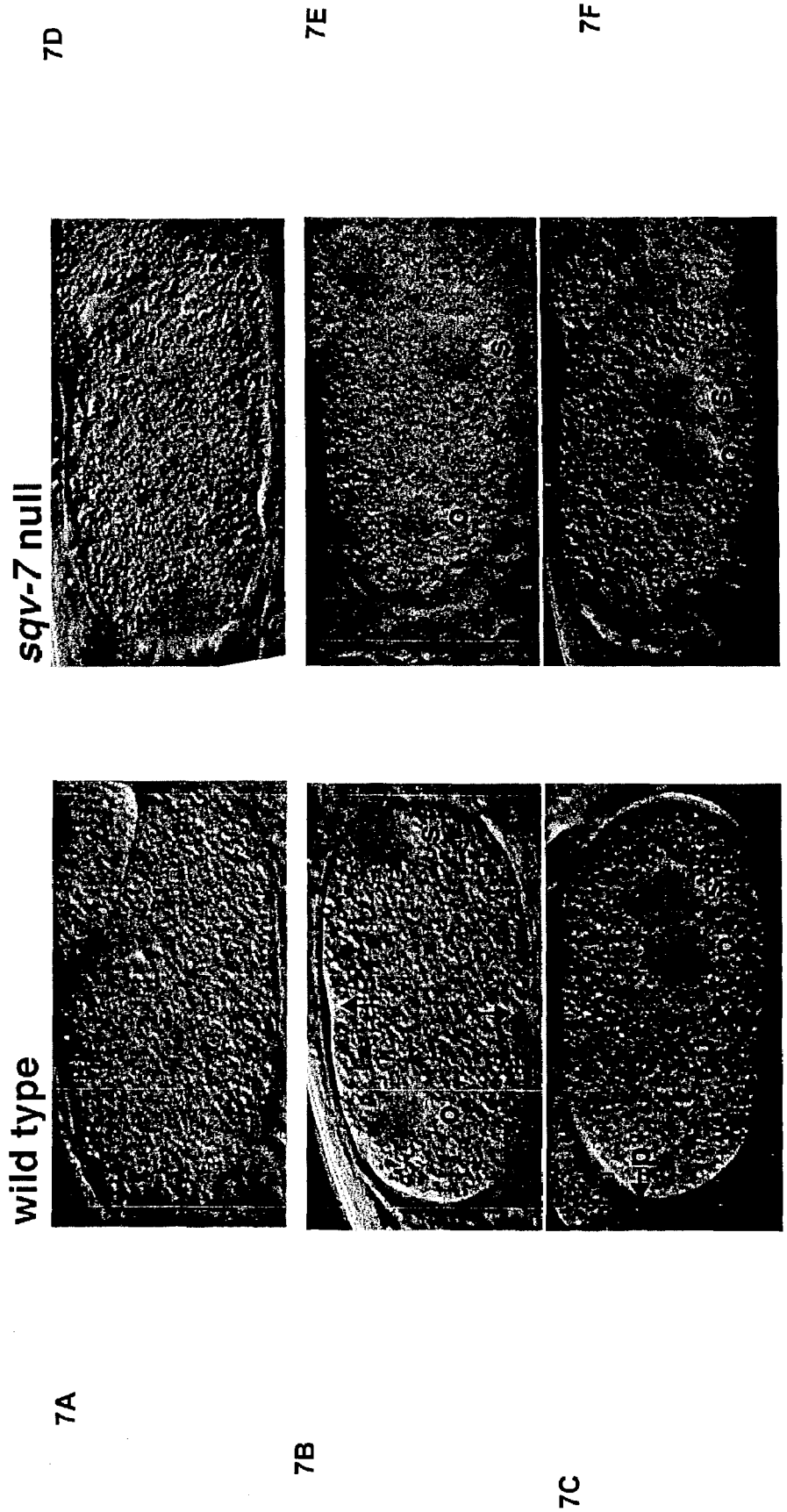

FIGS. 7A-7C are Nomarski photomicrographs of early embryogenesis in a wild-type embryo.

FIGS. 7D-7F are Nomarski photomicrographs of a sqv-7 (n3789) mutant embryo.

FIGS. 7A and 7D are Nomarski photomicrographs showing fertilized wild-type and sqv-7 null embryos, respectively FIGS. 7B and 7E are Nomarski photomicrographs showing the appearance of egg (o) and sperm (s) pronuclei in wild-type and sqv-7 null embryos, respectively, after fertilization. Constriction of the plasma membrane, or pseudocleavage, is indicated by arrows in the wild-type embryo.

FIGS. 7C and 7F are Nomarski photomicrographs showing the pronuclear meeting in wild-type and sqv-7 null embryos, respectively. A polar body (p) is indicated in the wild-type embryo. The space between the plasma membrane and eggshell is indicated by a bracket in the wild-type embryo.

FIGS. 8A-8C are Nomarski photomicrographs of early embryogenesis in a wild-type embryo.

FIGS. 8D-8F are Nomarski photomicrographs of a sqv-7 (n3789) mutant embryo.

FIGS. 8A and 8D are Nomarski photomicrographs showing the rotation of the mitotic spindle onto the anterior-posterior axis in wild-type and sqv-7 null embryos, respectively. The space between the plasma membrane and the eggshell in the wild-type embryo is indicated by a bracket.

FIGS. 8B and 8E are Nomarski photomicrographs showing the first mitosis in wild-type and sqv-7 null embryos, respectively. The initiation of cytokinesis is visible in the wild-type embryo, but not in the sqv-7 mutant embryo. The constriction of the plasma membrane in the wild-type embryo is indicated by arrows.

FIGS. 8C and 8F are Nomarski photomicrographs showing embryos after the first nuclear division in wild-type and sqv-7 null embryos, respectively. The wild-type embryo is a two-cell embryo with the daughter cells labeled (AB, P0). The sqv-7 mutant embryo contains more than two nuclei in a single cytoplasm. Multiple nuclei present in the sqv-7 mutant embryo are indicated by arrows.

Figures 9A, 9B:
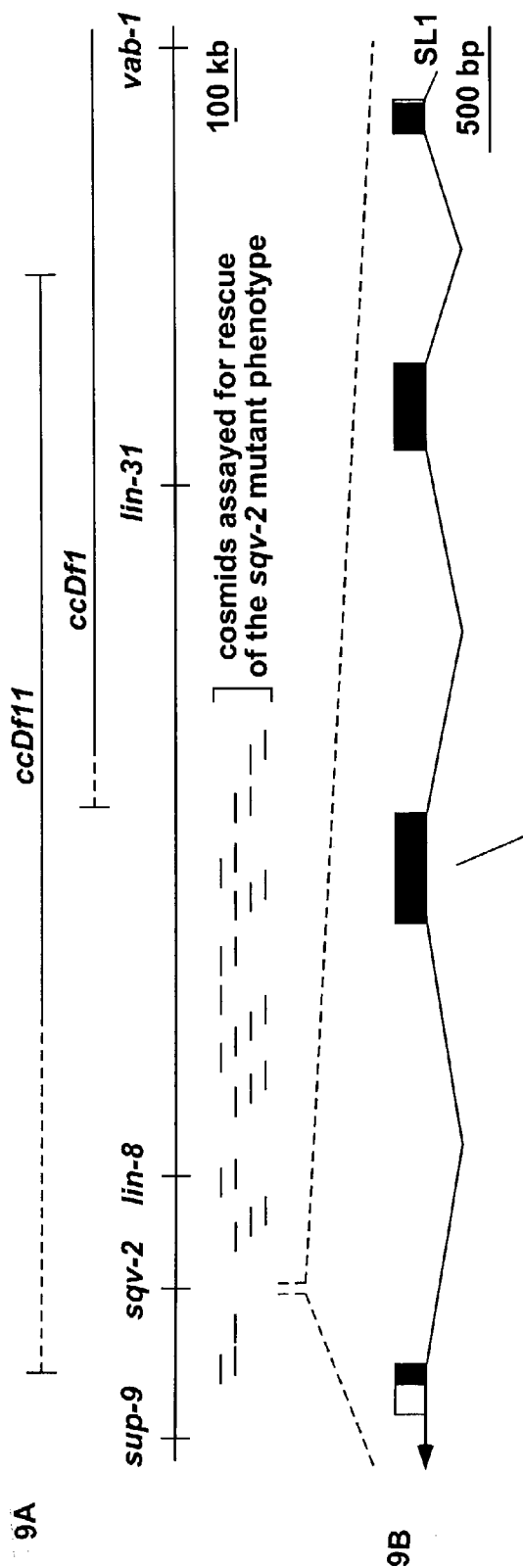

FIG. 9A shows the genetic and physical map of sqv-2. The dashed horizontal lines depicting deficiencies ccDf11 and ccDf1 indicate the possible extent of the left end points of these deletions. Short solid lines represent cosmid clones that were assayed in germline transformation experiments.

FIG. 9B shows the structure of the sqv-2 gene. Solid boxes indicate exons, and open boxes indicate untranslated sequences. The sqv-2 trans-spliced leader SL1 is indicated, and the arrow indicates the sqv-2 poly(A) tail.

FIG. 9C shows an alignment of the C. elegans sqv-2 genomic (Y110A2AL.1) (SEQ ID NO:7) and cDNA (SEQ ID NO:8) nucleic acid sequences. The start and stop codons are indicated in bold.

FIG. 9D shows the nucleic acid sequence of the human sqv-2 homolog (SEQ ID NOS:9, 98, 178-179).

FIG. 10 shows the alignment of SQV-2 (SEQ ID NOS:10 and 99-102), a Drosophila homolog (SEQ ID NOS:11 and 103-105), and human GAG galactosyltransferase II (SEQ ID NOS:12 and 106-111). Identities between two or more proteins are shaded in black. The predicted transmembrane domains are underlined. The three sqv-2 mutant alleles are indicated. The numbers on the right indicate amino acid positions.

Figures 11A, 11B:
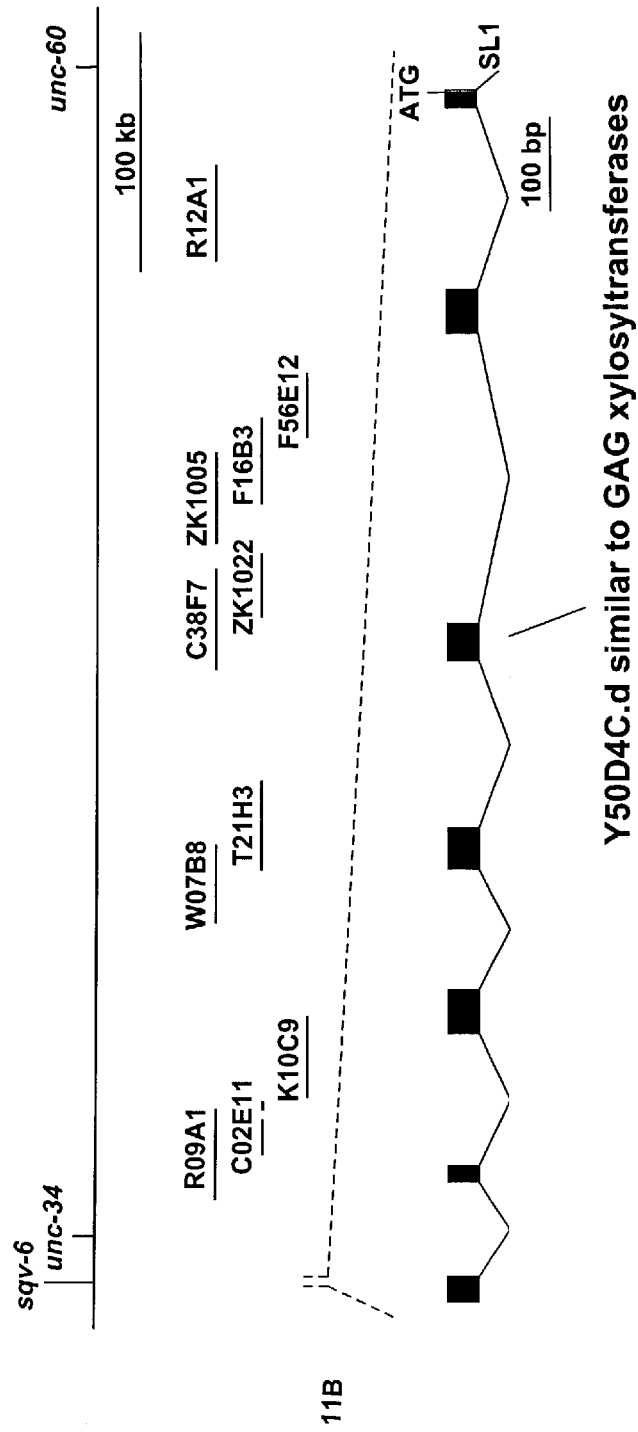

FIG. 11A shows the genetic and physical map of sqv-6. Short solid lines represent cosmid clones that were assayed in germline transformation experiments.

FIG. 11B shows the structure of the sqv-6 gene. Solid boxes indicate exons. The sqv-6 trans-spliced leader SLI and the sqv-6 start codon (ATG) are indicated.

FIG. 11C shows the nucleic acid sequence of C. elegans sqv-6 (SEQ ID NO:13) and cDNA sequences (SEQ ID NO:14). The start and stop codons are indicated.

FIG. 12A shows an alignment of SQV-6 (SEQ ID NOS:15 and 112-119) and two human GAG xylosyltranferases (SEQ ID NOS:16 and 120-127; SEQ ID NOS:17 and 128-131). Identities between two or more proteins are shaded in black. The predicted transmembrane domains are underlined. The single sqv-6 nonsense allele is indicated. The numbers on the right indicate amino acid positions.

Figure 12B:
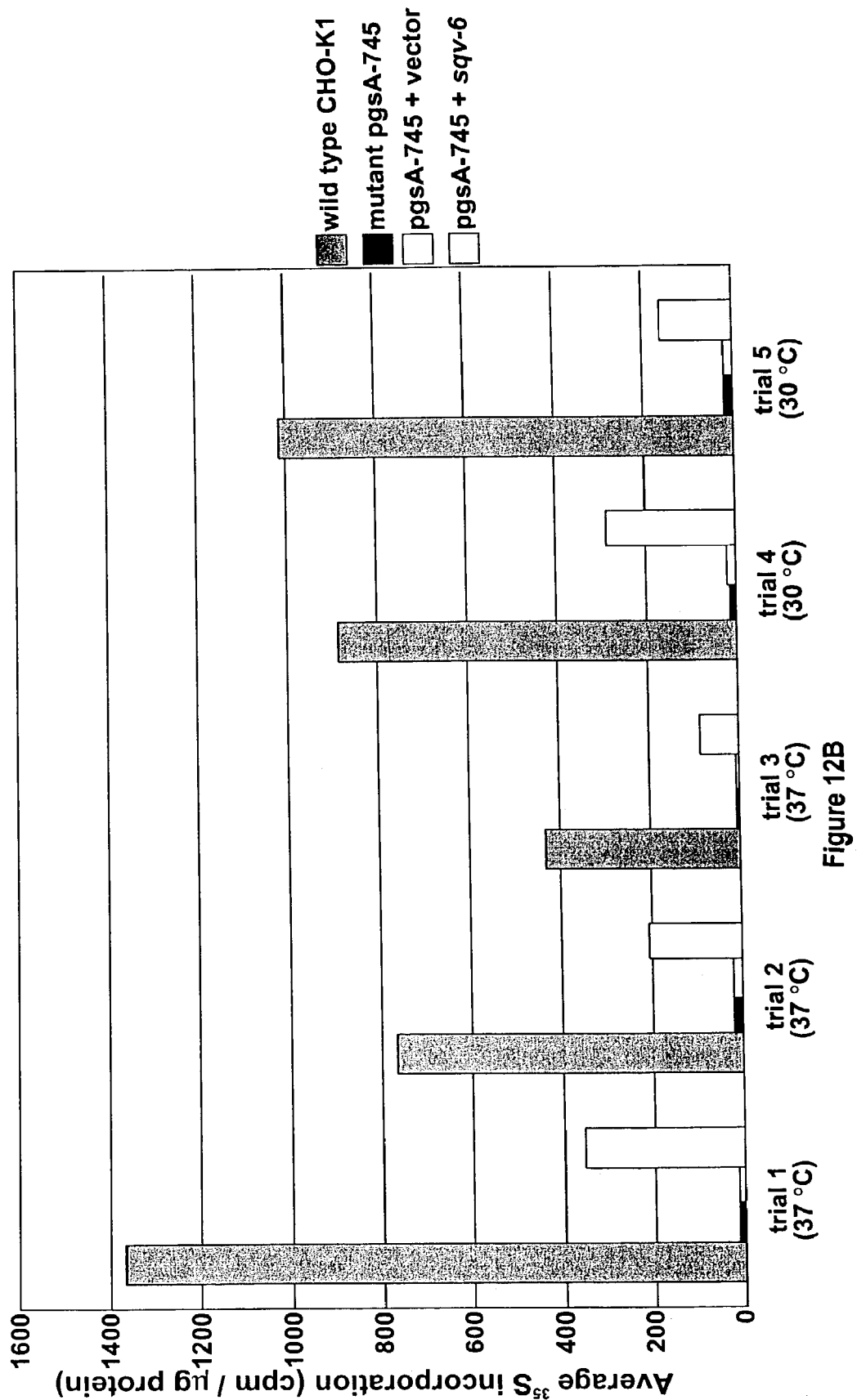

FIG. 12B is a bar graph showing, on the y axis, the average $^{35}$S incorporation (cpm/µg protein) and on the x axis, trials at various temperatures in wild-type CHO-K1 cells, xylosyltransferase deficient mutant pgsA-745 cells, xylosyltransferase deficient mutant pgsA-745 cells transfected with an empty vector, and xylosyltransferase deficient mutant pgsA-745 cells transfected with wild-type sqv-6.

Figures 13A, 13B, 13C:
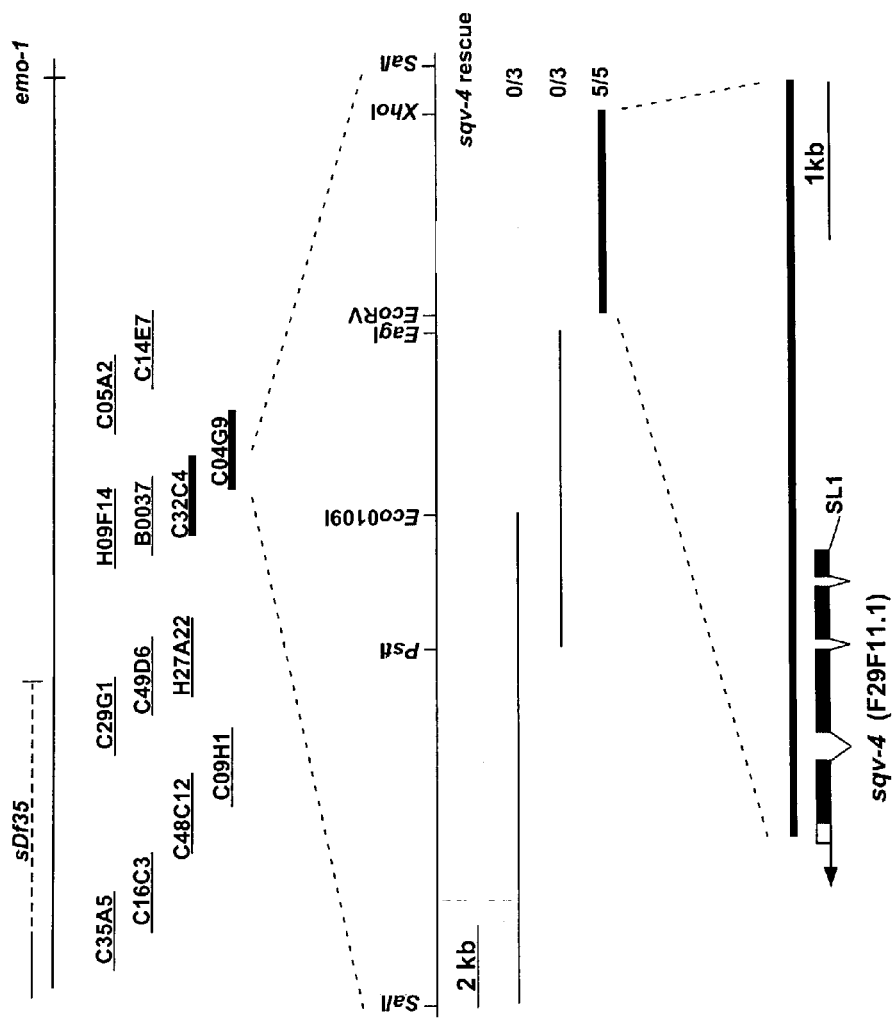

FIG. 13A shows the genetic and physical maps of the sqv-4 locus. The dashed horizontal line depicting deficiency sDf35 indicates the possible extent of the right end point of this deletion, between C35A5 and T21C9 (T21C9 is not shown.). The short solid horizontal lines represent cosmid clones that were assayed in germline transformation experiments. Overlapping cosmids C49D6 and H27A22 were assayed instead of T21 C9. The parallel vertical lines indicate a gap in the cosmid coverage of the C. elegans genome. Cosmids that rescued the sqv-4 mutant phenotype are shown in bold.

FIG. 13B shows subclones derived from the cosmids C32C4 and C04G9 that correspond to the common region shared by the two cosmids. Subdlones that rescued the sqv-4 mutant phenotype are shown in bold. The rescue data are shown as the number of transformed lines that rescued/total number of lines tested.

FIG. 13C shows the structure of the sqv-4 gene. Solid boxes indicate exons, and open boxes indicate untranslated sequences. The sqv-4 trans-spliced leader SL1 is indicated, and the arrow indicates the sqv-4 poly(A) tail.

FIG. 13D shows the nucleic acid sequence of C. elegans sqv-4 (SEQ ID NO:18) and genomic nucleic acid molecules (SEQ ID NO:19). Start and stop codons are indicated.

FIG. 14 shows the sequence alignmnent of *C. elegans* SQV-4 (SEQ ID NO:20) *Drosophila melanogaster* (Sugarless) (SEQ ID NO:21), human (SEQ ID NO:22), and *Arabidopsis thaliana* (SEQ ID NO:23) UDP-glucose dehydrogenases. The numbers on the right indicate amino acid positions. Amino acid identities between two (or more) proteins are shaded in black or gray. The positions of the two sqv-4 missense alleles are indicated.

Figure 15:
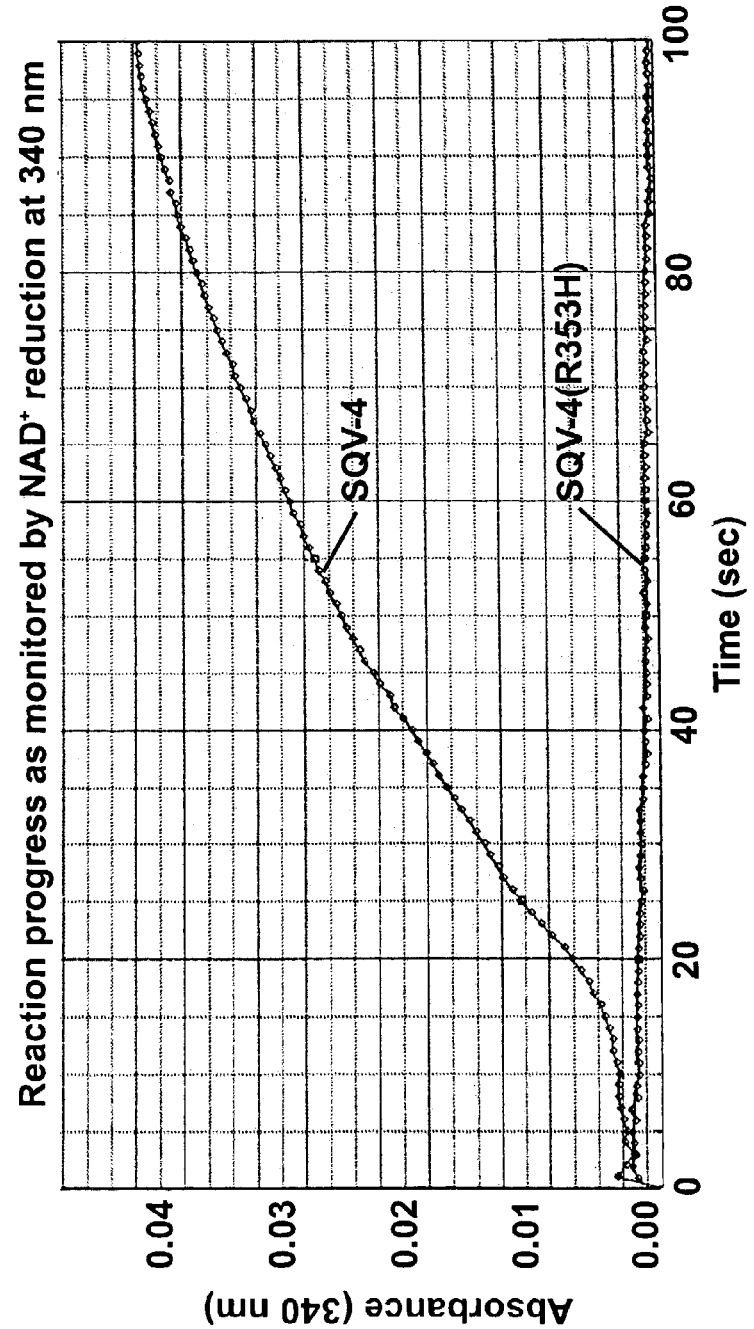

FIG. 15A is a diagram of the UDP-glucose dehydrogenase reaction. Two molecules of $NAD^+$ are reduced to NADH as one molecule of uridine diphosphate (UDP)-glucose and one molecule of water are converted to one molecule of UDP-glucuronic acid.

FIG. 15B shows the progress of the UDP-glucose dehydrogenase reaction as measured by $AND^+$ reduction at 340 nm. Reaction curves of wild-type, SQV-4 T2A (SQV-4 T2A contains a threonine-to-alanine substitution at the second amino acid position that was caused by the addition of an NcoI restriction site at the 5' end of the sqv-4 ORF), and mutant SQV-4 (R353H) (SQV-4 (R353H) contains the same mutation as the n2827 mutant allele) are shown. Approximately 3 mg of a soluble protein fraction containing SQV-4 was mixed with 50 µM UDP-glucose and 50 µM $AND^+$. Absorbance at 340 nm was measured at one second intervals for 100 seconds.

Figure 16:
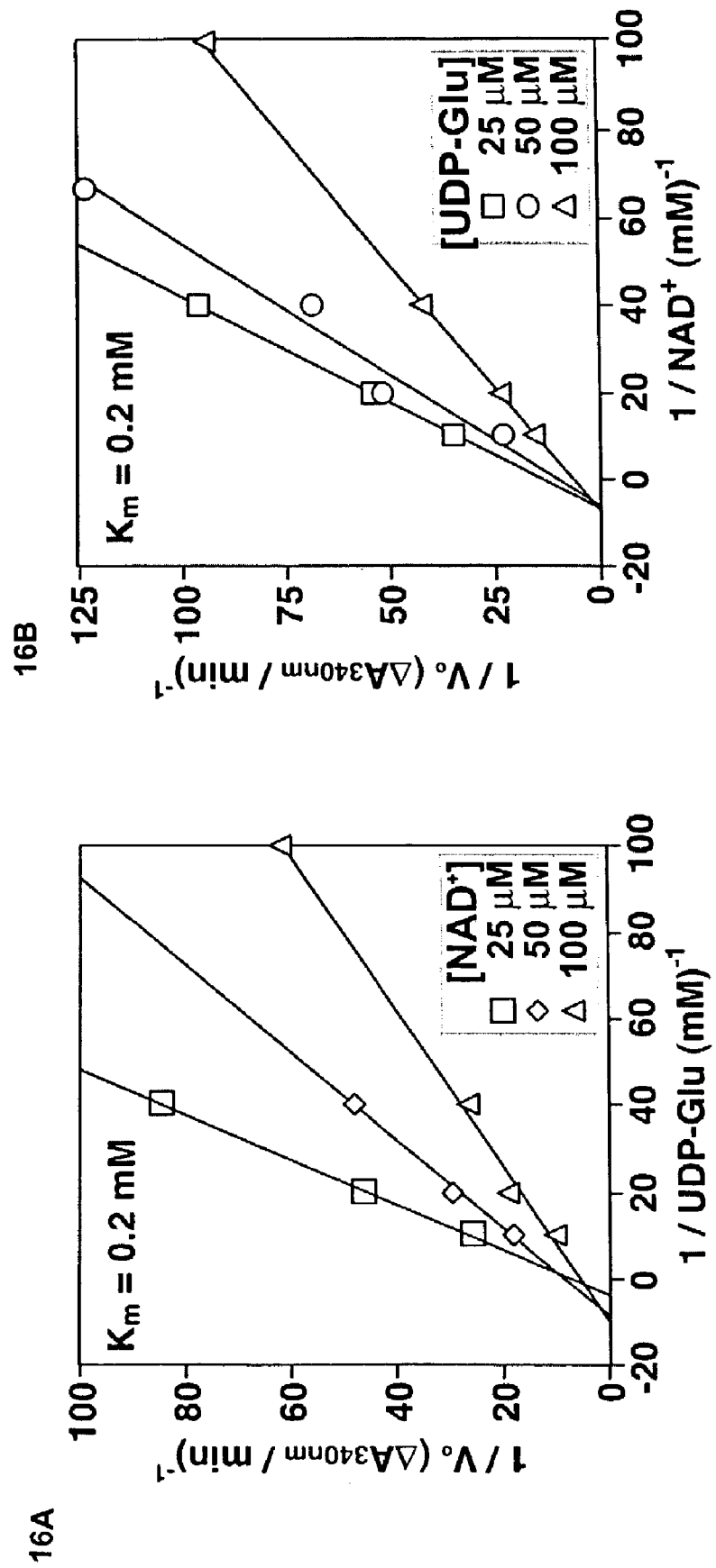

FIG. 16A shows a double-reciprocal plot of the initial reaction velocities with UDP-glucose as the variable substrate. Initial velocity was measured using the linear phase of the reaction curve (20 to 30 second intervals). $AND^+$ concentrations were 25 µM, 50 µM, or 100 µM.

FIG. 16B shows a double reciprocal plot of the initial reaction velocities with $AND^+$ as the variable substrate. Initial velocity was measured using the linear phase of the reaction curve (20 to 30 second intervals). UDP-glucose concentrations were 25 µM, 50 µM, or 100 µM. Km values were calculated by the method of Lineweaver and Burke (1934).

Figure 17:
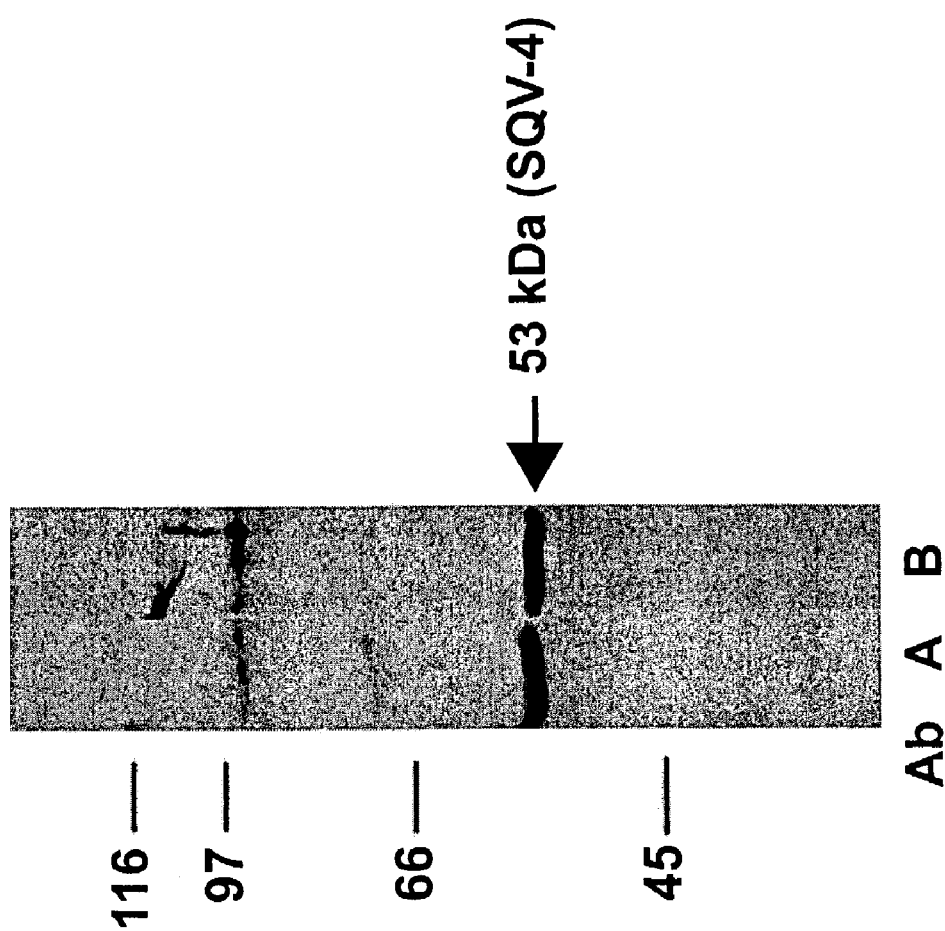

FIG. 17 shows Western blots probed with anti-SQV-4 antibodies raised from two different rabbits (Ab A and Ab B). The Anti-SQV-4 antibodies detected a protein of the expected size (53 kDa) in a wild-type protein extract. The molecular weights (kDa) of SDS-PAGE standard markers (Bio-Rad, Hercules, Calif.) are indicated. The protein of approximately 95 kDa is probably of bacterial origin, since a protein of the same size is detected in an immunoblot of proteins from *E. coli*.

Figure 18:
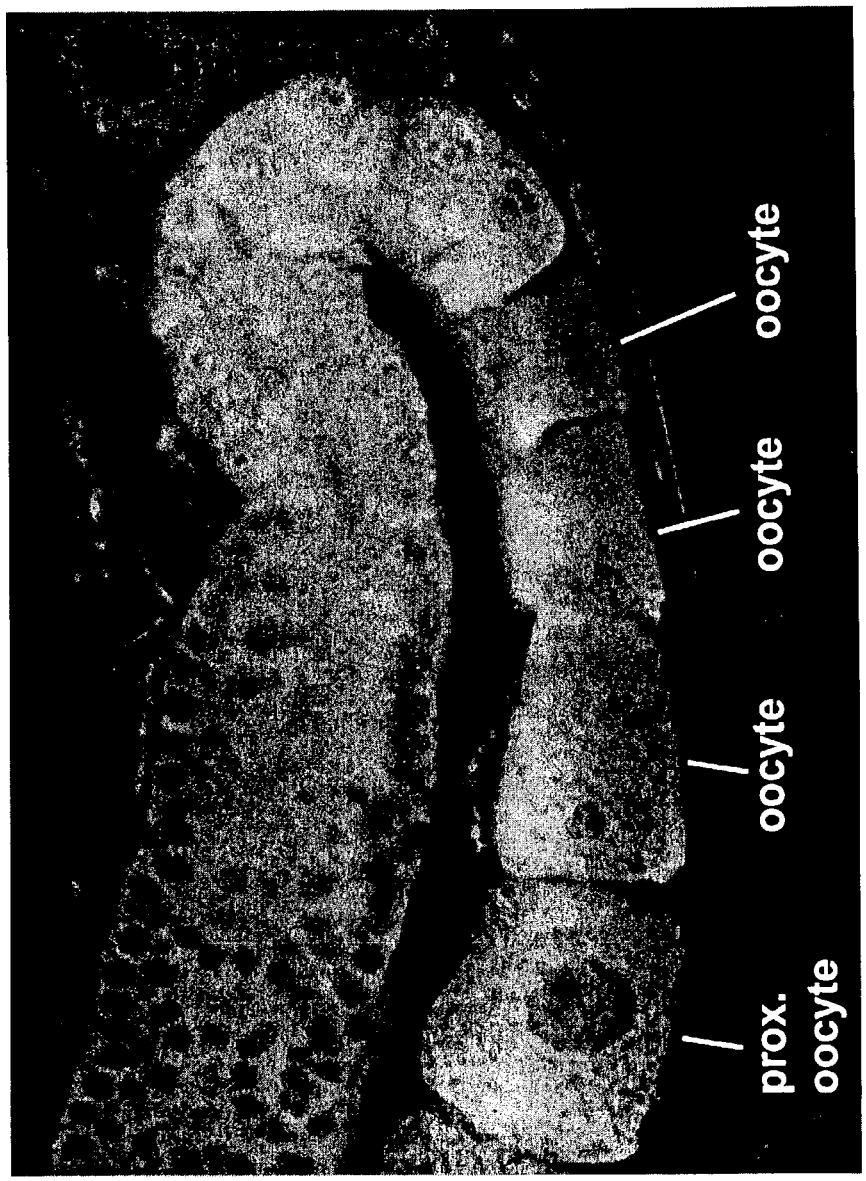

FIG. 18 is a photomicrograph showing anti-SQV-4 antibody staining in a row of oocytes in an adult hermaphrodite. This staining was absent in animals stained with pre-immune sera or antibodies that were pre-absorbed with GST-SQV-4. The oocyte most proximal to the uterus is located at the lower left.

FIGS. 19A-19C are confocal images showing that anti-SQV-4 antibodies stained a subset of vulval cells during early vulval morphogenesis.

FIGS. 20A and 20B are confocal images showing anti-SQV-4 antibody staining in vulval cells during later vulval morphogenesis.

FIG. 20A shows vulval cells containing four nuclei (P5.ppal, P6.paal, P6.pppl and P7.papl) on the left side of the worm.

FIG. 20B shows SQV-4 antibody staining in vulval cells containing two of the four dorsal-most nuclei (P6.papl and P6.ppal), which were not stained at an earlier stage.

FIG. 20C is a confocal image showing anti-SQV-4 antibody staining during later vulval morphogenesis in two vulval cells (P5.ppp and P7.paa) in the middle plane of the worm.

FIG. 20D shows anti-SQV-4 antibody staining in vulval cells containing two of the four dorsal-most nuclei (P6.papr and P6.ppar), which were not stained at an earlier stage.

FIG. 20E shows vulval cells containing four nuclei (P5.ppar, P6.paar, P6.pppr and P7.papr) on the right side of the worm.

FIG. 21A is a Nomarski photomicrograph of a lin-12 gain-of-function (gf) mutant nematode.

FIG. 21B is a photomicrograph showing anti-SQV-4 antibody staining in a lin-12 gain-of-function mutant nematode with multiple psuedovulva (pv) and one functional vulva (v). The formation of the pseduovulval extracellular space coincides with increased expression of SQV-4 in the pseudovulvae.

FIG. 22A is a Nomarski photomicrograph of a lin-11 loss-of-function (lf) mutant nematode with a reduced vulval extracellular space.

FIG. 22B is a photomicrograph showing anti-SQV-4 antibody staining in a lin-11 loss-of-function mutant nematode.

FIG. 23A is a Nomarski photomicrograph of a wild-type L4 larva with fully-grown vulval extracellular space (v). The vulval and uterine (u) extracellular spaces are separated by a thin planar cytoplasmic process of a uterine cell (utse).

FIG. 23B is a Nomarski photomicrograph of a sqv-4 (n2827) loss-of-function (lf) homozygous L4 larva carrying a transgene array (nEx(sqv-4-gfp)) that expresses a rescuing SQV-4-GFP fusion protein under the control of the native sqv-4 promoter. The vulval extracellular space (v) is larger than in the wild-type nematode.

FIG. 23C is a Nomarski photomicrograph of a wild-type L4 larva with a nearly undetectable uterine extracellular space. An almost fully-grown vulval extracellular space (v) is separated from the uterine extracellular space by the anchor cell (ac).

FIG. 23D is a Nomarski photomicrograph of a sqv-4 (n2827) heterozygous L4 larva carrying a transgene array (nEx($P_{hs}$::sqv-4)) that expresses SQV-4 under the control of the heat-shock promoter. The vulval extracellular space is larger than in the wild-type nematode and is larger at the dorsal end than at the ventral end.

FIG. 24A shows the genetic and physical maps for sqv-5. A dashed horizontal line depicts the deficiency qDf10 and indicates the possible extent of the left end point of this deletion, which is between cosmids K10C3 and C03C11. Short solid horizontal lines represent cosmid clones that were assayed in germnlie transformation experiments. Cosmid K09A8, which rescued the sqv-5 mutant phenotype, is shown in bold.

FIG. 24B shows a partial restriction map of K09A8, the cosmid that was used to derive subclones assayed for rescue of the sqv-5 phenotype. The structure of the sqv-5 gene, as deduced from the genomic and cDNA sequences, is shown below the restriction map. Predicted genes in the minimal rescuing fragment are shown with solid boxes indicating exons and an arrow indicating the 3' poly A sequence. The extent of the sqv-5(n3611) deletion is indicated by a horizontal line.

FIG. 24C shows sqv-5 rescue data, which is expressed as the number of transformed lines that rescue/total number of lines tested. The minimal rescuing fragment is indicated with a thick black line. The symbol, ˆ, indicates the introduction of a four base pair addition/frameshift in the T24D1.1 coding sequence. Asterisks (*) indicate the introduction of a nonsense codon (W664opal, Y160amber, G21 opal) in the T24D1.1 coding sequence.

FIG. 25 is a sequence alignment of SQV-5 (SEQ ID NOS: 24 and 132-146) and its human (SEQ ID NOS:25 and 162-177) and *Drosophila melanogaster* (SEQ ID NOS:26 and 147-161) homologs. The numbers on the right indicate amino acid positions. Amino acids that are identical between at least two proteins are shaded in black. The extent of the sqv-5 (n3611) deletion and the sqv-5(n3039) nonsense allele are indicated. The putative transmembrane domains are underlined. The addition of two amino acids (FQ) after the third amino acid in a longer alternatively spliced form of SQV-5 is indicated.

FIG. 26 shows the genomic sequence of the C. elegans sqv-5 (SEQ ID NO:27) minimal rescuing fragment.

FIG. 27 shows the nucleic acid sequence of a C. elegans sqv-5 cDNA (SEQ ID NO:28) containing 5' and 3' untranslated regions (UTR).

FIG. 28 shows the nucleic acid sequence of a human sqv-5 cDNA (ORF 477-2885) (SEQ ID NO:29).

Figure 29:
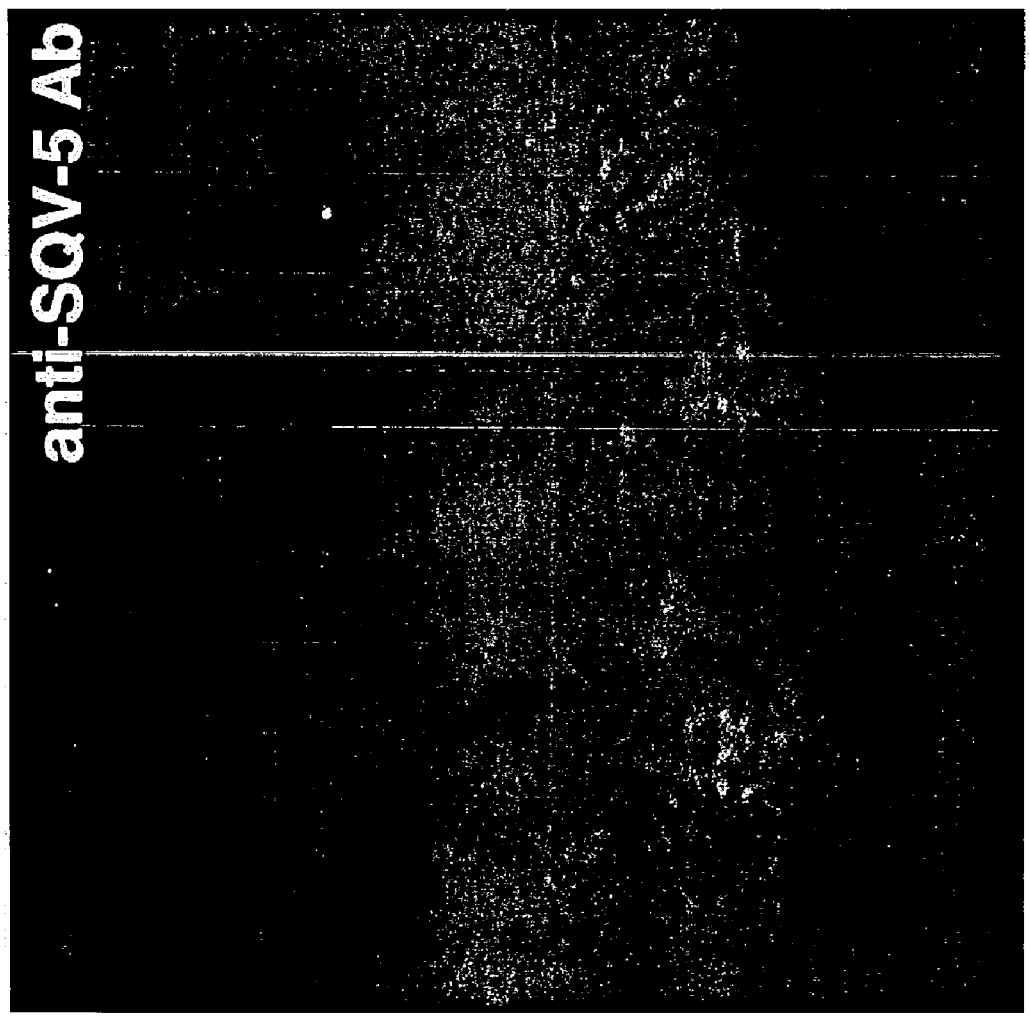

FIG. 29 is a photomicrograph showing that an anti-SQV-5 antibody stained punctuate foci in all vulval cells.

Figure 30:
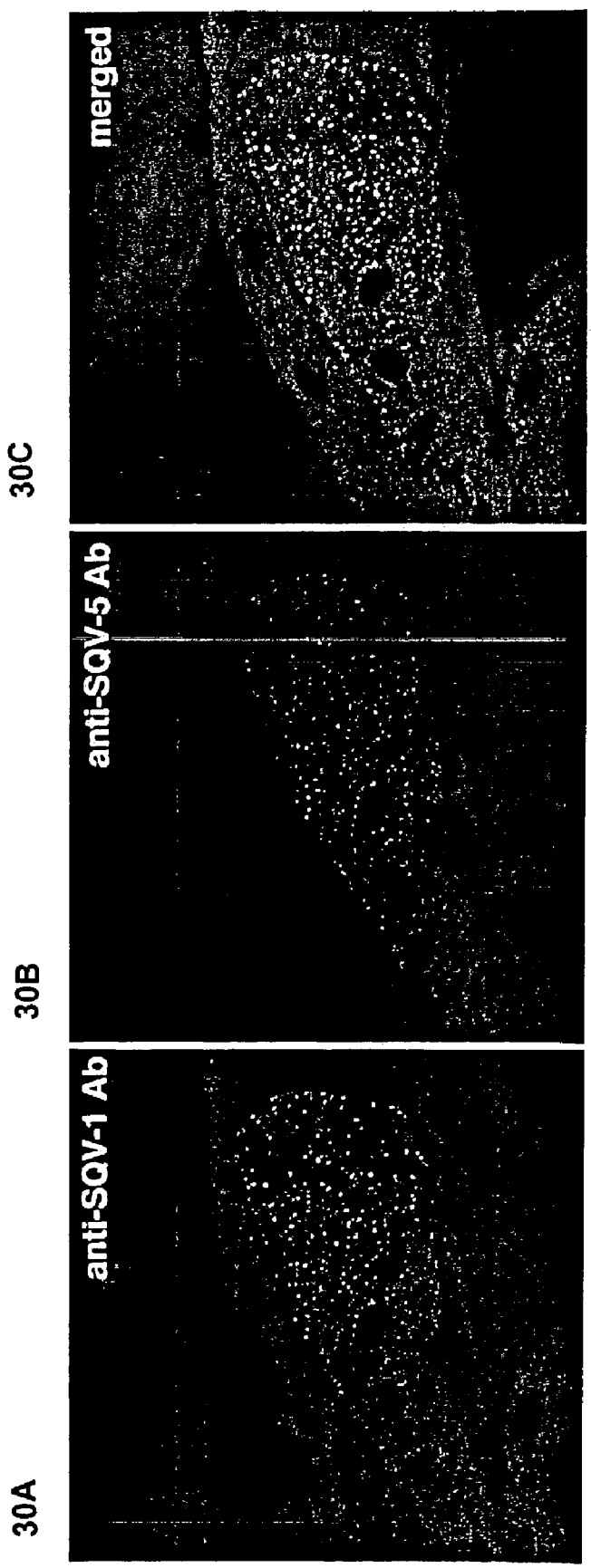

FIG. 30A shows anti-SQV-1 antibody staining in oocytes.

FIG. 30B shows anti-SQV-5 antibody staining in oocytes.

FIG. 30C is a merged image of FIGS. 30A and 30B, showing that SQV-5 and SQV-1 reside in the same subcellular compartment.

Figure 31:
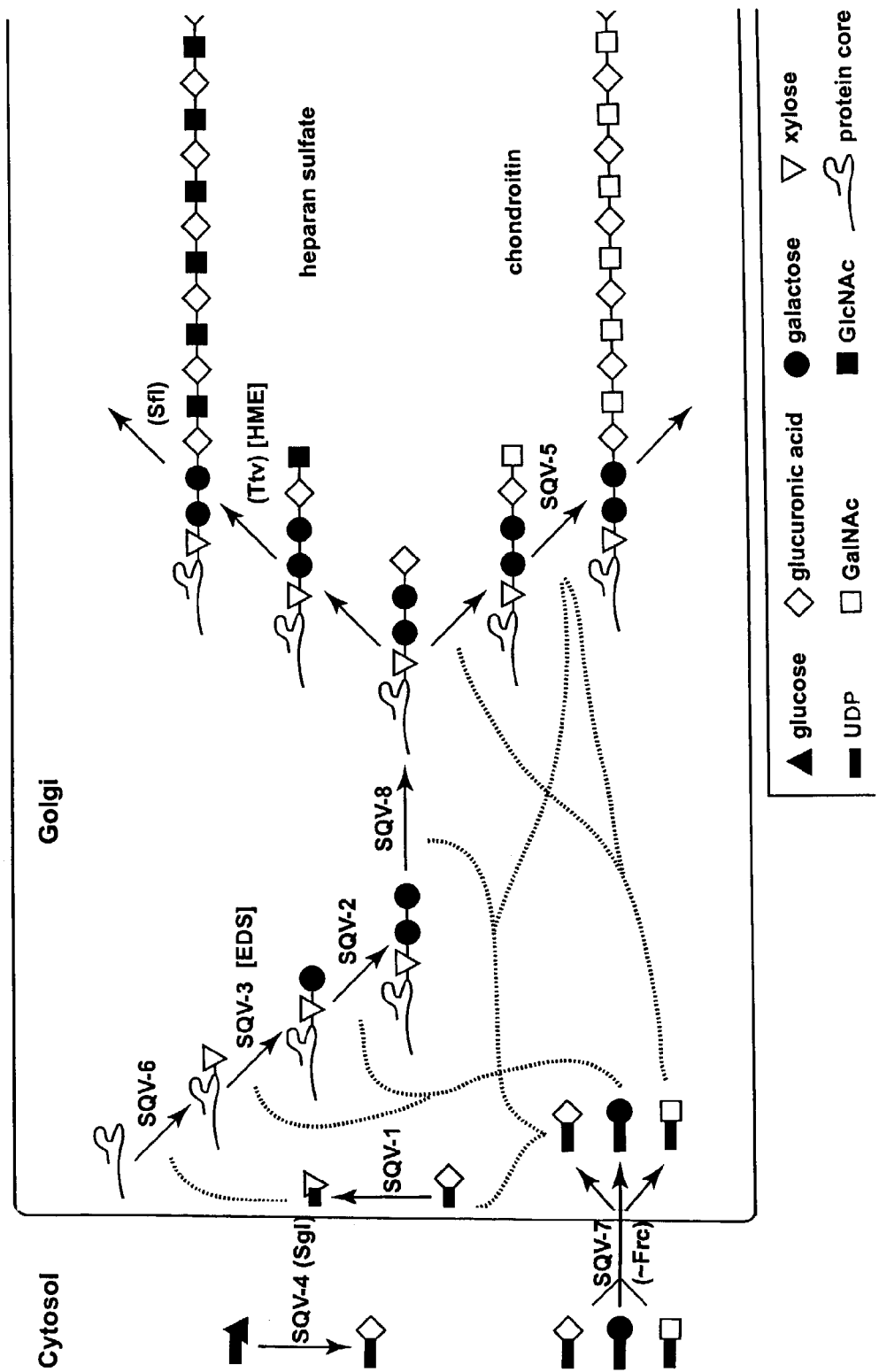

FIG. 31 is a schematic diagram showing a model for the function of the eight sqv genes.

DESCRIPTION OF THE INVENTION

We have identified and characterized five sqv genes, sqv-1, sqv-2, sqv-4, sqv-5, and sqv-6, that function together in a eukaryotic glycosylation pathway. These genes, or their encoded polypeptides, can be used to identify compounds useful in the treatment of a progeroid syndroms, connective tissue diseases, or glycosylation disorders. We have discovered that sqv-1 encodes a UDP-glucuronic acid decarboxylase; sqv-2 and sqv-6 encode glycosyltransferases; sqv-4 encodes a protein similar to UDP-glucose dehydrogenases; and sqv-5 encodes a chondroitin synthase (CS) that controls the biosynthesis of CS glycosaminoglycans (GAGs), but not of heparan sulfate (HS) GAGs.

SQV-1 and SQV-4 act in nucleotide-sugar biosynthesis and synthesize UDP-xylose and UDP-glucuronic acid, respectively. Although all developmental defects caused by mutations in these two genes have been observed in all other sqv mutants, we suspect that additional defects could be present in mutants defective in these two genes because both UDP-glucuronic acid and UDP-xylose are used in non-GAG glycosylation.

SQV-2 is the C. elegans GAG galactosyltransferase II, and SQV-6 is the C. elegans GAG xylosyltransferase; SQV-6, SQV-3, SQV-2, and SQV-8 act in the biosynthesis of the four-sugar linker region (xylose attached to serine-galactose-galactose-glucuronic acid (attached to a repeating disaccharide of glucuronic acid and N-acetylglucosamine or N-acetylgalactosamine) that is necessary for the biosynthesis of chondroitin and heparan sulfate GAGs and that covalently links the GAGs to the protein core of proteoglycans.

SQV-5 is the C. elegans chondroitin synthase. This finding represents the first characterization of developmental defects caused exclusively by defective CS biosynthesis. sqv-5 mutants share the phenotypes observed in other sqv mutants, including defects in cytokinesis during C. elegans embryogenesis and defects in vulval and uterine morphogenesis during postembryonic development. Because all of the developmental defects described in other sqv mutants, including defects in cytokinesis during C. elegans embryogenesis and defects in vulval morphogenesis during postembryonic development, are found in sqv-5 mutants, we propose that these developmental defects are also caused by defects in CS biosynthesis.

sqv-1 Cloning

Figure 1A:
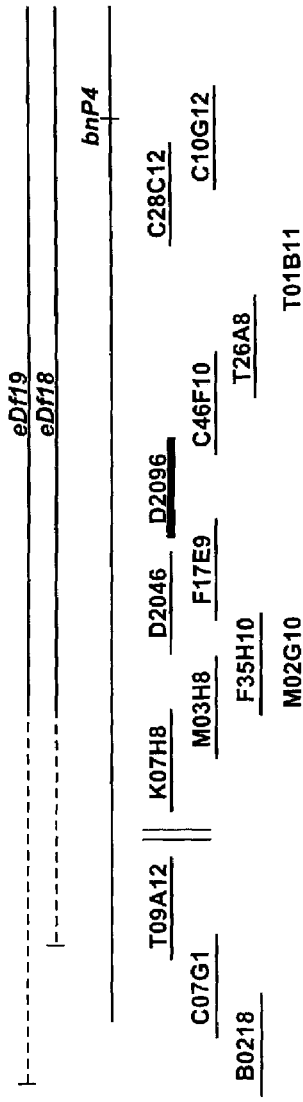
FIG. 1A is a diagram showing genetic and physical maps of the sqv-1 region. The horizontal lines at the top of the panel indicate the extent of a chromosomal deletion in deficiencies eDf18 and eDf19. Dashed horizontal lines depicting eDf18 and eDf19 indicate the possible extent of the left end points of eDf18 and eDf19. These endpoints are described relative to a series of cosmids that contain virtually the entire *C. elegans* genome. These endpoints are between cosmids B0218 and F35H10, for eDf19, and between cosmids C07G1/T09A12 and F35H10, for eDf18. Short solid horizontal lines represent cosmid clones that were assayed in germline transformation experiments (cosmids B0218 and C07G1 were not tested). The parallel vertical lines represent a gap in cosmid coverage of the *C. elegans* genome. The D2096 cosmid that rescued the sqv-1 mutant phenotype is shown in bold.
Figure 1B:
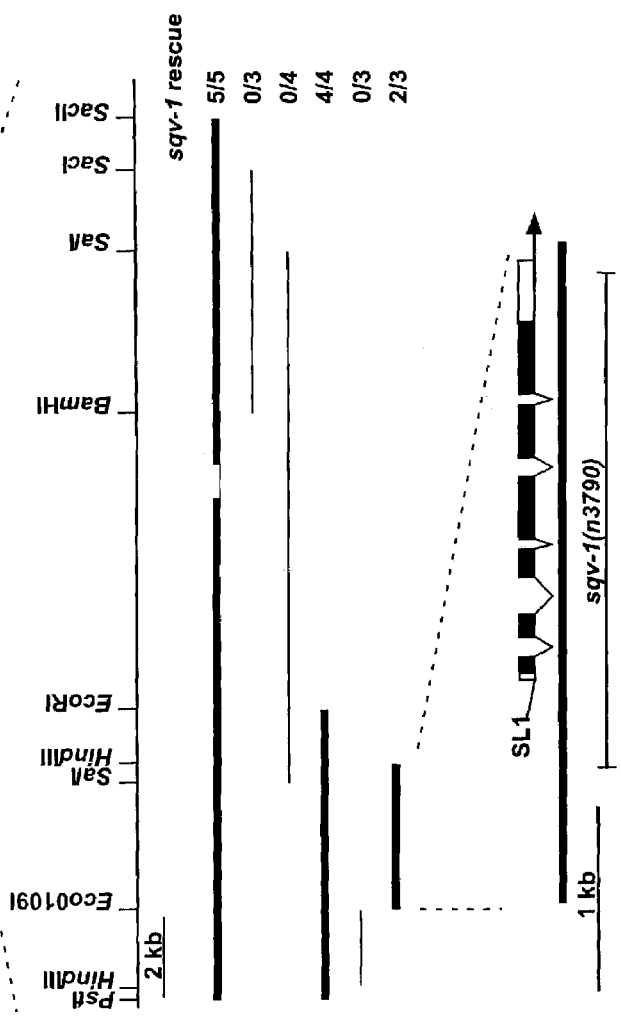
FIG. 1B is a diagram showing the D2096 cosmid subclones that were tested for sqv-1 rescuing activity. Subclones that rescued the sqv-1 mutant phenotype are shown in bold. The rescue results are expressed as the number of transformed lines that rescued/total number of lines tested. At the bottom of the panel is a schematic diagram showing the structure and location of the sqv-1 gene as deduced from the genomic and cDNA sequences relative to the minimal rescuing subclone. Solid boxes indicate exons, and open boxes indicate untranslated sequences. The sqv-1 5' trans-spliced leader, SL1, is indicated, and the arrow indicates the sqv-1 3' poly(A) tail. The extent of the deletion in sqv-1(n3790) is indicated by a horizontal line.

We used a positional approach to clone sqv-1. sqv-1 had been previously mapped between phenotypic markers unc-24 and dpy-20 on LGIV (Herman et al., Proc. Natl Acad. Sci. USA 96:968-73, 1999). We mapped sqv-1 to an approximately 400 kb region between bnP4 and the left endpoint of eDf18 and eDf19 (FIG. 1A). Thirteen cosmids in this interval were tested for the ability to rescue sqv-1 mutants. We found that a single cosmid, D2096, rescued sqv-1. A 3.6 kb Eco0109I-HindIII fragment of D2096, containing a single predicted gene D2096.4 (The C. elegans Sequencing Consortium, Science 282:2012-8, 1998), was sufficient to rescue sqv-1 mutants (FIG. 1B). The nucleic acid sequences of the C. elegans sqv-1 gene and human sqv-1 are shown in FIGS. 1C and 1D.

We used the 3.6 kb C. elegans minimal rescuing fragment as a probe to screen a C. elegans embryonic cDNA library and isolated seven cDNA clones. One of the cDNAs obtained contained 1771 bases of open reading frame, untranslated sequence, 3' poly-A sequence, and a 5' SL1 trans-spliced leader. The SL1 motif is found at the 5' end of many C. elegans transcripts (Krause et al., Cell 49:753-61, 1987). The longest open reading frame (ORF) in this cDNA was identical to that predicted for D2096.4 and was predicted to encode a protein of 467 amino acids. Using a fragment containing this ORF, we detected a single 2.1 kb transcript on a Northern blot of mixed-stage total RNA from wild-type nematodes. The expression of the sqv-1 ORF under the control of the C. elegans heat shock promoters (Stringham et al., Mol. Biol. Cell 3:221-33, 1992) rescued the vulval defect and maternal-effect lethality of sqv-1 mutants, indicating that the predicted coding sequence encoded a functional SQV-1 protein.

We identified six molecular lesions in D2096.4 in five of the six sqv-1 alleles. Five alleles, n2820, n2824, n2828, n2848 and ku246, were missense mutations and one allele, n2819, contained two missense mutations (FIG. 2). The molecular lesion in the sixth allele, n2849, has not been identified. A library of mutagenized worms was screened by PCR to obtain a deletion allele, n3790, which removed the entire coding sequence of sqv-1 (FIG. 1B). Animals homozygous for n3790 showed the same vulval and Mel phenotypes observed in the stronger missense mutations.

SQV-1 Enzymatic Activity

SQV-1 contains a potential transmembrane domain near the amino terminus, suggesting it may be a type II transmembrane protein. It is weakly similar to UDP-glucose epimerases and TDP-glucose dehydratases. SQV-1 is 14% (67/467 amino acids) identical to an E. coli UDP-glucose epimerase and 17% identical to a thymidine diphosphate (TDP)-glucose dehydratase (78/467 amino acids). UDP-glucose epimerases catalyze the interconversion of UDP-glucose and UDP-galactose, and TDP-glucose dehydratases convert TDP-glucose to TDP-4,6-keto-deoxy-glucose. Biochemical assays on bacterially expressed SQV-1 failed to detect either of these enzymatic activities. Because the C. elegans genome contains a UDP-glucose epimerase homolog, C47B2.6 (47% identity to the E. coli gene) and two TDP-glucose dehydratase homologs, F53B1.4 and C01F1.3 (35% and 30% identities to the E. coli genes respectively), we reasoned that SQV-1 is not likely to be the C. elegans UDP-glucose epimerase or TDP-glucose dehydratase.

Further analysis revealed that SQV-1 is more similar to predicted proteins whose function is undefined. We identified and determined the sequence of human cDNA clones from a National Cancer Institute EST project that encode a protein closely related to SQV-1. The most common form of the predicted human protein was 56% (236/420 amino acids) identical to SQV-1, and the *Drosophila melanogaster* CG7979 gene product was 54% identical (239/441 amino acids) to SQV-1 (FIG. 2).

Based on SQV-1's sequence similarity to UDP-glucose epimerases and TDP-glucose dehydratases, we hypothesized that sqv-1 encoded an enzyme that modifies a nucleotide sugar. Many of the previously cloned nucleotide-sugar modifying enzymes involved in GAG biosynthesis do not share a high degree of amino acid identity to SQV-1. Therefore, we tested SQV-1 for enzymatic activities for which the corresponding gene had not yet been cloned in any species. One such enzymatic activity was that of UDP-glucuronic acid decarboxylase, which converts UDP-glucuronic acid to UDP-xylose. UDP-xylose is a donor substrate necessary for the initiation of the GAG-protein core linker region (reviewed by Kjellen et al., *Annu. Rev. Biochem.* 60:443-75, 1991).

Figures 3A, 3B:
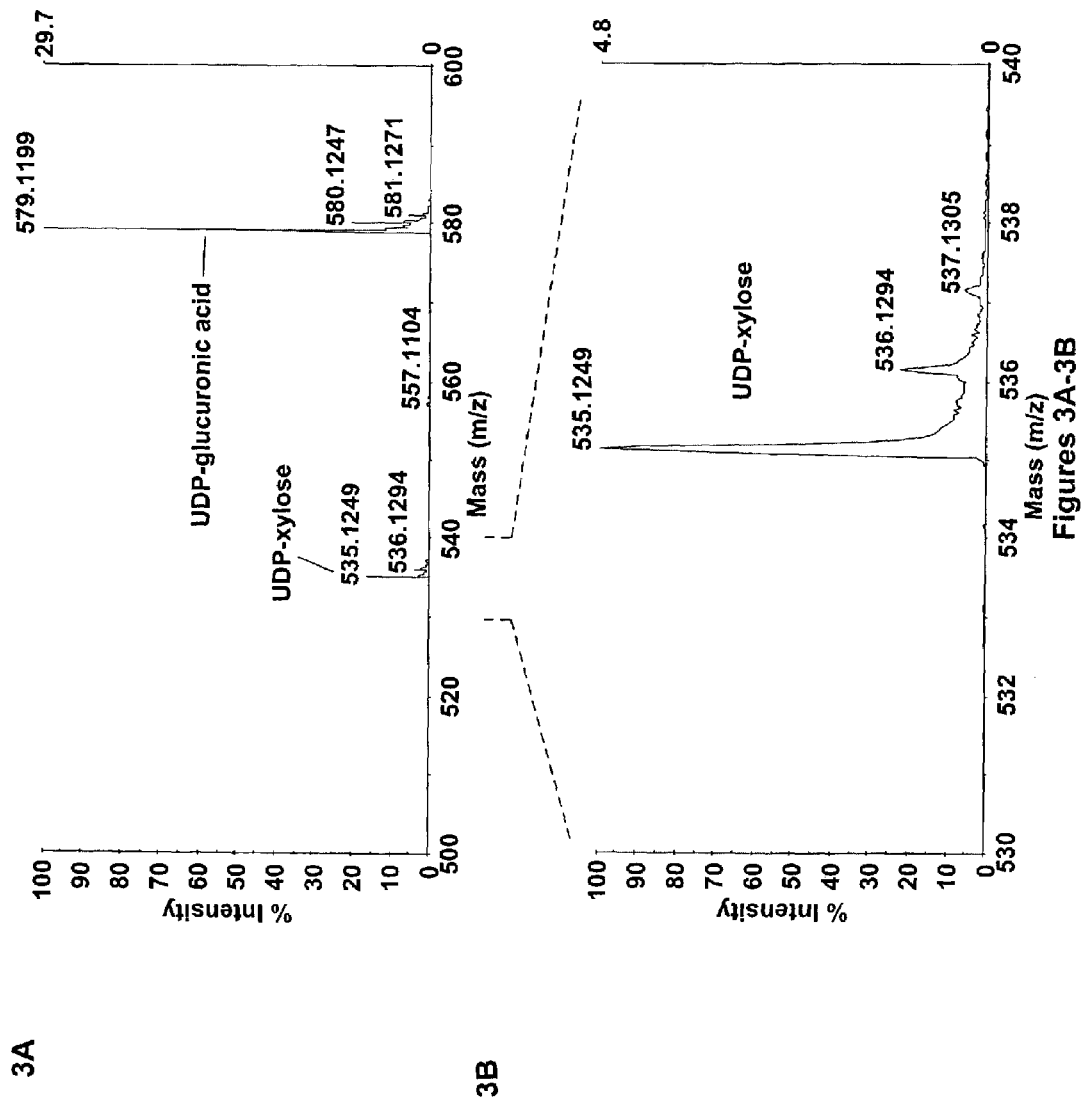
FIG. 3A is a UV trace of extracted ion chromatography (XIC) of mass of 500 to 700 from the SQV-1 reaction. It shows the negative polarity mass spectra of SQV-1 reaction sample. The y-axis indicates the intensity of the spectra, and the x-axis indicates the mass (mass to charge ratio (m/z)). Peaks of mass (m/z) of 500 to 600 are shown.
FIG. 3B shows the magnification of mass spectra for mass (m/z) of 530 to 540. The highest peak at ~535 represents the most abundant mass of UDP-xylose. Smaller peaks at ~536 and ~537 represent isotopic masses of UDP-xylose containing heavy isotopes of carbon, hydrogen, oxygen or nitrogen.
Figures 4A, 4B, 4C, 4D:
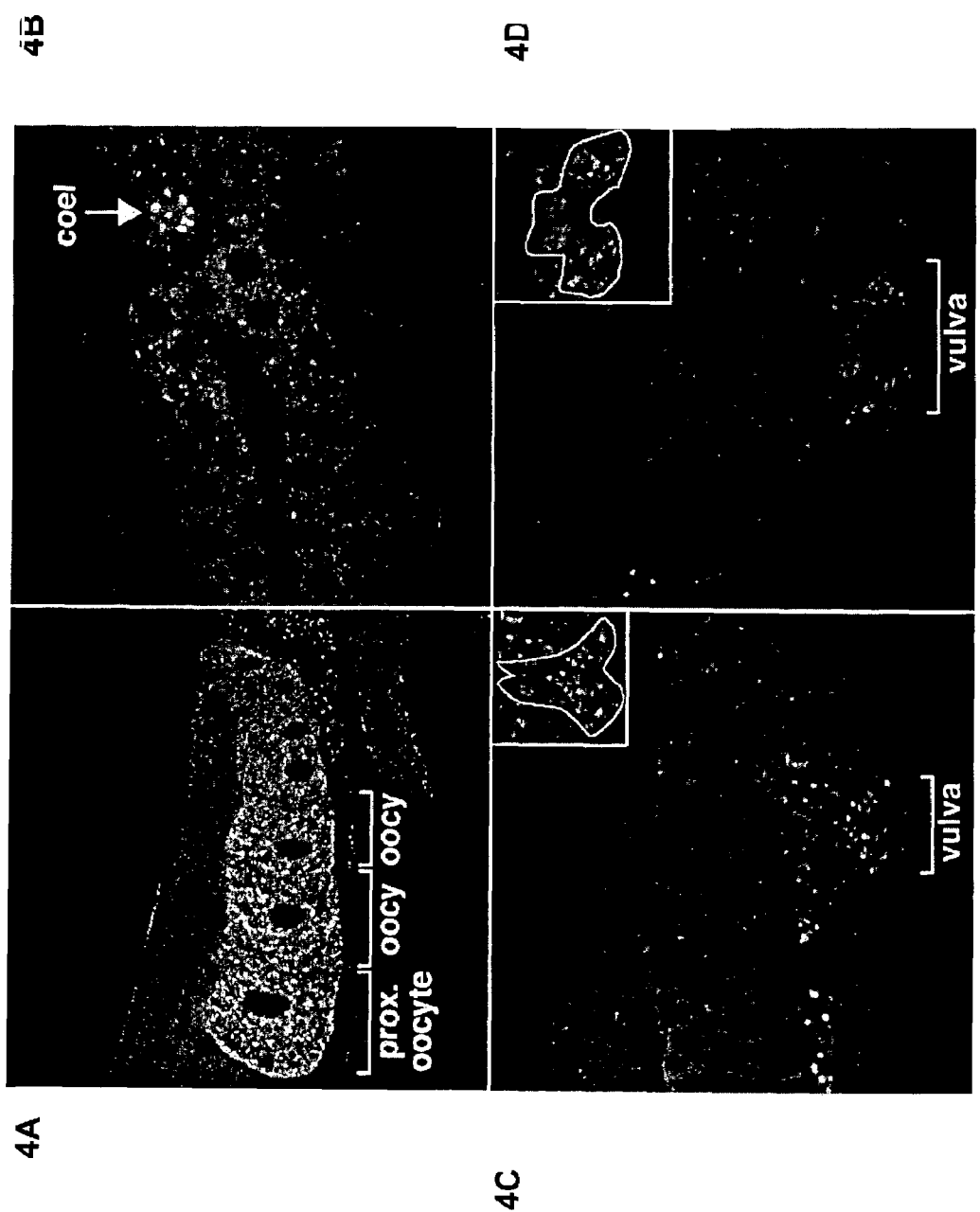
FIG. 4A is a photomicrograph showing anti-SQV-1 antibody staining of oocytes. The three most mature oocytes (oocy), including the most proximal oocyte (prox oocy), are indicated. The oocytes were prepared in a whole-mount staining of wild-type nematodes using an anti-SQV-1-myelin basic protein (MBP) rabbit polyclonal antibodies. SQV-1 antibodies localized to punctate cytoplasmic foci.
FIG. 4B is a photomicrograph showing anti-SQV-1 antibody staining of coelomocytes (coel) in an L4 larva. Coelomocytes are indicated by a white arrow.
FIGS. 4C and 4D are photomicrographs showing anti-SQV-1 antibody staining of vulval cells (v) during vulval morphogenesis in two different focal planes. The location of vulval cells is indicated by brackets. The inset indicates the boundaries of the vulval cells.

We found that purified myelin basic protein (MBP)-SQV-1 fusion protein, in the presence of $NAD^+$ cofactor, generated UDP-xylose from UDP-glucuronic acid. This enzymatic reaction mixture was analyzed using an HPLC coupled to a mass spectrometer. Ion phase reverse polarity HPLC separated the nucleotide sugars and $AND^+$ into three peaks of elution as detected by UV (FIG. 3A). These peaks were determined by mass spectrometry to be the substrate UDP-glucuronic acid, the product UDP-xylose, and the cofactor $NAD^+$. Negative polarity mass spectra identified the masses of the most abundant compounds in the reaction sample as 579 and 535 (FIG. 3B). These masses corresponded to the molecular masses of UDP-glucuronic acid (580) and UDP-xylose (536). The slight difference in molecular mass (579 versus 580 and 535 versus 536) was due to the negative ionization by the mass spectrometer, which removed one hydrogen atom from each compound. The presence of isotopic masses of 536 and 537 corresponded to subpopulations of UDP-xylose containing heavy isotopes such as $^{13}C$.

Even after a long incubation of the reaction mixture (>1 hour) with MBP-SQV-1 protein, a significant amount of UDP-glucuronic acid was left unconverted (FIG. 3B). In other species, the UDP-glucuronic acid decarboxylase reaction is irreversible, but is inhibited by the product, UDP-xylose (John et al., *J. Biol. Chem.* 252:6707-10, 1977). The presence of non-decarboxylated UDP-glucuronic acid in our reaction mixture was likely caused by the UDP-xylose inhibiting UDP-glucuronic acid decarboxylase.

SQV-1 Immunocytochemistry

We generated affinity-purified rabbit polyclonal antibodies raised against SQV-1-GST fusion protein, and rabbit and rat polyclonal antibodies raised against SQV-1-MBP fusion protein. These antibodies were used for immunolocalization experiments and were found to stain punctate foci in the cytoplasm of many cells in wild-type worms (FIGS. 4A-4D). Staining was observed in the vulval and uterine cells (FIGS. 4C and 4D), and stronger staining was observed in oocytes and coelomocytes (FIGS. 4A and 4B), cells in the pseudocoelom that may function as scavengers. This punctate staining was not seen in animals homozygous for the sqv-1 (n3790) null allele. The presence of SQV-1 in the vulva of wild-type animals is consistent with SQV-1 having a function in vulval morphogenesis. The presence of SQV-1 in oocytes is also consistent with a cell-autonomous role in embryonic development.

sqv-1 Rescuing Construct

A translational fusion of the sqv-1 open reading frame (ORF) and green fluorescent protein (GFP), fused to the sqv-1 carboxy terminus was expressed under the control of the endogenous sqv-1 promoter in sqv-1 mutants. This construct rescued sqv-1 mutants vulval defect and maternal-effect lethality. SQV-1-GFP was expressed in many of the same tissues in which SQV-1 antibody staining had been seen, including the vulva, gut, pharynx, seam cells and coelomocytes.

SQV-1 Colocalizes with the SQV-7 Nucleotide-Sugar Transporter

We reasoned that the punctate cytoplasmic staining of anti-SQV-1 antibodies was likely caused by the localization of SQV-1 to a specific subcellular compartment, such as the Golgi bodies. SQV-7, a multipass transmembrane protein capable of transporting nucleotide sugars required for GAG biosynthesis across membranes (Hennan et al., *Proc. Natl. Acad. Sci. USA* 96:974-9, 1999; Berninsone et al., *Proc. Natl. Acad. Sci. USA* 98:3738-43, 2001), was also expected to localize to the Golgi. SQV-7 was predicted to translocate UDP-glucuronic acid, UDP-galactose and UDP-N-acetylgalactosamine from the cytosol to the lumen of the Golgi (Berninsone et al., *Proc. Natl. Acad. Sci. USA* 98:3738-43, 2001). To test whether SQV-1 and SQV-7 colocalized, we raised rabbit polyclonal antisera against a 26 amino acid peptide corresponding to the SQV-7 carboxy-terminus and affinity-purified the antisera against the same SQV-7 peptide.

We found that anti-SQV-7 antibodies stained punctate foci in the cytoplasm of several tissues in wild-type nematodes, including the vulva, seam cells, distal tip cells, and oocytes (FIGS. 5A-5D). The presence of SQV-7 in the vulva and oocytes is consistent with SQV-7 functioning in both vulval morphogenesis and embryonic development. We obtained a null allele of sqv-7, (n3789), that deleted the entire ORF by PCR screening a deletion library (FIG. 5E). In animals homozygous for the sqv-7(n3789) null allele, SQV-7 antibodies did not stain punctate foci in the vulval, seam and distal tip cells or oocytes.

A translational fusion, which contained the sqv-7 ORF fused with GFP at the SQV-7 carboxy terminus, was expressed under the control of the endogenous sqv-7 promoter in wild-type nematodes that were assayed by fluorescence microscopy for GFP expression. Punctate GFP fluorescence was observed in seam cells, consistent with the seam cell staining observed with anti-SQV-7 antibodies. In cells that had only a low level of SQV-7-GFP fluorescence, the SQV-7 GFP colocalized with small granular bodies in seam cells, which had been previously identified as Golgi bodies by Singh et al. (Singh et al., *Nematologica* 24:63-71, 1978). SQV-7's localization to the Golgi membranes is consistent with its proposed function as a nucleotide-sugar transporter.

Using rat anti-SQV-1 antibodies and rabbit anti-SQV-7, we found that SQV-1 and SQV-7 colocalized in the same or adjacent compartments in oocytes (FIG. 6A-C), in vulval cells, and in the pharynx. Based on our results with SQV-1 and SQV-7 antibodies, we predicted that significant amounts of SQV-1 and SQV-7 protein would be present in the Golgi bodies of several cell types, including oocytes, and present at lower concentrations in most, if not all, other cells.

Through sequence analysis, we found that homologs of *C. elegans* SQV-1, in human and *Drosophila*, have a potential transmembrane domain near the amino terminus, suggesting that the conversion of UDP-glucuronic acid to UDP-xylose is made in the Golgi lumen in many other species. Indeed, Kearns et al. (*J. Biol. Chem.* 268, 11097-1041993) found that UDP-glucuronic acid decarboxylase activity and xylosyltransferase activities are similarly localized in chondrocytes. In chondrocytes, xylosylation of GAGs is carried out in the vesicular regions of endoplasmic reticulum (ER) and continues in the early Golgi (Vertel et al., *J. Biol. Chem.* 268:11105-12, 1993). Most glycosyltransferases, including all glycosyltransferases involved in the biosynthesis of GAGs, act in the lumen of the ER and Golgi (reviewed by Varki, *Trends Cell Biol.* 8:34-40, 1998). Production of UDP-xylose in the lumen of the Golgi may allow for more efficient feedback inhibition of the decarboxylation reaction by restricting the diffusion of UDP-xylose. It seems likely that SQV-1 and SQV-7 act in the late ER as well as in the Golgi. Decarboxylation of UDP-glucuronic acid is the only reaction known to produce UDP-xylose. Interestingly, mammalian UDP-xylose transporter activities for transporting UDP-xylose from the cytosol to the Golgi lumen have been described biochemically using purified Golgi and ER vesicles (Kearns et al., *J. Biol. Chem.* 268:11097-104, 1993).

sqv-7 Mutant Progeny Fail to Initiate Cytokinesis

Herman et al. (*Proc. Natl. Acad. Sci. USA* 96:968-73, 1999) reported that most progeny of mutants homozygous for stronger mutant alleles of sqv-1 to -7 arrest as one-cell stage embryos. We examined the embryonic arrest phenotype of sqv mutants by comparing the development of wild-type embryos and the progeny of mutants homozygous for the sqv-7(n3789) null allele.

In wild-type nematodes, fertilization triggers meiosis in oocytes and extrusion of a polar body, which contains the excess maternal DNA that remains after meiosis. We observed fertilization in wild-type embryos, and found that at about this time the oocyte plasma membrane and eggshell become visible, and the space between the plasma and vitelline membranes expands (FIG. 7A-7C). Shortly before the fusion of the maternal and paternal haploid pronuclei, the embryonic plasma membrane constricted in a process termed pseudocleavage (FIG. 7B). The maternal and paternal pronuclei, which were initially located at opposite ends of the embryo, then migrated to the middle of the embryo where they fused and then rotated around each other (FIGS. 7C and 7D). Aster and mitotic spindle formation and nuclear division then occurred, followed by cytokinesis (FIG. 8A-8C).

While sqv-7 null mutant oocytes were fertilized normally, we failed to detect polar body extrusion, pseudocleavage, or separation of the plasma membrane and eggshell in most sqv-7 null mutant embryos (FIG. 7D-7F). The timing of migration, fusion, rotation of the sperm and egg pronuclei, and separation of postmitotic nuclei was similar to that observed in wild-type embryos (FIG. 7D-7F). In sqv-7 null mutants, however, nuclear division was not accompanied by the initiation of cytokinesis (FIG. 8D-8F). Following the first nuclear division, the sqv-7 null mutant embryos contained at least three nuclei (FIG. 8F), in contrast to the two nuclei normally observed in wild-type embryos (FIG. 8C). We suspected that the extra nuclei were derived from unextruded polar bodies. DAPI staining confirmed that these extra nuclei contained DNA. These nuclei divided repeatedly in the absence of cytokinesis, resulting in a multinucleate embryo.

Cellular Express of SQV-1 and SQV-7

We found that SQV-1 is expressed at a high level in coelomocytes, but SQV-7 is not. Conversely, SQV-7 is expressed at a high level in seam cells, but SQV-1 is not. One possible explanation for these differences in cellular expression is that different levels of SQV proteins result in different compositions of GAGs. For example, if a large amount of nucleotide sugars, used in GAG biosynthesis, is present in a cell, but only a small amount of UDP-xylose is available, because of low expression of SQV-1, such a cell may have a smaller number of GAG molecules, but the length of each GAG molecule may be longer. Conversely, if UDP-xylose levels in a cell are high, but other nucleotide sugar levels are low, such a cell may have a larger number of short GAG molecules. Alternatively, the main function of SQV-1 and SQV-7 in coelomocytes and seam cells may not be the biosynthesis of chondroitin and heparan sulfate GAGs.

Cloning of sqv-2 sqv-2 was previously mapped to the left of lin-31 on LGII. We further mapped sqv-2 to an interval between sup-9 and lin-31. Although twenty-seven cosmids in this interval were assayed, none rescued the sqv-2 mutant phenotype (FIG. 9A).

We examined the DNA sequence corresponding to the gaps between the cosmids in this interval and found a predicted gene, Y110A2AL.14, that is weakly similar to galactosyltransferases. Because other sqv genes function in the biosynthesis of chondroitin and/or heparan sulfate GAGs, we reasoned that sqv-2 might also encode a protein involved in GAG biosynthesis. We sequenced the sqv-2 candidate gene, Y110A2AL.14 (FIG. 9B), in two of the strongest sqv-2 alleles, n3037 and n3038. n3037 and n3038 mutants display a maternal effect lethal (Mel) phenotype. The nucleic acid sequences of *C. elegans* SQV-2 and the SQV-2 human homolog are shown in FIGS. 9C and 9D, respectively. In the n3037 allele, we identified a nonsense mutation in the codon that codes for amino acid 225 (FIG. 10), and in n3038, we identified a missense mutation at the predicted start codon (FIG. 10). In a weak allele of sqv-2, n2826, which gives live progeny, we identified a missense mutation that encoded a glycine-to-arginine substitution at amino acid position 99. The molecular lesion present in the weakest allele of sqv-2, n2840, has not yet been identified.

We sequenced two cDNA clones, yk94e4 and yk292g2, that correspond to Y110A2AL.14. The yk292g2 clone contained 990 bases of ORF, 17 bases of 5' untranslated region (UTR), and 121 bases of 3' UTR. The 5' end contained three bases that corresponded to a 5' SL1 trans-spliced leader, which marks the 5' end of many *C. elegans* transcripts (Krause et al., *Cell* 49:753-61, 1987). The 3' end contained a poly A sequence. The longest ORF in this cDNA is identical to Y110A2AL.14 and is predicted to encode a protein of 330 amino acids. The yk94e4 clone lacked the 5' end of Y110A2AL.14. The expression of the longest ORF in yk292g2 under the control of the *C. elegans* heat-shock promoters (Stringham et al., *Mol. Biol Cell* 3:221-3, 1992) rescued the sqv-2 mutant phenotype.

RNA-mediated interference (RNAi), a method of specific gene inactivation (Fire et al., *Nature* 391:806-11, 1998), was induced by feeding wild-type nematodes *E. coli* expressing double-stranded Y110A2AL.14 RNA. The progeny of these animals exhibited a variable Mel phenotype very similar to the strongest alleles of sqv-2.

sqv-2 Encodes a Protein Similar to GAG Galactosyltransferase II

The predicted SQV-2 protein contains a putative transmembrane domain near the amino terminus, suggesting it may be a type TI transmembrane protein. All glycosyltransferases identified to date are type II transmembrane proteins that act in the lumen of the ER/Golgi. SQV-2 was 29% (95/330 amino acids) identical to a *Drosophila* homolog and 40% (132/330 amino acids) identical to a human homolog (FIG. 10). Recently, the human homolog of SQV-2 was identified as a GAG galactosyltransferase II by Bai et al. (*J. Biol. Chem.* 276:48189-95, 2001).

SQV-2 Has GAG Galactosyltransferase II Activity

We assayed a recombinant Protein A-SQV-2 fusion protein expressed in COS7 cells for galactosyltransferase II activity. The SQV-2 fusion protein specifically catalyzed addition of galactose to a disaccharide acceptor, galactose-(β1,4)-xylose (β1)-O-benzyl (Galβ1,4Xylβ1-O-Bn), which was used to demonstrate the acceptor substrate specificity of the human GAG galactosyltransferase II (Bai et al., *J. Biol. Chem.* 276: 48189-95, 2001) (Table 1).

TABLE 1

Acceptor substrate specificity of SQV-2 fusion protein.

| Acceptor Substrates | | Enzyme Activity (pmol/h/mL medium) |
|---|---|---|
| Monosaccharides (5 mM) | Xylβ1-O-Bn | 0 |
| | Xylβ1-O-naphthol | 0 |
| | Galβ1-O-NM | 0 |
| | GalNAcβ1-O-Bn | 0 |
| | GlcNAcβ1-O-NM | 0 |
| Disaccharides (5 mM) | Galβ1,4Xylβ1-O-Bn | 2660 |
| | Galβ1,3GalNAcα1-O-NM | 1 |
| | Galβ1,3Galβ1-O-NM | 3 |
| | Galβ1,4GlcNAcβ1-O-NM | 0 |
| | Galβ1,3GlcNAcβ1-O-NM | 0 |
| | GlcNAcβ1,3Galβ1-O-NM | 6 |
| | Manα1,6Manα1-O—C$_{10}$ | 0 |

Table Legend: NM, naphthalenemethanol, Bn, benzyl; C$_{10}$, O-decenyl (CH$_2$)$_8$ CH=CH$_2$ Galactosyltransferase activity was assayed in vitro using UDP-[$^3$H]galactose together with various acceptor substrates. None of the other acceptors tested acted as an acceptor for glycosylation by SQV-2, including the monosaccharide acceptor counterpart, xylose-(β1)-O-benzyl (Xylβ1-O-Bn) and a related acceptor, xylose-(β1)-O-naphthalenemethanol (Xylβ1-O-naphthol). Xylβ1-O-Bn, or a chemically similar acceptor, have previously been used to demonstrate the acceptor substrate specificity of SQV-3 GAG galactosyltransferase I and its human homologs (Almeida et al., *J. Biol. Chem.* 274:26165-71, 1999; Okajimaetal., *J. Biol. Chem.* 274:22915-8, 1999b; Bulik et al., *Proc. Natl. Acad. Sci. USA* 97:10838-43, 2000), which are predicted to catalyze a previous glycosylation step to that catalyzed by SQV-2.

Molecular Identification of sqv-6 sqv-6 was previously mapped to the left of the stP3 polymorphism of LGV (Herman et al., *Proc. Natl. Acad. Sci. USA* 96:968-73, 1999). We further mapped sqv-6 to the left of cosmid W07B8, near unc-34. Eleven cosmids to the right of unc-34 were assayed for the ability to rescue the sqv-6 mutant phenotype, but none rescued (FIG. 11A).

We examined the DNA sequence in the gaps in the cosmid coverage near the cosmid W07B8 and unc-34 and found a gene, Y50D4C.d, that is similar to two recently identified human GAG xylosyltransferases (Gotting et al., *J. Mol. Biol.* 304:517-28, 2000). We noticed that unc-34 is is located 5' to Y50D4C.d. By nucleic acid sequencing, we identified a molecular lesion, a nonsense mutation causing a deletion of the last 42 amino acids of the predicted protein product, corresponding to sqv-6 (n2845), in the ORF of Y50D4C.d (FIG. 11B). The nucleic acid sequence of *C. elegans* SQV-6 is shown in FIG. 11C.

We sequenced PCR-amplified cDNA and 5'-rapid amplification of cloned ends (RACE) products corresponding to Y50D4C.d. We determined that the cDNA contains a 5' SL1 trans-spliced leader, 23 bases of 5' UTR, and 2418 bases of ORF, including two additional 5' exons not found in Y50D4C.d. The longest ORF in this cDNA, including the additional exons, is predicted to encode a protein of 806 amino acids. The expression of this ORF under the control of the *C. elegans* heat-shock promoters (Stringham et al., *Mol. Biol. Cell* 3:221-33, 1992) rescued the sqv-6 mutant phenotype.

sqv-6 Encodes a Protein Similar to GAG Xylosyltransferases

The SQV-6 protein is 23% (182/806 amino acids) and 24% (193/806 amino acids) identical to human xylosyltransferases I and II, respectively (FIG. 12A). The predicted SQV-6 protein and human xylosyltransferase II contain a putative transmembrane domain near the amino terminus, and are likely type II transmembrane proteins. No start codon and no presumptive transmembrane domain has been defined in human xylosyltranferase I (Gotting et al., *J. Mol. Biol.* 304:517-28, 2000).

sqv-6 can Correct a Xylosyltransferase Defect in CHO Cells

We tested the ability of sqv-6 to act as a GAG xylosyltransferase by testing its ability to complement Chinese hamster ovary (CHO) mutant cells defective in this enzymatic activity (FIG. 12B). Wild-type CHO-K1 cells incorporated most exogeneous $^{35}$SO$_4$ into GAGs; 55% (+/−5%) and 40% (+/−5%) of incorporated $^{35}$SO$_4$ was present in chondroitin sulfate and heparan sulfate, respectively (Esko et al., *Proc. Natl. Acad. Sci. USA* 82:3197-201, 1985). The mutant CHO pgsA-745 cells, which are defective in the biosynthesis of GAGs, were dramatically reduced in GAG xylosyltransferase activity (Esko et al., *Proc. Natl. Acad. Sci. USA* 82:3197-201, 1985).

We transiently transfected mutant pgsA-745 cells with a plasmid encoding SQV-6. We then tested GAG xylosyltransferase activity in the mutant pgsA-745 cells and in the sqv-6 transiently transfected cells. We found that the sqv-6 transiently transfected cells were able to incorporate $^{35}$SO$_4$ into macromolecules inside and on the surface of the cells (Table 2).

TABLE 2

Content of sulfated GAGs in CHO cells transformed with sqv-6

| Strain | Temp. °C. | Average $^{35}$S incorporation cpm / μg protein | Percent incorporation |
|---|---|---|---|
| wild-type CHO-K1 trial 1 | 37 | 1364 | 100 |
| mutant pgsA-745 trial 1 | 37 | 16 | 1 |
| pgsA-745 + vector trial 1 | 37 | 16 | 1 |
| pgsA-745 + sqv-6 trial 1 | 37 | 354 | 26 |
| wild-type CHO-K1 trial 2 | 37 | 766 | 100 |
| mutant pgsA-745 trial 2 | 37 | 19 | 2 |
| pgsA-745 + vector trial 2 | 37 | 19 | 2 |
| pgsA-745 + sqv-6 trial 2 | 37 | 207 | 27 |
| wild-type CHO-K1 trial 3 | 37 | 436 | 100 |
| mutant pgsA-745 trial 3 | 37 | 10 | 2 |
| pgsA-745 + vector trial 3 | 37 | 10 | 2 |
| pgsA-745 + sqv-6 trial 3 | 37 | 88 | 20 |
| wild-type CHO-K1 trial 4 | 30 | 890 | 100 |
| mutant pgsA-745 trial 4 | 30 | 15 | 2 |
| pgsA-745 +vector trial 4 | 30 | 20 | 2 |
| pgsA-745 + sqv-6 trial 4 | 30 | 286 | 32 |
| wild-type CHO-K1 trial 5 | 30 | 1014 | 100 |
| mutant pgsA-745 trial 5 | 30 | 23 | 2 |
| pgsA-745 + vector trial 5 | 30 | 23 | 2 |
| pgsA-745 + sqv-6 trial 5 | 30 | 163 | 16 |

The average $^{35}$S incorporation into polysaccharides in two wells of CHO cells are shown in Table 2. In five separate trials, $^{35}$SO$_4$ incorporation in the sqv-6 transfected cells ranged from 16% to 27%. In contrast, $^{35}$SO$_4$ incorporation ranged from 1% to 2% in the untransfected pgsA-745 cells and in cells transfected with the vector alone.

Molecular Identification of sqv-4 sqv-4 had been mapped between unc-42 and sma-1 on LGV (Herman et al., *Proc. Natl. Acad. Sci. USA* 96:968-73, 1999). We then mapped sqv-4 to an approximately 300 kb region between the left endpoint of sDf35 and emo-1. We then carried out germline transformation rescue experiments. Of the 13 cosmids in this interval tested, two overlapping cosmids, C32C4 and C04G9, rescued sqv-4 (FIG. 13A). Within the overlapping region between C32C4 and C04G9, we identified a 4.8 kb EcoRV-XhoI fragment, containing a single gene, F29F11.1, that was sufficient to rescue the sqv-4 mutant phenotype (FIG. 13B).

We used this 4.8 kb minimal rescuing fragment as a probe to screen a *C. elegans* embryonic cDNA library and isolated six cDNA clones. One of the cDNAs we obtained appeared to be complete; it contained 1443 bases of open reading frame, 142 bases of untranslated sequence, a 3' poly-A sequence, and a 5' SL1 trans-spliced leader, a sequence found at the 5' end of many *C. elegans* transcripts (Krause et al., *Cell* 49:753-61, 1987). The longest open reading frame within this cDNA is identical to F29F11.1 (FIG. 13C) and is predicted to encode a 481 amino acid polypeptide. Using this cDNA as a probe, we detected a single 1.9 kb transcript in *C. elegans* mixed-stage total RNA on a northern blot. The nucleic acid sequence of *C. elegans* sqv-4 is shown in FIG. 13D.

We expressed this presumptive sqv-4 open reading frame (ORF) under the control of *C. elegans* heat-shock promoters (Stringham et al., *Mol Biol. Cell* 3:221-33, 1992) and found that this expression rescued the sqv-4 mutants vulval defect and maternal-effect lethality. This indicated that the predicted coding sequence encodes a functional SQV-4 protein (Table 3).

TABLE 3 sqv-4 mutant phenotype rescue by heat-shock induced expression of sqv-4.

| Heat shock (hours)[a] | Stage[b] | % non-Sqv[c] (n) | % Fertile[d] (n) |
|---|---|---|---|
| 1 | embryo | 13 (31) | 3 (31) |
| 7 | embryo | 32 (19) | 5 (19) |
| 16 | embryo | 100 (6) | 0 (6) |
| 22 | embryo/L1 | 95 (40) | 0 (40) |
| 38 | L1/L2 | 100 (24) | 0 (24) |
| 45 | L1/L2 | 100 (15) | 4 (24) |
| 54 | L2/L3 | 100 (13) | 0 (13) |
| 63 | L3/L4 | 33 (15) | 100 (15) |
| 88 | adult | — | 94 (17) |
| 117 | adult | — | 38 (24) |

[a]The time of heat shock after the eggs were laid.
[b]Developmental stage (as determined by visual examination using a dissecting microscope) at which heat-shock treatment occurred.
[c]% non-Sqv, percentage of Rol animals that rescued the L4 vulval phenotype.
[d]% Fertile, number of Rol animals that rescued the Mel phenotype (that had progeny grow to adulthood).
The numbers in parenthesis (n) indicate the total numbers of animals examined.

sqv-4(n2827)/nT1(n754) adult hermaphrodites carrying an extrachromosomal array of sqv-4 coding sequence fused to the *C. elegans* heat-shock promoters and a Rol marker were allowed to lay eggs at 20° C. for two hours. SQV-4 expression was then induced by a thiry minute heat-shock treatment at 33° C.

We found that heat-shock-induced expression of sqv-4 from late embryogenesis through the second larval (L2) stage was sufficient to rescue the sqv-4 vulval defect, but failed to rescue the maternal-effect lethality. To rescue maternal-effect lethality, heat-shock-induced expression of sqv-4 is required in third or fourth stage (L3-L4) larvae or in young adults. These data indicated that sqv-4 acts during at least two distinct phases of *C. elegans* delopment.

We identified molecular lesions in F29F11.1 in sqv-4 mutants. Both mutant alleles, n2827 and n2840, are missense mutations that are predicted to cause an arginine-to-histidine substitution at amino acid position 353 and a threonine-to-isoleucine substitution amino acid position 420, respectively (FIG. 14).

RNA-mediated interference (RNAi) is a method that allows the inactivation of specific genes (Fire et al., *Nature* 391:806-11, 1998). We injected wild-type nematodes with double-stranded sqv-4 RNA, and found that the progeny of these injected animals exhibited a Mel phenotype similar to that of sqv-4 mutants. When wild-type nematodes were fed a strain of *E. coli* that expresses double-stranded sqv-4 RNA (RNAi by feeding), the progeny of these animals exhibited a variable Sqv and Mel phenotype.

sqv-4 Encodes a Protein Similar to UDP-Glucose Dehydrogenases

The predicted SQV-4 protein is similar in amino acid sequence to a family of UDP-glucose dehydrogenases from vertebrates, insects and plants (FIG. 14). UDP-glucose dehydrogenase catalyzes the conversion of UDP-glucose and $NAD^+$ to UDP-glucuronic acid and NADH (Strominger et al., *J. Amer. Chem. Soc.* 76:6411-6412, 1954; Hempel et al., *Protein Science* 3:1074-1080, 1994) (FIG. 15A). Two molecules of $NAD^+$ are converted to NADH for each molecule of UDP-glucose that is converted to UDP-glucuronic acid (Strominger et al., *J. Amer. Chem. Soc.* 76:6411-6412, 1956). Of the 481 amino acids of SQV-4, 304 (63%), 304 (63%) and 271 (56%) amino acids are identical to human, *Drosophila melanogaster*, and *Arabidopsis thaliana* UDP-glucose dehydrogenases, respectively (FIG. 14). The two amino acids, R353 and T420, that are altered in the sqv-4 mutant alleles, are conserved among all known metazoan UDP-glucose dehydrogenases.

SQV-4 Has UDP-Glucose Dehydrogenase Activity

We expressed recombinant SQV-4 protein in *E. coli* and tested the bacterially-expressed protein for UDP-glucose dehydrogenase activity (FIG. 15A). Enzymatic activity was measured by monitoring the reduction of $NAD^+$ at 340 nm in the presence of UDP-glucose or other nucleotide sugars. Spectrophotometric measurement indicated that UDP-glucose dehydrogenase activity was increased at least 20-fold in lysates containing wild-type SQV-4 protein compared to lysates from cells transfected with either the vector alone or containing mutant SQV-4 protein. Bacterially-expressed SQV-4 protein that contained a histidine for arginine substitution at amino acid position 353, corresponding to the sqv-4 mutant allele, n2827, resulted in a greater than 20-fold decrease in UDP-glucose dehydrogenase activity (FIG. 15B). Substitution of isoleucine for threonine at amino acid position 420, corresponding to the mutant allele n2840, caused the SQV-4 protein to become insoluble. This insoluble protein could not be tested for enzymatic activity. $NAD^+$ reduction was undetectable if UDP-glucose was replaced with TDP-, ADP-, CDP- or GDP-glucose, or UDP-galactose, -mannose, -glucuronic acid, or —N-acetyl-glucosamine.

We measured the initial velocities of this reaction varying concentrations of either UDP-glucose or $NAD^+$. A double-reciprocal plot of the initial velocities revealed a $K_m$ of 0.2 mM for UDP-glucose (FIG. 16A), and a $K_m$ of 0.2 mM for $NAD^+$ (FIG. 16B). These $K_m$ values were comparable to those of UDP-glucose dehydrogenases from other species (e.g., chicken UDP-glucose dehydrogenase, which has $K_m$s of 0.5 mM for UDP-glucose and 0.9 mM for NAD$^+$; *E. coli*, which has K$_m$s of 1 mM for UDP-glucose and 0.05 mM for NAD$^+$; and *Streptococcus pyogenes* UDP-glucose dehydrogenase, which has K$_m$'s of 0.02 mM for UDP-glucose and 0.06 mM for NAD$^+$ (Bdolah et al., *Biochim. Biophys. Acta* 159:176-178, 1968; Schiller et al., *Biochim. Biophys. Acta* 293:1-10, 1973; Campbell et al., *J. Biol. Chem.* 272:3416-3422, 1997)).

SQV-4 Protein Expression is Dynamically Regulated in Vulval Cells during Vulval Morphogenesis We raised rabbit polyclonal antisera against a GST-SQV-4 fusion protein and affinity purified anti-SQV-4 antibodies using a MBP-SQV-4 fusion protein. The anti-SQV-4 antibodies recognized a protein of approximately 53 kDa in worm extracts (FIG. 17) that is the predicted size of the SQV-4 protein.

SQV-4 antibodies stained the cytoplasm of many cells, including (but not limited to) oocytes (FIG. 18) and vulval cells (FIG. 19A-C) as well as uterine, seam, pharyngeal and spermathecal cells. The cytoplasmic localization of SQV-4 is consistent with the idea that nucleotide sugar biosynthesis is catalyzed in the cytoplasm, and the nucleotide-sugars are then translocated into the endoplasmic reticulum and/or Golgi, where polymerization of sugars is catalyzed by glycosyltransferases for the biosynthesis of GAGs. SQV-4's expression in the developing vulva is consistent with its functioning in a cell-autonomous fashion in vulval morphogenesis. The presence of SQV-4 in oocytes is likely to be necessary for normal embryonic development.

In wild type nematodes, the vulva consists of the twenty-two descendants of the ventral hypodermal cells, P5.p, P6.p and P7.p. During the L3 larval stage, P5.p and P7.p divide to make seven vulval descendants each, while P6.p divides to make eight vulval descendants (Sulston et al., *Dev. Biol.* 56:110-56, 1977). During the L4 stage, the twenty-two vulval nuclei migrate inward and dorsally, with the inner nuclei of the P6.p descendants assuming the most dorsal positions and the outer nuclei of the P5.p and P7.p descendants assuming the most ventral positions (Sharma-Kishore et al., *Development* 126:691-9, 1999). During the L4 stage, the P5.p and the anterior half of the P6.p descendants are separated from the P7.p and the posterior half of the P6.p descendants by the expanding vulval extracellular space. This extracellular space expands so that the separation at the dorsal end is smaller than the separation at the ventral end. Then the middle of the vulval extracellular space widens, resulting in a bottle-like shape. Finally, the dorsal end of the vulval extracellular space expands toward the uterine cavity, and the vulval extracellular space fuses with the uterine cavity. Many of the vulval cells fuse homotypically at various points during vulval morphogenesis, ultimately generating nine cells containing 22 nuclei (Sharma-Kishore et al., *Development* 126:691-9, 1999). In sqv-4 mutants, the expansion of the vulval invagination space is impaired.

The twenty-two vulval nuclei define three classes of nuclei based on the levels and timing of their SQV-4 expression. In early L4 larva, ten nuclei are in vulval cells with dramatically increased SQV-4 expression. These 10 nuclei are the six inner nuclei of the P5.p and P7.p descendants, and the four outer nuclei of the P6.p descendants. In late L4 larva, the inner four nuclei of the P6.p descendants show increased SQV-4 expression. Thus, fourteen vulval nuclei are in cells that highly express SQV-4 (FIGS. 20A-20E).

The increased expression of SQV-4 in L4-stage vulval cells suggested that the nematode requires a high level of UDP-glucuronic acid for normal vulval morphogenesis. Increases in vulval cell UDP-glucuronic acid likely result in increases in the amount and length of chondroitin and heparan sulfate GAGs. The temporal and spatial increase of SQV-4 expression in a subset of the vulval cells corresponds to the stereotypical changes in the shape of the vulval extracellular space during the L4 stage. The widening of the middle of the vulval extracellular space coincides with increased SQV-4 expression in the cells containing 10 vulval nuclei located in the center of the dorso-ventral axis. The final expansion of the dorsal end of the extracellular space coincides with the increased expression of SQV-4 in the cells containing the four dorsal-most vulval nuclei.

SQV-4, tagged with GFP at its carboxy terminus, was expressed under the control of the endogenous sqv-4 promoter in transgenic sqv-4 mutant animals. We found that this expression was sufficient to rescue the vulval defect and maternal-effect lethality of sqv-4 mutants. We found SQV-4::GFP expression in many tissues that were stained by SQV-4 antibodies, including the vulva, uterus, gut, seam cells, and hypodermis. SQV-4::GFP expression was absent from oocytes; this absence was likely due to germline silencing of the SQV-4::GFP transgenic array (Kelly et al., *Genetics* 146:227-38, 1997). GFP expression was observed in vulval cells containing 10 nuclei in the early L4 stage, and in vulval cells containing 14 nuclei in the later L4 stage, consistent with the antibody staining.

SQV-4 Expression in lin-12 (gf) Mutants and lin-11 (lf) Mutants

In wild-type early L3 larvae, ventral hypodermal cells, P5.p, P6.p and P7.p, form a row along the ventral side of the worm. P3.p and P4.p are at the anterior end of this group and P8.p is posterior. P3.p, P4.p and P8.p divide once, each generating two descendants that do not participate in vulva formation. In lin-12 gain-of-function (gf) mutants, cells P3.p to P8.p divide aberrantly, generating seven descendants each. Anti-SQV-4 antibodies stained a subset of cells in pseudovulvae and vulva in lin-12 (g) mutants (FIGS. 21A and 21B). This resulted in the formation of four pseudovulvae and one functional, but abnormal, vulva. Each pseudovulvae contained seven nuclei, while the functional vulva contained fourteen nuclei (Greenwald et al., *Cell* 34:435-44, 1983). SQV-4 antibodies strongly stained three nuclei of each pseudovulva and six nuclei of the functional vulva of lin-12 (gf) mutant L4 stage larvae. This result was consistent with the elevated expression of SQV-4 in three of the seven descendants of P5.p and P7.p observed in wild-type worms.

In lin-11 loss-of-function (lf) mutants, P5.p and P7.p each generated eight vulval descendants. The lin-11(lf) P5.p and P7.p cell lineages were different from the wild-type P6.p cell lineage, which also generates eight descendants, in the orientation of the final cell division: the final wild-type P6.p divisions are along the left-right axis, while the final lin-11 P5.p and P7.p divisions are along the anterior-posterior axis (Freyd et al., *Nature* 344:876-9, 1990). lin-11 mutants have an abnormally small vulval extracellular space, which is distinct from that of the sqv mutants, as only the ventral region is reduced in lin-11 mutants. In lin-11 (lf) mutants, SQV-4 antibody staining was weaker and observed in fewer vulval cells relative to wild-type nematodes (FIGS. 22A and 22B). This difference in SQV-4 expression likely caused the smaller vulval extracellular space present in lin-11 mutants.

Nematodes with Multiple Copies of sqv-4 Exhibited Increased Vulval Extracellular Space We analyzed vulval extracellular space in rescued sqv-4 mutant animals expressing a transgenic array in which the sqv-4 open reading frame (ORF) was linked to GFP, and expressed under the control of the endogenous sqv-4 promoter. Many of these rescued transgenic animals had vulval extracellular spaces that were increased in size relative to wild-type nematodes (FIG. 23A-23B). When SQV-4 was expressed under the *C. elegans* heat-shock promoter in sqv-4 mutant animals, we found that some of these transgenic L4 larva also had a larger than wild-type vulval extracellular space. In these animals, however, the shape of the extracellular space was affected. The dorsal width of the vulval extracellular space in these $P_{hs}$Sqv-4 transgenic animals was approximately five times larger than that observed in wild-type animals (FIG. 23C-23D).

Nematodes carrying a sqv-4 trangenic array are likely to have many copies of the sqv-4 gene and abnormally high levels of SQV-4 protein. Increased SQV-4 levels likely increases the size of the vulval extracellular space. The abnormal shape of the vulval extracellular space observed when the sqv-4 transgene was expressed under the heat-shock promoter may be caused by premature SQV-4 expression in the four inner descendants of the P6.p. Thus, regulation of sqv-4 appears to control the shape of the vulval extracellular space and the surrounding vulval epithelia during vulval morphogenesis. This observation is consistent with the regulation of SQV-4 expression at the transcriptional level.

Molecular Identification of sqv-5

We used a positional approach to clone sqv-5. First, by physically mapping deficiency endpoints, we localized sqv-5 to a roughly 200-kilobase region between the left endpoint of qDf10 and fog-3 (FIG. 24A). Of nine cosmids that were injected, K09A8 rescued the sqv-5 mutant phenotype. A 18,448 base BamHI-PstI fragment of K09A8, containing a single complete gene, T24D1.1, was sufficient to rescue sqv-5 mutants (FIGS. 24B and C). The minimal rescuing fragment is shown in FIG. 26. Introducing a nonsense or a frameshift mutation in T24D1.1 abrogated the rescuing activity of the 18 kb Bam HI-PstI fragment. We identified the molecular lesion of the first sqv-5 mutant allele, n3039, as a late nonsense mutation in the open reading frame (ORF) of T24D1.1 (FIG. 25). We obtained a new deletion mutant allele of sqv-5, n3611, which showed the same Sqv mutant phenotype as n3039 (FIG. 25). We also found three DNA sequence discrepancies between our DNA sequencing results and results of the *C. elegans* Sequencing Consortium, which caused us to reevaluate and change the gene structure of T24D1.1 (FIG. 24B).

We sequenced two cDNA clones, yk20d7 and yk21g9, that roughly correspond to T24D1.1, and also sequenced six 5'-rapid amplification of cloned ends (RACE) products derived from mixed stage RNA. The 5' RACE products contained a 5' SL1 trans-spliced leader, which is found at the 5' end of many *C. elegans* transcripts. We determined that the sqv-5 cDNA contained 417 bases of 5' untranslated region (UTR), 2202 bases of open reading frame, and 657 bases of 3' UTR sequence. Two alternatively spliced forms of the transcript were identified; the shorter form is shown in FIG. 27. The longer form contains six additional bases in the ORF; the polypeptide encoded by this cDNA is shown in FIG. 25. The longest ORF in the sqv-5 cDNA was predicted to encode a protein of 734 or 736 amino acids; both proteins are larger than the protein predicted by T24D1.1. Using a 1827 bp fragment corresponding to the 3' segment of the ORF, we detected a single 3.6 kb transcript in mixed-stage total RNA on a Northern blot.

The short form of sqv-5 contains 734 amino acids; 277 of which are identical to a recently cloned human chondroitin synthase (38% identical) (Kitagawa et al., *J. Biol. Chem.* 276:38721-6, 2001). The sequence of a human sqv-5 homolog cDNA is shown in FIG. 28. We also identified and DNA sequenced a cDNA of a *Drosophila melanogaster* homolog that is predicted to encode a 832 amino acid protein, which shares 38% amino acid identity with SQV-5 (FIG. 25). Alternatively, 262 of 734 amino acids of SQV-5 are identical to the *Drosophila* genome project's deduced polypeptide which contains 788 amino acids (FIG. 25). All three proteins contain a single predicted transmembrane domain near the N-terminus, consistent with a type TT transmembrane topology typical of glycosyltransferases localized to the lumen of ER or Golgi.

sqv-5 Mutants Have Reduced Chondroitin Synthase Activity sqv-5(n3611), sqv-5(n3611)/hT2, and wild-type (N2) animals were used to prepare worm protein extracts. These extracts were tested for chondroitin synthase activity using standard methods, for example, in DeAngelis et al., (*J. Biol. Chem.* 27:24124-24129, 2000).

Table 4 shows the result of biochemical assays for chondroitin synthase activity in protein extracts from wild-type (+/+), sqv-5 heterozygotes (sqv-5(n3611)/hT2) (+/sqv-5), and sqv-5(n3611) homozygotes (sqv-5/sqv-5). A desulfated chondroitin acceptor was used for the GalNAcT (N-acetylgalactosamyl transferase) assay. Desulfated and β-glucuronidase-treated chondroitin acceptor was used for the GlcAT (glucuronyl transferase) assay.

TABLE 4 sqv-5 protein extracts have reduced chondroitin synthase activity

| Donor Sugar | Genotype | CPM |
| --- | --- | --- |
| UDP-glucuronic acid | +/+ | 1820 |
|  | +/sqv-5 | 1369 |
|  | sqv-5/sqv-5 | 109 |
| UDP-N-acetylgalactosamine | +/+ | 171 |
|  | +/sqv-5 | 134 |
|  | sqv-5/sqv-5 | <0 |

+/+ is wild-type; +/sqv-5 is sqv-5(n3611)/hT2; and sqv-5/sqv-5 is sqv-5 (n3611);

SQV-5 Expression

To study the expression and subcellular localization of SQV-5 protein in *C. elegans*, we generated affinity-purified rabbit polyclonal antibodies against SQV-5-GST fusion protein. Anti-SQV-5 antibodies stained multiple punctate foci in the cytoplasm of vulval cells, (FIG. 29), uterine cells, and oocytes. This punctate staining was not seen in nematodes homozygous for the sqv-5(n3611) null allele.

A similar punctate staining pattern was observed using antibodies against SQV-7 nucleotide sugar transporter and SQV-1 UDP-glucuronic acid decarboxylase. Anti-SQV-1 rat antibodies and anti-SQV-5 rabbit antibodies were used to determine whether SQV-1 and SQV-5 proteins colocalized to the same cytoplasmic compartment. We found that SQV-1 and SQV-5 staining colocalized to the same or adjacent compartment in oocytes (FIG. 30A-30C).

SQV-5 Mutants Fail to Initiate Cytokinesis sqv-5 mutants failed to initiate cytokinesis. This may have resulted from a failure of the plasma membrane to separate from the eggshell. We also noticed that the uterus in the sqv-5 mutant adult was unusually small. We measured the length of the uterus in young adults in various sqv mutant backgrounds, and found strong uterine defects in sqv-5 and sqv-1 mutant nematodes, and milder uterine defects in sqv-4, -7 and -8 mutant nematodes; the sqv-4 and sqv-8 mutant alleles tested may not represent null mutations. The length of the uterus was restored to wild type length in sqv-1 and sqv-4 mutant nematodes by expression of a sqv-1-gfp and sqv-4-gfp extrachromosomal array, respectively.

Function of the Eight sqv Genes

A model for the function of the eight sqv genes is shown in FIG. 31.

WORKING EXAMPLES sqv-1 Strains and Genetics

C. elegans strains were cultured as described by Brenner (*Genetics* 77:71-94, 1974)). The wild-type strain used was N2 (Brenner, *Genetics* 77:71-94, 1974). The mutant strains used were described by Riddle et al. (*C. elegans* II. Cold Spring Harbor, N.Y., Cold Spring Harbor Laboratory Press, 1997)), except as follows: LGII sqv-7(n3789) is described herein; mnC1 (dpy-10(e128) unc-52(e444)) was described by Herman, (*Genetics* 88:49-65, 1978); LGIV sqv-1(n2819, n2820, n2824, n2828, n2848, n2849, n3790) are described herein; LGIV sqv-1 (ku246) was obtained from Min Han; unc-24 (e138), dpy-20(e1282), fem-3(q20), mes-6(bn66), eDf18, and eDf19 were described by Hodgkin et al., (*Cold Spring Harb. Symp. Quant. Biol.* 50:585-93, 1985), and nT1(n754) was described by Ferguson et al., (*Genetics* 110:17-72, 1985). The strain RW7000, which displays multiple RFLPs relative to wild-type Bristol N2, was described by Emmons et al., (*Cell* 32:55-65, 1983) and Liao et al. (*Proc. Natl. Acad. Sci. USA* 80:3585-9, 1983).

sqv-1 had been previously mapped between unc-24 and dpy-20 on LGIV (Herman et al., *Proc. Natl. Acad. Sci. USA* 96:968-73, 1999). We further mapped sqv-1 to an approximately 400 kb region between the TC1 polymorphism bnP4 and the left endpoint of the deficiencies eDf18 and eDf19 (FIG. 1A). To map sqv-1, Unc non-Sqv progeny were obtained from unc-24(e138) sqv-1(n2819)/fem-3(q20) hermaphrodites. Dpy non-Sqv progeny were obtained from sqv-1(n2819) dpy-(n1282)/fem-3(q20) hermaphrodites. All 11 Unc non-Sqv progeny carried fem-3(q20) and 27 of 34 Dpy non-Sqv progeny carried fem-3(q20). We obtained Unc Dpy non-Sqv progeny from mes-6(bn66) dpy-20(e1282)/unc-24 (e138) sqv-1(n2819) hermaphrodites. All 8 Unc Dpy progeny carried mes-6(bn66).

We obtained Unc non-Sqvs from unc-24(e138) sqv-1 (n2819)/++ (RW7000) hermaphrodites and Dpy non-Sqvs from sqv-1(n2819) dpy-20(e1282)/++ (RW7000) hermaphrodites. An initial survey of 26 Dpy non-Sqvs indicated that two of them carried the Tc1 polymorphisms bnP3 and bnP2, but did not carry the Tc1 polymorphism bnP4. One Dpy non-Sqv carried only bnP2. We next determined whether bnP4 was present in additional recombinants. We found that all 35 Unc non-Sqvs carried bnP4 and 72 of 75 Dpy non-Sqvs carried bnP4. These results placed sqv-1 to the left of bnP4. Both dpy-20(e1282) sqv-1(n2819)/eDf18 and dpy-20 (e1282) sqv-1(n2819)/eDf19 animals were Sqv.

We obtained eDf18 and eDf19 dead eggs from unc-24 (e138) dpy-20(e1282)/eDf18 or unc-24(e138) dpy-20 (e1282)/eDf19 hermaphrodites. We attempted to PCR amplify genomic DNA sequences corresponding to cosmids B0218, C07G1 (overlapping with T09A12), F35H10, and D2096 (see FIG. 1A). Four eDf19 eggs contained the genomic DNA sequence from B0218, but not F35H10 and D2096. This placed the left endpoint of eDf19 between B0218 and F35H10. Three eDf18 eggs contained the genomic DNA sequence from B0218, but did not contain F35H10 and D2096. Eleven eDf18 eggs contained genomic DNA sequence from B0218 and C07G1, but did not contain F35H10. These results placed the left endpoint of eDf18 between C07G1 and F35H10, thus placing sqv-1 to right of C07G1/T09A12.

Isolation of sqv-1 Deletion Alleles

Null mutations sqv-1(n3790) and sqv-7(n3789) were isolated from a library of animals mutagenized with UV illumination and trimethylpsoralen essentially as described by Jansen et al (*Nat. Genet.* 17: 119-21, 1997) and Liu et al. (*Genome Res.* 9, 859-67, 1999) and backcrossed six times to N2. The deletion in sqv-1(n3790) removed bases 2981 to 5690 of the cosmid D2096 and the entire sqv-1 coding sequence. The deletion in sqv-7(n3789) removed bases 17746 to 19294 of the cosmid C52E12 and all but the first and part of the second exon of sqv-7. sqv-7(n3789) also contained a tandem duplication of bases 19295 to 19316 of the cosmid C52E12.

Generation of Transgenic Animals

We injected genomic DNA into unc-24(e138) sqv-1 (n2819)/dpy-20(e1282) hermaphrodites at concentrations of 3-7 µg/ml with the dominant roller marker pRF4 (80 µg/ml) as described by Mello et al. (*EMBO J.* 10: 3959-3970, 1991). Rol lines were established and Unc Rol animals were examined for rescue of the sqv-1 mutant phenotype.

sqv-1 Human cDNA Clones

The sequence of all PCR-amplified DNA used for cloning was confirmed to exclude unintended mutations. The human cDNA clones, 1875025, 1871770, 29917, 210962, 21151921, 32371, 208993, 2630577 and 54339, containing the human homolog of sqv-1, were provided to us by the I.M.A.G.E. consortium (Lennon et al., *Genomics* 33:151-2, 1996). The clones 1875025 and 1871770 have an identical 5' end. The clone 29917 contained an alternative spliced form of human sqv-1, which is predicted to encode five additional amino acids not found in 1875025 and 1871770.

C. elegans sqv-1 cDNAs

To identify sqv-1 cDNAs, a 3.6 kb Eco0109I-HindIII rescuing fragment was used to probe an embryonic stage lambda-gt11 cDNA library (Okkema et al., *Development* 120:2175-86, 1994) and to isolate cDNA clones. The isolated cDNA clone that contained the longest open reading frame (ORF) identical to D2096.4 is predicted to encode a protein of 467 amino acids. The D2096.4 ORF was PCR-amplified using the cDNA clone as a template and the oligonucleotides 5'-TCTGGTACCATGCTGAGCCCCAGACG-3' (SEQ ID NO:30) and 5'-TCTGAGCTCATCGTCGACTCTCAAG-3' (SEQ ID NO:31) as primers. The resulting product was digested with KpnI and SacI and cloned into pPD49.78 and pPD49.83 (from A. Fire). We injected sqv-1(n2828)/nT1 (n754) hermaphrodites with the full length sqv-1 ORF fused to the heat-shock promoters (Stringham et al., *Mol. Biol. Cell* 3:221-33, 1992) in the vectors pPD49.78 (90 µg/ml) and pPD49.83 (85 µg/ml) with pRF4 (80 µg/ml) as the coinjection marker. The expression of sqv-1 was then induced in the transgenic animals by a 30 minute heat-shock treatment at 33° C. Worms that expressed the coinjection marker displayed a characteristic "rolling" phenotype, these Rol animals were examined for rescue of the sqv-1 mutant phenotype.

UDP-Glucuronic Acid Decarboxylase Assay

Standard molecular biology techniques were used (Sambrook et al., *Molecular Cloning: A Laboratory Manual*. Plainview, N.Y., Cold Spring Harbor Laboratory Pess, 1989) to obtain a construct that encoded a SQV-1-maltose-binding protein (MBP) fusion protein. The sqv-1 coding sequence was cloned into the MBP encoding vector, pMAL-c2. The oligonucleotides 5'-TCTGAATTCATGCTGAGCCCCA-GACG-3' (SEQ ID NO:32) and 5'-TCTGGATCCT-CATCGTCGACTCTCAAG-3' (SEQ ID NO:33) were used to PCR-amplify the sqv-1 ORF. The resulting PCR product was cut with EcoRI and BamHI, purified using standard methods, and cloned into pMAL-c2. The resulting construct was then transformed into BL21 pLysS bacterial cells.

MBP-SQV-1 protein expression was induced by incubating the transformed cells with 1 mM IPTG at 20° C. for 15 hours. The *E. coli* were pelleted via centrifugation, resuspended in 0.1 M phosphate, pH 7, 1 mM glutathione and 2 mM EDTA, and lysed using a French Pressure Cell. The soluble fraction was separated from insoluble inclusion bodies by centrifugation at 12,000 g for 20 minutes. The soluble MBP-SQV-1 fusion protein was purified by binding the soluble fraction to amylose resin and then eluting the bound MBP-SQV-1 fusion protein with 10 mM maltose.

Approximately 10 μg of purified MBP-SQV-1 was then incubated with 2 mM UDP-glucuronic acid and 2 mM NAD$^+$ for one hour at 22 to 23° C. Nucleotide sugars were separated from protein by twenty minutes of centrifugation through a Microcon YM-10 (Millipore) filter equilibrated with water and methanol. The eluate was diluted 100-fold with water and mixed with an equal volume of methanol, injected into a capillary ion pair reverse phase-HPLC (C18), and eluted with increasing concentrations of methanol. The HPLC column was coupled to an electrospray time-of-flight mass spectrometer (Mariner Workstation, PerSeptive Biosystems, Inc.) to detect the mass of nucleotide sugars present in the reaction sample.

Anti-SQV-1 and SQV-7 Antibodies and Immunostaining

A twenty-six amino acid ((C)RSKSTTISYKPLPMTM-PIDVHKPRN) (SEQ ID NO:34) peptide corresponding to the carboxy-terminal end of SQV-7 was synthesized and injected into two rabbits. The anti-SQV-7 antisera was affinity purified by binding to the SQV-7 peptide conjugated to the SULFOLINK COUPLING GEL (Pierce) affinity column. Antibodies were then eluted with 100 mM glycine, pH 2.5, according to the manufacturer's instructions.

The full length sqv-1 ORF was cloned into the vectors pGEX-4T3 and pMAL-c2 to generate glutathion stransferase (GSl)-SQV-1 and MBP-SQV-1 fusion proteins, respectively. The oligonucleotides 5'-TCTCCCGGGGCATGCTGAGC-CCCAGAC-3' (SEQ ID NO:35) and 5'-TCTCTC-GAGTCGTCGACTCTCAAGACC-3' (SEQ ID NO:36) were used to PCR-amplify the sqv-1 ORF; the resulting PCR-product was cut with XmaIand XhoI, purified using standard methods, and cloned into pGEX-4T3. Expression of the GST-SQV-1 and MBP-SQV-1 fusion proteins was induced by incubation with 1 mM IPTG at 37° C. for three hours, and both fusion proteins were purified by isolating inclusion bodies, as described above, followed by SDS-PAGE and electroelution of the fusion proteins. GST-SQV-1 was injected into two rabbits (Covance). MBP-SQV-1 was injected into two rabbits and two rats (Covance). The anti-GST-SQV-1 antibodies were affinity purified by incubating the anti-GST-SQV-1 anti-sera with the MBP-SQV-1 fusion protein bound to OPTITRAN (S&S) reinforced nitrocellulose strips and then eluting the bound antibodies with 100 mM glycine, pH 2.5.

Anti-MBP-SQV-1 antibodies were affinity purified by incubating the anti-MBP-SQV-1 antisera with GST-SQV-1 fusion proteins bound to OPTITRAN reinforced nitrocellulose strips and eluting the purified antibodies with 100 mM glycine, pH 2.5.

Whole worms were fixed and stained using standard methods.

Expression of SQV-1-GFP and SQV-7-GFP in Nematodes

We isolated a 5.4 kb PstI-SalI fragment that included 3,520 bases of genomic DNA upstream of sqv-1 and all but 3 bases of the sqv-1 ORF. This piece of DNA was cloned into the vector pPD95.81 (from A. Fire), resulting in a sqv-1-GFP translational fusion construct. This construct was then injected into sqv-1(n2828)/nT1(n754) and sqv-1(n2849)/nT1 (n754) hermaphrodites at a concentration of 23 μg/ml. Transgenic progeny were used to establish GFP-positive lines that were determined to rescue both sqv-1 alleles.

We generated a NotI site at the 3' terminus of the sqv-7 ORF in a 14 kb MluI-PstI fragment containing bases 4250 to 8601, 11205 to 15320, and 16143 to 21512 of the cosmid C52E11. Two rounds of PCR amplification were done using the sqv-7 minimal rescuing MluI-PstI fragment minus the internal (bases 8602 to 11204 of the cosmid C52E11) SphI fragment (Herman et al., *Cold Spring Harb. Symp. Quant. Biol.* 62:353-9, 1999) as the template. The first round of PCR was used to amplify two overlapping sequences. The first sequence was amplified with 5'-GATCTTGGAAAGTATGG-3' (SEQ ID NO:37) and 5'-TTGAACATTTGCGGCCGCGTTCCTTG-GCTTGTG-3' (SEQ ID NO:38), the mutagenic primer, to introduce a NotI site to the 3' end of sqv-7 ORF. The second sequence was amplified using primers 5'-TACTACAACCT-GCGTTG-3' (SEQ ID NO:39) and 5'-GTTCGCTTTT-TAGTCCCG-3' (SEQ ID NO:40) to amplify an overlapping sequence. In the second round of PCR amplification, primers 5'-GATCTTGGAAAGTATGG-3' (SEQ ID NO:41) and 5'-GTTCGCTTTTTAGTCCCG-3' (SEQ ID NO:42) were used and two products from the first round of PCR acted as the templates. The resulting product was digested with ClaI and BsmI and cloned into a pBluescript II vector (Stratagene) containing a SalI-PstI fragment (bases 16041 to 21512 of C52E11) of cosmid C52E11. The resulting construct was digested with BamHI (using the BamHI site at the base 16143 of C52E11 and a second site in the multicloning site (MCS) of pBluescript II) and cloned into a second pBluescript II vector that contained the sqv-7 minimal rescuing MluI-PstI minus SphI fragment that was digested with BamHI (thus removing bases 15320 to 16143 of C52E11) and the NotI site of MCS blunted and self ligated. We then cloned a 1011 base pair NotI fragment that codes for GFP from pPD102.33 (from A. Fire) into the new NotI site of the final construct. We injected either DNA construct (40-50 μg/ml) into sqv-7(n2844) unc-4 (e120)/mnC1 (dpy-10(e128) unc-52(e444)) hermaphrodites with the dominant roller marker pRF4 (50 μg/ml). Although this GFP construct failed to rescue the sqv-7 mutant phenotype, an equivalent DNA construct that contained an HA tag (instead of GFP) rescued the sqv-7 mutant phenotype (Berninsone et al., *Proc. Nat. Acad. Sci. USA* 98:3738-43, 2001).

sqv-2 and sqv-6 Strains and Genetics

Nematode strains were cultured as described by Brenner, (*Genetics* 77:71-94, 1974) and were grown at 20° to 22° C. except where indicated. The mutations used were described in Riddle et al. (*C. elegans* II. Cold Spring Harbor, N.Y., Cold Spring Harbor Laboratory Press, 1997), except as follows: ccDf11 and ccDf11 were described by Chen et al. (*Science* 256:240-3, 1992); lin-8(n3646) was obtained from J. Doll; sDf28, sDf32, sDf34, sDf38, sDf39, sDf50, sDf53 were described by Rosenbluth et al.(*Genetics* 124:615-25, 1990) and nT1(n754) was described by Ferguson et al., (*Genetics* 110:17-72, 1985). CB4856 (Koch et al., *Genome Res.* 10:1690-6, 2000), which displays multiple single nucleotide polymorphisms (SNPs), relative to N2, was also used.

sqv-2 Mapping

We examined the vulval phenotypes of six sqv-2(n2826)/ccDf1 and nine sqv-2(n2826)/ccDf11 hermaphrodites. We found that sqv-2(n2826)/ccDf1 hermaphrodites had wild-type vulval phenotypes. The sqv-2(n2826)/ccDf11 hermaphrodites displayed a squashed vulval phenotype (Sqv). Thirteen of 73 Variable Abnormal morphology (Vab) progeny from vab-1(e2027)/sqv-2(n2826) hermaphrodites carried sqv-2(n2826), thus placing sqv-2 8.9 map units away from vab-1. Three of 99 Lin-8 progeny from lin-8(n3646)/sqv-2(n2826);nIs130 animals carried sqv-2(n2826), thus placing sqv-2 1.6 map units away from lin-8. Sqv and Sup-9 animals were obtained from sup-9(n1913)/sqv-2(n2826) lin-31(n301) unc-85(e1414);unc-93(e1500) hermaphrodites. Four of 167 Sqv animals gave Sup-9 progeny, thus placing sqv-2 1.2 map units away from sup-9. Five of 222 Sup-9 animals gave Sqv Lin-31 progeny, thus placing sqv-2 to the right of sup-9 and 1.1 map units away from sup-9 (FIG. 9A).

sqv-6 Mapping

We examined the vulval phenotype of the genotype sqv-6(n2845)/Df unc-46(e177) wherein Df is either sDf28, sDf32, sDf34, sDf38, sDf39, sDf50 or sDf53. Based on previous mapping of these deficiencies by the *C. elegans* research community reviewed by Rosenbluth et al., (*Genetics* 124: 615-25, 1990), we tentatively placed sqv-6 to the left of unc-60. We found that only sDf32, sDf34 and sDf53 failed to complement sqv-6(n2845). We obtained Dpy non-Unc and Unc non-Dpy progeny from unc-60(e677) dpy-11(e224)/sqv-6(n2845) hermaphrodites. All 26 Dpy non-Unc progeny carried sqv-6(n2845), and none of 27 Unc non-Dpy progeny carried sqv-6(n2845). This result is consistent with sqv-6 being located to the left of unc-60. One of 99 Unc progeny from unc-60(e677)/sqv-6(n2845) hermaphrodites carried sqv-6(n2845), thus placing sqv-6 0.5 map units away from unc-60. None of 265 Unc progeny from unc-34(s138)/sqv-6(n2845) carried sqv-6(n2845), suggesting sqv-6 is closely linked to unc-34. We obtained 21 Unc non-Sqv progeny from sqv-6(n2845) unc-60(e677)/CB4856. We PCR-amplified genomic DNA sequences in the region between unc-34 and unc-60, using animals wild-type for the sqv-6 locus as a template. We determined the presence of single-nucleotide polymorphisms using N2 and CB4856 as controls. CB4856-specific polymorphism was located in cosmid T21H3 in 15 of 21 recombinants, in the cosmid W07B8 in 17 of 21 recombinants, and in the gap between K10C19 and W07B8 in all 21 recombinants. These results placed sqv-6 to the left of W07B8 (FIG. 11A).

sqv-2 and sqv-6 Genomic Rescue

Genomic rescue of sqv-2 and sqv-6 mutant nematodes was assayed by injecting genomic DNA into sqv-2(n2821) and sqv-6(n2845) unc-60(e677)/unc-34(s138) nematodes at concentrations of 3-4 μg/ml. The dominant marker pRF4 (58 μg/ml) was co-injected as described in Mello et al. (*EMBO J.* 0:3959-3970, 1991) for germline rescue. Nematodes expressing the coinjection marker display a distinctive "roller" phenotype. The presence of Rol lines was established. Rol animals were examined for rescue of the sqv-2 mutant phenotype. Unc-60 Rol animals were examined for rescue of the sqv-6 mutant phenotype.

sqv-2 cDNA

Plasmids containing sqv-2 cDNA were excised from phage clones yk94e4 and yk292g2. The plasmid, derived from the yk292g2 clone, contained the full sqv-2 ORF. sqv-2 cDNA was also PCR-amplified using an embryonic stage pACT2 cDNA library (from Z. Zhou) as the template and oligonucleotides corresponding to the ORF of sqv-2 and a pACT2 primer. DNA sequence at the 5' end of the resulting product corresponding to the sqv-2 locus was identical to the 5' end of yk292g2.

The sqv-6 cDNA was PCR-amplified using the embryonic stage pACT2 cDNA library as the template and oligonucleotides corresponding to the ORF of sqv-6 as primers. DNA sequence of the resulting overlapping amplified cDNA fragments was determined, and a set of fragments was cloned into pBluescript II (Stratagene). To determine and clone the 5' end of sqv-6, we used 5'-rapid amplification of cloned ends (RACE).

cDNA Rescue of sqv-2

The sqv-2 ORF was PCR-amplified using the yk292g2 clone as a template and the oligonucleotides 5'-TCTGAATTCAATGAGATTCTACCGAAC-3' (SEQ ID NO:43) and 5'-TCTCTCGAGTTATGGAATATTCGATCC-3' (SEQ ID NO:44) as primers. The resulting product was digested with EcoRI and XhoI and cloned into a pENTR2B vector (Invitrogen). The sqv-6 ORF in pcDNA3.1 (see below) was digested with Asp718I and NotI and cloned into the pENTR3C vector. The GATEWAY LR cloning system, which is a site-specific recombination system (Invitrogen) of bacteriophage lambda, was then used to transfer the sqv-2 and sqv-6 ORF into pMB6 and pMB 12 (from M. Boxem and S. Heuvel).

We injected sqv-2(n2821) hermaphrodites with the sqv-2 ORF tagged with an N-terminal Myc tag and fused to the *C. elegans* heat-shock promoters (Stringham et al., *Mol. Biol. Cell* 3:221-33, 1992) in the vectors pMB6 (34 μg/ml) and pMB12 (52 μg/ml) with pRF4 (58 μg/ml) as the coinjection marker. We injected sqv-6(n2845)/nT1(n754) hermaphrodites with the sqv-6 ORF tagged with an N-terminal Myc tag in the vectors pMB6 (37 μg/ml) and pMB12 (58 μg/ml) with pRF4 (58 μg/ml) as the coinjection marker. Rol lines were established, and Rol (non-Unc) animals were examined for rescue of the sqv-2 and sqv-6 mutant phenotype following induction of sqv-2 and sqv-6 expression by thirty minutes of heat-shock treatment at 33° C.

Galactosyltransferase II Assay

A sqv-2 coding sequence encoding amino acids 25 to 330 of SQV-2, thus lacking the transmembrane domain at the amino terminus, was cloned into pDEST-CMV-protA vector as follows. The oligonucleotides 5'-TCTGAATTCAATTGTGGATGGGATG-3' (SEQ ID NO:45) and 5'-TCTCTCGAGTTATGGAATATTCGATCC-3' (SEQ ID NO:46) were used as the primers for PCR-amplification, and the resulting product was digested with EcoRI and XhoI and cloned into pENTR3C. The Gateway LR cloning reaction (Invitrogen) was used to transfer the sqv-2 ORF lacking TM into the Gateway destination vector pDEST-CMV-protA to generate a modified amino-terminal protein A fusion protein using the CMV promoter. The plasmid pDEST-CMV-protA was constructed by cloning the Gateway C.1 reading frame cassette, from the manufacturer, into pRK5F10ProteinA (Wei et al., *Proc. Natl. Acad. Sci. USA* 90:3885-8, 1993), which was digested with EcoRI and blunted using dNTPs, Klenow fragment and T4 DNA polymerase. This plasmid was designed to express a secreted protein A-SQV-2 (amino acids 25-330) fusion protein in mammalian cells.

COS7 cells were transiently transfected with pDEST-CMV-protA-sqv-2 using LIPOFECTAMINE (3:1 (w/w)) liposome formulation of the polycationic lipid 2,3-dioleyloxy-N-[2(sperminecarboxamido)ethyl]-N,N-dimethyl-1-propanaminium trifluoroacetate (DOSPA) (Chemical Abstracts Registry name: N-[2-(2,5-bis[(3-aminopropyl)

amino]-1-oxpentyl}amino)ethyl]-N,N-dimethyl-2,3-bis(9-octadecenyloxy)-1-propanaminium trifluoroacetate), and the neutral lipid dioleoyl phosphatidylethanolamine (DOPE) in membrane filtered water) (Life Technologies) in accordance with the manufacturer's instructions. The transfected cells expressed a secreted protein A-SQV-2 (amino acids 25-330) fusion protein. After seventy-two hours of incubation, the fusion protein was recovered and purified from the cell culture supernatant by affinity chromatography using IgG-agarose (Wei et al., *Proc. Natl. Acad. Sci. USA* 90:3885-8, 1993).

Galactosyltransferase II activity was assayed using UDP-[1-$^3$H]Gal (NEN Life Sciences Products, 12.8 Ci/mmol) and various mono- and di-saccharide acceptor substrates, including Xylβ-O-benzyl (Bn), Xylβ-O-naphthol, Galβ-O-naphthalenemethanol (NM), GalNAcβ-O-NM, GlcNAcβ-O-NM, Galβ,14Xylβ-O-Bn, Galβ1,3GlcNAc α-O-NM, Galβ1, 3Galβ-O-NM, Galβ1,4GlcNAcβ-O-NM, Galβ1,3GlcNAcβ-O-NM, GlcNAcβ1,3Galβ-O-NM, Manaα,1,6Man α-O-decenyl (Lugemwa et al., *J. Biol. Chem.* 271:19159-65, 1996; Sarkar et al., *Carbohydr Res* 329:221-33, 2000; Brown et al., *Bioorg. Med. Chem.* 9:815-24, 2001). The standard reaction (25 µl) contained 5 µl of IgG slurry containing the fusion protein, 50 mM 2-(N-Morpholino) ethanesulfonic acid (MES), pH 6.0, 0.3 µCi of UDP-[1-$^3$H]galactose, 150 µM UDP-galactose, 5 mM acceptor, 15 mM MnCl$_2$, 50 mM KCl and 1% TX-100. After incubation at room temperature for 3 hours, the reaction products were diluted with 1 mL of 0.5 M NaCl and applied to a Sep-Pak C18 (100 mg; Waters). After washing with 5 ml of 0.5 M NaCl and water, the radiolabeled products were eluted with 50% methanol, dried and counted by liquid scintillation.

sqv-6 Rescue of Xylosyltranferase Defect in CHO Cells

The sqv-6 coding sequence was cloned into pcDNA3.1 and transformed into Chinese hamster ovary (CHO) cells. The oligonucleotides 5'-TCTGGTACCACCATGGTAT-TCAACGGGACGAC-3'(SEQ ID NO:47) and 5'-TTC-CTCGTCGGAAATCG-3' (SEQ ID NO:48) were used for PCR-amplification of the 5' half of sqv-6, and the oligonucleotides 5'-CGATTTTGAGAGACTTATC-3' (SEQ ID NO:49) and 5'-TCTGCGGCCGCTAAATCAAGGTCTGCG-3' (SEQ ID NO:50) were used for PCR-amplification of the 3' half of sqv-6. The resulting products were digested with Asp718I and BamHI, for the 5' half of sqv-6, and BamHI and NotI, for the 3' half of sqv-6, and cloned into pcDNA3.1.

Six-well tissue culture dishes were seeded with 1×10$^5$ CHO-K1 or CHO pgsA-745 cells (ATCC) in 2 ml of Ham's F12 growth medium (Ham, *Proc. Natl. Acad. Sci. USA* 53:288-293, 1965) with 10% fetal bovine serum (FBS), 100 µg/ml streptomycin, and 100 U/ml penicillin G. CHO pgsA-745 cells are defective in the GAG xylosyltransferase activity (Esko et al., *Proc. Natl. Acad. Sci. USA* 82:3197-201, 1985). The following day, duplicate wells of pgsA-745 cells were left untreated, transfected with an empty pcDNA3.1 vector, or transfected with the pcDNA3.1-sqv-6 construct. After two days of incubation at 37° C. or 30° C., the medium was removed and replaced with 1 ml of Ham's F12 containing 10% dialyzed (to remove sulfate) FBS, 100 U/ml penicillin G, and 50 µCi/ml $^{35}$SO$_4$ (sulfuric acid form, NEN). After one to two hours of incubation, the labeling medium was removed and cell monolayers were washed with phosphate buffered saline. The cells were solubilized with 0.1 N NaOH and an aliquot was assayed for protein content by the method of Bradford. The remaining material was diluted with phosphate buffered saline (PBS) and neutralized with acetic acid, then digested with 2 mg/ml Pronase overnight at 4° C. in the presence of 2 mg carrier chondroitin sulfate A (Sigma).

Samples were diluted three-fold with water and run over a 0.5 ml DEAE-Sephacel (Pharmacia) column pre-equilibrated with 0.25 M NaCl, 20 mM NaOAc pH 6.0. After washing with the same buffer, radiolabeled GAGs were eluted with 2.5 ml 1 M NaCl, 20 mM NaOAc, pH 6.0. GAGs were precipitated overnight at 4° C. with four volumes of ethanol. The pellet was resuspended in water and counted by liquid scintillation.

sqv-4 Molecular Biology

Standard molecular biological techniques were used (Sambrook et al., *Molecular Cloning: A Laboratory Manual*. Plainview, N.Y., Cold Spring Harbor Laboratory Pess, 1989). The sequences of all amplified DNA were determined to ensure the absence of unintended mutations.

sqv-4 Strains and Genetics

*C. elegans* was cultured at 20° to 22° C. as described by Brenner (*Genetics* 77:71-94, 1974). N2 was the standard wild-type strain (Brenner, *Genetics* 77:71-94, 1974). Mutations used are described by Riddle et al. (*C. elegans II*. Cold Spring Harbor, N.Y., Cold Spring Harbor Laboratory Press, 1997) with the following exceptions. The following mutations were used: LGI, lin-11(n389); LGIII lin-12(n137), dpy-18(e364); LGV unc-60(e677), dpy-11(e224), odr-2(n2145), mec-1(e1066), unc-42(e270), sDf35 (McKim et al., *Genetics* 118:49-59, 1988), sqv-4(n2827, n2840), emo-1(oz1), sma-1 (e30) and nT1(n754) (Ferguson et al., *Genetics* 110:17-72, 1985). The wild-type strain RW7000, which contains many more Tc1 transposable elements than N2, was also used (Emmons et al., *Cell* 32:55-65, 1983; Liao et al., *Proc. Natl. Acad. Sci. USA* 80:3585-9, 1983).

We obtained Unc non-Sqv progeny from unc-42(e270) sqv-4(n2827)/++(RW7000) hermaphrodites and Sma non-Sqv progeny from sqv-4(n2827) sma-1(e30)/++(RW7000) hermaphrodites. All 12 Unc non-Sqv progeny carried the Tc1 polymorphism bP1 (Williams et al., *Genetics* 131:609-24, 1992), and 12 of 18 Sma non-Sqv progeny carried bP1. We obtained Unc non-Sqv progeny from unc-42(e270) sqv-4 (n2827)1emo-1(oz1) and Sma non-Sqv progeny from sqv-4 (n2827) sma-1(e30)/emo-1(oz1). All 15 Unc non-Sqv progeny carried emo-1(oz1), and 28 of 36 Sma non-Sqv progeny carried emo-1(oz1). We examined the vulval phenotype of six dpy-18(e364); unc-60(e677) dpy-11(e224) sDf35/sqv-4 (n2827) hermaphrodites, and all were non-Sqv. We obtained unc-60(e677) dpy-11(e224) sDf35 dead eggs from dpy-11 (e224) odr-2(n2145) mec-1(e1066) unc-42(e270) sqv-4 (n2827)/unc-60(e677) dpy-11(e224) sDf35 hermaphrodites or unc-42(e270) sqv-4(n2827)/unc-60(e677) dpy-11(e224) sDf35 hermaphrodites. Using single sDf35 eggs, we amplified genomic DNA sequence corresponding to the cosmids C35A5, T21C9 and/or C32C4 (see FIG. 13a). Cosmid F58E6, which contains unc-42 and is deleted in sDf35, was used as the negative amplification control, and C26B2 and D2096 from LGIV were used as positive controls. PCR products of expected length were amplified for C32C4 (n=3) and T21 C9 (n=5), but not for C35A5 (n=12), which placed the right endpoint of sDf35 between T21C9 and C35A5.

sqv-4 Rescue

We injected genomic DNA into unc-42(e270) sqv-4 (n2827)/emo-1(oz1) animals at concentrations of 3-7 µg/ml with the dominant roller marker pRF4 (80 µg/ml) as described by Mello et al. (*EMBO J.* 10, 3959-3970,1991) for germline rescue. Rol lines were established, and Unc Rol animals were examined for rescue of the sqv-4 mutant phenotype.

sqv-4 cDNA

To identify sqv-4 cDNAs, a 4.8 kb EcoRV-XhoI rescuing fragment was used to probe an embryonic stage lambda-gt11 cDNA library (Okkema et al., *Development* 120:2175-86, 1994) and isolate cDNA clones. The cDNA clone that contained the longest ORF identical to F29F11.1 was predicted to encode a protein of 481 amino acids. The F29F11.1 ORF was PCR-amplified using the cDNA clone as a template and the oligonucleotides 5'-TCTGGTACCATGACTGAT-CAAGTCTTC-3' (SEQ ID NO:51) and 5'-TCTGATATCT-TAATAACCAGCTGTTCC-3' (SEQ ID NO:52) as primers. The resulting product was digested with KpnI and EcoRV and cloned into pPD49.78 and pPD49.83 (from A. Fire). We injected sqv-4(n2827)/nT1(n754) animals with the sqv-4 coding sequence transcriptionally fused to the *C. elegans* heat-shock promoters (Stringham et al., *Mol. Biol. Cell* 3:221-33, 1992) in the vectors pPD49.78 (90 µg/ml) and pPD49.83 (85 µg/ml) with pRF4 (80 µg/ml), and Rol lines were established. Rol non-Unc animals were examined for rescue of the sqv-4 mutant phenotype following induction of sqv-4 expression by 30 minutes of heat-shock treatment at 33° C.

sqv-4 RNAi

For RNAi by injection, the sqv-4 cDNA was PCR-amplified using lambda-gt11 primers and the cDNA clone as a template. The resulting product was cloned into pBluescript II SK+ (Stratagene), digested with EcoRV and treated with dNTPs and Taq polymerase. RNA was synthesized using T3 and T7 polymerases and injected as described by Fire et al. (*Nature* 391:806-11, 1998). For RNAi by feeding, the sqv-4 ORF, cloned into a pMAL-c2 expression vector (New England Biological), was digested with XhaI and SalI and cloned into the pPD129.36 feeding vector (Timmons et al., *Nature* 395:854, 1998). Expression of dsRNA was induced as described by Kamath et al. (*Genome Biol*. 2:1-102000).

UDP-Glucose Dehydrogenase Assay

The sqv-4 coding sequences corresponding to the wild-type, n2827, and n2840 alleles were cloned into the pET21d *E. coli* expression vector and transformed into BL21 pLysS. The oligonucleotides 5'-GACACACACGAATCATCAGC-3' (SEQ ID NO:53) and 5'-GTACTTATCGAGTGGGATG-3' (SEQ ID NO:54) were used to generate R353H n2827 and T4101 n2840 mutations, respectively, by site-directed mutagenesis. The oligonucleotides 5'-TCTCCATGGCT-GATCAAGTCTTCGG-3' (SEQ ID NO:55) and 5'-TCTCTCGAGTTAATAACCAGCTGTTCC-3' (SEQ ID NO:56) were used for PCR-amplification of the sqv-4 ORF, and the resulting product was digested with NcoI and XhoI and cloned into pET21d. All three proteins have a threonine to alanine mutation in the second amino acid because of the addition of an NcoI site at the 5' end. SQV-4 expression was induced by incubation with 1 mM IPTG for three to four hours at 37° C. *E. coli* were pelleted and resuspended in 50 mM Tris-HCl pH 7.5, 1 mM DTT, 1 mM EDTA, 1 mM PMSF, 2 µg/ml pepstatin A, and aprotinin and lysed using a French pressure cell. The soluble fraction was separated from the insoluble inclusion bodies by centrifugation at 12,000 g for 20 minutes. Most of the recombinant SQV-4 protein was present in the soluble fraction, which was used for the UDP-glucose dehydrogenase assay without further purification.

UDP-glucose dehydrogenase activity was assayed spectrophotometrically by measuring the reduction of $NAD^+$ in the presence of UDP-glucose at 340 nm (Strominger et al., *J. Amer. Chem. Soc*. 224:79-90, 1954). All assays were performed at room temperature (20 to 22° C.) in 50 mM Tris-HCl, 2 mM dithiothrietol (DTT), pH 8.7. The initial velocity of the reaction was determined from time points during the first 60 seconds after addition of the SQV-4 extract. The substrate specificity of SQV-4 was examined by measuring $NAD^+$ reduction in the presence of 100 µM $NAD^+$ and 250 µM UDP-galactose, UDP-mannose, UDP-glucuronic acid, UDP-N-acetyl-glucosamine, TDP-glucose, ADP-glucose, CDP-glucose, or GDP-glucose.

Anti-SQV-4 Antibodies and Immunostaining

The full-length sqv-4 coding sequence was cloned into vectors pGEX-4T3 and pMAL-c2 to generate GST-SQV-4 and MBP-SQV-4 fusion proteins, respectively. The oligonucleotides used for PCR-amplifications were 5'-TCTC-CCGGGTAATGACTGATCAAGTCTTC-3' (SEQ ID NO:57) and 5'-TCTCTCGAGATAACCAGCTGTTC-CGAATAG-3' (SEQ ID NO :58), for pGEX-4T3, and 5'-TCT-TCTAGAATGACTGATCAAGTCTTC-3' (SEQ ID NO:59) and 5'-TCTGTCGACTTAATAACCAGCTGTTCC-3' (SEQ ID NO:60), for pMAL-c2. The amplified product was digested with XmaI and XhoI for cloning into pGEX4-3, and with XbaI and SalI, for cloning into pMAL-c2. The GST-SQV-4 and MBP-SQV-4 fusion proteins were purified by isolating the insoluble fusion proteins in inclusion bodies followed by SDS-PAGE and electroelution. GST-SQV-4 was injected into two rabbits (Covance, Princeton, N.J.). Anti-SQV-4 antisera were affinity purified by binding to MBP-SQV-4 fusion protein bound to OPTITRAN reinforced nitrocellulose (Schleicher & Schuell, Keene, N.H.) strips, and eluted with 100 mM glycine, pH 2.5. For western blots, SQV-4 was visualized using horseradish peroxidase conjugated secondary antibodies (Bio-Rad, Hercules, Calif.) and chemiluminescent detection reagents (Pierce, Rockford, Ill.).

Whole worms were fixed using 40:40:1 parts of Bouin's fixative (15:5:1 parts of saturated picric acid: 37% formnaldehyde:glacial acetic acid):methanol:β3-mercaptoethanol as described by Nonet et al. (*J. Neurosci* 17:8061-73, 1997). Briefly, the worms were incubated in fixative for thirty minutes at room temperature, frozen with liquid nitrogen, quickly thawed, and incubated at room temperature for an additional ten or thirty minutes. The worms were washed with a solution of BTB 1×Borate buffer, 0.5% Triton X-100, 2% β-mercaptoethanol) several times, until most of the yellow tinge was removed from the worms. The worms were incubated with fresh BTB for two to three hours with a change of BTB after the first hour. The worms were washed with BT (BTB minus the β-mercaptoethanol) once, and with PBST-A (1×PBS, 1% BSA, 0.5% Triton X-100, 5 mM sodium azide, 1 mM EDTA) once. The worms were blocked with PBST-A for 30 minutes and stored at 4° C. The fixed worms were incubated with anti-SQV-4 antibodies and goat anti-rabbit FITC-conjugated secondary antibodies (Jackson) as described by Finney and Ruvkun (1990).

The staining patterns observed by whole-mount immunohistochemistry using antibodies from both rabbits were indistinguishable. Pre-immune antisera showed staining comparable to that seen with the secondary antibodies only, and pre-absorption of the antibody using GST-SQV-4 fusion protein reduced the whole-mount staining to background level indicating that the SQV-4 staining was specific.

Expression of SQV-4-GFP Under a sqv-4 Promoter

The oligonucleotides 5'-TCTCCCGGGATAACCAGCT-GTTCCGAATAG-3' (SEQ ID NO:61) and 5'-CCAATATAC-GAGGTGAGC-3' (SEQ ID NO:62) were used to amplify a genomic fragment of sqv-4. The resulting 1.5 kb fragment was digested with XmaI (at the 3' of sqv-4) and PstI (in the middle of the sqv-4 locus) and ligated with a PstI-SalI fragment containing genomic DNA spanning the middle of the sqv-4 locus to 6253 bases upstream of the predicted ATG of sqv-4 and a SalI-XmaI fragment of the GFP vector pPD95.79 (from A. Fire). We injected sqv-4(n2827)/nT1(n754) animals with the sqv-4 genomic locus and 6253 bases upstream of the predicted ATG transcriptionally fused to GFP in the vector pPD95.79 (80 μg/ml). GFP-positive lines were established and were found to rescue sqv-4.

sqv-5 Mapping

We obtained Unc non-Vul and Vul non-Unc progeny from unc-29(e1072) lin-11(n566)lsqv-5(n3039) hermaphrodites. Five often Unc non-Vul progeny carried sqv-5(n3039), and three of ten Vul non-Unc progeny carried sqv-5(n3039), suggesting sqv-5(n3039) was located to the left of lin-11(n566). We examined the vulval phenotype of animals with the genotype ces-1(n703) Df/sqv-5(n3039) where the Df used was qDf5, qDf7, qDf8, qDf9 and qDf10. All were Sqv except for ces-1(n703) qDf5/sqv-5(n3039). Because qDf5, qDf7, qDf8, qDf9 and qDf10 were previously shown to deletefog-3, but only qDf5 and qDf7 was shown to delete lin-11 (10), this mapping placed sqv-5 to the left of fog-3. Using single qDf10 eggs, we amplified genomic DNA sequence corresponding to cosmids K10C3 and C03C11. PCR product of expected length was amplified for K10C3, but not for C03C11 (n=10), which placed the left end point of qDf10 between K10C3 and C03C11.

Site-Directed Mutagenesis of Genomic sqv-5 Locus

To generate genomic sqv-5 fragments with nonsense mutations in T24D1.1, two rounds of PCR were done for each mutation using the 18448 base pair BamHI-PstI rescuing fragment of K09A8 as the template. Two primer pairs were used to amplify overlapping products in the first cycle, and a second round of PCR was done using the two 'outer' primers of the first cycle and the two amplified products from the first round as the template. The primers are listed as the 'outer' 5' primer, 'inner' 3' primer, 'inner' 5' primer and 'outer' 3' primer: (1) the outer primer 5'-AAAGTTCCAACACGAG-GAG-3' (SEQ ID NO:63) (f0a), 5'-GTGTATCAACG-TATTTTGCAGC-3' (SEQ ID NO:64) (r8), the mutagenic primer 5'-CCTACTCTGAATCCTGTTTGG-3' (SEQ ID NO:65) (m167), 5'-CAACACGCATGTATCCATATTG-3' (SEQ ID NO:66)(r5) to generate G21opal mutation; (2) 5'-AAAGTTCCAACACGAGGAG-3' (SEQ ID NO:67) (F0a), 5'-ATCGGTAGATCCAAGAGC-3' (SEQ ID NO:68) (r7), the mutagenic primer 5'-GATGAATAGGATTGGT-TCTTG-3' (SEQ ID NO:69) (m528), 5'-CAACACGCATG-TATCCATATTG-3' (SEQ ID NO:70) (r5) to generate Y160amber mutation; (3) 5'-CGTCCACCAAACAGAA-CAAC-3' (SEQ ID NO:71) (f7a), 5'-GATGTGAACAAGTC-CAGG-3' (SEQ ID NO:72) (r1), the mutagenic primer 5'-GAAGGATGAGGAAAGGAAGATG-3' (SEQ ID NO:73) (mn3039), 5'-AGCATGGGACAATTACTCG-3' (SEQ ID NO:74) (r0a) to generate W664opal sqv-5(n3039). The amplified product containing G21opal or Y160 amber mutation was digested with AatII and StuI, and the amplified product containing W664opal sqv-5(n3039) was digested with PacI and MluI. The resulting digested product was cloned into pBluescriptII (Stratagene) containing the 18448 base BamHI-PstI rescuing fragment of K09A8, and digested with the same pair of restriction enzymes. To generate a genomic sqv-5 fragment with a four base insertion and frameshift mutation in T24D1.1, a pBluescriptII containing the 18448 base BamHI-PstI rescuing fragment was digested witl MluI and blunted with dNTP, Klenow fragment, and T4 DNA polymerase, and then self ligated.

Deletion Allele

Null mutation sqv-5(n3611) was isolated from a library of animals mutagenized with UV illumination and trimethylpsoralen (Jansen et al., Nat Genet 17:119-21, 1997) using an outer primer pair, KOF1 5'-CACTATCCAGTGCAAACG-3' (SEQ ID NO:75) and KOR3 5'-CAGCTCTTCCTCT-TAATGG-3' (SEQ ID NO:76), and a nested primer pair, KOF2 5'-GGTAATCGAGAAGACACG-3' (SEQ ID NO:77) and KOR2 5'-GATCGGAACACTCCTTC-3' (SEQ ID NO:78). The mutant animals containing sqv-5(n3611) were backcrossed six times. The sqv-5(n3611) deletion removed bases 6124 to 7767 of cosmid T24D1, or 1641 bases. A two base discrepancy results from a DNA sequencing error by the C. elegans Sequencing Consortium. Sqv-5(n3611) is predicted to encode a truncated SQV-5 that is missing 385 amino acids (amino acids 130 to 447) from the middle of SQV-5, and also contains an alanine-to-phenylalanine substitution at amino acid 129.

Site-Directed Mutagenesis of sqv-5 cDNA

A pBluescript VECTOR (Stratagene) containing the sqv-5 cDNA corresponding to yk21g9 was popped out of the LAMBDA-ZAP II (Stratagene) phage according to the manufacturer is directions, and transformed into CJ236 E. coli. Single-stranded plasmid was isolated using R408 helper phage. Site-directed mutagenesis was performned to generate restriction sites at the ends of the sqv-5 coding sequence. The primers used were 5'-AGAAGACACGGGATCCAGTAT-GCGAGTGCGG-3' (SEQ ID NO:79) to generate a 5' BamHI site, 5'-GATAGCCTTGTCGACTTTCCACCTCTATC-3' (SEQ ID NO:80) to generate a 3' SalI site and 5'-CACAT-GATAGCGGCCGCGGTTTTCCACCTC-3' (SEQ ID NO:81) to generate a 3' NotI site.

Anti-SQV-5 Antibody Generation

A sqv-5 expression vector was generated as follows: sqv-5 coding sequence was cloned into an expression vector by a three-way ligation. The constructs with the newly introduced 5' and 3' restriction sites were digested with BamHI, SalI, or NotI, as appropriate, and MluI, which cuts a site located in the middle of the sqv-5 coding sequence.

The full-length sqv-5 coding sequence was then cloned into expression vectors pGEX-4T3 and pMAL-c2, which were used to generate GST-SQV-5 and MBP-SQV-5 fusion proteins. The GST-SQV-5 and MBP-SQV-5 fusion proteins were then purified by isolating insoluble proteins in inclusion bodies, SDS-PAGE, and electroelution. The GST-SQV-5 fusion protein was injected into two rabbits (Covance). Anti-SQV-5 antisera were affinity purified by incubating the antisera with MBP-SQV-5 fusion protein bound to Optitran (Schleicher & Schuell) strips and eluting the purified antisera with 100 mM glycine, pH 2.5. Whole-mount staining of worms was done according to methods previously described herein.

Generating Worms For Biochemical Assays sqv-5(n3611), sqv-5(n3611)/hT2, and wild-type N2 hermaphrodites were picked as L4 larvae by visual examination using a dissecting microscope. The staged worms were allowed to grow for 23 to 27 hours at 22° C., re-examined, then transferred to 1.7-ml plastic tubes containing sterile water. The worms were washed once with water, twice with 50 mM Tris, pH 7.5, and then frozen in 50 μl volumes using liquid nitrogen and maintained at −70° C. Worm protein extracts were obtained by sonication.

Biochemistry

The enzymatic activity of SQV-5 was assayed as follows. SQV-5(n3611), sqv-5(n3611)/hT2, and wild-type N2 hermaphrodites were picked as L4 larvae by visual examination of the vulva using a dissecting microscope. The worms staged were allowed to grow for an additional twenty-three to twenty-seven hours at 22° C., re-examined, then transferred to 1.7-ml plastic tubes containing sterile water. The staged worms were washed once with water and twice with 50 mM Tris, pH 7.5, then frozen in a 50 µl volume using liquid nitrogen, and stored at −70° C.

Worm extracts were assayed for GlcAT glucoronosyltransferase activity by combining $1.3 \times 10^5$ cpm UDP-$^3$H-glucuronic acid donor (NEN), 6 µg β-glucuronidase-treated chondroitin acceptor, and 2.7 µg worm extract in a 25 µl reaction volume containing 0.05% Triton X-100, 10 mM $MnCl_2$, and 100 µM ATP, pH 6.5. GalNAcT activity was detected by combining 1.3 to $3 \times 10^5$ cpm UDP-$^3$H-GalNAc donor (NEN), 12 µg chondroitin acceptor, and 6.7 µg worm extract in a 25 µl reaction volume containing 0.05% Triton X-100 and 10 mM $MnCl_2$, pH 6.5. Reactions were incubated for 3 hours at 25° C., after which time 1 mg carrier chondroitin sulfate A and 500 µl GlcAT or GalNAcT loading buffer were added (GlCAT loading buffer: 20 mM NaOAc, pH 6.0, 2 mg/ml BSA, 10 mM UDP, and 10 mM GlCA; GalNAcT loading buffer: 20 mM NaOAc, pH 6.0, 2 mg/ml BSA, and 10 mM uridine). Samples were loaded onto 0.2 ml DEAE-Sephacel columns equilibrated with 0.1 M NaCl and 20 mM NaOAc, pH 6. Radiolabeled chondroitin was eluted with 1 M NaCl and 20 mM NaOAc, pH 6 and precipitated overnight with 4 volumes of ethanol at 4° C. Pelleted material was resuspended in water and counted by liquid scintillation.

The chondroitin acceptor used was prepared as follows. Chondroitin sulfate C (Sigma, St. Louis, Mo.) was passed over a DOWEX 50 WX8 ion exchange resin column ($H^+$ form, 200-400 mesh) (Bio-Rad, Hercules, Calif.), neutralized with pyridine, and lyophilized. The sample was desulfated with 90% dimethyl sulfoxide, partially deacetylated with lp% hydrazine sulfate in 70% anhydrous hydrazine, cleaved by high pH nitrous treatment, and reduced by sodium borohydride. Some of the CS preparation was digested with β-glucuronidase (Sigma) to generate GalNAc residues at the reducing end of the oligosaccharide. Uronic acid concentration of both preparations was determined by the Carbazole method (Bitter, et al., *Anal. Biochem.* 4:330-334, 1962).

Polypeptide Expression

In general, polypeptides of the invention may be produced by transformation of a suitable host cell with all or part of a polypeptide-encoding nucleic acid molecule or fragment thereof in a suitable expression vehicle.

Those skilled in the field of molecular biology will understand that any of a wide variety of expression systems may be used to provide the recombinant protein. The precise host cell used is not critical to the invention. A polypeptide of the invention may be produced in a prokaryotic host (e.g., *E. coli*) or in a eukaryotic host (e.g., *Saccharomyces cerevisiae*, insect cells, e.g., Sf21 cells, or mammalian cells, e.g., NIH 3T3, HeLa, or preferably COS cells). Such cells are available from a wide range of sources (e.g., the American Type Culture Collection, Rockland, Md.; also, see, e.g., Ausubel et al., supra). The method of transformation or transfection and the choice of expression vehicle will depend on the host system selected. Transformation and transfection methods are described, e.g., in Ausubel et al. (supra); expression vehicles may be chosen from those provided, e.g., in *Cloning Vectors: A Laboratory Manual* (P. H. Pouwels et al., 1985, Supp. 1987).

A variety of expression systems exist for the production of the polypeptides of the invention. Expression vectors useful for producing such polypeptides include, without limitation, chromosomal, episomal, and virus-derived vectors, e.g., vectors derived from bacterial plasmids, from bacteriophage, from transposons, from yeast episomes, from insertion elements, from yeast chromosomal elements, from viruses such as baculoviruses, papova viruses, such as SV40, vaccinia viruses, adenoviruses, fowl pox viruses, pseudorabies viruses and retroviruses, and vectors derived from combinations thereof.

One particular bacterial expression system for polypeptide production is the *E. coli* pET expression system (Novagen, Inc., Madison, Wis.). According to this expression system, DNA encoding a polypeptide is inserted into a pET vector in an orientation designed to allow expression. Since the gene encoding such a polypeptide is under the control of the T7 regulatory signals, expression of the polypeptide is achieved by inducing the expression of T7 RNA polymerase in the host cell. This is typically achieved using host strains that express T7 RNA polymerase in response to IPTG induction. Once produced, recombinant polypeptide is then isolated according to standard methods known in the art, for example, those described herein.

Another bacterial expression system for polypeptide production is the pGEX expression system (Pharmacia, Peapack, N.J.). This system employs a GST gene fusion system that is designed for high-level expression of genes or gene fragments as fusion proteins with rapid purification and recovery of functional gene products. The protein of interest is fused to the carboxyl terminus of the glutathione S-transferase protein from *Schistosoma japonicum* and is readily purified from bacterial lysates by affinity chromatography using Glutathione Sepharose 4B. Fusion proteins can be recovered under mild conditions by elution with glutathione. Cleavage of the glutathione S-transferase domain from the fusion protein is facilitated by the presence of recognition sites for site-specific proteases upstream of this domain. For example, proteins expressed in pGEX-2T plasmids may be cleaved with thrombin; those expressed in pGEX-3X may be cleaved with factor Xa.

Once the recombinant polypeptide of the invention is expressed, it is isolated, e.g., using affinity chromatography. In one example, an antibody (e.g., produced as described herein) raised against a polypeptide of the invention may be attached to a column and used to isolate the recombinant polypeptide. Lysis and fractionation of polypeptide-harboring cells prior to affinity chromatography may be performed by standard methods (see, e.g., Ausubel et al., supra).

Once isolated, the recombinant protein can, if desired, be further purified, e.g., by high performance liquid chromatography (see, e.g., Fisher, *Laboratory Techniques In Biochemistry and Molecular Biology*, eds., Work and Burdon, Elsevier, 1980).

Polypeptides of the invention, particularly short peptide fragments, can also be produced by chemical synthesis (e.g., by the methods described in *Solid Phase Peptide Synthesis*, 2nd ed., 1984 The Pierce Chemical Co., Rockford, Ill.).

These general techniques of polypeptide expression and purification can also be used to produce and isolate useful peptide fragments or analogs (described herein).

Antibodies

To generate antibodies, a coding sequence for a polypeptide of the invention may be expressed as a C-terminal fusion with glutathione S-transferase (GST) (Smith et al., *Gene* 67:31-40, 1988). The fusion protein is purified on glutathione-Sepharose beads, eluted with glutathione, cleaved with thrombin (at the engineered cleavage site), and purified to the degree necessary for immunization of rabbits. Primary immunizations, for example, are carried out with Freund's complete adjuvant and subsequent immunizations with Freund's incomplete adjuvant. Antibody titers are monitored by Western blot and immunoprecipitation analyses using the thrombin-cleaved protein fragment of the GST fusion protein. Immune sera are affinity purified using CNBr-Sepharose-coupled protein. Antiserum specificity is determined using a panel of unrelated GST proteins.

As an alternate or adjunct immunogen to GST fusion proteins, peptides corresponding to relatively unique immunogenic regions of a polypeptide of the invention may be generated and coupled to keyhole limpet hemocyanin (KLH) through an introduced C-terminal lysine. Antiserum to each of these peptides is similarly affinity purified on peptides conjugated to BSA, and specificity tested in ELISA and Western blots using peptide conjugates, and by Western blot and immunoprecipitation using the polypeptide expressed as a GST fusion protein.

Alternatively, monoclonal antibodies which specifically bind any one of the polypeptides of the invention are prepared according to standard hybridoma technology (see, e.g., Kohler et al., *Nature* 256:495-497, 1975; Kohler et al., *Eur. J Immunol.* 6:511-519, 1976; Kohler et al., *Eur. J Immunol.* 6:292-295, 1976; Hammerling et al., In *Monoclonal Antibodies and T Cell Hybridomas*, Elsevier, N.Y., 1981; Ausubel et al., supra). Once produced, monoclonal antibodies are also tested for specific recognition by Western blot or immunoprecipitation analysis (by the methods described in Ausubel et al., supra). Antibodies that specifically recognize the polypeptide of the invention are considered to be useful in the invention; such antibodies may be used, e.g., in an immunoassay. Alternatively monoclonal antibodies may be prepared using the polypeptide of the invention described above and a phage display library (Vaughan et al., *Nature Biotech* 14:309-314, 1996).

Preferably, antibodies of the invention are produced using fragments of the polypeptide of the invention that lie outside generally conserved regions and appear likely to be antigenic, by criteria such as high frequency of charged residues. In one specific example, such fragments are generated by standard techniques of PCR and cloned into the pGEX expression vector (Ausubel et al., supra). Fusion proteins are expressed in *E. coli* and purified using a glutathione agarose affinity matrix as described in Ausubel et al. (supra). To attempt to minimize the potential problems of low affinity or specificity of antisera, two or three such fusions are generated for each protein, and each fusion is injected into at least two rabbits. Antisera are raised by injections in a series, preferably including at least three booster injections.

Screening Assays

A number of novel nucleic acids and polypeptides are described above that function in a eukaryotic glycosaminoglycan (GAG) biosynthetic pathway; a pathway important in human medicine. As a result these novel compounds and related materials (e.g., antibodies and nucleic acids for RNA interference) may therefore be used to screen for compounds that modulate a eukaryotic GAG biosynthetic pathway. Any number of methods are available for carrying out such screening assays. According to one approach, candidate compounds are added at varying concentrations to the culture medium of cells expressing one of the nucleic acid sequences of the invention. Gene expression is then measured, for example, by standard Northern blot analysis (Ausubel et al., *Current Protocols in Molecular Biology*, Wiley Interscience, New York, 2000), using any appropriate fragment prepared from the nucleic acid molecule as a hybridization probe. The level of gene expression in the presence of the candidate compound is compared to the level measured in a control culture medium lacking the candidate molecule. A compound that modulates the expression of a sqv gene is considered useful in the invention; such a molecule may be used, for example, as a therapeutic to treat a connective tissue disease or disorder related to a defect in GAG biosynthesis, or to treat the normal effects of aging on connective tissues.

If desired, the effect of candidate compounds may, in the alternative, be measured at the level of polypeptide production using the same general approach and standard immunological techniques, such as Western blotting or immunoprecipitation with an antibody specific for a SQV polypeptide. For example, immunoassays may be used to detect or monitor the expression of at least one of the polypeptides of the invention.

Polyclonal or monoclonal antibodies (produced as described above) that are capable of binding to such a polypeptide may be used in any standard immunoassay format (e.g., ELISA, Western blot, or RIA assay) to measure the level of the SQV polypeptide. A compound that increases the expression of a SQV polypeptide is considered particularly useful. Again, such a molecule may be used, for example, as a therapeutic to treat a connective tissue disease or disorder.

Alternatively, or in addition, candidate compounds may be identified that specifically bind to a SQV polypeptide of the invention. The efficacy of such a candidate compound is dependent upon its ability to interact with the SQV polypeptide. Such an interaction can be readily assayed using any number of standard binding techniques and functional assays (e.g., those described in Ausubel et al., supra). For example, a candidate compound may be tested in vitro for interaction and binding with a polypeptide of the invention and its ability to modulate a GAG biosynthetic pathway may be assayed by any standard assays (e.g., those described herein).

Potential antagonists include organic molecules, peptides, peptide mimetics, polypeptides, nucleic acid ligands, and antibodies that bind to a nucleic acid sequence or polypeptide of the invention and thereby inhibit or extinguish its activity. Potential antagonists also include small molecules that bind to and occupy the binding site of the polypeptide thereby preventing binding to cellular binding molecules, such that normal biological activity is prevented. Other potential antagonists include antisense molecules.

In one particular example, a candidate compound that binds to a SQV polypeptide may be identified using a chromatography-based technique. For example, a recombinant polypeptide of the invention may be purified by standard techniques from cells engineered to express the polypeptide (e.g., those described above) and may be immobilized on a column. A solution of candidate compounds is then passed through the column, and a compound specific for the SQV polypeptide is identified on the basis of its ability to bind to the SQV polypeptide and be immobilized on the column. To isolate the compound, the column is washed to remove non-specifically bound molecules, and the compound of interest is then released from the column and collected. Compounds isolated by this method (or any other appropriate method) may, if desired, be further purified (e.g., by high performance liquid chromatography). In addition, these candidate compounds may be tested for their ability to render a pathogen less virulent (e.g., as described herein). Compounds isolated by this approach may also be used, for example, as therapeutics to treat or prevent the onset of a connective tissue disease or disorder. Compounds that are identified as binding to SQV polypeptides with an affinity constant less than or equal to 10 mM are considered particularly useful in the invention.

Each of the DNA sequences provided herein may also be used in the discovery and development of compounds. The encoded protein, upon expression, can be used as a target for the screening of drugs. Additionally, the DNA sequences encoding the amino terminal regions of the encoded protein or Shine-Delgarno or other translation facilitating sequences of the respective mRNA can be used to construct antisense sequences to control the expression of the coding sequence of interest.

In one embodiment, a candidate compound that inhibits a eukaryotic GAG biosynthetic pathway is identified by growing wild-type nematodes in the presence of a candidate compound and assaying the effect of the compound on vulval development. Vulval development is compared between nematodes contacted with the candidate compound and control nematodes not contacted with the candidate compound. A candidate compounds that causes a sqv phenotype in at least 10%, 20%, 30%, 40%, 50%, 60%, 70%, 80%, 90%, or even 100% of contacted nematodes is a candidate compound that inhibits a eukaryotic GAG biosynthetic pathway.

In another embodiment, a candidate compound that enhances a eukaryotic GAG biosynthetic pathway is identified by growing Sqv mutant nematodes in the presence of a candidate compound, and assessing the effect of the compound on vulval development. A candidate compound that suppresses the Sqv phenotype in at least 10%, 20%, 30%, 40%, 50%, 60%, 70%, 80%, 90%, or even 100% of contacted nematodes is identified as a candidate compound that enhances a GAG biosynthetic pathway.

Test Compounds

Compounds that may be tested for the ability to modulate the expression of sqv-1, sqv-2, sqv-4, sqv-5 or sqv-6 can be from natural as well as synthetic sources. Those skilled in the field of drug discovery and development will understand that the precise source of test extracts or compounds is not critical to the methods of the invention. Examples of such extracts or compounds include, but are not limited to, plant-based, fungal-based, prokaryotic-based, or animal-based extracts, fermentation broths, and synthetic compounds, as well as modifications of existing compounds. Numerous methods are also available for generating random or directed synthesis (e.g., semi-synthesis or total synthesis) of any number of chemical compounds, including, but not limited to, saccharide-, lipid-, peptide-, and nucleic acid-based compounds. Synthetic compound libraries are commercially available from Brandon Associates (Merrimack, N.H.) and Aldrich Chemical (Milwaukee, Wis.). For example, libraries of natural compounds in the form of bacterial, fungal, plant, and animal extracts are commercially available from a number of sources, including Biotics (Sussex, UK), Xenova (Slough, UK), Harbor Branch Oceanographics Institute (Ft. Pierce, Fla.), and PharmaMar, U.S.A. (Cambridge, Mass.). Natural and synthetically produced libraries may be produced, if desired, according to methods known in the art, e.g., by standard extraction and fractionation methods. If desired, any library or compound is readily modified using standard chemical, physical, or biochemical methods.

A test compound that modulates the expression of sqv-1, sqv-2, sqv-4, sqv-5 or sqv-6, or its encoded protein, may be used to treat a connective tissue diseases, progeroid disorders, or cellular damage caused by aging.

Treatment

The invention provides methods for treating connective tissue diseases, progeroid disorders, or the connective tissue damage caused by aging. These treatments may be administered by any of a variety of routes known to those skilled in the art, such as, for example, intraperitoneal, subcutaneous, parenteral, intravenous, intramuscular, or subdermal injection. However, sqv-1, sqv-2, sqv-4, sqv-5 or sqv-6 nucleic acids or their encoded proteins may also be administered as an aerosol, as well as orally, nasally, or topically. Standard concentrations used to administer a sqv-1, sqv-2, sqv-4, sqv-5 or sqv-6 nucleic acid or encoded protein include, for example, $10^2$, $10^3$, $10^4$, $10^5$, or $10^6$ plaque forming units (pfu)/animal, in a pharmacologically acceptable carrier. Appropriate carriers or diluents, as well as what is essential for the preparation of a pharmaceutical composition are described, e.g., in Remington's Pharmaceutical Sciences ($18^{th}$ edition), ed. A. Gennaro, 1990, Mack Publishing Company, Easton, Pa., a standard reference book in this field.

Formulations for parenteral administration may, for example, contain excipients, sterile water, or saline. For inhalation, formulations may contain excipients, for example, lactose. Aqueous solutions may be used for administration in the form of nasal drops, or as a gel for topical administration. The exact dosage used will depend on the severity of the condition, or the general health of the patient and the route of administration. sqv-1, sqv-2, sqv-4, sqv-5 or sqv-6 nucleic acids or their encoded proteins may be administered once, or it may be repeatedly administered as part of a regular treatment regimen over a period of time.

In addition, the invention provides methods for treating connective tissue disease. A sqv-1, sqv-2, sqv-4, sqv-5 or sqv-6 nucleic acid sequence may be introduced into a cell, for example, by using liposome-based transfection techniques, to treat the connective tissue disease, progeroid disorder, or cellular damage caused by aging (Units 9.1-9.4, Ausubel et al., Current Protocols in Molecular Biology, John Wiley & Sons, New York, 2001). Such DNA constructs may also be introduced into mammalian cells using an adenovirus, or retroviral or vaccinia viral vectors (Units 9.10 and 16.15-16.19, Ausubel et al., Current Protocols in Molecular Biology, John Wiley & Sons, New York, 2001). These standard methods of introducing DNA into cells are applicable to a variety of cell-types.

Recombinant adenoviral vectors offer several significant advantages for gene transfer therapies. The adenoviruses can be prepared at extremely high titer, infect non-replicating cells, and confer high-efficiency and high-level transduction of target cells in vivo after directed injection or perfusion. Either directed injection or perfusion are appropriate for delivery of vectors containing a sqv-1, sqv-2, sqv-4, sqv-5 or sqv-6 gene in a clinical setting.

In animal models, adenoviral gene transfer has generally been found to mediate high-level expression for at least one week. The duration of transgene expression may be prolonged, and ectopic expression relatively reduced, by using tissue-specific promoters in combination with the sqv gene of choice. Other improvements in the molecular engineering of the adenoviral vector itself have produced more sustained transgene expression and with less inflammation. This is seen with so-called "second generation" vectors harboring specific mutations in additional early adenoviral genes and "gutless" vectors in which virtually all the viral genes are deleted utilizing a Cre-Lox strategy (Engelhardt, et al., Proc. Natl. Acad. Sci. USA 91:6196-6200, 1994; Kochanek, et al., Proc. Natl. Acad. Sci. USA 93:5731-5736, 1996).

In addition, recombinant adeno-associated viruses (rAAV), derived from non-pathogenic parvoviruses, may be used to express a sqv-1, sqv-2, sqv-4, sqv-5 or sqv-6 gene as these vectors evoke almost no cellular immune response, and produce transgene expression lasting months in most systems. Incorporation of a tissue-specific promoter is, again, beneficial. Furthermore, besides adenovirus vectors and rAAVs, other vectors and techniques are known in the art, for example, those described by Wattanapitayakul and Bauer (*Biomed. Pharmacother.* 54:487-504, 2000), and citations therein.

A vector carrying a sqv-1, sqv-2, sqv-4, sqv-5 or sqv-6 gene can be delivered to the target organ through in vivo perfusion by injecting the vector into the target organ, or into blood vessels supplying this organ (e.g., for the liver, the portal vein (Tada, et al., *Liver Transpl. Surg.* 4:78-88, 1998)).

Diagnosis

The methods of the present invention can be used to diagnose connective tissue diseases or progeroid disorders in a patient, or a predisposition to acquiring such disorders, by determining whether the cells of the patient are defective in the expression of a sqv-1, sqv-2, sqv-4, sqv-5 or sqv-6. nucleic acid molecules or polypeptides.

A genetic lesion in a sqv-1, sqv-2, sqv-4, sqv-5 or sqv-6 may be identified in a biological sample obtained from a patient using a variety of methods available to those skilled in the art. Generally, these techniques icnlude PCR amplification of nucleic acid from the patient sample, followed by identification of the genetic lesion by either altered hybridization, aberrant electrophoretic gel migration, restriction fragment, length polymorphism (RFLP) analysis, binding or cleavage mediated by mismatch binding proteins, or direct nucleic acid sequencing, such as identification of single nucleic acid polymorphisms (SNPs).

Any of these techniques may be used to facilitate detection of a genetic. lesion in a candidate gene, and each is well known in the art; examples of particular techniques are described, without limitation, in Orita et al. (*Proc. Natl. Acad. Sci. USA* 86:2766-2770, 1989) and Sheffield et al. (*Proc. Natl. Acad. Sci. USA* 86:232-236, 1989). Furthermore, expression of the sqv-1, sqv-2, sqv-4, sqv-5 or sqv-6 in a biological sample (e.g., a biopsy) may be monitored by standard Northern blot analysis or may be aided by PCR (see, e.g., Ausubel et al., *Current Protocols in Molecular Biology*, John Wiley & Sons, New York, N.Y., 2001; *PCR Technology: Principles and Applications for DNA Amplification*, H. A. Ehrlich, Ed., Stockton Press, NY; Yap et al., *Nucl. Acids. Res.* 19:4294, 1991).

Once a genetic lesion is identified using the methods of the invention (as is described above), the genetic lesion is analyzed for association with an increased risk of developing a connective tissue disease or progeroid disorder.

Antibodies against a protein produced by the gene which has the genetic lesion, for example, a SQV-1, SQV-2, SQV-4, SQV-5 or Sqv-6 protein, may be used to detect altered expression levels of the protein. Such altered expression may include a lack of expression, or a change in its mobility on a gel, which in turn indicates a change in the protein structure or size. In addition, antibodies may be used for detecting an alteration in the expression pattern or the sub-cellular localization of the protein. Such antibodies include those that recognize both the wild-type and mutant protein, as well as those antibodies that are specific for either the wild-type or an altered form of the protein. If desired, monoclonal antibodies may also be prepared using the SQV-1, SQV-2, SQV-4, SQV-5 or SQV-6 protein described above using standard hybridoma technology (see, e.g., Kohler et al., *Nature* 256: 495, 1975; Kohler et al., *Eur. J. Immunol.* 6:511, 1976; Kohler et al., *Eur. J. Immunol.* 6:292, 1976; Hammerling et al., In *Monoclonal Antibodies and T Cell Hybridomas*, Elsevier, New York, N.Y., 1981; Ausubel et al., *Current Protocols in Molecular Biology*, John Wiley & Sons, New York, N.Y., 2001). Once produced, monoclonal antibodies are also tested for specific SQV-1, SQV-2, SQV-4, SQV-5 or Sqv-6 protein recognition by Western blot or immunoprecipitation analysis (by the methods described in, for example, Ausubel et al. (*Current Protocols in Molecular Biology*, John Wiley & Sons, New York, N.Y., 1995).

Antibodies used in the methods of the invention may be produced using amino acid sequences that do not reside within highly conserved regions, and that appear likely to be antigenic, as analyzed by criteria such as those provided by the Peptide Structure Program (Genetics Computer Group Sequence Analysis Package, Program Manual for the GCG Package, Version 7, 1991) using the algorithm of Jameson and Wolf (*CABIOS* 4:181, 1988). These fragments can be generated by standard techniques, e.g., by the PCR, and cloned into the pGEX expression vector (Ausubel et al., *Current Protocols in Molecular Biology*, John Wiley & Sons, New York, N.Y., 1995). GST fusion proteins are expressed in *E. coli* and purified using a glutathione agarose affinity matrix as described in Ausubel et al. (*Current Protocols in Molecular Biology*, John Wiley & Sons, New York, N.Y., 1995).

RNA Interference

RNA interference (RNAi) is a form of post-transcriptional gene silencing initiated by the introduction of double-stranded RNA (dsRNA). Elbashir et al. reported that 21-nucleotide RNA duplexes introduced into cultured mammalian cells could elicit gene-specific silencing (Nature 411: 494-498, 2001). Based on these results, one would predict that a double stranded RNA corresponding to one of the sqv genes (e.g., sqv-1, sqv-2, sqv-4, sqv-5, or sqv-6) described herein could be used to specifically silence sqv gene expression. To this end, the antisense nucleic acids described herein are contemplated to be employed as double-stranded RNA molecules. One in the art will recognize that the other strand of the RNA molecule has the reverse complement sequence of the depicted antisense sequence.

Use of Transgenic and Knockout Animals in Diagnosis

This invention also features transgenic and knockout animals that may be used as research tools to determine genetic and physiological features of connective tissue diseases, progeroid disorders, or the cellular damage associated with aging and for identifying therapeutic compounds. Knockout animals also include animals where the endogenous gene has been inactivated or removed and replaced with a known polymorphic or other mutant allele of the gene of interest. These animals can serve as a model system for the risk of acquiring a connective tissue disease or progeroid disorder that is associated with a particular allele.

In general, the methods of identifying markers associated with a progeroid syndromes, such as Ehlers-Danlos, or connective tissue disease, involves comparing the presence, absence, or level of expression of genes, either at the RNA level or at the protein level, in tissue from an animal and in tissue from a matching unaffected or unaltered animal. Standard techniques for detecting RNA expression, e.g., by Northern blotting, or protein expression, e.g., by Western blotting, are well known in the art. Differences between animals such as the presence, absence, or change in the level of expression of a gene indicate that the expression of the gene is a marker associated with a connective tissue disease or progeroid disorder.

To assess the effectiveness of a treatment paradigm, a transgene, such as a sqv-1, sqv-2, sqv-4, sqv-5 or sqv-6 gene, may be conditionally expressed (e.g., in a tetracycline sensitive manner) and the phenotype assessed. For example, the promoter for the transgene may contain a sequence that is regulated by tetracycline and expression of the sqv-1, sqv-2, sqv-4, sqv-5 or sqv-6 gene product ceases when tetracycline is administered to the mouse. In this example, a tetracycline-binding operator, tetO, is regulated by the addition of tetracycline, or an analog thereof, to the organism's water or diet. The tetO may be operably-linked to a coding region, for example a sqv-1, sqv-2, sqv-4, sqv-5 or sqv-6 gene. The system also may include a tetracycline transactivator (tTA), which contains a DNA binding domain that is capable of binding the tetO as well as a polypeptide capable of repressing transcription from the tetO (e.g., the tetracycline repressor (tetR)), and may be further coupled to a transcriptional activation domain (e.g., VP16). When the tTA binds to the tetO sequences, in the absence of tetracycline, transcription of the target gene is activated. Binding of tetracycline to the tTA prevents activation. Thus, a gene operably-linked to a tetO is expressed in the absence of tetracycline and is repressed in its presence. Alternatively, this system could be modified such that a gene is expressed in the presence of tetracycline and repressed in its absence. Tetracycline regulatable systems are well known to those skilled in the art and are described in, for example, WO 94/29442, WO 96/40892, WO 96/01313, and Yamamoto et al. (*Cell* 101:57-66, 2000).

In another example of conditional expression, FRT sequences may be introduced into the organism so that they flank the gene of interest. Transient or continuous expression of the FLP protein may then be used to induce site-directed recombination, resulting in the excision of the gene of interest. The use of the FLP/FRT system is well established in the art and is described in, for example, U.S. Pat. No. 5,527,695, and in Lyznik et al. (*Nucleic Acid Research* 24:3784-3789, 1996).

Conditional, i.e., somatic knockout organisms, may also be produced using the Cre-lox recombination system. Cre is an enzyme that excises DNA between two recognition sites termed loxP. The cre transgene may be under the control of an inducible, developmentally regulated, tissue specific, or cell-type specific promoter. In the presence of Cre, the gene, for example a sqv-1, sqv-2, sqv-4, sqv-5 or sqv-6 gene, flanked by loxP sites is excised, generating a knockout. This system is described, for example, in Kilby et al. (Trends in Genetics 9:413-421, 1993).

Particularly desirable is a rodent model for a progeroid syndrome (e.g., Ehlers-Danlos syndrome) or connective tissue diseases, wherein the nucleic acid having an alteration in a sqv-1, sqv-2, sqv-4, sqv-5 or sqv-6 gene, for example, an altered human chondroitin synthase gene, is expressed in the connective tissue cells of the transgenic rodent such that the transgenic rodent develops a progeroid syndrome (e.g., Ehlers-Danlos syndrome) or a connective tissue disorder. The rodents may also contain a sqv-1, sqv-2, sqv-4, sqv-5 or sqv-6 transgene, such as one expressing an appropriate (e.g., N-terminally truncated) fragment of sqv-1, sqv-2, sqv-4, sqv-5 or sqv-6 under the control of a tissue specific promoter, or have a knockout of the murine sqv-1, sqv-2, sqv-4, sqv-5 or sqv-6 gene. In addition, cell lines from these rodents may be established by methods standard in the art.

Construction of transgenes can be accomplished using any suitable genetic engineering technique, such as those described in Sambrook et al., (*Molecular Cloning: A Laboratory Manual*, Cold Spring Harbor Laboratory, N.Y., 1989). Many techniques of transgene construction and of expression constructs for transfection or transformation in general are known and may be used for the disclosed constructs. Although the use of an altered sqv-1, sqv-2, sqv-4, sqv-5 or sqv-6 gene in the transgene constructs is used as an example, wild-type sqv-1, sqv-2, sqv-4, sqv-5 or sqv-6 may also be used.

One skilled in the art will appreciate that a promoter is chosen that directs expression of the chosen gene in the cells which are affected by a progeroid syndrom or a connective tissue disease, for example, connective tissue cells. As noted above, any promoter that promotes expression of sqv-1, sqv-2, sqv-4, sqv-5 or sqv-6 in connective tissue cells can be used in the expression constructs of the present invention. One skilled in the art is aware that the modular nature of transcriptional regulatory elements and the absence of position-dependence of the function of some regulatory elements, such as enhancers, make modifications such as, for example, rearrangements, deletions of some elements or extraneous sequences, and insertion of heterologous elements possible. Numerous techniques are available for dissecting the regulatory elements of genes to determine their location and function. Such information can be used to direct modification of the elements, if desired. It is desirable, however, that an intact region of the transcriptional regulatory elements of a gene is used. Once a suitable transgene construct has been made, any suitable technique for introducing this construct into embryonic cells can be used.

Animals suitable for transgenic experiments can be obtained from standard commercial sources such as Taconic (Germantown, N.Y.). Many strains are suitable, but Swiss Webster (Taconic) female mice are desirable for embryo retrieval and transfer. B6D2F (Taconic) males can be used for mating and vasectomized Swiss Webster studs can be used to stimulate pseudopregnancy. Vasectomized mice and rats are publicly available from the above-mentioned suppliers. However, one skilled in the art would also know how to make a transgenic mouse or rat. An example of a protocol that can be used to produce a transgenic animal is provided below.

Production of Transgenic Mice and Rats

The following is but one desirable means of producing transgenic mice. This general protocol may be modified by those skilled in the art.

Female mice six weeks of age are induced to superovulate with a 5 IU injection (0.1 cc, IP) of pregnant mare serum gonadotropin (PMSG; Sigma) followed 48 hours later by a 5 IU injection (0.1 cc, IP) of human chorionic gonadotropin (hCG, Sigma). Females are placed together with males immediately after hCG injection. Twenty-one hours after hCG injection, the mated females are sacrificed by $CO_2$ asphyxiation or cervical dislocation and embryos are recovered from excised oviducts and placed in Dulbecco's phosphate buffered saline with 0.5% bovine serum albumin (BSA, Sigma). Surrounding cumulus cells are removed with hyaluronidase (1 mg/ml). Pronuclear embryos are then washed and placed in Earle's balanced salt solution containing 0.5% BSA (EBSS) in a 37.5 C incubator with humidified atmosphere at 5% $CO_2$, 95% air until the time of injection. Embryos can be implanted at the two-cell stage.

Randomly cycling adult female mice are paired with vasectomized males. Swiss Webster or other comparable strains can be used for this purpose. Recipient females are mated at the same time as donor females. At the time of embryo transfer, the recipient females are anesthetized with an intraperitoneal injection of 0.015 ml of 2.5% avertin per gram of body weight. The oviducts are exposed by a single midline dorsal incision. An incision is then made through the body wall directly over the oviduct. The ovarian bursa is then torn with watchmakers forceps. Embryos to be transferred are placed in DPBS (Dulbecco's phosphate buffered saline) and in the tip of a transfer pipet (about 10 to 12 embryos). The pipet tip is inserted into the infundibulum and the embryos are transferred. After the transferring the embryos, the incision is closed by two sutures.

A desirable procedure for generating transgenic rats is similar to that described above for mice (Hammer et al., *Cell* 63:1099-112, 1990). For example, thirty-day old female rats are given a subcutaneous injection of 20 IU of PMSG (0.1 cc) and 48 hours later each female placed with a proven, fertile male. At the same time, 40-80 day old females are placed in cages with vasectomized males. These will provide the foster mothers for embryo transfer. The next morning females are checked for vaginal plugs. Females who have mated with vasectomized males are held aside until the time of transfer. Donor females that have mated are sacrificed ($CO_2$ asphyxiation) and their oviducts removed, placed in DPBA (Dulbecco's phosphate buffered saline) with 0.5% BSA and the embryos collected. Cumulus cells surrounding the embryos are removed with hyaluronidase (1 mg/ml). The embryos are then washed and placed in EBSs (Earle's balanced salt solution) containing 0.5% BSA in a 37.5 C incubator until the time of microinjection.

Once the embryos are injected, the live embryos are moved to DPBS for transfer into foster mothers. The foster mothers are anesthetized with ketamine (40 mg/kg, IP) and xulazine (5 mg/kg, IP). A dorsal midline incision is made through the skin and the ovary and oviduct are exposed by an incision through the muscle layer directly over the ovary. The ovarian bursa is torn, the embryos are picked up into the transfer pipet, and the tip of the transfer pipet is inserted into the infundibulum. Approximately 10 to 12 embryos are transferred into each rat oviduct through the infundibulum. The incision is then closed with sutures, and the foster mothers are housed singly.

Generation of Knockout Mice

The following is but one example for the generation of a knockout mouse and the protocol may be readily adapted or modified by those skilled in the art.

Embryonic stem cells (ES), for example, $10^7$ AB1 cells, may be electroporated with 25 μg targeting construct in 0.9 ml PBS using a Bio-Rad Gene Pulser (500 μF, 230 V). The cells may then be plated on one or two 10-cm plates containing a monolayer of irradiated STO feeder cells. Twenty-four hours later, they may be subjected to G418 selection (350 μg/ml, Gibco) for 9 days. Resistant clones may then be analyzed by Southern blotting after Hind III digestion, using a probe specific to the targeting construct. Positive clones are expanded and injected into C57BL/6 blastocysts. Male chimeras may be back-crossed to C57BL/6 females. Heterozygotes may be identified by Southern blotting and intercrossed to generate homozygotes.

The targeting construct may result in the disruption of the gene of interest, e.g., by insertion of a heterologous sequence containing stop codons, or the construct may be used to replace the wild-type gene with a mutant form of the same gene, e.g., a "knock-in." Furthermore, the targeting construct may contain a sequence that allows for conditional expression of the gene of interest. For example, a sequence may be inserted into the gene of interest that results in the protein not being expressed in the presence of tetracycline. Such conditional expression of a gene is described in, for example, Yamamoto et al. (*Cell* 101:57-66, 2000).

These examples are provided for the purpose of illustrating the invention and should not be construed as limiting.

All publications and patent applications mentioned in this specification are herein incorporated by reference to the same extent as if each independent publication or patent application was specifically and individually indicated to be incorporated by reference.

Other embodiments are within the scope of the claims.

SEQUENCE LISTING

```
<160> NUMBER OF SEQ ID NOS: 81

<210> SEQ ID NO 1
<211> LENGTH: 3120
<212> TYPE: DNA
<213> ORGANISM: Caenorhabditis elegans

<400> SEQUENCE: 1
tcaaattttc gtatttctg ctgaactttt aatattcata gtctccaagg ctatgttaat      60
attcttggtt taagagtttg ctttgttgct ttctaaatat attttttta ctttctcttt     120 gtaacttttt taaatttcat atttggaagc gtaatacatt ttccaaaact tcaggcatct    180
gcatgcaacc aatcaataat caacgcgcat gctgagcccc agacgtatcc gtaacaactc    240
gatttcgatg gcaacacgtg gagcatgtgc tgtactaatc acattttttc tcatatttgg    300
ttagtgaaaa caatttttaa caatacaatc aatttcata aatattcgtc aactccaata     360
attttttgac aaagtttgt ttaatgatta cggttttcag tgttgataac aaatacatcg     420
aacaaatcat tgtcgagtga cgtcattgaa aaaagcgagc aaaaaatcag tcagatggag    480
gaggaaggac gaggagatac gattgtcgaa tttaataagt atggattaat tttttttgaaa   540 acatttttgc ttatcgtctg gtagggtttt tcttcacaga aaaattgatt tttctctaat    600 ttagacttt ttcaaaaaat gatcaacaca tagaaacaga aaaaaaatct atcaatttaa     660
aaataccaat taaagttatc aacgtgaaga tatgaaatgt ataattttttc agaaacaata   720
```

```
ttcctgacga cactgtctca tcattactgg aaagaataaa attacttgaa gacgaacttt    780
cgtcgatgag aactcggatg gatgatgctg aaaatcgaga aggaaatgct gcaaatggag    840
atgaaattgt tgcacctctc ccgacaacgt aagatatccg agtttatcaa aatgctttaa    900
aaaaagattt tcagaaagtc attcccatct gttcgatacc ggaatgagga aactcgaaaa    960
cgtattctga ttactggagg agctggtttt gttggatcac atttggtaga taagctgatg   1020
ttagacgggc atgaagtcat cgcactggat aattatttca ctggaagaaa gaaaaatgtt   1080
gagcattgga ttggacatcc aaatttcgaa atggttcatc acgatgttgt gaatccatat   1140
tttgtggaag ttgatcagat ttatcacttg gcttctcctg catcaccacc tcattatatg   1200
tataatcctg tcaaaactat caaaacgaac acattgggga ctattaatat gcttggattg   1260
gcaaagttcg tttttttttt caaatattca attttgtgaa actactatac tcatacttaa   1320
atcgaatgtt ctgtaatcct tacttttcag acgcgtcaaa gccacagttc ttcttgcatc   1380
aacttcagaa gttacggag atccagaagt tcacccacag ccagaaactt attggggaca   1440
tgttaataca attggaccac gagcatgtta tgatgagggt aaacgagttg ccgaatcgct   1500
tatggttgct acaataaac aagaaaatat caagattcga attgctcgaa ttttcaacac   1560
ttttggacca agaatgcaca tgaatgatgg acgagttgtt tcgaatttta taattcaggc   1620
acttcaggat aaaccaatca cggtgagcaa tagcttctta tacttaatat gaaaaaatta   1680
ttctgaacat tgtagatcta cgggaacgga actcaaacgc gatcattcca atatgtgaca   1740
gatcttgttg atggactgat taagctgatg aacagtaatt actctctccc agtcaacatt   1800
ggaaacccag aagaacatac aatcgggcag tttgcaacaa ttattcgtga tcttgttcca   1860
ggatcaacaa gtgaaattgt gaatttggaa tctcaacagg atgatcctca acaaagaagg   1920
ccagatatcc ggagagctgc tgaacaaata tcatgggctc acaagttcca tatgaaagac   1980
ggactcctta aaactgttga ctactttcgt gctgaaattg accgaaataa acgaggaggg   2040
aaacctgtac cggagcctgt aaggcttgca ggtcttgaga gtcgacgatg agaacgcaac   2100
aagcaaggct cgaaccgaaa cttccaattt atatcatttc tttttccaaa atatttcctg   2160
tcttttaaat acgggtaatt tccttattct aggcattatt ttacattctt ccaatcctgg   2220
tttacatgta aaaacgtgct tcattatcag tgcgttttct ccggtatttt tgcttttca    2280 aaatcgatat catcttgatt taaatacgcg gttcacattt tcctctaatt cacagtctat   2340
tttccgcttt catgttgtat atttcaattt tatagaattt ttaaatgcac ccgtctttga   2400
taaaaattga acttcgtac aagtgctcga cttttttttg ttttttgttg tgaagtgata   2460
gatgttggtt gtcgtgcctg gtttcattac ataaaaaagc tttctaattc catattgccg   2520
gaaaatttca agagactttg tatttcagga atggccgctg agcctatgga agaggacgat   2580
agcttcaatg atccactacc tagagctgta cctttttcctc gacattctgt aactcagact   2640
gctgctccgc tttcatcaaa acctgtagat tctgatcctg attcagatga ttcttttgaa   2700
acttttgcac cgacacaaac aacaacagga aattcactga aagttcagc aagcagtaca   2760 caatctacgg aagctagtaa tattttcgag aataataatg agaaattaat ttttttttcg   2820
ttttcagaac cacctcctgt gcaattccca ccaccgtcca aaaatcctcc aaaacacgta   2880
catcaacaaa acgtttcaag tgagaacaac taatattgat cttaaggcaa tcttctgaat   2940
tacagaatcc ccactgattc cacaacttcc gcgaaatcaa gttccgactc gacctcaaat   3000
aaatacagtt caatctgtac aacagaaacc atcagcgagt gccactggca gagtaggaat   3060
aggtgtgcat tcagcagttg cgaataccag aaatggtgtg atgacaaaaa gtgcggcaaa   3120
```

<210> SEQ ID NO 2
<211> LENGTH: 1771
<212> TYPE: DNA
<213> ORGANISM: Caenorhabditis elegans

<400> SEQUENCE: 2

| | | | | | |
|---|---|---|---|---|---|
| aggcatctgc | atgcaaccaa | tcaataatca | acgcgcatgc | tgagccccag | acgtatccgt | 60 |
| aacaactcga | tttcgatggc | aacacgtgga | gcatgtgctg | tactaatcac | attttttctc | 120 |
| atatttgtgt | tgataacaaa | tacatcgaac | aaatcattgt | cgagtgacgt | cattgaaaaa | 180 |
| agcgagcaaa | aaatcagtca | gatggaggag | gaaggacgag | gagatacgat | tgtcgaattt | 240 |
| aataaaaaca | atattcctga | cgacactgtc | tcatcattac | tggaaagaat | aaaattactt | 300 |
| gaagacgaac | tttcgtcgat | gagaactcgg | atggatgatg | ctgaaaatcg | agaaggaaat | 360 |
| gctgcaaatg | gagatgaaat | tgttgcacct | ctcccgacaa | caaagtcatt | cccatctgtt | 420 |
| cgataccgga | atgaggaaac | tcgaaaacgt | attctgatta | ctggaggagc | tggttttgtt | 480 |
| ggatcacatt | tggtagataa | gctgatgtta | gacgggcatg | aagtcatcgc | actggataat | 540 |
| tatttcactg | gaagaaagaa | aaatgttgag | cattggattg | acatccaaa | tttcgaaatg | 600 |
| gttcatcacg | atgttgtgaa | tccatatttt | gtggaagttg | atcagattta | tcacttggct | 660 |
| tctcctgcat | caccacctca | ttatatgtat | aatcctgtca | aaactatcaa | acgaacaca | 720 |
| ttggggacta | ttaatatgct | tggattggca | aaacgcgtca | aagccacagt | tcttcttgca | 780 |
| tcaacttcag | aagtttacgg | agatccagaa | gttcacccac | agccagaaac | ttattgggga | 840 |
| catgttaata | caattggacc | acgagcatgt | tatgatgagg | gtaaacgagt | tgccgaatcg | 900 |
| cttatggttg | cttacaataa | acaagaaaat | atcaagattc | gaattgctcg | aattttcaac | 960 |
| acttttggac | caagaatgca | catgaatgat | ggacgagttg | tttcgaattt | tataattcag | 1020 |
| gcacttcagg | ataaaccaat | cacgatctac | gggaacggaa | ctcaaacgcg | atcattccaa | 1080 |
| tatgtgacag | atcttgttga | tggactgatt | aagctgatga | acagtaatta | ctctctccca | 1140 |
| gtcaacattg | gaaacccaga | agaacataca | atcgggcagt | ttgcaacaat | tattcgtgat | 1200 |
| cttgttccag | gatcaacaag | tgaaattgtg | aatttggaat | ctcaacagga | tgatcctcaa | 1260 |
| caaagaaggc | cagatatccg | gagagctgct | gaacaaatat | catgggctcc | acaagttcat | 1320 |
| atgaaagacg | gactccttaa | aactgttgac | tactttcgtg | ctgaaattga | ccgaaataaa | 1380 |
| cgaggaggga | aacctgtacc | ggagcctgta | aggcttgcag | gtcttgagag | tcgacgatga | 1440 |
| gaacgcaaca | agcaaggctc | gaaccgaaac | ttccaattta | tatcatttct | tttttcaaaa | 1500 |
| tatttcctgt | cttttaaata | cgggtaattt | ccttattcta | ggcattattt | tacattcttc | 1560 |
| caatcctggt | ttacatgtaa | aaacgtgctt | cattatcagt | gcgttttctc | cggtattttt | 1620 |
| gcttttcaa | aatcgatatc | atcttgattt | aaatacgcgg | ttcacatttt | cctctaattc | 1680 |
| acagtctatt | ttccgctttc | atgttgtata | tttcaatttt | atagaatttt | taaatgcacc | 1740 |
| cgtctttgat | aaaaattgaa | ctttcgtaca | a | | | 1771 |

<210> SEQ ID NO 3
<211> LENGTH: 2077
<212> TYPE: DNA
<213> ORGANISM: Homo sapiens

<400> SEQUENCE: 3

| | | | | | |
|---|---|---|---|---|---|
| tcctacatca | gaatggtaac | agggcccccg | cgcggcaggg | ccctggaccc | gcgcggctcc | 60 |

-continued

```
cggggatggt gagcaaggcg ctgctgcgcc tcgtgtctgc cgtcaaccgc aggaggatga    120
agctgctgct gggcatcgcc ttgctggcct acgtcgcctc tgtttggggc aacttcgtta    180
atatgaggtc tatccaggaa aatggtgaac taaaaattga agcaagatt gaagagatgg     240
ttgaaccact aagagagaaa atcagagatt tagaaaaaag ctttacccag aaatacccac    300
cagtaaagtt tttatcagaa aaggatcgga aaagaatttt gataacagga ggcgcagggt    360
tcgtgggctc ccatctaact gacaaactca tgatggacgg ccacgaggtg accgtggtgg    420
acaatttctt cacgggcagg aagagaaacg tggagcactg gatcggacat gagaacttcg    480
agttgattaa ccacgacgtg gtggagcccc tctacatcga ggttgaccag atataccatc    540
tggcatctcc agcctcccct ccaaactaca tgtataatcc tatcaagaca ttaaagacca    600
atacgattgg gacattaaac atgttggggc tggcaaaacg agtcggtgcc cgtctgctcc    660
tggcctccac atcggaggtg tatggagatc ctgaagtcca ccctcaaagt gaggattact    720
ggggccacgt gaatccaata ggacctcggg cctgctacga tgaaggcaaa cgtgttgcag    780
agaccatgtg ctatgcctac atgaagcagg aaggcgtgga agtgcgagtg ccagaatct    840
tcaacacctt tgggccacgc atgcacatga acgatgggcg agtagtcagc aacttcatcc    900
tgcaggcgct ccaggggag ccactcacgg tatacggatc cgggtctcag acaagggcgt    960
tccagtacgt cagcgatcta gtgaatggcc tcgtggctct catgaacagc aacgtcagca    1020
gcccggtcaa cctggggaac ccagaagaac acacaatcct agaatttgct cagttaatta    1080
aaaaccttgt tggtagcgga agtgaaattc agtttctctc cgaagcccag gatgacccac    1140
agaaaagaaa accagacatc aaaaaagcaa agctgatgct ggggtgggag cccgtggtcc    1200
cgctggagga aggtttaaac aaagcaattc actacttccg taaagaactc gagtaccagg    1260
caaataatca gtacatcccc aaaccaaagc ctgccagaat aaagaaagga cggactcgcc    1320
acagctgaac tcctcacttt taggacacaa gactaccatt gtacacttga tgggatgtat    1380
ttttggcttt tttttgttgt cgtttaaaga aagactttaa caggtgtcat gaagaacaaa    1440
ctggaattc attctgaagc ttgctttaat gaaatggatg tgcctaaaag ctcccctcaa    1500
aaaactgcag attttgcctt gcacttttg aatctctctt tttatgtaaa atagcgtaga    1560
tgcatctctg cgtattttca agttttttta tcttgctgtg agagcatatg ttgtgactgt    1620
cgttgacagt tttatttact ggtttctttg tgaagctgaa aaggaacatt aagcgggaca    1680
aaaaatgccg atttatttta taaaagtggg tacttaataa atgagtcgtt atactatgca    1740
taaagaaaaa tcctagcagt attgtcaggt ggtggtgcgc cggcattgat tttagggcag    1800
ataaagaat tctgtgtgag agctttatgt ttctcttta attcagagtt tttccaaggt     1860
ctacttttga gttgcaaact tgactttgaa atattcctgt tggtcatgat caaggatatt    1920
tgaaatcact actgtgtttt gctgcgtatc tggggcgggg gcaggttggg gggcacaaag    1980
ttaacatatt cttggttaac catggttaaa tatgctattt taataaaata ttgaaactca    2040
aaaaaaaaaa aaaaaaaaaa aaaaaaaaaa aaaaaaa                             2077
```

<210> SEQ ID NO 4
<211> LENGTH: 467
<212> TYPE: PRT
<213> ORGANISM: Caenorhabditis elegans

<400> SEQUENCE: 4

```
Met Leu Ser Pro Arg Arg Ile Arg Asn Asn Ser Ile Ser Met Ala Thr
 1               5                  10                  15
```

```
            Arg Gly Ala Cys Ala Val Leu Ile Thr Phe Phe Leu Ile Phe Val Leu
                         20                  25                  30

Ile Thr Asn Thr Ser Asn Lys Ser Leu Ser Ser Asp Val Ile Glu Lys
                         35                  40                  45

Ser Glu Gln Lys Ile Ser Gln Met Glu Glu Gly Arg Gly Asp Thr
             50                  55                  60

Ile Val Glu Phe Asn Lys Asn Ile Pro Asp Asp Thr Val Ser Ser
             65                  70                  75                  80

Leu Leu Glu Arg Ile Lys Leu Leu Glu Asp Glu Leu Ser Ser Met Arg
                             85                  90                  95

Thr Arg Met Asp Asp Ala Glu Asn Arg Glu Gly Asn Ala Ala Asn Gly
                         100                 105                 110

Asp Glu Ile Val Ala Pro Leu Pro Thr Thr Lys Ser Phe Pro Ser Val
                         115                 120                 125

Arg Tyr Arg Asn Glu Glu Thr Arg Lys Arg Ile Leu Ile Thr Gly Gly
                         130                 135                 140

Ala Gly Phe Val Gly Ser His Leu Val Asp Lys Leu Met Leu Asp Gly
            145                 150                 155                 160

His Glu Val Ile Ala Leu Asp Asn Tyr Phe Thr Gly Arg Lys Lys Asn
                         165                 170                 175

Val Glu His Trp Ile Gly His Pro Asn Phe Glu Met Val His His Asp
                         180                 185                 190

Val Val Asn Pro Tyr Phe Val Glu Val Asp Gln Ile Tyr His Leu Ala
                         195                 200                 205

Ser Pro Ala Ser Pro Pro His Tyr Met Tyr Asn Pro Val Lys Thr Ile
            210                 215                 220

Lys Thr Asn Thr Leu Gly Thr Ile Asn Met Leu Gly Leu Ala Lys Arg
            225                 230                 235                 240

Val Lys Ala Thr Val Leu Leu Ala Ser Thr Ser Glu Val Tyr Gly Asp
                         245                 250                 255

Pro Glu Val His Pro Gln Pro Glu Thr Tyr Trp Gly His Val Asn Thr
                         260                 265                 270

Ile Gly Pro Arg Ala Cys Tyr Asp Glu Gly Lys Arg Val Ala Glu Ser
                         275                 280                 285

Leu Met Val Ala Tyr Asn Lys Gln Glu Asn Ile Lys Ile Arg Ile Ala
                         290                 295                 300

Arg Ile Phe Asn Thr Phe Gly Pro Arg Met His Met Asn Asp Gly Arg
            305                 310                 315                 320

Val Val Ser Asn Phe Ile Ile Gln Ala Leu Gln Asp Lys Pro Ile Thr
                         325                 330                 335

Ile Tyr Gly Asn Gly Thr Gln Thr Arg Ser Phe Gln Tyr Val Thr Asp
                         340                 345                 350

Leu Val Asp Gly Leu Ile Lys Leu Met Asn Ser Asn Tyr Ser Leu Pro
                         355                 360                 365

Val Asn Ile Gly Asn Pro Glu Glu His Thr Ile Gly Gln Phe Ala Thr
                         370                 375                 380

Ile Ile Arg Asp Leu Val Pro Gly Ser Thr Ser Glu Ile Val Asn Leu
            385                 390                 395                 400

Glu Ser Gln Gln Asp Asp Pro Gln Gln Arg Arg Pro Asp Ile Arg Arg
                         405                 410                 415

Ala Ala Glu Gln Ile Ser Trp Ala Pro Gln Val His Met Lys Asp Gly
                         420                 425                 430

Leu Leu Lys Thr Val Asp Tyr Phe Arg Ala Glu Ile Asp Arg Asn Lys
```

```
                        435                 440                 445
Arg Gly Gly Lys Pro Val Pro Glu Pro Val Arg Leu Ala Gly Leu Glu
    450                 455                 460

Ser Arg Arg
465

<210> SEQ ID NO 5
<211> LENGTH: 420
<212> TYPE: PRT
<213> ORGANISM: Homo sapiens

<400> SEQUENCE: 5

Met Val Ser Lys Ala Leu Leu Arg Leu Val Ser Ala Val Asn Arg Arg
  1               5                  10                  15

Arg Met Lys Leu Leu Leu Gly Ile Ala Leu Leu Ala Tyr Val Ala Ser
                 20                  25                  30

Val Trp Gly Asn Phe Val Asn Met Arg Ser Ile Gln Glu Asn Gly Glu
             35                  40                  45

Leu Lys Ile Glu Ser Lys Ile Glu Glu Met Val Glu Pro Leu Arg Glu
 50                  55                  60

Lys Ile Arg Asp Leu Glu Lys Ser Phe Thr Gln Lys Tyr Pro Pro Val
 65                  70                  75                  80

Lys Phe Leu Ser Glu Lys Asp Arg Lys Arg Ile Leu Ile Thr Gly Gly
                 85                  90                  95

Ala Gly Phe Val Gly Ser His Leu Thr Asp Lys Leu Met Met Asp Gly
                100                 105                 110

His Glu Val Thr Val Val Asp Asn Phe Phe Thr Gly Arg Lys Arg Asn
                115                 120                 125

Val Glu His Trp Ile Gly His Glu Asn Phe Glu Leu Ile Asn His Asp
            130                 135                 140

Val Val Glu Pro Leu Tyr Ile Glu Val Asp Gln Ile Tyr His Leu Ala
145                 150                 155                 160

Ser Pro Ala Ser Pro Pro Asn Tyr Met Tyr Asn Pro Ile Lys Thr Leu
                165                 170                 175

Lys Thr Asn Thr Ile Gly Thr Leu Asn Met Leu Gly Leu Ala Lys Arg
                180                 185                 190

Val Gly Ala Arg Leu Leu Leu Ala Ser Thr Ser Glu Val Tyr Gly Asp
            195                 200                 205

Pro Glu Val His Pro Gln Ser Glu Asp Tyr Trp Gly His Val Asn Pro
210                 215                 220

Ile Gly Pro Arg Ala Cys Tyr Asp Glu Gly Lys Arg Val Ala Glu Thr
225                 230                 235                 240

Met Cys Tyr Ala Tyr Met Lys Gln Glu Gly Val Glu Val Arg Val Ala
                245                 250                 255

Arg Ile Phe Asn Thr Phe Gly Pro Arg Met His Met Asn Asp Gly Arg
                260                 265                 270

Val Val Ser Asn Phe Ile Leu Gln Ala Leu Gln Gly Glu Pro Leu Thr
            275                 280                 285

Val Tyr Gly Ser Gly Ser Gln Thr Arg Ala Phe Gln Tyr Val Ser Asp
            290                 295                 300

Leu Val Asn Gly Leu Val Ala Leu Met Asn Ser Asn Val Ser Ser Pro
305                 310                 315                 320

Val Asn Leu Gly Asn Pro Glu Glu His Thr Ile Leu Glu Phe Ala Gln
                325                 330                 335
```

-continued

```
Leu Ile Lys Asn Leu Val Gly Ser Gly Ser Glu Ile Gln Phe Leu Ser
            340                 345                 350

Glu Ala Gln Asp Asp Pro Gln Lys Arg Lys Pro Asp Ile Lys Lys Ala
        355                 360                 365

Lys Leu Met Leu Gly Trp Glu Pro Val Val Pro Leu Glu Glu Gly Leu
370                 375                 380

Asn Lys Ala Ile His Tyr Phe Arg Lys Glu Leu Glu Tyr Gln Ala Asn
385                 390                 395                 400

Asn Gln Tyr Ile Pro Lys Pro Lys Pro Ala Arg Ile Lys Lys Gly Arg
                405                 410                 415

Thr Arg His Ser
            420

<210> SEQ ID NO 6
<211> LENGTH: 441
<212> TYPE: PRT
<213> ORGANISM: Drosophila melanogaster

<400> SEQUENCE: 6

Met Thr Ala Thr Lys Lys Arg Leu Lys Ile Val Ala Ala Ile Ser Leu
1               5                   10                  15

Leu Leu Leu Leu Leu Val Tyr Leu Tyr Arg Met Ala Ser Phe Cys Pro
            20                  25                  30

Ser Gly Lys Val Ala Val Ser Val Pro Gly Val Glu Glu Val Gln Ala
        35                  40                  45

Lys Trp Pro Pro Thr Glu Ser Pro Leu Gln Arg Ser Leu Gln Met Ala
    50                  55                  60

Tyr Glu Glu Gln Ser Ser Leu Ile Arg Glu Gln Lys Ala Glu Leu Gln
65                  70                  75                  80

Arg Thr Arg Glu Asn Leu Ala Arg Leu Glu Glu Gln Val Arg Ser Leu
                85                  90                  95

Gln Thr Ser Thr Pro Arg Lys Tyr Pro Lys Val Lys Tyr Leu Asn Tyr
            100                 105                 110

Lys Asn Arg Lys Arg Ile Leu Ile Thr Gly Gly Ala Gly Phe Val Gly
        115                 120                 125

Ser His Leu Val Asp Asp Leu Met Val Gln Gly His Glu Val Ile Val
    130                 135                 140

Val Asp Asn Phe Phe Thr Gly Arg Lys Arg Asn Val Glu His Trp Leu
145                 150                 155                 160

Gly His Glu Asn Phe Glu Leu Ile His His Asp Ile Val Asn Pro Leu
                165                 170                 175

Phe Ile Glu Ile Asp Glu Ile Tyr His Leu Ala Ser Pro Ala Ser Pro
            180                 185                 190

Pro His Tyr Met Tyr Asn Pro Val Lys Thr Ile Lys Thr Asn Thr Met
        195                 200                 205

Gly Thr Ile Asn Val Leu Gly Leu Ala Lys Arg Val Met Ala Lys Val
    210                 215                 220

Leu Ile Ala Ser Thr Ser Glu Val Tyr Gly Asp Pro Thr Val His Pro
225                 230                 235                 240

Gln Pro Glu Thr Tyr Trp Gly His Val Asn Pro Ile Gly Pro Arg Ala
                245                 250                 255

Cys Tyr Asp Glu Gly Lys Arg Val Ser Glu Thr Leu Ser Tyr Ala Tyr
            260                 265                 270

Ala Lys Gln Glu Lys Val Gln Val Arg Val Ala Arg Ile Phe Asn Thr
        275                 280                 285
```

```
Tyr Gly Pro Arg Met His Met Asn Asp Gly Arg Val Val Ser Asn Phe
            290                 295                 300
Ile Leu Gln Ala Leu Arg Asn Glu Thr Ile Thr Val Tyr Gly Asn Gly
305                 310                 315                 320
Lys Gln Thr Arg Ser Phe Gln Tyr Val Ser Asp Leu Val Asp Gly Met
                325                 330                 335
Ile Ala Leu Met Ala Ser Asn Tyr Thr Gln Pro Val Asn Leu Gly Asn
            340                 345                 350
Pro Val Glu Gln Thr Ile Gly Glu Phe Ala Glu Ile Ile Lys Lys Leu
        355                 360                 365
Val Gly Gly Pro Ser Val Ile Lys Gln Ser Lys Ala Met Glu Asp Asp
370                 375                 380
Pro Gln Arg Arg Lys Pro Asp Ile Thr Arg Ala Arg Gln Leu Leu His
385                 390                 395                 400
Trp Glu Pro Lys Val Pro Leu Glu Thr Gly Leu Gln Arg Thr Ile Ser
                405                 410                 415
Tyr Phe Arg Asn Glu Leu Ala Arg Ser Asp Arg Phe Gln Glu Ser Ser
            420                 425                 430
Asn Lys Tyr Phe Asp Thr His Thr Pro
            435                 440

<210> SEQ ID NO 7
<211> LENGTH: 5759
<212> TYPE: DNA
<213> ORGANISM: Caenorhabditis elegans

<400> SEQUENCE: 7
gaatataaac atgacaaggt tcggagaagt ttgaaattta tgtgggtctc tcggcgagct      60
gagtttaaaa attaaaaaat ttagagaaaa aaagagtccc aacgcgaaaa aattccaaaa     120
actatgggat ctcgtggcgg gttttttcca atttttcact actgaaatgt tgttttttt     180 ttcagccaaa tgctgccgga atgagattct accgaacata tttgctcgta gctggcgctt    240
tttgctcatt gtgcacactt gcagtaatat tcaattgtgg atgggatgat tcaccgccag    300
caacaccttc agccatcaat ggttcggagc aattttaagc ggaaaaattt gaaaaaatcc    360
tcgaaatttc ggaaaaaact ttgaattttg atttttagc tcgaaaattg ccattttag     420 ccattttcgg agattttgac ccaaaaattt gaattttcc attaaaaaac ccgaaattcc     480
cgagaattat cagtagagcg cagtttcatt tttcgaaaaa ttcaaatttt ttgaatttc     540 aaataatgcg ccgcgctcta ctgatatttt ttctaaaaat ttcaaatttt ttagaagcag    600
agtgcacttg cattattcga aaatttagaa aaatataaaa ttttagtttt tgaaaaatgc    660
aaccgtgctc tactgataat ttttctaaaa ttttcgaatt tgagctaaa ttgcataaat     720 ttcgttccga gacccatttt ttccacaaaa ttccaatttt ttaaaggaaa attaacagta    780
gagtgcagtt gcattattcg gaaatttaaa aaacatgaaa attgaatttt tgaagaatgc    840
aaccgcgctc taatgataac ttttctaaaa atttcaaatt ttgggcacaa aattgtttaa    900
atctcgtttc gagacatcaa aattttagaa aaattgtcag taaagcgaat tttgaatttt    960
tgaaaaatgc agcaaccgcg ctctactgat aattttcaa aatttggaa attcgagctc    1020 aaaaattgca aaatttcgt ttcgagactc atttctccgc aaaattttga ttttcagtga   1080 ttttgctcc aaatgtcagc agcaactgcg ccctattgat aattttgcga aaaatttcga   1140
attttgagct cagaaattgc tcaaatttcg cttcaagacc cgattttttc tccaaatttc   1200
```

```
cgattttttt tccagaaaaa tcgataattt tccccaattt tcaggcggtg gctccaatgc    1260
tcctttaatc tcctctccaa ctaatcttcc cgaaacattt ctgtacattt caattctgac    1320
gtcaccaaac gaaacagaac gacgtcaaaa tgtccgtgac acatggttcc gcctatcaac    1380
taaaggaccg tccgttttta tcgcaaaatt cgccgtcgga acgatgggcc tcgcggccga    1440
agatcgtcgg ttgctggccg aggaaaatga gaaattcggc gatttggcgc ttctcgaccg    1500
ccatgaagag tcctatgaga ggctggcaaa gaagactttg gcctgttttg tacacgcttt    1560
tgccaatttt aaattcaaat ttttcttgaa ggtatacaac tggaatttgg ctggaaatcc    1620
gcactgcaac ttttcctga cgagggacga ggaaaagtgg tttctaggcc atggccgagg    1680
ggccgacaag tttcatcggc catttatctt gctctgtttt ccgcctgttt tctttcgttt    1740
ttcatcgatt tttttcgttt tttcttaata aaactgataa ataaatattt tttgcagatg    1800
ctaaaacaat ttccgagtaa aaaattatgt attcagtggg caagcagcgg tgaaagtggt    1860
caatgtaaaa tgatggatta cgggaataca aaacctaaac ttttctgaa acatgataca    1920 tatgatgctt agatgttgaa attacctgat tttcataacg agaccgctga aaaagttttg    1980
aggttttcaa aattcaaatt ttttagtgaa aaagtcgaga ttttcgcaca aaaagtttaa    2040
ttttgaaaat ctcaaaactt tttcagcggt ctcgttatga aaatcaggta atttcagcat    2100
ctaagcatca tatgtatcat gtttcagaaa aagtttaggt tttgtattcc cgtaatccat    2160
cattttacat tgaccacttt caccgctgct tgcccactga atacataatt ttttactcgg    2220
aaattgtttt agcatctgtg caaaaagtat ttatttatca gttttattaa gaaaaaacga    2280
aaaaaaatcg atgaaaaacg aaagaaaaca ggcggaaaac aaagcaagat aaatggccgc    2340
tgaaacttgt cggcccctcg gccatggcct agaaaccact tttcctcgtc cctcgtgtgg    2400
aaaaagttgc agtgattttg tagattttca cggaaaaatt catttattct tataaaaaaa    2460
cttgaagttt tagtctaaca attaagattc tcggtcagtt ttagagataa attactccaa    2520
agttgggaga ttttttgcgaa aaatcgttaa aaattatcaa aaatgccata ttttgtcagg    2580
aaaaatgttt ataatttaat aaacccgaaa aatatcgaaa atcggctaaa tttttagatt    2640
tttcagcaca aaaaaatgat gagaaactgt tgtgaaaaac ggttttaatc ctcaaatttt    2700
ttttaaatcg gcaaaatgtg aaattttgcc caattttgtg caaattttga ctcaaaaacc    2760
tcaattttcc tgtggcaaat ggatgtatct attgagtatt gtgatgtgca aaacctcgtt    2820
aattcgccaa tagaattacg atattctcat cacaattccc gatgggctcc atttagtcac    2880
gtttacgggg aacctctgcc caattttca ttttttggct aaaaacatta aatttttcaa    2940
caaaaaaaaa actccggtag aattattatt gttattattt gcattaaaat tttccaattt    3000
ttcactctaa aaccaccgcc gattttcccc caaaatctcc catttttca tcagaccgac    3060 atcgactcat tcgtccgaat caccccacta atcataaatc tcaaacaaat tcaagatcca    3120
atgctctact ggggattcct agatggtcga gctaaaccat tccgtaaagg aaaatggaaa    3180
gaacccgaat ggaatctgtg tgatcgttat cttccatatc aacttggcgg tggttatgtg    3240
ctctcttatg agctcattcg attccttggca atcaatgccc aactcttccg acactatcgg    3300
aatgaagatg tgtcggtagg cgcctggata ggcggcctag atgttaaata tgtacatgat    3360
ccgagatttg taccgaatg gagatcccgt ggatgtaata atgagtattt aattactcat    3420
aagcacacgg agcaagagat gcaagagatg tttgaaaatt tgaagaaaac tggaaaactt    3480
tgtgctaaag agttccagta agtcagcgga aatggacgaa aaatcatcgc atttttggg    3540 attttttgaac caatttttcaa taaaaatcaa ttttttagtgc tgaaaattga attttcgcgc    3600
```

```
gaatttttag gttttactg tgaaaattgt gggtgattta gagcttttt ggccatttt     3660
ccgcgaaaat gccagatttt aggctgaaaa atgaagaaaa atcgattaaa aacccatttt   3720
tccgggtaaa attagagaaa atcgcatttt tttgggattt ttgagaacca attttcata   3780
ataaaaaaca atttttagtg ctgaaaatcc gcattttggg ggtttaaaat gtgaaaaatc   3840
cggattttc cgagaaaaat ttagtatttg agctaaacag ccgaaaaact tgccatttc    3900
atgaaaattt cactaatttt ccgctaaaaa tcagaaaatt ggcaatttc gggttaaaac   3960
tctaaaaaat cgtaattttt cggggtttca acgcgatttt tcaattaaaa atcggttttt   4020
tgcggaaaat tggccaaaaa tttggaaatt ttggatttt aaaattaaaa aaaaaattt    4080
aagatttttt aaaaataatt ttgatttttt ggcctaaaaa tcaaaattt ggccttaaca   4140
ttaaaggatt tagccttaaa attttggatt ttttgaattt aaaaacaaaa aaaaattgaa   4200
tttttggttt aaaaatcgtc aaaatcgccc ggaaaattgg aaaattcact ttttcctaag   4260
aaaaatcgga aaaatggtc cattttcga aaaactgaat ttttgacaa aattttacg     4320
ccaaatttg gattttcca ccaaaaaaaa cccatgaaat cgctcgaaaa attagaaaaa   4380
tcgcctttt tttcggaaat ttttaagccg attttgtgaa aaatgcgaaa aaattgcccc   4440
ggattcgcta atttttggg ttttttagt aaaaaaatcg tcaaaatctc ccggaaaatt   4500
ggacaaatcg caatttcac caattttcag cccaaaaaac cgaaatttag cctaaaactg   4560
ccaaatcgct cggataatta gaaaattcac aagtttcacc aattttttaa agctattttc   4620
tcagatttt gcctaaaaat tgccaaaatc tgctggacaa attagaaaat tcgcaatttt   4680
tacccattt tggccatttt ctgggttttt ccgcaaaaaa accagatttt tgtgttaaaa   4740
tcggccggaa aattggaaaa atcggataaa aatggtcgat tttaccgaa aatcgtccaa   4800
ttttcgacat tcttgtacaa aaccccgaaa aattccaatt ttttgccaat tttttccattt   4860
ttcgaccaaa aaactgattt ttcgtgcgaa aattgcgcca atcactcga aaaattgcaa   4920
aattcgcatt tataggccga ttttttagaa agtcggcgaa acattaagcc attttcgaag   4980
tttctcggga aaaacagcg aaaaaatcga attttcgctt gttttttgct ggattcgtat   5040
ttaaaatgca atttcatca attttcccat cgaaaaaccg gaaataacct gcaaaaaccc   5100
cttttaatcg ccaaaattat gcgaaattcg cgaaattatt aattcacctc ttctccgaga   5160
ggactccgtg gccgcgacga ccgattctcc atagagcgcg cttgcctaaa atcgatttct   5220
cggccgcgtt aatcaatttc catcattttt caccaatttt taaccaattt cttgcagaaa   5280
acatccatcc tacgtgtacg atttctcgaa agcacccagc gaatgttgta caagagtcaa   5340
cggatcgaat attccataat ttattgcatt ttatcgcatt ttttactgaa tacgggccaa   5400
ttttccagat ttctacggtt tttccgcgca taataattgt cttctcgta taaatattgc   5460
attttccac atttaaaccg atttattca ttttcccccc cgaaaaatcg ttgatttttc   5520
ccagaaatac ctatttttac gcaaaatccc cagaaaaacc catacattct cacagatgtc   5580
cgataattcg ctgccagccg gatgggaaaa gcgtcagagc cgctcgaatg gttgaaaatt   5640
cgcgaaattc tgcgaaaaaa atcgataatt tttccagatc gcgtctacta cttcaacacg   5700
gccaccggcc gcagccaatg ggagcgccca gacgagtcgg cgtttggaaa agtgagaaa    5759
```

<210> SEQ ID NO 8
<211> LENGTH: 1126
<212> TYPE: DNA
<213> ORGANISM: Caenorhabditis elegans

<400> SEQUENCE: 8

```
ccaaatgctg ccggaatgag attctaccga acatatttgc tcgtagctgg cgcttttttgc    60
tcattgtgca cacttgcagt aatattcaat tgtggatggg atgattcacc gccagcaaca   120
ccttcagcca tcaatggcgg tggctccaat gctcctttaa tctcctctcc aactaatctt   180
cccgaaacat ttctgtacat ttcaattctg acgtcaccaa acgaaacaga acgacgtcaa   240
aatgtccgtg acacatggtt ccgcctatca actaaaggac cgtccgtttt tatcgcaaaa   300
ttcgccgtcg gaacgatggg cctcgcggcc gaagatcgtc ggttgctggc cgaggaaaat   360
gagaaattcg gcgatttggc gcttctcgac cgccatgaag agtcctatga gaggctggca   420
aagaagactt tggcctgttt tgtacacgct tttgccaatt ttaaattcaa attttttcttg   480
aagaccgaca tcgactcatt cgtccgaatc accccactaa tcataaatct caaacaaatt   540
caagatccaa tgctctactg gggattccta gatggtcgag ctaaaccatt ccgtaaagga   600
aaatggaaag aacccgaatg gaatctgtgt gatcgttatc ttccatatca acttggcggt   660
ggttatgtgc tctcttatga gctcattcga ttcttggcaa tcaatgccca actcttccga   720
cactatcgga tgaagatgt gtcggtaggc gcctggatag gcggcctaga tgttaaatat   780
gtacatgatc cgagatttga taccgaatgg agatcccgtg gatgtaataa tgagtattta   840
attactcata gcacacggag caagagatg caagagatgt ttgaaaattt gaagaaaact   900
ggaaaacttt gtgctaaaga gttccaaaaa catccatcct acgtgtacga tttctcgaaa   960
gcacccagcg aatgttgtac aagagtcaac ggatcgaata ttccataatt tattgcattt  1020
tatcgcattt tttactgaat acgggccaat tttccagatt tctacggttt ttccgcgcat  1080
aataattgtc tttctcgtat aaatattgca tttttccaca tttaaa              1126
```

<210> SEQ ID NO 9
<211> LENGTH: 1928
<212> TYPE: DNA
<213> ORGANISM: Homo sapiens

<400> SEQUENCE: 9

```
atagccacat ccctgaatgt cacctgtccc tgggtgagag ccatgcctga cttgtctttc    60
tttcctcttc ctcttccggc gcgggcgcca tgaatctgct gcggcgggcg tggcggcggc   120
gggcggcgct aggcctgggc acgctggcgc tgtgcggggc ggcgctgctc tacctggcgc   180
gctgcgcggc cgagcccggg gaccccaggg cgatgtcggg ccgcagcccg cctccccccg   240
cgcccgcgcg cgccgccgcc ttcctggcag tgctggtggc cagcgcgccc cgcgccgccg   300
agcgccgcag cgtgatccgc agcacgtggc ttgcgcggcg cggggccccg ggcgacgtgt   360
gggcgcgctt gccgtgggc acggccggcc tgggcgccga ggagcggcgc gccctggagc   420
gggagcaggc gcggcacggg gacctgctgc tgctgcccgc gctgcgcgac gcctacgaaa   480
acctcacggc caaggtgctg gccatgctgg cctggctgga cgagcacgtg gccttcgagt   540
tcgtgctcaa ggcggacgac gactccttcg cgcggctgga cgcgctgctg ccgagctgc   600
gcgcccgcga gcccgcgcgc cgccgccgcc tctactgggg cttcttctcg ggccgcggcc   660
gagtcaagcc ggggggggcgc tggcgcgagg ccgcctggca actctgcgac tactacctgc   720
cctacgcgct gggcggcggc tacgtgctct cggccgacct ggtgcactac ctgcgcctca   780
gccgcgacta cctgcgcgcc tggcacagcg aggacgtgtc tctgggcgcc tggctggcgc   840
cggtggacgt ccagcgggag cacgacccgc gcttcgacac cgaataccgg tcccgcggct   900
gcagcaacca gtacctggtg acgcacaagc agagcctgga ggacatgctg gagaagcacg   960
```

```
cgacgctggc gcgcgagggc cgcctgtgca agcgcgaggt gcagctgcgc ctgtcctacg   1020
tgtacgactg gtccgcgccg ccctcgcagt gctgccagag aagggagggc atcccctgag   1080
ccgccgcggc cggcccctcc gggacacctg cttcacccgg cggcgccttg ggcaggtgc    1140 cgagcgggcg catacgcccg ggccccaagg ccccgtccc gcagccacgc ttgtggtcgc    1200
tgcgtcccgg tctgcgtttg ggagacccct gggggttgcc ggggcagcgc gccgtgtcca   1260
ggtggaggtg cccgttcctg gacctcagcg agcctgagcc gggcccggcc gcacgctgac   1320
ccccgtgctg tccccgaccg gctcacgggg ctgggctccg atcttccgtg tctcttatca   1380
gtggcgtttc tcacgtctgc gtctcagatc taacgtggtt tcacatcaat ccgctttcat   1440
gggattttgg tctctgtcca gtgacttcgt ggtaaatgta actcagtgtt tgcttgcgac   1500
ttatttataa atattgtaag tttgtgtcga tgagtgtaag ttggcagtgc gcacgtctcg   1560 gttttttttac atgatttaag gaaagacttt tatgtcagaa cttggtgcct gtaccgtcaa   1620
ccccgctgct gcccgtgttt aaacgcagga gcactttaaa actggccatc tatctttca   1680 gtgtacaagt cactgaaccc attgtttctt tctgaagaga ctttcctttc aaggcttccc   1740
atgggtccgc gccacacagg gccggtgctg ctttatttca gactctgccc caggttccag   1800
gaatccgaac cccggagtgc tgacgcggtt ccccaacttc cgccttaaga aaacaggacc   1860
agccggcacc aggcccgtct ctcacgtact ttaacacatc cttgaaagcc cctcgtttaa   1920
tgagaaaa                                                            1928
```

<210> SEQ ID NO 10
<211> LENGTH: 330
<212> TYPE: PRT
<213> ORGANISM: Caenorhabditis elegans

<400> SEQUENCE: 10

```
Met Arg Phe Tyr Arg Thr Tyr Leu Leu Val Ala Gly Ala Phe Cys Ser
  1               5                  10                  15

Leu Cys Thr Leu Ala Val Ile Phe Asn Cys Gly Trp Asp Asp Ser Pro
             20                  25                  30

Pro Ala Thr Pro Ser Ala Ile Asn Gly Gly Ser Asn Ala Pro Leu
         35                  40                  45

Ile Ser Ser Pro Thr Asn Leu Pro Glu Thr Phe Leu Tyr Ile Ser Ile
     50                  55                  60

Leu Thr Ser Pro Asn Glu Thr Glu Arg Arg Gln Asn Val Arg Asp Thr
 65                  70                  75                  80

Trp Phe Arg Leu Ser Thr Lys Gly Pro Ser Val Phe Ile Ala Lys Phe
                 85                  90                  95

Ala Val Gly Thr Met Gly Leu Ala Ala Glu Asp Arg Arg Leu Leu Ala
            100                 105                 110

Glu Glu Asn Glu Lys Phe Gly Asp Leu Ala Leu Leu Asp Arg His Glu
        115                 120                 125

Glu Ser Tyr Glu Arg Leu Ala Lys Lys Thr Leu Ala Cys Phe Val His
    130                 135                 140

Ala Phe Ala Asn Phe Lys Phe Lys Phe Phe Leu Lys Thr Asp Ile Asp
145                 150                 155                 160

Ser Phe Val Arg Ile Thr Pro Leu Ile Ile Asn Leu Lys Gln Ile Gln
                165                 170                 175

Asp Pro Met Leu Tyr Trp Gly Leu Asp Gly Arg Ala Lys Pro Phe
            180                 185                 190
```

```
Arg Lys Gly Lys Trp Lys Glu Pro Glu Trp Asn Leu Cys Asp Arg Tyr
            195                 200                 205

Leu Pro Tyr Gln Leu Gly Gly Tyr Val Leu Ser Tyr Glu Leu Ile
    210                 215                 220

Arg Phe Leu Ala Ile Asn Ala Gln Leu Phe Arg His Tyr Arg Asn Glu
225                 230                 235                 240

Asp Val Ser Val Gly Ala Trp Ile Gly Gly Leu Asp Val Lys Tyr Val
                245                 250                 255

His Asp Pro Arg Phe Asp Thr Glu Trp Arg Ser Arg Gly Cys Asn Asn
            260                 265                 270

Glu Tyr Leu Ile Thr His Lys His Thr Glu Gln Glu Met Gln Glu Met
    275                 280                 285

Phe Glu Asn Leu Lys Lys Thr Gly Lys Leu Cys Ala Lys Glu Phe Gln
290                 295                 300

Lys His Pro Ser Tyr Val Tyr Asp Phe Ser Lys Ala Pro Ser Glu Cys
305                 310                 315                 320

Cys Thr Arg Val Asn Gly Ser Asn Ile Pro
                325                 330

<210> SEQ ID NO 11
<211> LENGTH: 382
<212> TYPE: PRT
<213> ORGANISM: Drosophila melanogaster

<400> SEQUENCE: 11

Met Arg Arg Leu Asn Asn Leu Val Thr Phe Phe Thr Ala Ile Thr Ala
1               5                   10                  15

Phe Phe Phe Gly Ser Phe Leu Thr Lys Ile Leu Ser Ser Val Asp Gln
                20                  25                  30

Cys Pro Ala His Arg Ser Arg Ile Pro His Leu Glu Pro His Pro Asn
            35                  40                  45

Leu Phe Leu Met Val Leu Val Leu Ser Ala Pro His Asn Ala Asp Glu
    50                  55                  60

Arg Asn Ala Met Arg Arg Thr Trp Leu Ala Asn Ala Gly Gln Ser Ile
65                  70                  75                  80

Ala Gln Pro Tyr Leu Pro Glu Glu Leu Ile Tyr Leu Pro Thr Phe Asn
                85                  90                  95

Ala Gln Gly His Leu Gln Val Glu Leu Val Ala Glu Gln Ala Ser Arg
            100                 105                 110

Leu Arg Gln Tyr Thr Asn Trp Gln Gln Ser Leu Leu Thr Glu Gly Pro
    115                 120                 125

Pro Arg Thr Lys Arg Leu Ile Thr Val Lys His Val Phe Ser Ile Gly
130                 135                 140

Thr Leu Asp Leu Ser Ser Ser Ala Leu Ala Glu Leu Glu Lys Glu Gln
145                 150                 155                 160

Asn Gln Asn Asn Asp Leu Leu Leu Leu Asn Arg His His Asp Thr Tyr
                165                 170                 175

Lys Asn Leu Thr Ala Lys Leu Met Gln Ser Leu Tyr Ile Leu Arg Arg
            180                 185                 190

His Tyr Glu Phe Ser Tyr Met Leu Lys Val Asp Asp Thr Tyr Val
    195                 200                 205

Lys Leu Asp Ser Leu Val Asn Thr Leu Val Ser Tyr Asp Arg Lys Leu
210                 215                 220

Leu Arg Lys Arg Ser Glu Tyr Arg Asp His Val Leu Pro Gln Leu Tyr
225                 230                 235                 240
```

```
Trp Gly Tyr Phe Asn Gly Arg Ser Thr Ile Lys Thr Lys Gly Gln Trp
                245                 250                 255

Lys Glu Ser Ser Tyr Tyr Leu Ser Lys Asn Tyr Leu Pro Tyr Ala Leu
            260                 265                 270

Gly Gly Gly Tyr Val Leu Ser Arg Ser Leu Cys Asp Tyr Ile Val Asn
        275                 280                 285

Asn Ser Gln Leu Leu Ser His Tyr Gly Ser Glu Asp Val Ser Val Gly
    290                 295                 300

Thr Trp Leu Ala Pro Leu Arg His Val Tyr Arg Trp His Asp Pro Arg
305                 310                 315                 320

Phe Asp Thr Ser Tyr Ala Pro Arg Lys Cys Arg Ser Tyr His Met Val
                325                 330                 335

Leu His Lys Arg Asn Gly Gln Met Met Arg Asp Ile His Asp Gly Glu
            340                 345                 350

Leu Cys Ser Gly Ile Gly Ser Ser Ile Leu Ser Asp Tyr Tyr Tyr Asp
        355                 360                 365

Trp Thr Arg Thr Ala Asp Lys Cys Cys Asp Ser Leu Val Ala
    370                 375                 380

<210> SEQ ID NO 12
<211> LENGTH: 329
<212> TYPE: PRT
<213> ORGANISM: Homo sapiens

<400> SEQUENCE: 12

Met Asn Leu Leu Arg Arg Ala Trp Arg Arg Ala Ala Leu Gly Leu
1               5                   10                  15

Gly Thr Leu Ala Leu Cys Gly Ala Ala Leu Leu Tyr Leu Ala Arg Cys
            20                  25                  30

Ala Ala Glu Pro Gly Asp Pro Arg Ala Met Ser Gly Arg Ser Pro Pro
        35                  40                  45

Pro Pro Ala Pro Ala Arg Ala Ala Ala Phe Leu Ala Val Leu Val Ala
    50                  55                  60

Ser Ala Pro Arg Ala Ala Glu Arg Arg Ser Val Ile Arg Ser Thr Trp
65                  70                  75                  80

Leu Ala Arg Arg Gly Ala Pro Gly Asp Val Trp Ala Arg Phe Ala Val
                85                  90                  95

Gly Thr Ala Gly Leu Gly Ala Glu Glu Arg Arg Ala Leu Glu Arg Glu
            100                 105                 110

Gln Ala Arg His Gly Asp Leu Leu Leu Pro Ala Leu Arg Asp Ala
        115                 120                 125

Tyr Glu Asn Leu Thr Ala Lys Val Leu Ala Met Leu Ala Trp Leu Asp
    130                 135                 140

Glu His Val Ala Phe Glu Phe Val Leu Lys Ala Asp Asp Ser Phe
145                 150                 155                 160

Ala Arg Leu Asp Ala Leu Leu Ala Glu Leu Arg Ala Arg Glu Pro Ala
                165                 170                 175

Arg Arg Arg Arg Leu Tyr Trp Gly Phe Phe Ser Gly Arg Gly Arg Val
            180                 185                 190

Lys Pro Gly Gly Arg Trp Arg Glu Ala Ala Trp Gln Leu Cys Asp Tyr
        195                 200                 205

Tyr Leu Pro Tyr Ala Leu Gly Gly Gly Tyr Val Leu Ser Ala Asp Leu
    210                 215                 220

Val His Tyr Leu Arg Leu Ser Arg Asp Tyr Leu Arg Ala Trp His Ser
```

```
                225                 230                 235                 240
Glu Asp Val Ser Leu Gly Ala Trp Leu Ala Pro Val Asp Val Gln Arg
                    245                 250                 255
Glu His Asp Pro Arg Phe Asp Thr Glu Tyr Arg Ser Arg Gly Cys Ser
                260                 265                 270
Asn Gln Tyr Leu Val Thr His Lys Gln Ser Leu Glu Asp Met Leu Glu
            275                 280                 285
Lys His Ala Thr Leu Ala Arg Glu Gly Arg Leu Cys Lys Arg Glu Val
        290                 295                 300
Gln Leu Arg Leu Ser Tyr Val Tyr Asp Trp Ser Ala Pro Pro Ser Gln
305                 310                 315                 320
Cys Cys Gln Arg Arg Glu Gly Ile Pro
                325

<210> SEQ ID NO 13
<211> LENGTH: 14000
<212> TYPE: DNA
<213> ORGANISM: Caenorhabditis elegans

<400> SEQUENCE: 13
aggcaacaaa acatatttt ttcaatgttt tttctacgga aaaccagcga aaatgttgat        60
ttttgaagga aattttcata tttttaaaac attttctatt tttctctcgt ccataatttt       120
agttttcaaa aaataaaca ttaaatagta cttcggcgg ccccacatct gtttcgtgat        180
cccaataaac attttgaacg tttaaactct ccgttttgca aacattttgc acttttttcc       240
tcattttctc aagtttttac agggcgtgct cctcatgtta ttcaacggga cgactaaata       300
tcgagattat gcgattgtga tatcattatt cttcctgcta acgtctatt tattgtacaa        360 tacggctcaa cacacgcaag tcggaaattc gaagcatatt tcgtcggata gcggtgaaaa       420
agttagattt tctggctaaa aattgaattt tctgcatatt cggatgaatc ccggcgcttt       480
ttttggcttt ttcttgcata ttcatctgaa ttatttcatt tttcggtcaa gaacgcattt       540
tttagcgaaa aacattatt aaactgtttt aaaatgtgtt ttatcaaaga aaacgacaaa        600
attcgcgcta aaaatgaagt aattttcatg aaaaagcact aaaaaattcg atttttttc        660 gatttcagca cgccgagcct tcaactaact aaatttatgc tcctgattcc gaaaatcgat       720
atgaaaaaac tcaaaaaaat ttccgtgatt ttatataaat ttttgaaaat caggaaaatc       780
cactggtttg ttaaattcaa cgatatctt tttgccgccc gataaccgtg ccgaaggtgt        840
ggatttccga cgagattaat attttcatt caattttatt taattttctt accgattttt        900
tcgtttttcg ttgttttaca tttaatttct tgtgatttcc attaatttat gactttttaa       960
cactgaaaat gaataaaatt acatgaaata ccctattttc atggaatttt atttatttta      1020
attaaaggtg gtgtagtcga ttttttttat tgctttatta gactcgaaat tgtctgaaaa      1080
caccgatttt ttaaatgaaa cttcttgaaa acttttcaga aaaagttgt gacgactcaa       1140 aaatgtccta aaattagtta aaatttgaaa tttgaccgac ttgtcaatgt cgcagcggct      1200
ggaaacaatt ttttttgaag tcactgtcaa atttgagta tgcaattcaa ttatcttgcg       1260
ttttaaactt gattaaggtg tttaaaagtc gatggacggc gagaattgat tttaaaagaa      1320
ttaaaaatct cgccgtccat cgactttaa ataccttaat caagtttgaa acgcaagata       1380
atcgcactgt atactcaaaa tttgacggtg atttcaaaaa agttagttc cagccgctga       1440 caagtcaaat ttcaatttt aactgatttt aggccatttt tgagcggtc ataacttttt        1500 tttggagaag ttttcaagaa gttcattat gaaattcggt gttttcagac aattttgagt       1560
```

```
ccagtaaagc aataaaaaaa ttcgactaca ccatctttat aattaaaagg tacttttccg    1620
atttctgccc cccaaaatgt ttttcaatct tattaaactc aatatttcag tttaaattca    1680
cacatgaatg tttatttcaa tactatttca attttaggc ttagaaacca acaatactaa     1740
gcctgaaatt ttcaaaaaaa gttcacgttt cattgataaa aatatcgaaa acactttggg    1800 ggggggggc agaaatcgga aaagtaccaa ttaaaagtga cttcaaaaaa attgtttcca     1860
gccgctgcga cattgacaag tcggtcaaat ttcaaatttt aactaatttt aggacatttt    1920
tgagtcgtca caactttttt ctgaaaagtt ttcaagaagt ttcatttaaa aaatcggtgt    1980
tttcaaacaa tttcgagtct aataaagcaa taaaaaaaat cgactacacc acctttaatt    2040
aaaataaata aaattccatg aaaatagga tttcatttaa ttgaattttg ttttcattaa     2100
taaaagcaat aaattaatga aaaccacaat aaatgcagtg taaaacaacg aaaaatgaga    2160
ggaattggga aaatcggtat gaaaatttaa taaaattgaa tgaaaatat ccatctcgta     2220 aattcaactt tatcgtttga atttaaagaa ccaatggatt ttcctaatat taaaaaatta    2280
atataaaata tcaggggcat tttttttgaa ttttttcaca agggtattcg gaatcaggag    2340
cataaataga gtctatcgta aattttttt ttttttggta aattaaatat ttttcagacg     2400
tcgaatcctc ttccatcatg cgaaatcaca gatgacctgg cgaaaagtgc aatttcccgt    2460
gcaattactc catcctgcaa agcaaaactg cagctggaag cttgtcaact gaaaaatggg    2520
acttttacaa taaattttcc ggaaaatcaa tgcccgaacc acgatagccg gcttatcgac    2580
caacgaatcg gctgttttt ggacaaaaaa gaggctcgag tgctcacaga gttcgagtac     2640
aaacttccaa agtcaaatgg gaaagcgacg tgtcgaaagc actgctataa agctggtttt    2700
ttgtatttcg gacttgaatt cggacacgaa tgcttctgtg ggaatgatgt atcaaatgcg    2760
acggcggttg atgacgtgga atgtcgggcg tataaatgtc cgggaaatga gaactcggag    2820
gagttctgtg gtggattcaa tgcagtcgag atttttagga caggatttag aagtaatatt    2880
aggtctccaa ataagttccg ggtcaaaaat cataactttg ttcgctgcgt atcgattttt    2940
atgaaattgt gggaatttat gttatcaacc atgatctttc atttgacaat actcacaaaa    3000 ttttttttgcc gtccgaagtg ccctaactcg gagccaaatt tttcaggcat ttttcagatc   3060
tcgcttcttt tacgctttga tttgaggttt gtgtgcggat ttagctttgt ttagtacata    3120
atgtaagaaa acaagaaaag tttggaaaaa atccgtccaa aaaaaaaatt ttttgtcgg     3180 tcgtcaaaaa atgttcaaaa aaattttgt cgaaaattct tgatttttca tacaaaaatg     3240
atgtaaccat gtgcaaacta tttgttcaca tacaaaacat ttaaatttag tgcgtcacac    3300
taaaataaaa acagaaaaca cacctttttt gaattatttt cgagttttg gagtgtttct     3360 cgagatccaa atttcatact caaatgtttt gtatgcgaaa aaatagtttg cacatggtta    3420
catcattttt gtataaaaaa tcaagaattt tcgacaaaaa ctttttttgag cattttttaa    3480 cgaccgacaa aaaattttt tttttggacg gattttttc taaactttc ttgtttttctt      3540 acattgtgta ctgaacaaag ctaaatccgc acacaaacct cgaatcaaag cgtaaaagaa    3600
gcgagatctg aaaaaattgg ctccgaatta gggcacttcg gatggcaaaa aaatttttgtg   3660 actattgtca aatgaaagat cacggttgat aacataaatt tccacagttt cataaaaatc    3720
gatacgcagc gaacaaagtt atgatttttg acccggaact tatttggaga cctaatatat    3780
tttgaaattt tagaaaattt gaagaaaaag tttacaaatg tttaaaaacc aaaaaattgt    3840
tcattttgtt agaaatgtca tgtgtttttt tgtttaaaaa acgccgattt tctcggtttt    3900
```

```
tccctgtaat ttagtctgaa acacgttttt ttttctcgtt ttcgggcacg aaattaacga  3960
caaaaaccca aaaatcgttt ttttttttta attttttgctt taaaaattgc tcgaattttc  4020
caattttgga aaacattttt attaaatttt tattaaaaaa tcacacattc ttcttaattt  4080
tcgggtattt tttttaattct tagctagaaa attgaaataa aatcaaaaaa cgttgaagaa  4140
aaaaccttaa aatacctgga aatgttgaac aaaatgtagt aaaaatctcg gagaaaggtc  4200
tttatatcta cactatttta ttttaaaaaa aacattgaaa atttaggaaa aaaatgcaaa  4260
gaatcgggga accccttaa gttttatttt aaattaaaca aaaaattcca aaaaacttgc  4320
gaaataaact aaaatatttt tggaaaagtt actctttta atatatcgaa atccaaatt  4380 aaaaaattcc aaatttcgtt aaaatttaac caaaaattct cctaataatc cagaagaata  4440
atctgaaaaa tttgaggaaa tgaatcaaaa aatctcacaa aataccgaaa ataggtcta  4500 aaaagcattg aaagttttg aaaaaaaaat taatttaaac attttggaaa agtaacgttt  4560
tttgaaaaaa tattggaaat ctacaaaaaa aaaattttcg aaaaattcac caaatttgat  4620
attaaaaaaa ttgcgaaata ctgaaaactt tcttgaaaat ttgaaaaaaa aatcttcaaa  4680
ttatcgttcc cgaaatgctc gacaagcaaa cgcgccctgt tgaacaactt ctgcgcgcgc  4740 attcaaatttt agtttttttt tgcttccaaa tattttata cggaaaagtg atagtttcac  4800 actgaattttg caattttaa agaacatttt taacaaattt tttttaatg ccgcaaaatg  4860 aataaaaaat atcccaaaaa accgaaaaat ttcttttaaa aaacgagaat tcgattattt  4920
cctaaattta ttatgctgaa aattttttata tggaaaatat cgaaaaatca tctgaaaaaa  4980
tctgaaaaat gtcgatcaat taaaaaaaaa tgtacaaaaa cactaaaat tgaacaaaaa  5040 atcgaaatat caggtaaaaa cccctacagt ttacggataa ttttcaaaaa aaaacggaaa  5100
tactttgata attttttagac agagtgaatc accaaaattg aaaaaaaaa ttgcaaaata  5160 ttcgccaaaa aaccgaaaaa tttctataaa tatccttaat tgaacaaaaa aaaaattcta  5220
gaaacaagat gtatttcaaa aattttcctg aaaattcaca ctgaaccgct aaaattcaaa  5280
ttctaaaaat tatcgaacat cgacgatacc gtaaaattaa aacaaagaat attccgaaaa  5340
ttcgagaaaa aagcaccttg caactttacc ctcacgaggg acgaggaaaa gtggtttcta  5400
ggccatggcc gagtccccga caagtttcag cggccattta tcttgctttg ttttccgcct  5460
gttttctttc gttttttcatc gatttttttc gtttttttctt aataaaactg ataaataaat  5520
attttttgca gatgctaaaa caattttccaa gtaaaaaaaa tcatgtattc agtgggcaag  5580
cagcggtgaa agtgggcatt gtaatatgat ggattacggg aatacaaaac ctaaactttt  5640
tctgaaacat gatacatatg atgcttagat gctgaaatta cctgatttt ataacgagac  5700 cgctgaaaaa gttttgagat tttcaaaatt caacttttt ggtgaaaaag tcgttacatt  5760
gcccactttc accgctgctt gcccactgaa tacataattt ttttacttgg aaattgtttt  5820
agcatctgca aaaatatttt atttatcagt tttaataaga aaaacggca aaatcggtg  5880 aaaaacaaaa gaaacaggc ggaaaacaaa gcaagataaa tggccgctga acttgtcgg  5940 cccctcggcc atggcctaga aaccactttt cctcgtccct cgtgaggaaa agttgcagt  6000 gaaacactga aaaatgcaaa aattcaaatt ttcaggcaaa gtgaatcacc gcaagccgac  6060
atatcttcca cctagcagcg attctatcaa aaatcccgtc aaaattctct tccttcttca  6120
attaaatggt agaaatgagc gtcaagtgaa acgatttctc aaatcaattt atcttccaca  6180
tcattattac tatatccacg tggatgcacg tcagaattac atgttctcag aaatgcaaaa  6240
agttgctgat tttctggata atattcatat aaccgaacgg agattcagca caatttgggg  6300
```

```
tggagcatca cttttacaaa tgtttctgca agtgattagg gattcgatga aaattgagaa    6360
attcaaggat tgggattata ttattaattt ctcggaaagt gatttcccga ttctaccgat    6420
ttccgatttt gagagactta tcactgtgta agttggagtg atttgaaaca tgttttagga    6480
ttaaaacgag ggaaaagttg aaattcaaaa atctgaatat tccactgcaa ctttttcctc    6540
acgagggacg aggaaaagtg gcttctaggc cacggccgag gggccgacaa gtttcagcgg    6600
ccatttatct tgctttgttt tccgcctgtt ttctttcgtt tttcatcgat ttttttcgtt    6660
ttttcttaat aaaactgata aataaatatt ttttgcagat gctaaaacaa tttccaagta    6720
aaaaaaatca tgtattcagt gggcaagcag cggtgaaagt gggcattgta atatgatgga    6780
ttacgggaat acaaaccta aactttttct gaaacatgat acatatgatg cttagatgct    6840
gaaattacct gattttcata cgagaccgc tgaaaaagtt ttgaggtttt caaaattcaa    6900 cttttttgtgc gaaaatctcg acttttttcac caaaaaagtt gaattttgaa atcctcaaaa    6960 cttttttcagc agtctcgtta tgaaaatcag gtagtctcag catttaagca gcatatgtat    7020
catgtttcag aaaagtttta ggttttgtat tcccgtaatc catcatatta caatgaccac    7080
tttcaccgct gcttgcccac tgaatacatg attttttttac ttggaaattg ttttagcatc    7140
tgcaaaaaat atttatttat cagtttttatt aagaaaaaac gaaaaaaatc ggtgaaaaac    7200
gaaagaaaac aggcggaaaa caaagcaaga taaatggccg atgaaacttg tcggcccctc    7260
ggccatggcc tagaaaccac ttttcctcgt ccctcgtgag gaaaaagttg cagagtattc    7320
cagaattttt atggaaattt cagatttata ttcctaaaaa ctcacaaaaa aacaattttta    7380 tggaaaaaaa atcgattttt tttcaccgga aaaattaaat tttcagagat ttttagatta    7440
aaataagaaa aaatagattt tttggagaaa tccgcttatt ttttttggaaa attccggaga    7500 tttttccgaa atatgaaaaa aaaacatttt tggaattcaa aaatctgatt aatccggaat    7560
tttcataaaa atcgacgaaa atcaccgaaa atttcagatt ttaatttaga aaaatcacaa    7620
aaagaaaaca attttatgga aaaaaaatcg attttttccg gaacaaaaat cgaaaccgga    7680
aaatctgaaa tttaacacag aaattttttg aaagtgagag aaaataaaat gaaaaaaaaa    7740 tcgattttttc ttgaaaaagt taattttcag cgttttttaa atcgaccatt tgaaaacaat    7800
taaaatttga aaaaaaaaac aatattttac gacaatttac tcggaatttc aaaattttca    7860
ttttaaaaaa tcaaaaaatt ttgctttttt ctagacaaaa ttgattttca gcgaattttc    7920
ctgaaaaaaa tttagaacgg attttttatcc gacaatatcg gaagttaaca ttttttaatga    7980 aaaaaaaaca cttttttcca aaaaaaaaaa aaatagaatt ttcgcaaaaa gtaaattcga    8040
aaaaaaattt aacaacctat cgaattctaa atttttttcag attaaaatcg atttttttttg    8100 tagaatttt gaagatttca tctagttttt tttttgttga taagttgcaa aaaattattt    8160
tttttgattt aaaaaagtgc taaaatatat ataagaaaaa tatgaacata agtaacttt    8220 tagaaatcga aaaaaaaaaa ttttttttta aattatttcg aatttccaat tttccagaaa    8280
caacggaaaa tcattcctgg cctcacacgg ctacaacact ggaaaattca ttcaaaaaca    8340
aggattcgaa tacgtgttct ccgaatgcga taatcgaatg ttccgtatcg gaaacgcga    8400 atttccacaa aatctacgaa ttgacggcgg atccgattgg gttggaattc atcgaaatct    8460
cgccgaattt tcgatttccg acgaggaatt gcctcgaaaa ttgcgaaaaa cgtatgaaag    8520
tatacttcta ccactggaat cattctatca tactcttgcg ttcaattccg aattctgtga    8580
tgatctactg atgagcaatt tgcggcttac gaattggtac aggaaacagg gatgtcggtg    8640
```

```
tgcttcattg aagcctattg ttgattggtg tggatgttcg ccgctggttt ttcgtgaaga    8700
aactatgaag aaatttgagc ttcaagtatg gccaattttg gttgtggagc tgaaaaattc    8760
tgaaattttg gtcttaaaaa aatcaaaaaa attcaaattt ctgtttgaat ttcaaagca     8820 ttatttacat gaaaaccata attttcgttt attttttttgc gattttttga aaaaaaaagc   8880
cgaacatttt cgttttttt ttcaattttt ttctgaaaaa aatctttaaa aattgaagtt     8940
ttttcgtgtt tcttttctc tgaaaaaaac cgttaaaatc aattttttt ttcgattttt      9000 ttttgaaaaa atgttttcaa aaaacctttt atccgaaaaa gcgataattt tggttttctt    9060
tcgatcttct cagaaaaaac cgtaaaaatc aataatttaa tagtttttgt ttcattttg     9120 ctgaaaaaaa aaacctttaa aaatggaagc ttttcgtttt tcagcgattt tctcagaaaa    9180
aaactttaaa aaatcaataa ttttttgaaaa acgctgaaaa ttttcggttt ttagcgattt   9240
tctcatgaaa aaaaccgtaa tcgtcgtagg cttaagctta ggcttgggcg taggcttagg    9300
atttggatta agcctaggga caatcccaac ttccgaagga tttccagaaa aagaaaaaa    9360 tattataagt aaaaatccaa aaatacaaa aaaaaccttaa taaaatcgtc aaaaaattat    9420
tcaaaaaatt agtaattaaa aaaaaataat ttttcaaatt tccagaaagc catctgaata    9480
taactttaaa aatctgaact gtccgttttg tagtgatttt ctcagaaaaa aaaaacaaaa    9540
acccaaaaaa aaccccaaaa aacttacaaa aaccggaaaa aaaaattaaa tttaaagttt    9600
ctaaatttcc agaaatccat cgcttaagct gaggcttggg cttactatta ggcttaggct    9660
cccatagttt taggcttagg gacaatccca acttacaaag gatttccaga aaaatatat     9720 aaaaaattaa tttataagta aaaatcccaa aatcctaaaa accccaaaaa tataccaaaa    9780
accttgtaga atcgaaaata aattaatttt ctaaatttcc agaaagccat cgcttaagct    9840
gaggcttggg cttactacta ggctttgtct taggctcagg cttagaaata gttttaggct    9900
taaggaaaat cccaacttcc aaaggatttc tagaaaaaaa aaattataag taaaaaatcc    9960
caaaatccta aaaactccaa aaatataaca aaaaccggga aaaaaaaaat taaattttaa   10020
ttttctaaat ttccagaaag ccatctccaa accaacctac tttgcccgaa aattcgatag   10080
tatggtagat atcgattcaa ttgaagccgc cgaaatgcaa tcaatttcac ctgaaaaact   10140
tcaattaaat catccaacct atcatttcgc ttttgcaaat attttcaaaa ctggaatcga   10200
cgagcagaag cttcatttcg aaagtttggc gaatttcgcg ctgaaatcca ccgaaactcg   10260
ggcaaaattc cgaaaagttt tgcgaatcga tgctcttcga gctcatcata atgctctcat   10320
cgagattgtc atgaaaatcg aaacgacgga cggcgcgacg tttgaatttt tgattcatag   10380
actgtcccat gtgaatttga cggaaaatga ggagaagctt gtggagcacg gatatctatt   10440
gagagctgta tcgtttggaa caaaatttga atggaaagag gagctttgca gggaatatat   10500
gggatttgtc actgatgttc gttggttttt tcggcggaaa attttgaaga aaatattttg   10560 gtctttttc tacgaaaaat gaaaaaaaaa aaacaaaaa ttattgattt ttgaggtttt     10620
ttttttcaga aaaaactgt ttaaaaaaac ggattttttt tgattatttt ggtatttcc     10680 tgaaaaaatc gaaaatgaa catttcggt ttttaaaagt tttttgacaa aaatttttta     10740
ttagaaaatc tagacaatga agaactaaaa attaaaaaaa aacttaaatt atcgatttt    10800 ccagatttt tcagaaaaaa cactcaaatt actgaaaatt tcttggagtt ttttttttcag   10860 aaaattgaca aaccgaaaaa gtccgatttg tggggttttt ttttcggaga aaaatatttt   10920
taaaaacgaa aaaaatcgaa aaactttttt ttttcacaaa aaatttggaa aaactcaaaa   10980
atttagattt tttttatttta gaaaaattcg aagaataaac aaaaattacc aaaaaatttc   11040
```

```
cgcggttttt tcaaaaaatc gaaaaaaaaa caaaaaattt cgatttttca gatattttt    11100
cagaaaaata ataataataa caaaagtatt cgattttttt ttttcggaga aaatcgaaaa    11160
attgaaaatt ctcgtcagaa ttgattaaaa aaccggtttt tttttgttga aaagggcta    11220
attaaaaact ataataataa tatttaacac gattaatttt ttgccgattc actgcaactt    11280
tttcctcacg agggacgagg aaaagtggtt tctaggccat ggccgaggga ccgacaagtt    11340
tcagcggcca tttatcttgc tttgttttcc gcctgttttc tttcgttttt catcgatttt    11400
tttcgttttt tcttaataaa actgataaat aaatatttt tgcagatgct aaaacaattt     11460
ccaagtaaaa aaattatgta ttcagtgggc aagcagcggt gaaagtgggc aatgtaacga    11520
ctttttcacc aaaaaagttg aattttgaaa acctcaaaac tttttcagcg gtctcgttat    11580
gaaaatcagg taatttcagc atctaagcat catatgtatc atgtttcaga aaagtttag     11640
gttttgtatt cccgtaatcc atcatattac aatgcccact ttcaccgctg cttgcccact    11700
gaatacatga ttttttttac ttggaaattg ttttagcatc tgcaaaaaat atttatttat    11760
cagtttatt aggaaaaaac gaaaaaaatc gatgaaaaac gaaagaaaac aggcggaaaa     11820
caaagcaaga taaatggccg atgaaacttg tcggcccctc ggccgtggcc tagaagccac    11880
ttttcctcgt ccctcgtgag gaaaagttg cagtgcgatt tttataaaag ttatttttt      11940
taaaatttt atttccagaa cgacactctt cacacccgct tgcaatggca tccgacagaa     12000
catgtgaaaa aagttggaga caagacgagt cccgaaatga tattcaaata tcgaaaggc     12060
gatgagctca ttgagcaaac tgttgtaaag ccgtacgatt cagtgtttgg aggacaattt    12120
gatagttgga atgttgggaa aaagttcgtg ttctactaga aattggatgg tccccccgaa    12180
aatttaaaaa taccacaaaa agaaaaagga aaaaactcgg gaaagtttc gttaaaaaaa     12240
tgttttttgt tgaaaatccc ttttttataa tattaaaatg ttgaattttc gcaacatagg    12300
tttgagacaa caaaaaaata attaaaaatc caacttataa aaacatattt tgaagttttt    12360
tgcaaagtta tctccaaaac gagaactacg actaatcagc gacttgcccc gcccacactt    12420
ttgaaccaat cagcgtcttc cgaagcctga ttggttcaaa agaagtgatc gtggtttctt    12480
atttagaacg gattacggaa aaatcgggtt tttcgatatt ttcttacgtt ttttgggggt    12540
cgggcgtaaa aatgtgctag cgaattaaaa aaaaaacgc cgaaaaattt agttttttcg     12600
tttttctctg caaaaaagcc caaaaaaaat cggaaaaaaa caaaaaaaac gaaaatttcg    12660
taattctgaa gaaaaaccc aaaaaatcca aattcgtagt ttttttttcga ttttctgaaa    12720
tttttattta aatcgaaaaa aaaacgaaaa cattagttaa tttttttcga tttttctatt    12780
ttaggaaaac atcccgaaaa atctaaattt gtagttttt tttcgattt ctcaaaaaa      12840
aaacctaaaa aatcaatttt ttcgattttt cgaaattctt tttaaaaaaa gattcaaaaa    12900
aatcaaacaa atttaaaatg tttgccgaaa atcgggggaa caacgaaaaa aaaaacgaac    12960
attttttttc gattttctca gaaaacaaa cttttaagt caataatttt tttttagttt      13020
tctcgatttt tcgatttct gaaaaaattc caaaaaagc aataatttta atttttta       13080
acttaatttt taattttaa ctgtaaattt tcggttttaa caacaaaaaa aatttttt       13140
ttttcgtttt ttttccaatt caaaaatttc cagactctcc aacctgacga cctgttccaa    13200
tttcttcgtc gacatcatct ccccatcgtc acccgatgat gctccaccgc tcgccacact    13260
acattttccc gttacactg atcaaaacgc gcattccac gtggattacc tacgccagtt      13320
cttcaaaatt gccgattttt gcacttccgg cgacgcttgc aaggaaaaga tctggagtac    13380
```

```
gagctatccc gatccgaaat cagatatttt tgtcggatac gatgaggata cgcagacctt    13440
gatttagaac acattttttt gtttgtagaa atttctgatt ttttttcttc aaattttaat    13500
tgttttatag tgctcaacga ttggcttttg caatgtgtta ttttcagcga aaacccctg     13560 aaaaaacagt ttttctggca aaagccgca aaaacggtt tttttaagct taaaacccaa      13620
aaaaaaaagg ggttttttt tttgctgaaa acgcgaaaa aataggcaat tctgctattt      13680
ttcaacacaa aaatgtcaaa tttatggcct tttctgtaaa tttactcctt tttgggcaac    13740
atttcagaaa caaattcttt ttttttttt tttttggaa aaatacgatt aaaatccaga      13800
aattcacgtg ttttttcac gaaaatacg aaaaccaaa aattcaccgt acctacatgt       13860
agcaaaagcc aatttaaata aaaactggag caccggaatc tgggaaatat gtttaaattt    13920
ttcccccgac tccaaatttt ccctgattc cgaaaatcta tgcaaaaaaa atgcatttaa     13980
aaaattccca gattttatat                                                14000

<210> SEQ ID NO 14
<211> LENGTH: 2444
<212> TYPE: DNA
<213> ORGANISM: Caenorhabditis elegans

<400> SEQUENCE: 14
agtttttaca gggcgtgctc ctcatgttat tcaacgggac gactaaatat cgagattatg     60
cgattgtgat atcattattc ttcctgctaa acgtctatt attgtacaat acggctcaac      120
acacgcaagt cggaaattcg aagcatattt cgtcggatag cggtgaaaaa acgtcgaatc     180
ctcttccatc atgcgaaatc acagatgacc tggcgaaaag tgcaatttcc cgtgcaatta     240
ctccatcctg caaagcaaaa ctgcagctgg aagcttgtca actgaaaaat gggacttta      300 caataaattt tccggaaaat caatgcccga accacgatag ccggcttatc gaccaacgaa     360
tcggctgttt tttggacaaa aaagaggctc gagtgctcac agagttcgag tacaaacttc     420
caaagtcaaa tgggaaagcg acgtgtcgaa agcactgcta taaagctggt ttttttgtatt    480 tcggacttga attcggacac gaatgcttct gtgggaatga tgtatcaaat gcgacggcgg     540
ttgatgacgt ggaatgtcgg gcgtataaat gtccgggaaa tgagaactcg gaggagttct    600
gtggtggatt caatgcagtc gagattttta ggacaggatt tagaagcaaa gtgaatcacc     660
gcaagccgac atatcttcca cctagcagcg attctatcaa aaatcccgtc aaaattctct    720
tccttcttca attaaatggt agaaatgagc gtcaagtgaa acgatttctc aaatcaattt    780
atcttccaca tcattattac tatatccacg tggatgcacg tcagaattac atgttctcag    840
aaatgcaaaa agttgctgat tttctggata atattcatat aaccgaacgg agattcagca    900
caatttgggg tggagcatca ctttttacaaa tgtttctgca agtgattagg gattcgatga    960
aaattgagaa attcaaggat tgggattata ttattaattt ctcggaaagt gatttcccga   1020
ttctaccgat ttccgatttt gagagactta tcactgtaaa caacgaaaaa tcattcctgg    1080
cctcacacgg ctacaacact ggaaaattca ttcaaaaaca aggattcgaa tacgtgttct    1140
ccgaatgcga taatcgaatg ttccgtatcg gaaaacgcga atttccacaa aatctacgaa    1200
ttgacggcgg atccgattgg gttggaattc atcgaaatct cgccgaattt tcgatttccg    1260
acgaggaatt gcctcgaaaa ttgcgaaaaa cgtatgaaag tatacttcta ccactggaat    1320
cattctatca tactcttgcg ttcaattccg aattctgtga tgatctactg atgagcaatt    1380
tgcggcttac gaattggtac aggaaacagg gatgtcggtg tgcttcattg aagcctattg    1440
ttgattggtg tggatgttcg ccgctggttt ttcgtgaaga aactatgaag aaatttgagc    1500
```

| | | |
|---|---|---|
| ttcaaaaagc catctccaaa ccaacctact tgcccgaaa attcgatagt atggtagata | 1560 |
| tcgattcaat tgaagccgcc gaaatgcaat caatttcacc tgaaaaactt caattaaatc | 1620 |
| atccaaccta tcatttcgct tttgcaaata ttttcaaaac tggaatcgac gagcagaagc | 1680 |
| ttcatttcga agtttggcg aatttcgcgc tgaaatccac cgaaactcgg caaaattcc | 1740 |
| gaaaagtttt gcgaatcgat gctcttcgag ctcatcataa tgctctcatc gagattgtca | 1800 |
| tgaaaatcga aacgacggac ggcgcgacgt ttgaatttt gattcataga ctgtcccatg | 1860 |
| tgaatttgac ggaaaatgag gagaagcttg tggagcacgg atatctattg agagctgtat | 1920 |
| cgtttggaac aaaatttgaa tggaaagagg agctttgcag ggaatatatg ggatttgtca | 1980 |
| ctgataacga cactcttcac acccgcttgc aatggcatcc gacagaacat gtgaaaaaag | 2040 |
| ttggagacaa gacgagtccc gaaatgatat tcaaatatcg aaaggcgat gagctcattg | 2100 |
| agcaaactgt tgtaaagccg tacgattcag tgtttggagg acaatttgat agttggaatg | 2160 |
| ttgggaaaaa actctccaac tgacgacct gttccaattt cttcgtcgac atcatctccc | 2220 |
| catcgtcacc cgatgatgct ccaccgctcg ccacactaca ttttcccgtt tacactgatc | 2280 |
| aaaacgcgca ttgccacgtg gattacctac gccagttctt caaaattgcc gatttttgca | 2340 |
| cttccggcga cgcttgcaag gaaaagatct ggagtacgag ctatcccgat ccgaaatcag | 2400 |
| atatttttgt cggatacgat gaggatacgc agaccttgat ttag | 2444 |

<210> SEQ ID NO 15
<211> LENGTH: 806
<212> TYPE: PRT
<213> ORGANISM: Caenorhabditis elegans

<400> SEQUENCE: 15

```
Met Leu Phe Asn Gly Thr Thr Lys Tyr Arg Asp Tyr Ala Ile Val Ile
  1               5                  10                  15

Ser Leu Phe Phe Leu Leu Asn Val Tyr Leu Leu Tyr Asn Thr Ala Gln
             20                  25                  30

His Thr Gln Val Gly Asn Ser Lys His Ile Ser Ser Asp Ser Gly Glu
         35                  40                  45

Lys Thr Ser Asn Pro Leu Pro Ser Cys Glu Ile Thr Asp Asp Leu Ala
     50                  55                  60

Lys Ser Ala Ile Ser Arg Ala Ile Thr Pro Ser Cys Lys Ala Lys Leu
 65                  70                  75                  80

Gln Leu Glu Ala Cys Gln Leu Lys Asn Gly Thr Phe Thr Ile Asn Phe
                 85                  90                  95

Pro Glu Asn Gln Cys Pro Asn His Asp Ser Arg Leu Ile Asp Gln Arg
            100                 105                 110

Ile Gly Cys Phe Leu Asp Lys Lys Glu Ala Arg Val Leu Thr Glu Phe
        115                 120                 125

Glu Tyr Lys Leu Pro Lys Ser Asn Gly Lys Ala Thr Cys Arg Lys His
    130                 135                 140

Cys Tyr Lys Ala Gly Phe Leu Tyr Phe Gly Leu Glu Phe Gly His Glu
145                 150                 155                 160

Cys Phe Cys Gly Asn Asp Val Ser Asn Ala Thr Ala Val Asp Val
                165                 170                 175

Glu Cys Arg Ala Tyr Lys Cys Pro Gly Asn Glu Asn Ser Glu Glu Phe
            180                 185                 190

Cys Gly Gly Phe Asn Ala Val Glu Ile Phe Arg Thr Gly Phe Arg Ser
        195                 200                 205
```

-continued

```
Lys Val Asn His Arg Lys Pro Thr Tyr Leu Pro Pro Ser Ser Asp Ser
    210                 215                 220

Ile Lys Asn Pro Val Lys Ile Leu Phe Leu Leu Gln Leu Asn Gly Arg
225                 230                 235                 240

Asn Glu Arg Gln Val Lys Arg Phe Leu Lys Ser Ile Tyr Leu Pro His
                245                 250                 255

His Tyr Tyr Tyr Ile His Val Asp Ala Arg Gln Asn Tyr Met Phe Ser
                260                 265                 270

Glu Met Gln Lys Val Ala Asp Phe Leu Asp Asn Ile His Ile Thr Glu
                275                 280                 285

Arg Arg Phe Ser Thr Ile Trp Gly Gly Ala Ser Leu Leu Gln Met Phe
290                 295                 300

Leu Gln Val Ile Arg Asp Ser Met Lys Ile Glu Lys Phe Lys Asp Trp
305                 310                 315                 320

Asp Tyr Ile Ile Asn Phe Ser Glu Ser Asp Phe Pro Ile Leu Pro Ile
                325                 330                 335

Ser Asp Phe Glu Arg Leu Ile Thr Val Asn Asn Gly Lys Ser Phe Leu
                340                 345                 350

Ala Ser His Gly Tyr Asn Thr Gly Lys Phe Ile Gln Lys Gln Gly Phe
                355                 360                 365

Glu Tyr Val Phe Ser Glu Cys Asp Asn Arg Met Phe Arg Ile Gly Lys
                370                 375                 380

Arg Glu Phe Pro Gln Asn Leu Arg Ile Asp Gly Gly Ser Asp Trp Val
385                 390                 395                 400

Gly Ile His Arg Asn Leu Ala Glu Phe Ser Ile Ser Asp Glu Glu Leu
                405                 410                 415

Pro Arg Lys Leu Arg Lys Thr Tyr Glu Ser Ile Leu Leu Pro Leu Glu
                420                 425                 430

Ser Phe Tyr His Thr Leu Ala Phe Asn Ser Glu Phe Cys Asp Asp Leu
                435                 440                 445

Leu Met Ser Asn Leu Arg Leu Thr Asn Trp Tyr Arg Lys Gln Gly Cys
450                 455                 460

Arg Cys Ala Ser Leu Lys Pro Ile Val Asp Trp Cys Gly Cys Ser Pro
465                 470                 475                 480

Leu Val Phe Arg Glu Glu Thr Met Lys Lys Phe Glu Leu Gln Lys Ala
                485                 490                 495

Ile Ser Lys Pro Thr Tyr Phe Ala Arg Lys Phe Asp Ser Met Val Asp
                500                 505                 510

Ile Asp Ser Ile Glu Ala Ala Glu Met Gln Ser Ile Ser Pro Glu Lys
                515                 520                 525

Leu Gln Leu Asn His Pro Thr Tyr His Phe Ala Phe Ala Asn Ile Phe
                530                 535                 540

Lys Thr Gly Ile Asp Glu Gln Lys Leu His Phe Glu Ser Leu Ala Asn
545                 550                 555                 560

Phe Ala Leu Lys Ser Thr Glu Thr Arg Ala Lys Phe Arg Lys Val Leu
                565                 570                 575

Arg Ile Asp Ala Leu Arg Ala His His Asn Ala Leu Ile Glu Ile Val
                580                 585                 590

Met Lys Ile Glu Thr Thr Asp Gly Ala Thr Phe Glu Phe Leu Ile His
                595                 600                 605

Arg Leu Ser His Val Asn Leu Thr Glu Asn Glu Glu Lys Leu Val Glu
610                 615                 620
```

```
His Gly Tyr Leu Leu Arg Ala Val Ser Phe Gly Thr Lys Phe Glu Trp
625                 630                 635                 640

Lys Glu Glu Leu Cys Arg Glu Tyr Met Gly Phe Val Thr Asp Asn Asp
            645                 650                 655

Thr Leu His Thr Arg Leu Gln Trp His Pro Thr Glu His Val Lys Lys
        660                 665                 670

Val Gly Asp Lys Thr Ser Pro Glu Met Ile Phe Lys Tyr Arg Lys Gly
    675                 680                 685

Asp Glu Leu Ile Glu Gln Thr Val Val Lys Pro Tyr Asp Ser Val Phe
690                 695                 700

Gly Gly Gln Phe Asp Ser Trp Asn Val Gly Lys Lys Leu Ser Asn Leu
705                 710                 715                 720

Thr Thr Cys Ser Asn Phe Phe Val Asp Ile Ile Ser Pro Ser Ser Pro
            725                 730                 735

Asp Asp Ala Pro Pro Leu Ala Thr Leu His Phe Pro Val Tyr Thr Asp
        740                 745                 750

Gln Asn Ala His Cys His Val Asp Tyr Leu Arg Gln Phe Phe Lys Ile
    755                 760                 765

Ala Asp Phe Cys Thr Ser Gly Asp Ala Cys Lys Glu Lys Ile Trp Ser
770                 775                 780

Thr Ser Tyr Pro Asp Pro Lys Ser Asp Ile Phe Val Gly Tyr Asp Glu
785                 790                 795                 800

Asp Thr Gln Thr Leu Ile
            805

<210> SEQ ID NO 16
<211> LENGTH: 827
<212> TYPE: PRT
<213> ORGANISM: Homo sapiens

<400> SEQUENCE: 16

Thr Gln Asp Gly Tyr Phe Ser His Arg Pro Lys Glu Lys Val Arg Thr
1               5                   10                  15

Asp Ser Asn Asn Glu Asn Ser Val Pro Lys Asp Phe Glu Asn Val Asp
            20                  25                  30

Asn Ser Asn Phe Ala Pro Arg Thr Gln Lys Gln Lys His Gln Pro Glu
        35                  40                  45

Leu Ala Lys Lys Pro Pro Ser Arg Gln Lys Glu Leu Leu Lys Arg Lys
    50                  55                  60

Leu Glu Gln Gln Lys Gly Lys Gly His Thr Phe Pro Gly Lys Gly
65                  70                  75                  80

Pro Gly Glu Val Leu Pro Pro Gly Asp Arg Ala Ala Ala Asn Ser Ser
                85                  90                  95

His Gly Lys Asp Val Ser Arg Pro Pro His Ala Arg Lys Thr Gly Gly
            100                 105                 110

Ser Ser Pro Glu Thr Lys Tyr Asp Gln Pro Lys Cys Asp Ile Ser
        115                 120                 125

Gly Lys Glu Ala Ile Ser Ala Leu Ser Arg Ala Lys Ser Lys His Cys
130                 135                 140

Arg Gln Glu Ile Gly Glu Thr Tyr Cys Arg His Lys Leu Gly Leu Leu
145                 150                 155                 160

Met Pro Glu Lys Val Thr Arg Phe Cys Pro Leu Glu Gly Lys Ala Asn
                165                 170                 175

Lys Asn Val Gln Trp Asp Glu Asp Ser Val Glu Tyr Met Pro Ala Asn
            180                 185                 190
```

-continued

```
Pro Val Arg Ile Ala Phe Val Leu Val His Gly Arg Ala Ser Arg
        195                 200                 205
Gln Leu Gln Arg Met Phe Lys Ala Ile Tyr His Lys Asp His Phe Tyr
        210                 215                 220
Tyr Ile His Val Asp Lys Arg Ser Asn Tyr Leu His Arg Gln Val Leu
225                 230                 235                 240
Gln Val Ser Arg Gln Tyr Ser Asn Val Arg Val Thr Pro Trp Arg Met
                245                 250                 255
Ala Thr Ile Trp Gly Gly Ala Ser Leu Leu Ser Thr Tyr Leu Gln Ser
            260                 265                 270
Met Arg Asp Leu Leu Glu Met Thr Asp Trp Pro Trp Asp Phe Phe Ile
        275                 280                 285
Asn Leu Ser Ala Ala Asp Tyr Pro Ile Arg Thr Asn Asp Gln Leu Val
        290                 295                 300
Ala Phe Leu Ser Arg Tyr Arg Asp Met Asn Phe Leu Lys Ser His Gly
305                 310                 315                 320
Arg Asp Asn Ala Arg Phe Ile Arg Lys Gln Gly Leu Asp Arg Leu Phe
                325                 330                 335
Leu Glu Cys Asp Ala His Met Trp Arg Leu Gly Asp Arg Arg Ile Pro
            340                 345                 350
Glu Gly Ile Ala Val Asp Gly Gly Ser Asp Trp Phe Leu Leu Asn Arg
        355                 360                 365
Arg Phe Val Glu Tyr Val Thr Phe Ser Thr Asp Asp Leu Val Thr Lys
        370                 375                 380
Met Lys Gln Phe Tyr Ser Tyr Thr Leu Leu Pro Ala Glu Ser Phe Phe
385                 390                 395                 400
His Thr Val Leu Glu Asn Ser Pro His Cys Asp Thr Met Val Asp Asn
                405                 410                 415
Asn Leu Arg Ile Thr Asn Trp Asn Arg Lys Leu Gly Cys Lys Cys Gln
            420                 425                 430
Tyr Lys His Ile Val Asp Trp Cys Gly Cys Ser Pro Asn Asp Phe Lys
        435                 440                 445
Pro Gln Asp Phe His Arg Phe Gln Gln Thr Ala Arg Pro Thr Phe Phe
        450                 455                 460
Ala Arg Lys Phe Glu Ala Val Val Asn Gln Ile Ile Gly Gln Leu
465                 470                 475                 480
Asp Tyr Tyr Leu Tyr Gly Asn Tyr Pro Ala Gly Thr Pro Gly Leu Arg
                485                 490                 495
Ser Tyr Trp Glu Asn Val Tyr Asp Glu Pro Asp Gly Ile His Ser Leu
            500                 505                 510
Ser Asp Val Thr Leu Thr Leu Tyr His Ser Phe Ala Arg Leu Gly Leu
        515                 520                 525
Arg Arg Ala Glu Thr Ser Leu His Thr Asp Gly Glu Asn Ser Cys Arg
        530                 535                 540
Tyr Tyr Pro Met Gly His Pro Ala Ser Val His Leu Tyr Phe Leu Ala
545                 550                 555                 560
Asp Arg Phe Gln Gly Phe Leu Ile Lys His His Ala Thr Asn Leu Ala
                565                 570                 575
Val Ser Lys Leu Glu Thr Leu Glu Thr Trp Val Met Pro Lys Lys Val
            580                 585                 590
Phe Lys Ile Ala Ser Pro Pro Ser Asp Phe Gly Arg Leu Gln Phe Ser
        595                 600                 605
```

```
Glu Val Gly Thr Asp Trp Asp Ala Lys Glu Arg Leu Phe Arg Asn Phe
    610                 615                 620
Gly Gly Leu Leu Gly Pro Met Asp Glu Pro Val Gly Met Gln Lys Trp
625                 630                 635                 640
Gly Lys Gly Pro Asn Val Thr Val Thr Val Ile Trp Val Asp Pro Val
                645                 650                 655
Asn Val Ile Ala Ala Thr Tyr Asp Ile Leu Ile Glu Ser Thr Ala Glu
                660                 665                 670
Phe Thr His Tyr Lys Pro Pro Leu Asn Leu Pro Leu Arg Pro Gly Val
                675                 680                 685
Trp Thr Val Lys Ile Leu His His Trp Val Pro Val Ala Glu Thr Lys
    690                 695                 700
Phe Leu Val Ala Pro Leu Thr Phe Ser Asn Arg Gln Pro Ile Lys Pro
705                 710                 715                 720
Glu Glu Ala Leu Lys Leu His Asn Gly Pro Leu Arg Asn Ala Tyr Met
                725                 730                 735
Glu Gln Ser Phe Gln Ser Leu Asn Pro Val Leu Ser Leu Pro Ile Asn
                740                 745                 750
Pro Ala Gln Val Glu Gln Ala Arg Arg Asn Ala Ala Ser Thr Gly Thr
                755                 760                 765
Ala Leu Glu Gly Trp Leu Asp Ser Leu Val Gly Gly Met Trp Thr Ala
    770                 775                 780
Met Asp Ile Cys Ala Thr Gly Pro Thr Ala Cys Pro Val Met Gln Thr
785                 790                 795                 800
Cys Ser Gln Thr Ala Trp Ser Ser Phe Ser Pro Asp Pro Lys Ser Glu
                805                 810                 815
Leu Gly Ala Val Lys Pro Asp Gly Arg Leu Arg
                820                 825

<210> SEQ ID NO 17
<211> LENGTH: 865
<212> TYPE: PRT
<213> ORGANISM: Homo sapiens

<400> SEQUENCE: 17

Met Val Ala Ser Ala Arg Val Gln Lys Leu Val Arg Arg Tyr Lys Leu
1               5                   10                  15
Ala Ile Ala Thr Ala Leu Ala Ile Leu Leu Gln Gly Leu Val Val
                20                  25                  30
Trp Ser Phe Ser Gly Leu Glu Glu Asp Glu Ala Gly Glu Lys Gly Arg
    35                  40                  45
Gln Arg Lys Pro Arg Pro Leu Asp Pro Gly Glu Gly Ser Lys Asp Thr
    50                  55                  60
Asp Ser Ser Ala Gly Arg Arg Gly Ser Thr Gly Arg His Gly Arg
65              70                  75                  80
Trp Arg Gly Arg Ala Glu Ser Pro Gly Val Pro Val Ala Lys Val Val
                85                  90                  95
Arg Ala Val Thr Ser Arg Gln Arg Ala Ser Arg Val Pro Pro Ala
                100                 105                 110
Pro Pro Pro Glu Ala Pro Gly Arg Gln Asn Leu Ser Gly Ala Ala Ala
                115                 120                 125
Gly Glu Ala Leu Val Gly Ala Ala Gly Phe Pro Pro His Gly Asp Thr
    130                 135                 140
Gly Ser Val Glu Gly Ala Pro Gln Pro Thr Asp Asn Gly Phe Thr Pro
145                 150                 155                 160
```

-continued

```
Lys Cys Glu Ile Val Gly Lys Asp Ala Leu Ser Ala Leu Ala Arg Ala
            165                 170                 175
Ser Thr Lys Gln Cys Gln Gln Glu Ile Ala Asn Val Val Cys Leu His
            180                 185                 190
Gln Ala Gly Ser Leu Met Pro Lys Ala Val Pro Arg His Cys Gln Leu
            195                 200                 205
Thr Gly Lys Met Ser Pro Gly Ile Gln Trp Asp Glu Ser Gln Ala Gln
            210                 215                 220
Gln Pro Met Asp Gly Pro Pro Val Arg Ile Ala Tyr Met Leu Val Val
225                 230                 235                 240
His Gly Arg Ala Ile Arg Gln Leu Lys Arg Leu Leu Lys Ala Val Tyr
                245                 250                 255
His Glu Gln His Phe Phe Tyr Ile His Val Asp Lys Arg Ser Asp Tyr
                260                 265                 270
Leu His Arg Glu Val Val Glu Leu Ala Gln Gly Tyr Asp Asn Val Arg
            275                 280                 285
Val Thr Pro Trp Arg Met Val Thr Ile Trp Gly Gly Ala Ser Leu Leu
290                 295                 300
Thr Met Tyr Leu Arg Ser Met Arg Asp Leu Leu Glu Val Pro Gly Trp
305                 310                 315                 320
Ala Trp Asp Phe Phe Ile Asn Leu Ser Ala Thr Asp Tyr Pro Thr Arg
                325                 330                 335
Thr Asn Glu Glu Leu Val Ala Phe Leu Ser Lys Asn Arg Asp Lys Asn
            340                 345                 350
Phe Leu Lys Ser His Gly Arg Asp Asn Ser Arg Phe Ile Lys Lys Gln
            355                 360                 365
Gly Leu Asp Arg Leu Phe His Glu Cys Asp Ser His Met Trp Arg Leu
            370                 375                 380
Gly Glu Arg Gln Ile Pro Ala Gly Ile Val Val Asp Gly Gly Ser Asp
385                 390                 395                 400
Trp Phe Val Leu Thr Arg Ser Phe Val Glu Tyr Val Val Tyr Thr Asp
                405                 410                 415
Asp Pro Leu Val Ala Gln Leu Arg Gln Phe Tyr Thr Tyr Thr Leu Leu
            420                 425                 430
Pro Ala Glu Ser Phe Phe His Thr Val Leu Glu Asn Ser Leu Ala Cys
            435                 440                 445
Glu Thr Leu Val Asp Asn Asn Leu Arg Val Thr Asn Trp Asn Arg Lys
            450                 455                 460
Leu Gly Cys Lys Cys Gln Tyr Lys His Ile Val Asp Trp Cys Gly Cys
465                 470                 475                 480
Ser Pro Asn Asp Phe Lys Pro Gln Asp Phe Leu Arg Leu Gln Gln Val
                485                 490                 495
Ser Arg Pro Thr Phe Phe Ala Arg Lys Phe Glu Ser Thr Val Asn Gln
                500                 505                 510
Glu Val Leu Glu Ile Leu Asp Phe His Leu Tyr Gly Ser Tyr Pro Pro
            515                 520                 525
Gly Thr Pro Ala Leu Lys Ala Tyr Trp Glu Asn Thr Tyr Asp Ala Ala
            530                 535                 540
Asp Gly Pro Ser Gly Leu Ser Asp Val Met Leu Thr Ala Tyr Thr Ala
545                 550                 555                 560
Phe Ala Arg Leu Ser Leu His His Ala Ala Thr Ala Ala Pro Pro Met
                565                 570                 575
```

-continued

```
Gly Thr Pro Leu Cys Arg Phe Glu Pro Arg Gly Leu Pro Ser Ser Val
            580                 585                 590

His Leu Tyr Phe Tyr Asp Asp His Phe Gln Gly Tyr Leu Val Thr Gln
        595                 600                 605

Ala Val Gln Pro Ser Ala Gln Gly Pro Ala Glu Thr Leu Glu Met Trp
    610                 615                 620

Leu Met Pro Gln Gly Ser Leu Lys Leu Leu Gly Arg Ser Asp Gln Ala
625                 630                 635                 640

Ser Arg Leu Gln Ser Leu Glu Val Gly Thr Asp Trp Asp Pro Lys Glu
                645                 650                 655

Arg Leu Phe Arg Asn Phe Gly Gly Leu Leu Gly Pro Leu Asp Glu Pro
            660                 665                 670

Val Ala Val Gln Arg Trp Ala Arg Gly Pro Asn Leu Thr Ala Thr Val
        675                 680                 685

Val Trp Ile Asp Pro Thr Tyr Val Val Ala Thr Ser Tyr Asp Ile Thr
    690                 695                 700

Val Asp Thr Glu Thr Glu Val Thr Gln Tyr Lys Pro Pro Leu Ser Arg
705                 710                 715                 720

Pro Leu Arg Pro Gly Pro Trp Thr Val Arg Leu Leu Gln Phe Trp Glu
                725                 730                 735

Pro Leu Gly Glu Thr Arg Phe Leu Val Leu Pro Leu Thr Phe Asn Arg
            740                 745                 750

Lys Leu Pro Leu Arg Lys Asp Asp Ala Ser Trp Leu His Ala Gly Pro
        755                 760                 765

Pro His Asn Glu Tyr Met Glu Gln Ser Phe Gln Gly Leu Ser Ser Ile
    770                 775                 780

Leu Asn Leu Pro Gln Pro Glu Leu Ala Glu Glu Ala Ala Gln Arg His
785                 790                 795                 800

Thr Gln Leu Thr Gly Pro Ala Leu Glu Ala Trp Thr Asp Arg Glu Leu
                805                 810                 815

Ser Ser Phe Trp Ser Val Ala Gly Leu Cys Ala Ile Gly Pro Ser Pro
            820                 825                 830

Cys Pro Ser Leu Glu Pro Cys Arg Leu Thr Ser Trp Ser Ser Leu Ser
        835                 840                 845

Pro Asp Pro Lys Ser Glu Leu Gly Pro Val Lys Ala Asp Gly Arg Leu
    850                 855                 860

Arg
865

<210> SEQ ID NO 18
<211> LENGTH: 1446
<212> TYPE: DNA
<213> ORGANISM: Caenorhabditis elegans

<400> SEQUENCE: 18
atgactgatc aagtcttcgg aaaggtgtcg aaagtcgttt gcgtcggagc tggatacgtt    60
ggtggaccaa catgtgcaat gattgcgcac aagtgtccac acattacagt aactgtcgtg   120
gacatgaaca ccgctaagat tgccgagtgg aactctgata aattgccaat atacgagcct   180
ggacttgacg agattgtttt cgccgctcgt ggtcgcaatc tattcttctc ctctgatatt   240
ccaaaagcga ttgctgaagc cgatcttatt tttatctcgg tgaacactcc cacaaaaatg   300
tacggacgtg gcaaaggaat ggctccagat ctgaaatatg tcgagtcagt ctcgcgtacc   360
atcgctcaat acgcgggtgg tccaaagatt gttgtggaaa aagtacagt tccggtaaag   420
```

```
gctgcagaat caattggttg cattttgaga gaagcacaaa aaaataacga aaatctaaag      480
ttccaagtcc tacttgttcg aatctacgaa aactgggtgc cacgcaatcg tattattact      540
actaatacat ggagcagcga actttcgaaa cgtcaaatcc agagttcttg gctgaaggaa      600
cagctatgaa ggatcttgcc aatccagatc gtgtgctcat tggaggagaa tcctctccag      660
aaggacttca agccgtcgct gatcgttgcc aacgcattct tggctcaaag aatttcatcg      720
atcaattcaa tttctgccgt ttgcgaagct accggagctg aaatctcgga agttgctcac      780
gcagttggat atgacactcg aattggtagc aagttcctac aagcatctgt tggctttgga      840
gggagctgct tccaaaaaga tgtactctca cttgtatatc tttgcgaatc tctcaatctt      900
ccacaagtcg ctgattattg gcaaggagtg attaatatta caactggca acgaagacgt       960 ttcgcagaca agattattgc ggagttgttt aacacggtga ctgataagaa aattgcaatc     1020
ttcggattcg ctttcaagaa gaacacaggt gacacacgcg aatcatcagc cattcacgta     1080
atcaaacact tgatggagga gcatgcaaaa ttatcagtct acgatccaaa agtgcagaaa     1140
tcgcaaatgc tcaacgatct ggcttcggtg acaagtgcgc aagatgttga gcgtctcatt     1200
actgttgagt cggatccata tgctgctgca cgtggtgctc acgcaattgt tgtacttacc     1260
gagtgggatg aattcgttga attgaactac agtcagattc ataatgacat gcagcatcca     1320
gctgccatat tcgatggaag actcattctg gatcagaaag cattgcgtga aatcgggttc     1380
cgtacattcg ccattggaac ttctccagat caagcttata atctattcgg aacagctggt     1440
tattaa                                                                1446

<210> SEQ ID NO 19
<211> LENGTH: 2000
<212> TYPE: DNA
<213> ORGANISM: Caenorhabditis elegans

<400> SEQUENCE: 19
ttgtgcatat tctgcattgt acgagttgat tttctgtagg gcggcaattc aaatgtaaaa       60 gtttttttt tcattttcat gtcttgacgc ctttcgagtt gttaaaaatc gtgttccttt       120
tgaaagcttt tctttatcgc ttactaattt tacttttcat tttaaatatt ttcaaatttc      180
agtaatgact gatcaagtct tcggaaaggt gtcgaaagtc gtttgcgtcg agctggata       240 cgttggtgga ccaacatgtg caatgattgc gcacaagtgt ccacacatta cagtaactgt       300
cgtggacatg aacaccgcta agattgccga gtggaactct gataaattgc caatatacga       360
ggtgagctat atttttttaa attttctct aataaacata ttgcagcctg acttgacga        420 gattgttttc gccgctcgtg gtcgcaatct attcttctcc tctgatattc caaaagcgat      480
tgctgaagcc gatcttattt ttatctcggt gaacactccc acaaaaatgt acggacgtgg      540
caaaggaatg gctccagatc tgaaatatgt cgagtcagtc tcgcgtacca tcgctcaata      600
cgcgggtggt ccaaagattg ttgtggaaaa agtacagtt ccggtaaagg ctgcagaatc       660
aattggttgc attttgagag aagcacaaaa aaataacgaa atctaaagt tccaagtcct       720 gtcaaatcca gagttcttgg ctgaaggtgg gctacacatt cacagtttt gccattaaat       780 accttgtatt ttcaggaaca gctatgaagg atcttgccaa tccagatcgt gtgctcattg      840
gaggagaatc ctctccagaa ggacttcaag ccgtcgctga acttgttcga atctacgaaa      900
actgggtgcc acgcaatcgt attattacta ctaatacatg gagcagcgaa ctttcgaaac      960
tcgttgccaa cgcattcttg gctcaaagaa tttcatcgat caattcaatt tctgccgttt     1020
gcgaagctac cggagctgaa atctcggaag ttgctcacgc agttggatat gacactcgaa     1080
```

-continued

```
ttggtagcaa gttcctacaa gcatctgttg gctttggagg gagctgcttc caaaaagatg   1140
tactctcact tgtatatctt tgcgaatctc tcaatcttcc acaagtcgct gattattggc   1200
aaggagtgat taatattaac aactggcaac gaagacgttt cgcagacaag attattgcgg   1260
agttgtttaa cacggtgact gataagaaaa ttgcaatctt cggattcgct ttcaagaaga   1320
acacaggtga gtataagcgc aaaaagctgt tcaacattaa tctaaaaata caccgagaat   1380
atacatacgt tacatgcttg ttttacaatt tacaggtatt ttaaagctat gcatattgcc   1440
atattgtcaa gaaatgaat attattacaa gtttggtttt tcaggtgaca cacgcgaatc   1500
atcagccatt cacgtaatca aacacttgat ggaggagcat gcaaaattat cagtctacga   1560
tccaaaagtg cagaaatcgc aaatgctcaa cgatctggct tcggtgacaa gtgcgcaaga   1620
tgttgagcgt ctcattactg ttgagtcgga tccatatgct gctgcacgtg gtgctcacgc   1680
aattgttgta cttaccgagt gggatgaatt cgttgaattg aactacagtc agattcataa   1740
tgacatgcag catccagctg ccatattcga tggaagactc attctggatc agaaagcatt   1800
gcgtgaaatc gggttccgta cattcgccat tggaacttct ccagatcaag cttataatct   1860
attcggaaca gctggttatt aatcgtgtct tggaaaatct ccaattctca ctattgactt   1920
caaaattatt tatctgcatg cttcttcttt ttactcataa tttattgcat tttatgatat   1980
ctaactgcct taatagtaaa                                              2000
```

<210> SEQ ID NO 20
<211> LENGTH: 481
<212> TYPE: PRT
<213> ORGANISM: Caenorhabditis elegans

<400> SEQUENCE: 20

```
Met Thr Asp Gln Val Phe Gly Lys Val Ser Lys Val Val Cys Val Gly
  1               5                  10                  15

Ala Gly Tyr Val Gly Gly Pro Thr Cys Ala Met Ile Ala His Lys Cys
             20                  25                  30

Pro His Ile Thr Val Thr Val Val Asp Met Asn Thr Ala Lys Ile Ala
         35                  40                  45

Glu Trp Asn Ser Asp Lys Leu Pro Ile Tyr Glu Pro Gly Leu Asp Glu
     50                  55                  60

Ile Val Phe Ala Ala Arg Gly Arg Asn Leu Phe Phe Ser Ser Asp Ile
 65                  70                  75                  80

Pro Lys Ala Ile Ala Glu Ala Asp Leu Ile Phe Ile Ser Val Asn Thr
                 85                  90                  95

Pro Thr Lys Met Tyr Gly Arg Gly Lys Gly Met Ala Pro Asp Leu Lys
            100                 105                 110

Tyr Val Glu Ser Val Ser Arg Thr Ile Ala Gln Tyr Ala Gly Gly Pro
        115                 120                 125

Lys Ile Val Val Glu Lys Ser Thr Val Pro Val Lys Ala Ala Glu Ser
    130                 135                 140

Ile Gly Cys Ile Leu Arg Glu Ala Gln Lys Asn Asn Glu Asn Leu Lys
145                 150                 155                 160

Phe Gln Val Leu Ser Asn Pro Glu Phe Leu Ala Glu Gly Thr Ala Met
                165                 170                 175

Lys Asp Leu Ala Asn Pro Asp Arg Val Leu Ile Gly Gly Glu Ser Ser
            180                 185                 190

Pro Glu Gly Leu Gln Ala Val Ala Glu Leu Val Arg Ile Tyr Glu Asn
        195                 200                 205
```

-continued

```
Trp Val Pro Arg Asn Arg Ile Ile Thr Thr Asn Thr Trp Ser Ser Glu
    210                 215                 220

Leu Ser Lys Leu Val Ala Asn Ala Phe Leu Ala Gln Arg Ile Ser Ser
225                 230                 235                 240

Ile Asn Ser Ile Ser Ala Val Cys Glu Ala Thr Gly Ala Glu Ile Ser
                245                 250                 255

Glu Val Ala His Ala Val Gly Tyr Asp Thr Arg Ile Gly Ser Lys Phe
                260                 265                 270

Leu Gln Ala Ser Val Gly Phe Gly Ser Cys Phe Gln Lys Asp Val
    275                 280                 285

Leu Ser Leu Val Tyr Leu Cys Glu Ser Leu Asn Leu Pro Gln Val Ala
    290                 295                 300

Asp Tyr Trp Gln Gly Val Ile Asn Ile Asn Asn Trp Gln Arg Arg
305                 310                 315                 320

Phe Ala Asp Lys Ile Ile Ala Glu Leu Phe Asn Thr Val Thr Asp Lys
                325                 330                 335

Lys Ile Ala Ile Phe Gly Phe Ala Phe Lys Lys Asn Thr Gly Asp Thr
                340                 345                 350

Arg Glu Ser Ser Ala Ile His Val Ile Lys His Leu Met Glu Glu His
                355                 360                 365

Ala Lys Leu Ser Val Tyr Asp Pro Lys Val Gln Lys Ser Gln Met Leu
    370                 375                 380

Asn Asp Leu Ala Ser Val Thr Ser Ala Gln Asp Val Glu Arg Leu Ile
385                 390                 395                 400

Thr Val Glu Ser Asp Pro Tyr Ala Ala Ala Arg Gly Ala His Ala Ile
                405                 410                 415

Val Val Leu Thr Glu Trp Asp Glu Phe Val Glu Leu Asn Tyr Ser Gln
                420                 425                 430

Ile His Asn Asp Met Gln His Pro Ala Ala Ile Phe Asp Gly Arg Leu
    435                 440                 445

Ile Leu Asp Gln Lys Ala Leu Arg Glu Ile Gly Phe Arg Thr Phe Ala
450                 455                 460

Ile Gly Thr Ser Pro Asp Gln Ala Tyr Asn Leu Phe Gly Thr Ala Gly
465                 470                 475                 480

Tyr
```

<210> SEQ ID NO 21
<211> LENGTH: 476
<212> TYPE: PRT
<213> ORGANISM: Drosophila melanogaster

<400> SEQUENCE: 21

```
Met Lys Val Cys Cys Ile Gly Ala Gly Tyr Val Gly Gly Pro Thr Cys
1               5                   10                  15

Ala Val Met Ala Leu Lys Cys Pro Asp Ile Val Ile Thr Leu Val Asp
                20                  25                  30

Lys Ser Ser Glu Arg Ile Ala Gln Trp Asn Ser Asp Lys Leu Pro Ile
            35                  40                  45

Tyr Glu Pro Gly Leu Asp Glu Val Val Lys Arg Cys Arg Asn Val Asn
    50                  55                  60

Leu Phe Phe Ser Thr Asp Ile Glu Thr Ala Ile Lys Glu Ala Asp Leu
65                  70                  75                  80

Ile Phe Ile Ser Val Asn Thr Pro Thr Lys Thr Cys Gly Asn Gly Lys
                85                  90                  95
```

-continued

```
Gly Arg Ala Ala Asp Leu Lys Tyr Val Glu Ser Ala Ala Arg Met Ile
            100                 105                 110
Ala Glu Ile Ala Gln Ser Asn Lys Ile Val Val Glu Lys Ser Thr Val
        115                 120                 125
Pro Val Arg Ala Ala Glu Ser Ile Met His Ile Leu Arg Ala Asn Gln
    130                 135                 140
Lys Pro Gly Ile His Tyr Asp Ile Leu Ser Asn Pro Glu Phe Leu Ala
145                 150                 155                 160
Glu Gly Thr Ala Ile Asn Asp Leu Leu Asn Ala Asp Arg Val Leu Ile
                165                 170                 175
Gly Gly Glu Glu Thr Pro Glu Gly His Gln Ala Val Glu Lys Leu Ser
            180                 185                 190
Trp Ile Tyr Glu His Trp Ile Pro Lys Gln Asn Ile Leu Thr Thr Asn
        195                 200                 205
Thr Trp Ser Ser Glu Leu Ser Lys Leu Ala Ala Asn Ala Phe Leu Ala
    210                 215                 220
Gln Arg Ile Ser Ser Ile Asn Ser Leu Ser Ala Val Cys Glu Ala Thr
225                 230                 235                 240
Gly Ala Asp Val Ser Glu Val Ala Arg Ala Val Gly Leu Asp Ser Arg
                245                 250                 255
Ile Gly Ser Lys Phe Leu Gln Ala Ser Val Gly Phe Gly Gly Ser Cys
            260                 265                 270
Phe Gln Lys Asp Ile Leu Asn Leu Ile Tyr Ile Cys Glu Asn Leu Asn
        275                 280                 285
Leu Pro Glu Val Ala Ala Tyr Trp Gln Gln Val Ile Asp Met Asn Glu
    290                 295                 300
Tyr Gln Lys Arg Arg Phe Ser Gln Lys Ile Ile Glu Ser Leu Phe Asn
305                 310                 315                 320
Thr Val Ser Asp Lys Arg Ile Ala Ile Leu Gly Phe Ala Phe Lys Lys
                325                 330                 335
Asn Thr Gly Asp Thr Arg Glu Thr Ala Ala Ile Thr Val Cys Gln Thr
            340                 345                 350
Leu Leu Glu Glu Gly Ala Ala Leu Asp Ile Tyr Asp Pro Lys Val Glu
        355                 360                 365
Pro Glu Gln Ile Ile Asp Asp Leu Thr His Pro Ser Val Thr Glu Ser
    370                 375                 380
Pro Glu Lys Val Lys Lys Ala Val Gln Ile His Ser Asp Pro Tyr Ser
385                 390                 395                 400
Ala Val Arg Ala Thr His Ala Leu Val Ile Cys Thr Glu Trp Asp Glu
                405                 410                 415
Phe Val Asp Leu Asp Phe Lys Arg Ile Tyr Gln Ser Met Met Lys Pro
            420                 425                 430
Ala Tyr Ile Phe Asp Gly Arg Lys Ile Leu Asp His Glu Arg Leu Gln
        435                 440                 445
Gln Ile Gly Phe His Val Gln Thr Ile Gly Lys Lys Tyr Gln Arg Thr
    450                 455                 460
Gly Leu Leu Arg Ser Trp Gly Ile Val Pro Gln Leu
465                 470                 475

<210> SEQ ID NO 22
<211> LENGTH: 494
<212> TYPE: PRT
<213> ORGANISM: Homo sapiens
```

-continued

```
<400> SEQUENCE: 22

Met Phe Glu Ile Lys Lys Ile Cys Cys Ile Gly Ala Gly Tyr Val Gly
  1               5                  10                  15

Gly Pro Thr Cys Ser Val Ile Ala His Met Cys Pro Glu Ile Arg Val
             20                  25                  30

Thr Val Val Asp Val Asn Glu Ser Arg Ile Asn Ala Trp Asn Ser Pro
         35                  40                  45

Thr Leu Pro Ile Tyr Glu Pro Gly Leu Lys Glu Val Val Glu Ser Cys
     50                  55                  60

Arg Gly Lys Asn Leu Phe Phe Ser Thr Asn Ile Asp Asp Ala Ile Lys
 65                  70                  75                  80

Glu Ala Asp Leu Val Phe Ile Ser Val Asn Thr Pro Thr Lys Thr Tyr
                 85                  90                  95

Gly Met Gly Lys Gly Arg Ala Ala Asp Leu Lys Tyr Ile Glu Ala Cys
            100                 105                 110

Ala Arg Arg Ile Val Gln Asn Ser Asn Gly Tyr Lys Ile Val Thr Glu
        115                 120                 125

Lys Ser Thr Val Pro Val Arg Ala Ala Glu Ser Ile Arg Arg Ile Phe
130                 135                 140

Asp Ala Asn Thr Lys Pro Asn Leu Asn Leu Gln Val Leu Ser Asn Pro
145                 150                 155                 160

Glu Phe Leu Ala Glu Gly Thr Ala Ile Lys Asp Leu Lys Asn Pro Asp
                165                 170                 175

Arg Val Leu Ile Gly Gly Asp Glu Thr Pro Glu Gly Gln Arg Ala Val
            180                 185                 190

Gln Ala Leu Cys Ala Val Tyr Glu His Trp Val Pro Arg Glu Lys Ile
        195                 200                 205

Leu Thr Thr Asn Thr Trp Ser Ser Glu Leu Ser Lys Leu Ala Ala Asn
    210                 215                 220

Ala Phe Leu Ala Gln Arg Ile Ser Ser Ile Asn Ser Ile Ser Ala Leu
225                 230                 235                 240

Cys Glu Ala Thr Gly Ala Asp Val Glu Glu Val Ala Thr Ala Ile Gly
                245                 250                 255

Met Asp Gln Arg Ile Gly Asn Lys Phe Leu Lys Ala Ser Val Gly Phe
            260                 265                 270

Gly Gly Ser Cys Phe Gln Lys Asp Val Leu Asn Leu Val Tyr Leu Cys
        275                 280                 285

Glu Ala Leu Asn Leu Pro Glu Val Ala Arg Tyr Trp Gln Gln Val Ile
    290                 295                 300

Asp Met Asn Asp Tyr Gln Arg Arg Phe Ala Ser Arg Ile Ile Asp
305                 310                 315                 320

Ser Leu Phe Asn Thr Val Thr Asp Lys Lys Ile Ala Ile Leu Gly Phe
                325                 330                 335

Ala Phe Lys Lys Asp Thr Gly Asp Thr Arg Glu Ser Ser Ser Ile Tyr
            340                 345                 350

Ile Ser Lys Tyr Leu Met Asp Glu Gly Ala His Leu His Ile Tyr Asp
        355                 360                 365

Pro Lys Val Pro Arg Glu Gln Ile Val Val Asp Leu Ser His Pro Gly
    370                 375                 380

Val Ser Glu Asp Asp Gln Val Ser Arg Leu Val Thr Ile Ser Lys Asp
385                 390                 395                 400

Pro Tyr Glu Ala Cys Asp Gly Ala His Ala Val Val Ile Cys Thr Glu
                405                 410                 415
```

```
Trp Asp Met Phe Lys Glu Leu Asp Tyr Glu Arg Ile His Lys Lys Met
            420                 425                 430

Leu Lys Pro Ala Phe Ile Phe Asp Gly Arg Arg Val Leu Asp Gly Leu
            435                 440                 445

His Asn Glu Leu Gln Thr Ile Gly Phe Gln Ile Glu Thr Ile Gly Lys
            450                 455                 460

Lys Val Ser Ser Lys Arg Ile Pro Tyr Ala Pro Ser Gly Glu Ile Pro
465                 470                 475                 480

Lys Phe Ser Leu Gln Asp Pro Pro Asn Lys Lys Pro Lys Val
            485                 490

<210> SEQ ID NO 23
<211> LENGTH: 480
<212> TYPE: PRT
<213> ORGANISM: Arabidopsis thaliana

<400> SEQUENCE: 23

Met Val Lys Ile Cys Cys Ile Gly Ala Gly Tyr Val Gly Gly Pro Thr
1               5                   10                  15

Met Ala Val Ile Ala Leu Lys Cys Pro Asp Ile Glu Val Ala Val Val
            20                  25                  30

Asp Ile Ser Val Pro Arg Ile Asn Ala Trp Asn Ser Asp Gln Leu Pro
        35                  40                  45

Ile Tyr Glu Pro Gly Leu Asp Asp Ile Val Lys Gln Cys Arg Gly Lys
    50                  55                  60

Asn Leu Phe Phe Ser Thr Asp Val Glu Lys His Val Arg Glu Ala Asp
65                  70                  75                  80

Ile Val Phe Val Ser Val Asn Thr Pro Thr Lys Thr Thr Gly Leu Gly
                85                  90                  95

Ala Gly Lys Ala Ala Asp Leu Thr Tyr Trp Glu Ser Ala Ala Arg Met
            100                 105                 110

Ile Ala Asp Val Ser Val Ser Asp Lys Ile Val Val Glu Lys Ser Thr
        115                 120                 125

Val Pro Val Lys Thr Ala Glu Ala Ile Glu Lys Ile Leu Met His Asn
    130                 135                 140

Ser Lys Gly Ile Lys Phe Gln Ile Leu Ser Asn Pro Glu Phe Leu Ala
145                 150                 155                 160

Glu Gly Thr Ala Ile Ala Asp Leu Phe Asn Pro Asp Arg Val Leu Ile
                165                 170                 175

Gly Gly Arg Glu Thr Pro Glu Gly Phe Lys Ala Val Gln Thr Leu Lys
            180                 185                 190

Glu Val Tyr Ala Asn Trp Val Pro Glu Gly Gln Ile Ile Thr Thr Asn
        195                 200                 205

Leu Trp Ser Ala Glu Leu Ser Lys Leu Ala Ala Asn Ala Phe Leu Ala
    210                 215                 220

Gln Arg Ile Ser Ser Val Asn Ala Met Ser Ala Leu Cys Glu Ser Thr
225                 230                 235                 240

Gly Ala Asp Val Thr Gln Val Ser Tyr Ala Val Gly Thr Asp Ser Arg
                245                 250                 255

Ile Gly Ser Lys Phe Leu Asn Ala Ser Val Gly Phe Gly Gly Ser Cys
            260                 265                 270

Phe Gln Lys Asp Ile Leu Asn Leu Val Tyr Ile Cys Gln Cys Asn Gly
        275                 280                 285

Leu Pro Glu Val Ala Glu Tyr Trp Lys Gln Val Ile Lys Ile Asn Asp
```

```
                    290                 295                 300
Tyr Gln Lys Asn Arg Phe Val Asn Arg Ile Val Ser Ser Met Phe Asn
305                 310                 315                 320

Thr Val Ser Asn Lys Lys Val Ala Ile Leu Gly Phe Ala Phe Lys Lys
                325                 330                 335

Asp Thr Gly Asp Thr Arg Glu Thr Pro Ala Ile Asp Val Cys Lys Gly
            340                 345                 350

Leu Leu Gly Asp Lys Ala Gln Ile Ser Ile Tyr Asp Pro Gln Val Thr
        355                 360                 365

Glu Glu Gln Ile Gln Arg Asp Leu Ser Met Lys Lys Phe Asp Trp Asp
370                 375                 380

His Pro Leu His Leu Gln Pro Met Ser Pro Thr Thr Val Lys Gln Val
385                 390                 395                 400

Ser Val Thr Trp Asp Ala Tyr Glu Ala Thr Lys Asp Ala His Ala Val
                405                 410                 415

Cys Val Leu Thr Glu Trp Asp Glu Phe Lys Ser Leu Asp Tyr Gln Lys
            420                 425                 430

Ile Phe Asp Asn Met Gln Lys Pro Ala Phe Ile Phe Asp Gly Arg Asn
        435                 440                 445

Ile Met Asn Val Asn Lys Leu Arg Glu Ile Gly Phe Ile Val Tyr Ser
    450                 455                 460

Ile Gly Lys Pro Leu Asp Pro Trp Leu Lys Asp Met Pro Ala Phe Val
465                 470                 475                 480

<210> SEQ ID NO 24
<211> LENGTH: 736
<212> TYPE: PRT
<213> ORGANISM: Caenorhabditis elegans

<400> SEQUENCE: 24

Met Arg Val Phe Gly Arg Ser Thr Cys Arg Met Pro Val Ser Arg Ala
  1               5                  10                  15

Thr Val Thr Ile Leu Leu Gly Ile Leu Phe Gly Phe Ser Ile Thr Tyr
                 20                  25                  30

Tyr Leu Thr Ala Leu Lys Ser Leu Thr Asn Pro Ile Ile Cys Gly Pro
            35                  40                  45

Glu Gln Gln Ile Gly Gly Phe Asp Tyr Leu Asp Val Ile Ser Gln Arg
        50                  55                  60

Ala Asp Ala Asp Val Phe Thr Arg Ser Gln Ser Leu Pro Gly His Arg
65                  70                  75                  80

Arg Gly Leu Ile Leu Val Ala Ile Met Thr Ala Ala Lys Tyr Val Asp
                 85                  90                  95

Thr Arg Ala Tyr Asn Val Trp Lys Thr Trp Ala Gln His Ile Pro Gly
            100                 105                 110

Arg Val Leu Ile Phe Val Ala Glu Gly Thr Glu Ser Val His Glu Asp
        115                 120                 125

Met Pro Leu Ile Arg Leu Lys Gly Val Asp Asp Thr Tyr Pro Pro Gln
130                 135                 140

Lys Lys Ser Phe Ala Met Val Lys Trp Leu Ala Glu Asn Met Ala Asp
145                 150                 155                 160

Glu Tyr Asp Trp Phe Leu Arg Ala Asp Asp Asp Leu Tyr Ile Arg Gly
                165                 170                 175

Glu Glu Leu Ala Leu Phe Leu Arg Ser Val Asp Ser Ser Lys Ala His
            180                 185                 190
```

-continued

```
Ile Ile Gly Gln Ala Gly Leu Gly Asn Ser Ala Glu Tyr Gly Leu Leu
            195                 200                 205

Ala Leu Gly Ser Thr Asp Asn Tyr Cys Met Gly Gly Pro Gly Ile Val
            210                 215                 220

Met Ser Arg Asp Thr Leu Leu Lys Val Ser Pro His Leu Glu Ser Cys
225                 230                 235                 240

Leu Gln His Met Leu Thr Ser His Glu Asp Val Glu Leu Gly Arg Cys
            245                 250                 255

Ile Arg Lys His Val Gly Val Ala Cys Thr Trp Asn Tyr Glu Met Gln
            260                 265                 270

Lys Leu Phe His Asn Asn Gln Ser Ala Ile Lys Glu Ser Tyr Ala Lys
            275                 280                 285

Asn Met Lys Glu Leu Lys Asp Ala Ile Thr Leu His Pro Ile Lys Asp
            290                 295                 300

Pro Ala Val Met Arg Lys Val His Leu Arg Asn Arg Glu Ile Lys Leu
305                 310                 315                 320

Arg Glu Ala Arg Ala Lys Arg Ser Leu Leu Ser Ser Glu Leu Ser Thr
            325                 330                 335

Ala Lys Ala Gln Thr Leu Val Arg Met Thr Pro Asn Arg Thr Asn Asp
            340                 345                 350

Leu Thr Pro Trp Glu Tyr Ile Asn Asn Asn Lys Ile Leu Phe Cys Ala
            355                 360                 365

Asp Arg Val Asn Cys Pro Arg His Thr Val Asp Leu Ser Ile Arg Thr
            370                 375                 380

Glu Met Ala Asp Thr Ile Thr Gln Leu Phe Asp Glu Phe Asn Thr Asn
385                 390                 395                 400

Ala Arg Gln Arg Gly Arg Val Leu Gln Phe Gln Ser Leu Gln Tyr Gly
            405                 410                 415

Tyr Met Arg Val Glu Pro Thr Lys Gly Val Asp Tyr Val Leu Asp Met
            420                 425                 430

Leu Leu Trp Phe Lys Lys Phe Arg Pro Pro Asn Arg Thr Thr Ile Ser
            435                 440                 445

Val Arg Arg His Ala Tyr Val Gln Gln Thr Phe Gly Lys Leu Arg Ser
450                 455                 460

Leu Ser Glu Gly Val Phe Arg Ser Asn Met Arg Ala Asn Ser Thr Leu
465                 470                 475                 480

Ile Glu Asp Pro Thr Leu His Met Ile Met Pro Leu Arg Gly Arg Ala
            485                 490                 495

Ala Ile Phe Ala Arg Phe Ala Gln His Leu Lys Ser Ile Cys Ala Arg
            500                 505                 510

Gly Gly Asp Asp Leu Ala Val Ser Leu Thr Ile Val Leu Tyr Ser Ser
            515                 520                 525

Glu Asp Glu Met Glu Asn Arg Glu Thr Ile Glu Met Leu Arg Ala Ser
            530                 535                 540

Phe Ile Pro Val Thr Val Ile Glu Met Gly Asp Val Ser Phe Ser Arg
545                 550                 555                 560

Gly Val Ala Leu Met Arg Gly Ala Glu Thr Leu Pro Ala Asn Ala Leu
            565                 570                 575

Leu Phe Phe Thr Asp Val Asp Met Leu Phe Thr Cys Asp Ala Leu Lys
            580                 585                 590

Arg Ile Lys Ser Asn Thr Ile Leu Asn Ala Gln Ile Tyr Phe Pro Ile
            595                 600                 605
```

-continued

```
Val Phe Ser Glu Phe Ser His Glu Ser Trp Ser Glu Asn Asp Lys Leu
610                 615                 620

Leu Ala Asp Ala Phe His Tyr Gly Arg Gly Arg Gly Tyr Phe Arg His
625                 630                 635                 640

Phe Gly Tyr Gly Leu Ala Ala Met Tyr Lys Ala Asp Leu Met Asp Val
                645                 650                 655

Gly Gly Phe Asp Thr Lys Ile Glu Gly Trp Gly Lys Glu Asp Val Asp
                660                 665                 670

Leu Phe Glu Lys Ala Ile Lys Asn Gly Arg Leu Arg Val Ile Arg Val
675                 680                 685

Pro Glu Pro Gly Leu Val His Ile Tyr His Pro Ile His Cys Asp Glu
690                 695                 700

Asn Met Pro Thr Ala Gln Lys Asp Met Cys His Gly Ser Lys Ala Ala
705                 710                 715                 720

Ser Leu Ala Ser Ile Asp Thr Leu Val Glu Gln Ile Ala Gln Tyr Thr
                725                 730                 735
```

<210> SEQ ID NO 25
<211> LENGTH: 802
<212> TYPE: PRT
<213> ORGANISM: Homo sapiens

<400> SEQUENCE: 25

```
Met Ala Ala Arg Gly Arg Arg Ala Trp Leu Ser Val Leu Leu Gly Leu
1               5                   10                  15

Val Leu Gly Phe Val Leu Ala Ser Arg Leu Val Leu Pro Arg Ala Ser
                20                  25                  30

Glu Leu Lys Arg Ala Gly Pro Arg Arg Ala Ser Pro Glu Gly Cys
            35                  40                  45

Arg Ser Gly Gln Ala Ala Ser Gln Ala Gly Ala Arg Gly Asp
    50                  55                  60

Ala Arg Gly Ala Gln Leu Trp Pro Pro Gly Ser Asp Pro Asp Gly Gly
65                  70                  75                  80

Pro Arg Asp Arg Asn Phe Leu Phe Val Gly Val Met Thr Ala Gln Lys
                85                  90                  95

Tyr Leu Gln Thr Arg Ala Val Ala Ala Tyr Arg Thr Trp Ser Lys Thr
                100                 105                 110

Ile Pro Gly Lys Val Gln Phe Phe Ser Ser Glu Gly Ser Asp Thr Ser
            115                 120                 125

Val Pro Ile Pro Val Val Pro Leu Arg Gly Val Asp Asp Ser Tyr Pro
            130                 135                 140

Pro Gln Lys Lys Ser Phe Met Met Leu Lys Tyr Met His Asp His Tyr
145                 150                 155                 160

Leu Asp Lys Tyr Glu Trp Phe Met Arg Ala Asp Asp Val Tyr Ile
                165                 170                 175

Lys Gly Asp Arg Leu Glu Asn Phe Leu Arg Ser Leu Asn Ser Ser Glu
                180                 185                 190

Pro Leu Phe Leu Gly Gln Thr Gly Leu Gly Thr Thr Glu Glu Met Gly
            195                 200                 205

Lys Leu Ala Leu Glu Pro Gly Glu Asn Phe Cys Met Gly Gly Pro Gly
    210                 215                 220

Val Ile Met Ser Arg Glu Val Leu Arg Arg Met Val Pro His Ile Gly
225                 230                 235                 240

Lys Cys Leu Arg Glu Met Tyr Thr Thr His Glu Asp Val Glu Val Gly
                245                 250                 255
```

-continued

```
Arg Cys Val Arg Arg Phe Ala Gly Val Gln Cys Val Trp Ser Tyr Glu
            260                 265                 270
Met Gln Gln Leu Phe Tyr Glu Asn Tyr Glu Gln Asn Lys Lys Gly Tyr
        275                 280                 285
Ile Arg Asp Leu His Asn Ser Lys Ile His Gln Ala Ile Thr Leu His
    290                 295                 300
Pro Asn Lys Asn Pro Pro Tyr Gln Tyr Arg Leu His Ser Tyr Met Leu
305                 310                 315                 320
Ser Arg Lys Ile Ser Glu Leu Arg His Arg Thr Ile Gln Leu His Arg
            325                 330                 335
Glu Ile Val Leu Met Ser Lys Tyr Ser Asn Thr Glu Ile His Lys Glu
        340                 345                 350
Asp Leu Gln Leu Gly Ile Pro Pro Ser Phe Met Arg Phe Gln Pro Arg
    355                 360                 365
Gln Arg Glu Glu Ile Leu Glu Trp Glu Phe Leu Thr Gly Lys Tyr Leu
370                 375                 380
Tyr Ser Ala Val Asp Gly Gln Pro Pro Arg Arg Gly Met Asp Ser Ala
385                 390                 395                 400
Gln Arg Glu Ala Leu Asp Asp Ile Val Met Gln Val Met Glu Met Ile
            405                 410                 415
Asn Ala Asn Ala Lys Thr Arg Gly Arg Ile Ile Asp Phe Lys Glu Ile
        420                 425                 430
Gln Tyr Gly Tyr Arg Arg Val Asn Pro Met Tyr Gly Ala Glu Tyr Ile
    435                 440                 445
Leu Asp Leu Leu Leu Tyr Lys Lys His Lys Gly Lys Lys Met Thr
    450                 455                 460
Val Pro Val Arg Arg His Ala Tyr Leu Gln Gln Thr Phe Ser Lys Ile
465                 470                 475                 480
Gln Phe Val Glu His Glu Glu Leu Asp Ala Gln Glu Leu Ala Lys Arg
            485                 490                 495
Ile Asn Gln Glu Ser Gly Ser Leu Ser Phe Leu Ser Asn Ser Leu Lys
        500                 505                 510
Lys Leu Val Pro Phe Gln Leu Pro Gly Ser Lys Ser Glu His Lys Glu
    515                 520                 525
Pro Lys Asp Lys Lys Ile Asn Ile Leu Ile Pro Leu Ser Gly Arg Phe
530                 535                 540
Asp Met Phe Val Arg Phe Met Gly Asn Phe Glu Lys Thr Cys Leu Ile
545                 550                 555                 560
Pro Asn Gln Asn Val Lys Leu Val Val Leu Leu Phe Asn Ser Asp Ser
            565                 570                 575
Asn Pro Asp Lys Ala Lys Gln Val Glu Leu Met Thr Asp Tyr Arg Ile
        580                 585                 590
Lys Tyr Pro Lys Ala Asp Met Gln Ile Leu Pro Val Ser Gly Glu Phe
    595                 600                 605
Ser Arg Ala Leu Ala Leu Glu Val Gly Ser Ser Gln Phe Asn Asn Glu
610                 615                 620
Ser Leu Leu Phe Phe Cys Asp Val Asp Leu Val Phe Thr Thr Glu Phe
625                 630                 635                 640
Leu Gln Arg Cys Arg Ala Asn Thr Val Leu Gly Gln Gln Ile Tyr Phe
            645                 650                 655
Pro Ile Ile Phe Ser Gln Tyr Asp Pro Lys Ile Val Tyr Ser Gly Lys
        660                 665                 670
```

```
Val Pro Ser Asp Asn His Phe Ala Phe Thr Gln Lys Thr Gly Phe Trp
            675                 680                 685

Arg Asn Tyr Gly Phe Gly Ile Thr Cys Ile Tyr Lys Gly Asp Leu Val
        690                 695                 700

Arg Val Gly Gly Phe Asp Val Ser Ile Gln Gly Trp Gly Leu Glu Asp
705                 710                 715                 720

Val Asp Leu Phe Asn Lys Val Val Gln Ala Gly Leu Lys Thr Phe Arg
                725                 730                 735

Ser Gln Glu Val Gly Val Val His Val His His Pro Val Phe Cys Asp
            740                 745                 750

Pro Asn Leu Asp Pro Lys Gln Tyr Lys Met Cys Leu Gly Ser Lys Ala
            755                 760                 765

Ser Thr Tyr Gly Ser Thr Gln Gln Leu Ala Glu Met Trp Leu Glu Lys
        770                 775                 780

Asn Asp Pro Ser Tyr Ser Lys Ser Ser Asn Asn Gly Ser Val Arg
785                 790                 795                 800

Thr Ala

<210> SEQ ID NO 26
<211> LENGTH: 827
<212> TYPE: PRT
<213> ORGANISM: Drosophila melanogaster

<400> SEQUENCE: 26

Met Thr Lys Arg Lys Thr Leu Ile Ile Gly Phe Phe Gly Ile Ala Leu
  1               5                  10                  15

Gly Leu Cys Ile Gly Thr Met Leu Lys Asn Tyr Leu Ala Leu Glu Ile
             20                  25                  30

Val Lys Arg Cys Ser Leu Arg Pro Thr Asn Leu Lys Thr Pro Ala Asp
         35                  40                  45

Ile Ile Gly Leu Arg Asp Glu Asp Thr Ile Gln Asn Ser Gln Arg Asn
     50                  55                  60

Leu Val Phe Val Gly Val Met Thr Ala Lys Ser Phe Leu Glu Gly Arg
 65                  70                  75                  80

Ala Arg Ala Val Tyr Asp Thr Trp Gly Lys Glu Val Pro Gly Arg Met
                 85                  90                  95

Ala Phe Phe Ser Ser Glu Gly Ser Tyr Ser Asp Asp Leu Pro Val Val
            100                 105                 110

Gly Leu Lys Asn Val Asp Asp Arg Tyr Pro Pro Gln Lys Lys Ser Phe
        115                 120                 125

Met Met Leu Tyr Tyr Met Tyr Glu His Tyr Ile Asp Arg Phe Glu Trp
    130                 135                 140

Phe Ile Arg Ala Asp Asp Asp Val Tyr Met Glu Pro Asp Lys Leu Glu
145                 150                 155                 160

Arg Phe Leu Arg Ser Ile Asp Ser Ser Lys Pro Gln Phe Ile Gly Gln
                165                 170                 175

Ala Gly Lys Gly Asn Ser Glu Glu Phe Gly Leu Leu Ser Leu Glu Phe
            180                 185                 190

Asp Glu Asn Phe Cys Met Gly Gly Pro Gly Val Ile Leu Ser Ser Glu
        195                 200                 205

Thr Leu Arg Arg Val Ala Pro His Ile Pro Ser Cys Leu Lys Asn Leu
    210                 215                 220

Tyr Ser Thr His Glu Asp Val Glu Val Gly Arg Cys Val Gln Lys Phe
225                 230                 235                 240
```

-continued

```
Ala Gly Ile Pro Cys Thr Trp Asn Tyr Glu Met Gln Tyr Ile Leu Arg
            245                 250                 255

His Asn Ser Ser Gly Arg Asn Ala Tyr Thr Gly Lys Leu Lys Arg Lys
        260                 265                 270

Glu Ile His Asn Ala Ile Thr Leu His Pro Ile Lys Gln Ala Pro Leu
            275                 280                 285

Met Tyr Arg Leu His Ser Tyr Val Gln Gly Leu Lys Ala Glu Glu Met
290                 295                 300

Arg Gln Glu Ser Leu Leu His Arg Asp Ile Lys Arg Met Ala Lys
305                 310                 315                 320

Tyr Leu Glu Val Pro Asp Glu Ser Thr Tyr Met Leu Pro Ser Val Ser
                325                 330                 335

Pro Glu Ser Asp Ser Thr Lys Arg His Phe Gln Asp His Asn Ile Leu
            340                 345                 350

Gly Ile Ser Pro Glu Leu Asn Lys Phe Val Pro Ala Ser Thr Asp Asp
        355                 360                 365

Leu Leu Asp Trp Ser Phe Ile Ala Arg Ser Leu Tyr Ser Ala Ser Ser
370                 375                 380

Ala Asn Pro Lys Gln Lys Ile Asp Ser Ala Met Arg Glu Gly Leu Glu
385                 390                 395                 400

Asp Ala Ile Thr Glu Val Met Glu Asn Ile Asn Asn Tyr Ser Arg Gln
                405                 410                 415

Arg Gly Arg Val Ile Glu Phe Arg Glu Leu Leu Tyr Gly Tyr His Arg
            420                 425                 430

Leu Asp Ala Leu His Gly Gln Asp Met Ile Leu Asp Leu Leu Leu Ile
        435                 440                 445

Tyr Lys Lys Tyr Arg Gly Lys Lys Met Thr Val Pro Val Arg Arg His
450                 455                 460

Leu Tyr Val Gln Arg Ala Phe Thr Gly Ile Phe Val Lys Glu Val Asp
465                 470                 475                 480

Glu Asp Phe Tyr Asn Val Thr Leu Gln Gln Ser Leu Leu Gly Ser Leu
                485                 490                 495

Phe Gln Asn Gly Met Ala Arg Leu Ser Ser His Phe Thr Met Pro Ser
            500                 505                 510

Gly Leu Leu Ser Pro Thr Gln Asp Lys Ile Val Phe Val Leu Pro Ile
        515                 520                 525

Ala Gly Arg Leu Gly Thr Phe Glu Arg Phe Leu Arg Thr Tyr Glu Arg
530                 535                 540

Val Cys Val Arg Gly Glu Gln His Cys Asp Leu Leu Val Val Ile Phe
545                 550                 555                 560

Gly Ser Pro Asp Glu Leu Gly Asp His Leu Gln Leu Leu His Asp Leu
                565                 570                 575

His Ala Arg His Val Tyr Gln Gln Val Asn Trp Ile Gln Arg Ser Ser
            580                 585                 590

Ala Phe Ser Arg Gly Val Ala Leu Asp Val Ala Ala Arg Ser Ser Tyr
        595                 600                 605

Ile Arg Gln Glu Asp Ile Ile Leu Phe Ile Asp Val Asp Met Val Phe
610                 615                 620

Glu Val Glu Thr Leu Gln Arg Val Arg Met His Thr Gln Arg Gly Lys
625                 630                 635                 640

Gln Val Tyr Leu Pro Ile Val Phe Ser Gln Tyr Asp Pro Gln Arg Arg
                645                 650                 655

Ser Gly Asp Ala Gly Gly Ser Glu Asp Glu Gly Glu Thr Pro Arg Ile
```

-continued

```
                    660             665             670
Asp Asp Glu Arg Gly Tyr Phe Arg Gln Phe Gly Phe Gly Ile Cys Ala
            675                 680                 685
Ile Tyr Lys Ser Asp Ile Leu Asp Glu Asp Ile Asn Gly Phe Asp Lys
        690                 695                 700
Asp Ile Thr Gly Trp Gly Leu Glu Asp Val Lys Phe Leu Glu Lys Ile
705                 710                 715                 720
Val Arg Val Gly Thr Arg Gln Arg Gly Phe Leu Ala Asn Thr Ala Glu
                725                 730                 735
Leu Ala Met Asp Tyr Asn Glu Ala Ala Glu Gln Trp Arg Arg Leu Ser
            740                 745                 750
Val Phe Arg Ala Pro Asp Pro Thr Leu Val His Ile Tyr His Asp Ile
            755                 760                 765
Ser Cys Asp Val Gln Leu Asp Ala Pro Gln Tyr Asn Met Cys Leu Gly
        770                 775                 780
Thr Lys Ala Asn Ser Leu Gly Ser Thr Arg Leu Met Glu Gln Leu Phe
785                 790                 795                 800
His Ser Ser Pro Glu Asn Val Gln Phe Ala Ala Asp Phe Asn Arg Gln
                805                 810                 815
Lys Gln Gln Gln Gln Gln Gln Gln Ala Arg
            820                 825

<210> SEQ ID NO 27
<211> LENGTH: 18446
<212> TYPE: DNA
<213> ORGANISM: Caenorhabditis elegans

<400> SEQUENCE: 27
acggatccaa gagttcctct tccaatcagc ctgaaaaaat aattttttta aaataaattt      60
cttttgtaaa tttatcttac tttcccaagc tataacgcct cggtatactt ggcaattttt     120
cggaatatct gcttgcttga ctcggcaatc cgtacgatcg accagccaat gttcctgcgt     180
aactttgtcg atcaaggtca ttctgtaaga tgaacaaaaa ttataataac tttattttc      240
cattttctcg aaaaaaaatg caacgatttg ttcacaaaaa aagcctttaa aagtaatttt     300
aaaaagtttg ttcaatgttt tgaaaaccgt agccgaaaaa tattcaaatc gagtgatggg     360
tctcgccacg aaatgatttt tgtgcgcctt taactgaaaa ctacggttct cttttttgttt    420
caacggattt tgttcttcat ttttgagatc ttttcttgct ttttttcttcg agtttacttt   480
ttaaatgata ttttcatttt ctatttagat aagaaaattc taaattacat ttcaatagc     540
tattttatac ttacggtatt cggcaaactg tccattagcg ctttcataac gatattaggc    600
tcaggttcta tttcatcagg ttctgaaacc gttattatat ttcctgtttt cactcgaact    660
gtgtcctctt catattttg caacacaaat tccaccacta gtttctttcc attgtgctga     720
aatcttacta attagctttt ctgtcaatcg tctctctttt ttcttttaaa attactttaa    780
ttgcctcgtc tagcgttttc tgtccatcta tgaccatttc gtactttccc atctcgtaca    840
aaatacggaa catgtccaga tttgtcgtct tccggcattt atcgacaagt tgctcgtaat    900
tattacatgc tctcgccaaa acttccactt ttttcctcag cttctgtttt tcgttcattg    960
atgagaccgc cattcgaatt taatgacgac ggtaaccgat gactcttcgt tttcgtctgc   1020
ttctgattct tccgaataac cattacatta cgggcgaagt ggattgagag tggagtagcc   1080
ggcagaagaa aaagtggac aagttttgag gtgaaggcac ctggaaaata gaagaatggc    1140
catgtgtggg cacacaccga gacgagaaaa aagagttttg gctgagagaa aaaagaaaag   1200
```

```
agtgaggacc aatcgaagtg aattcgtgtg cacgctctcg tccaacagaa gccgcttaac    1260
atcgcccgca gtgagagcag tgctgagtaa acgaacccat gagggggttca cgagaaaagc   1320 gcccgtcgct caataactga cgttttttgtgt gtgcgtgcaa atgttagaac ccctttgtca   1380
taaaaatgtc tgattgaggc aatcttatca taacgctttc cgcgttttga tgatgattat    1440
gactttctct ggtgttagct tgattgcagt ggcgtcactg tccagaatta tcagtggcat    1500
ggaattgggg aattaaagag agcaaaagta cgcggaaaca atccgatttt aatttaatgt    1560
gagattgctt aacatctacg atgattccaa tgctgcaatg ccctatcctt tgcgataaac    1620
ttaattcgat tagttgcttt tacagggttt agctctaatt tcgacgttta cagaagcgtc    1680
tatgccgcgt gttagaacag caaggttatt ttaagaattg attcttcatt ggaaaatgat    1740
tgtgtacttt tggccaaatt gtcatgtgcg aactattgag catttgtgtt ttagaattga    1800
cacgttctca tattaccatc tcgatgatca agtactact gatcactacg caagcttatc     1860
caaagaatct atacaagaac agcgaaggtg acaggctcat cactatttga acttgcctga    1920
acttgtttga actacgaccg ccaagttttgc accctttgta ctacagctgc aactatttca   1980
acgtgtccga ttcaattttc gtgttctcca gatgtttgcc gtttccgaaa ttcccgctat    2040
gcttgttctt tttttttgctg gcatgttgaa agaaagagcg actacttgaa tcgtcgagaa   2100
tacaccttat caatcgtcgc acctgagaga tgtctcgcgc ccaaatgcga tccggtgtat   2160
atgaataaga gaatgcgtct gatttcgaaa aaaagaaca caatcgaaaa acaccaatca    2220
ttctcgtttt ggcattaact atatcctcct cctcattctc ttctcactca tccacgacgt    2280
catcaattgt cgtagttgtc tcctttcgtg gaatgattac gccagaagac attcccatcg    2340
tttgtgatgc cacaactttg tgtccggcaa tctcatcgtt ggcaattccg ttcgtttcgt    2400
ttgcaaatca acttgactcg ctgtccactt cttgatttca ttcattttc ctattctacc     2460 tctttctttt cttcatgttc gtttaggatt cgaggacgtg tcggttttgg tattggtgtg    2520
tgtcagtgtg tgtgtacatg cccagtttgg taatcaaatg agatttctat gttaggccta    2580
gctaaagtgc acccgtacga cgagacaagg atatgtttcg ttctccgttc gtgtccgacc    2640
ttgatgtcta caggcctcca cgcttttttgc cacgtcttct tgtgttactc aaaaaaggaa    2700
agaacgacat cgcacaactt cctgccgtcg ctttcgttttt actttcaaag tggattgaga   2760
gcgaaattta cagctggtca cagatcttaa gttgaattct agatttatct ctatgaccaa    2820
catgacttac gaaaaaaaaa tttgtgtgct ttagaaatat caaaaatcaa aattttctgt    2880
acatttcaac atcttcaacc tcctttttca aaattttgga ctccataaat ttttttgttga    2940 gaaattttca aagtgaaata cgcttttaaa aaaaatttttt tatgaatctt tcaaagcgat   3000
caaaaaagtt tgctattcca gttttttttg tacaccacga aaattcaata tatctccaga    3060
gccttatctc aattgttttc atgattcact gatatacgtc acgaaatgct gaatcagtgt    3120
tcatcatttt acacgcaccg atcatttctg aaggccgcaa aaacttgaat gcgctcttga    3180
aagtactttc ttcttgggca ctatgccaga attttcctca ttgaagtgg aaatcaaaga     3240 tctctatata atcttggtct agattttaca aaattgtagt ttgctgcacc acaagtaggt    3300
tcagagttcg gcatggtaaa acttgaggaa ctataaaaag ctatttgcac aacattttcg    3360
cttttaaaag ttgaacgcga tgcttcacaa ttatctttgt tctggattta tcatttggat    3420 tatttttagat taagttctac tgattattca ttgaaattct ctcctagaaa aggaaattct   3480
cgtgccctca actttaaaaa atgtaattac tgggacgaat agttcaaaaa atttctttga    3540
```

```
agtgttggag tgctctatcg ttgcgtcaca aacgttgcac atctggcaca taacatgaat    3600
gtccctcttt tttacaattg ggaaaaaacg cacagccgaa tctaaatgat atggtattaa    3660
ttctatcacc tgctgcacac aattcaatta aaattccacc ctcattcgct tcttcagtca    3720
tatcttggta ttacgcagga ggtacgcaca cagatgttgc gcagttcagt gtcgcatttc    3780
tcattcctcc tccttttctt ccacaacgca atcatctctt ctccggtcga ctgcggccag    3840
tggaggttga gccgcgtgta tgtgttggcc ctccaaacca tttacaatag attgccgtct    3900
cctcctcttg tattcttta tcccattcca atcataattt cttttggaat tgcaagtgag    3960
catcgcacag acaaaacggt cattgtctgt caaagtcggt ctcttgtctt cgtctacttg    4020
acgtcacctc ttatccttca tattgtttct cttaccgggt catcttgttc ttcacatcta    4080
ttttcttaca tctaaccatt ttaatgcagt ttatctaaat atacactttc tgccctcgtg    4140
aaaaaatcat gcgaaaatga taataaaata gaaaacaaga aaatctttat catatcgagg    4200
cgcatagttt cattttgaaa caagtctttg atctatttac attctttgac tagcctgctg    4260
actgagaatg tagtttcgaa aaatataaag ctatgaccaa tagaaagaaa agtgtgaatg    4320
ataatgatgg ttttttaggc ttgcagtcga attttctgta aaattgccaa atctttggta    4380
aataccaaaa ttttgtgaaa tccctaattt tttggtaaat tgcaaacttt tttcataagt    4440
tgccaaatt ttggtaaatt tcaatttttg taaaatcctt aatttttttt ttggtaaatt    4500
accacatttt tcatggtaaa ttgctaattt tcgctaagtt gcctaatttt tgtaaaattg    4560
ctaatttttt cggtaaatta caattttttt tgtaaattgc caaatgtgtc ataaataggc    4620
aattttttt tggtagattg tcaaattttt tggtaaattg ccaaattgtc gagaaatgaa    4680
aattttctag tacttttgag cattgctgca acccctcagc ttagatacta acaattgtaa    4740
cgagattaaa gtatattact caataaaaac caataaaaaa tgtagttgta tattccgtgg    4800
gtttaaaggt tattagtgaa atccctgttt tgtatgatca gctgtatcta gtaccaggtt    4860
caaccatatc agttttttgat acaaaaccga tttcctatat ggtatagttt gaaagtgtac    4920
tcatactcta acaaaagatc agtcagtcgt tctcaattta aatctaggcc aactttagtt    4980
tctcattatc cgaaacgaaa cgctcacagt ttcatctcga tcttctcatt ttttttctac    5040
tctaataaca cctttgctgg tgttctcgga ttccttgaaa aacgccccca cacacacact    5100
ttctacttct tccgaaaata aaaataaaag tcaacgaacg actgtttgga tacgctgacc    5160
gcaaacactt ttggaactcc gccgactcgc cctggcttaa ctctttttc ttttcagttt    5220
gcgcccagat gtttcaagtt tcaattgata catatcatct ggctttctga aataaatgaa    5280
tggagagccg agtgtcggag atgaagctat gttgaaaaaa tattgtacag agcggcgaat    5340
ggttttccat gtctccagta ctgttgtgca ctcaatttgt ctctcttcat ctcctccact    5400
cgtgtgaatc tgtttgaaca gtggcgccgc ggctcgtttc tctccttctc tctctctctc    5460
tttgggccct ttggggtaaa atcaacgaag atgaagaaga agcgtgtcgt tttgtcggta    5520
gctatgctgc cagttcatcg gcaaataagc atgcttgtcc tacattatgt tctcatggat    5580
gacaatcctt ttttgtccct catttataat ttttttattta tttttattgt catggaagta    5640
gacatagtag ttgttttctc cgaaggtttt cacgaattga atgtacaagt atcggaatga    5700
gaatgaacgt atttaggttc ctcataacaa tttgtgcata tatcaggtga cataaatcgt    5760
tatgtcgtaa aattatctag atttaatttc aaatttatcc ctcctcgtcc cactaacatt    5820
gtcacatgaa agggttattc agtagtagag aagtagcatc atccgacctc aactgtgatg    5880
cttatctctg ccgcatttc atcgacctct ctagtaggca gtaggcgaat atgcgtgaag    5940
```

```
aaaagatctc attctcaccc ggttttttg tctttctacc tcaacctatt catctagaaa     6000
ctgaacataa gtttcacttt tcttgtattt ttcacccttta tcatcaccac atccttcttt    6060
attttgaata ggccatgttc ttacgtggaa tcactgtcca ttcactcaaa aaatgttgcg    6120
aaaattactt ttttaatagc ttttccattc ggttcaacag atgacgatca gaaattcctg    6180
gtttgaacga taaagtgctt gcttcttctt tctaccacat ttagacccac catgggctta    6240
tctgtgggtg atctaggatt atatgagagt tgttaagacg cagagtgaaa gtgttgaggt    6300
cagatatagc caaaagtcg gttgagttat attatcagat tatcttttcg ccgatatcaa     6360
gactatttag ttatgttgcc gactatatag ccagctcttg tcatatcgac ttccattttt    6420
ctattttcag tactgtttag agatatttt cggatttgtc gcatttttc ttagttggaa      6480
aaaaaagtaa accgcacata taatgaaa ccctcattcc ggggttttc taattttttt       6540
gtataaagaa tgaaataatt ttcgattccg tcctttgcta gagatcagta ccatcagaat    6600
attctctttt ttctcgccca cgactcatgc ttttgaaaca gagatgttaa atgaatgtgt    6660
atttataata taaattatta taacattcat cggcgtagtc aatcggcgtc tcacacattc    6720
ccattcttct caccatcttc aatttcaatc ggtcattacc acaccaacac taccaaaagc    6780
cgatggaaat tcgacgattt gtttataagt gacatgtgtg tctaagtctc gaactctctc    6840
cttctgactt ccaccaagtt gctccaatca ctttctgctg caccagtcta cgtaccactt    6900
gccactattt catttctttt ttccaatctc tgatctatct gcgtctctat ttctctacct    6960
ctactaatct tgttccacaa ttgtttgata gttgaaagtg caaaaaacgt ctcgtataac    7020
ggaccgcgaa aagtcgtcga gtgttcatat acttctttt tctcctcatt tttctcgtag    7080
taatgtgcta taattgttgt tgctgtgacc gttttcacat gactaccgtg atgctctaaa    7140
tgaccttttc gttctgtccg caattagtac gaacactgcc gagataattg caagttgaga    7200
gggataccaa aaaaaacgaa taagtgatag attggaatgg tcatggcgcg tagcagtttg    7260
aatgttgaga aaggtcatcg aagagcattt atttgcacat agaaggtgca aaattagtga    7320
tgttcaggta cttatgagc tagttctcaa caagtcggcg gttttctta agatgatcaa      7380
caaatgttcg atctccttgt tcttttttgtc tgatcaaaga tttatatttt cgaaaaaaat  7440
gcaaaaaaag tgtttaatgc gttatttttg aaattttatt ttggaattaa aaaattccaa    7500
tatttcaatg gctaactgat aatttaattt accaaaaaaa ttgacgaaat cagtgaaatt   7560
ttcccaagga cgaatgagaa aatacactat ttttaattta gatttgtagt ctcttcaaat   7620
atcttttttt taactgaaat gatttcaatt tttcgttgta tttattggta acaaaacaat   7680
tatatttctt tcctgtcaaa cataaaatag gcaaacaatt attatttgaa ccatatttac   7740
ttttatgttt actctctaga aagtaaactt tggtagtact tccatgcttg agttattctt   7800
ttcacaatgt aaaaatcaac gaaaaaaagg acaataagaa acatttagt gtactttttt    7860
agtgaatcgt cgagaatata aaggtcacac ctgtttctca gctgtctttt cactcatttt   7920
gtgtcttcca tcatcatcca aaattcatta aattcggttc tgcaataata gcagatcgag   7980
aatgttttt tacagccgtg ctaattttta accgaaaaat gtgtccggta aataaaaaat    8040
cgtcatacgg ctaattaaaa aagtgaaagc attccgttcg tctttgggtt tagataggta   8100
tctcttttta tttttaaatt tagtttaatg aatcacgagg tggatggtaa tatagttacc   8160
gccatccaac attttttgag tcatttaggt caattgcagg tgactttgtt caaaagaatt   8220
cacttattat caagtaccac ccctccagcc gaatgcttat cactcatgca tttgatctag   8280
```

```
tattgttaac acagttttcg tcatcgtttg tcaagaaaat gaaagaagac gttatgtagt    8340
tgtcgacaac ttcttgtcaa tcgctgtggt tgcaacattt tgcttttctc tttctgattc    8400
gctttcctct tactctccgt tttttctcga tcaagagagg aggtcggaca ctattatttt    8460
ctgtgatttt cctttgattc tttcttttg tgtctcggtt atcattgatt catgttgtat     8520
ctccttaata tcaatccgaa ccatttttat tcgaattcca tttgattcct cggatttcgt    8580
ttatcaggag gtatagcaca caaatcaagg attgacgact aaaacatcga aatctctttc    8640
acattatttt tttgaaaaaa gtggtattaa aatatttta attttttga aattaatttt      8700 tatgttattg aaatattgca aaaattcttt ccggattttt cgtttcgaat gttaaaaatc    8760
ccaaattaaa cccttctgta ggagctgcta agagtaattt ccaattaaat cctaacatgc    8820
gacaccttaa aattcagaag gtttatttgt tttaatagtt tggaacaaag tatccaaaac    8880
tataaattct ggagaatttt atatagatat cggtcactca agataacctg ctaagaaaga    8940
gttcatcctg acaccttccg acacatttt tttttcacaa aatcatatgt ttcaatcact     9000
ctcactctct ctctctcaat acctttcct ttatccattc agtataccac ccaagtgttg     9060
gattttatgg gctgatgaga aagtgagaac gtgtcaaagt ttcacacatg tttgcggtt     9120 cgaaaagtta tcaactatcc ctctctctct ctctactctc taatatatat ctacccattt    9180
ttatgtgtgt ttttgttatt tttcagtcaa gatttgatag atagctattg agtatgtgtt    9240
gttagtgggt acattctccc accttgtgat cacctttgt tccgcctatt ttcacgctct     9300
catcttgaag tatctacatc agtatcgaac attttggcgg cgagtgaaac tgaaaacagt    9360 agttttgtt tcgaccctc gaaaatttt tgtgttgcca actttctatt ttaagaggcc       9420
atcggttgct aacctattaa ccagtttaaa tttcagacaa aatgtcttaa gagggtttgg    9480
acaaatttat ataataggtg gcgcgcgatt gtccggcttg aacttttttt tctgtgtgaa    9540
aaagttgaac tttcactatt actccaaaaa taagtctagt ttcatcttgg cttactgaaa    9600
aaatccaatt ttctctttga tttatcgaaa aaaaagaac aaactaggtg aaaattatga     9660
atttatcaag aaaagatgta tattttgatt atcaacattt tctaacagag aaattatggg    9720
aaatttgaat ttttaccgaa aaatcgaaaa aatcgtaaaa atcctggttt acaaaactaa    9780
ggttttgaaa ttagctctaa ctaatttcct cattttcgtg tttctttct taatcaaatc     9840 attatcggct gtccacaaga taccataatt ttagttaata tgcaattcca aagaatgctt    9900
cgctttttta tgttagaaac cattaaaatc gaatatttcc ataaattctc aaagaaatcg    9960 gccaatttc ttgcctttct cttcatcgga aatgtcgcaa tcattcataa tcgaaggggg    10020
aagtgagttt tattcttttt ctcgtgcctc ggaatttcat gaattttcgc gtaccgctcg   10080
tcgccgtcac tttaattgtt gggcctctgt gtttcttacg atctttcaag tgctaattca   10140
ctgtctttcc catccgttac tagccttatt tcattccttt tgtttcgctg attccgtttc   10200
tgcaaaaatg aaagaaaaaa aaacattttc acatagacta ggtggctgcg atctgttttt   10260
ttcttgctcc ttgctctttg tgtgttttct catgccaacc gttgtattgt ttttcatatc   10320
gtcttggtct atgtttgtc gatattcact ttaaaaactc agatattatt ggatttttt     10380 tttcaaaagt tgagtttttg atttagacaa aattttaaaa aatctgaaat tcttataata   10440 tcaatttac aacaaaaaaa ttctgaagaa attttttttt cgaattaaat tttctaaaaa    10500
tttgaataaa ttgacaagat gttttataat ttgatagaca tattgaaatt aaattttttt   10560
ttctagaatt ctcttcgtat acttcttcat atatatttat tatttttaat ttcatgtgt    10620 attttttgca gctttctgct caaagttcca acacgaggag cggcggtgcg gtgcgattcg   10680
```

```
cgacgaaaat caatgaatca gagtgccatc tgacgtgcaa ttatatgtcg ccacctgctc   10740
atcttctcag tgttaatcat cttcatcaaa tccacgagaa gttcatcaca atcatctcac   10800
tacgaccacc aacatcatca gcaacaacaa aacacctgac gaacacacca cactatccag   10860
tgcaaacgtt cagcagaaaa aacacagaaa ataacaaaaa taacagtgag aaccatcatc   10920
agtcgatttt ggatcggagg aggagagaag gcggcggacg aggagacgca gacactcttg   10980
ctcgacgact catccggtaa tcgagaagac acggaagaga gtatgcgagt ggtgagtcat   11040
tttttgatat aattctaaaa tcaaaagaaa tatgattcat ttatgcataa cggggtcagc   11100
agatgaatga caccagtttc ttcataatga acaaattttg gtcaacaata ggcctgagtt   11160
tacgtgattg tcgaaaaatt aaaataaaag cctgtttttt cttctataaa aattcccaga   11220
tctgaaaatt cgtcattttt gttccaagaa atacggtacc cggtttcgaa gcgaccgatt   11280
ttctcaaatg taaagagtg tgctccttta aggagtactg tagtctccag ttttttttaaa   11340 actgttcaat ttttctgttt ttctagagct aatcgaaaaa ttgtaaattt ctgcttaaaa   11400 tttttaaat tgaaatccag ttttttgatta ttcggaaaat cgaaaaaaaa ttttaaaata   11460
ataaaaacat ttcaaatttt aacaaaaaat aatttgatac gaggaaaaaa gcccaaaatt   11520
tgaagtgatt ttttttcgaaa actcgtaaaa tttaaaatcc aaaaatagtg tgcgctttaa   11580
aggagtactg tagttcccaa ctgctcgaaa aaactttctt tgatgtctca taagtttcac   11640
cctccaaatt ttcttctttt ttttcaaca attaataaaa catcgaagaa aattccgcag   11700
tgagaagatg agaactacag tactcttttaa aggcgcaaac tttttttttaa accgaaaata   11760 gagtgtttta ggtttttttt ttgttacaga aaaaaataaa attcctaaaa tctctgaaat   11820
ttctgggaaa atttttttatt tcagatttga ataaactaaa agttttataa aaattaaaat   11880
gctcacattg tttaatctat tgtcagtttc agcggagcac atgcagaatg ccggtctccc   11940
gagccaccgt cacaatccta ctcggaatcc tgtttggttt tcaatcact tactatctga   12000 cggctctcaa atctctgaca aatccaataa tctgtggccc agaacaacaa attggcggtt   12060
tcgattatct cgatgtgata agtcaacgtg ctgatgctga tgttttcaca agatcccaaa   12120
gtcttcccgg tcatcgaagg ggtctgattc ttgtggctat tatgactgct gcaaaatacg   12180
ttgatacacg tgcttataat gtttggaaaa catgggctca acacattccc ggacgagttt   12240
taatatttgt tgccgaagga actgaatcag tgcatgagga tatgccatta attcgtctga   12300
aaggagttga tgatacttat ccaccacaga agaaaagttt cgcaatggta aaatggttgg   12360
cagagaatat ggctgatgaa tatgattggt tcttgcgagc agacgacgac ctctacatta   12420
gaggagaaga gctcgcttta ttcctaagat ctgtcgattc atccaaagct catatcatcg   12480
gacaggctgg acttggtaac agtgcggaat atggtcttct agctcttgga tctaccgata   12540
attattgtat gggaggacct ggaattgtta tgagcaggga cacccttattg tacgttgttt   12600 ttaagagaat ttgtgggggt tttgtcaaaa taactgaaac tgacttctca acaaatttcc   12660
aaattttgct aaaatctaaa atttcgtcat ttttccttgt tgcagctgct gaaatacagt   12720
tttattaaat tatcactctt tcattgagta atttggtagt ttatctcgca ctaattcgac   12780
gatttagtca caaatcgaat ttatagttaa aatatgcaag aaaaaaagat ttttgataac   12840
aactatattt cagcttctac aacagggaca aattgatgaa atttaagatt tgagcaaaat   12900
ttggaaattt tttgagaatt ctcactatga aattcgactg tttcggggca gttttaatct   12960
atttgatgaa aaactcaaac cttttctctc tttcagtgat aacaattata atattatata   13020
```

```
tttttcagaa aagtatctcc tcatctcgaa tcatgcctcc aacacatgct gacttctcac    13080
gaggacgtcg aactcgggcg gtgtattcga aaacatgtcg gtgtagcttg cacgtggaat    13140
tatgaaatgc aaaagttgtt ccataataat caaagtgcaa tcaaggagtc atatgcaaaa    13200
aatatgaaag aattgaaaga tgcaattact cttcatccga ttaaagatcc agctgtaatg    13260
aggaaggttc atcttcgaaa tcgagaaatt aaacttcgtg aagcacgagc taaacgaagt    13320
cttttgagtt cggagctcag tactgcaaaa gcacagacat tggtacgaat gacaccgaat    13380
agaacgaatg atttgacacc atgggaatat attaataaca ataaaattct gttttgtgcg    13440
gatcgggtca attgtcctcg gcatactgta gatttgagta ttcggacgga aatggccgac    13500
actatcacac aggtttgttc aaaattcaga tcaagtattg aaattttttaa atgctttttt    13560 cgaattttcg gaaaatcgga aactcaaaaa ttttcgtatg tctatttcca aattttctgg    13620
atgctacagt acttcttaaa ggcgcacact cttttacgct ataaaatcgg ccgtgtcgag    13680
actgagttcc gtattttttaa agcaaaattc gcaaaaacat tcgagtaaat aatttttcca    13740
aaaaactatc ccatttttcag ttattcgacg agttcaacac aaatgctcgc caaagaggtc    13800
gtgttcttca atttcaaagt cttcaatatg gatacatgcg tgttgaacct acaaaaggag    13860
tcgattatgt tcttgacatg ttactttggt tcaaaaagtt ccgtccacca aacagaacaa    13920
caatttccgt tcgaagacac gcgtatgttc aacaaacatt cggaaaactt cgaagtctct    13980
ctgaaggagt gttccgatca aatatgagag caaactctac acttattgaa gatccaacat    14040
tgcatatgat tatgccatta agaggaagag ctgccatatt tgcaagattt gctcaacatt    14100
tgaagagtat ttgtgcgaga ggaggagatg atttagctgt ttcattgaca attgtattat    14160
actcgagtga agatgaaatg gagaataggt aagttttgga aattttaaaa tctacctatt    14220
tcggaatgaa aatccaattt ataaatcaaa aatgaatgtg tttacaaata tcgaacaaaa    14280
tttaattgat tcgaaagaaa gaataatttt tggtctaatt ggatctcaaa aacttttgagc    14340 tctagaagaa attttttaaaa cccaattggg atattttata atttacagag aaacgattga    14400
aatgctccgt gcaagcttca tcccagtaac agtaatcgaa atgggtgatg tttcattctc    14460
acgtggtgtt gctcttatgc gtggagctga aactcttcca gccaatgctc ttctattctt    14520
tactgatgtt gatatgctat tcacatgtga tgcattgaaa cgtataaaat cgaatacaat    14580
tctcaacgca caaatctact tcccgatcgt ttttctgaa ttctcacatg agagttggtc    14640
tgaaaatgac aagttattgg ctgacgccct ccattatgga cgtggacgtg gatatttttag    14700 acatttggt tatggtctcg cagcgatgta caaggtaaga tattttgaga aaatattttt    14760
tcttcaataa attttttaatt tcaggcggat ttgatggatg tcggagggtt tgacacaaag    14820
atcgaaggat ggggaaagga agatgttgac ttgtttgaga aggtaataca caagaccagg    14880
aatgcaaatt caaaaaatcg caaacatcca cttttcagtg tgtctaaaga atgatctgta    14940
aaacctacaa aaatcttttt ttatgtttag aataaatttg aagcttctct gaaatatctc    15000
ttttagaaat attttctgcg acttcatttt gacaaaataa aaactgggag tttgtagttt    15060
tttaaaattt tttccatttt tttcgaaaaa tttttccatgc agaattaaat acgcatgtta    15120
cagaaattca actttcttct ttttgcaaaa ccccaaaaat agtttttaaa gttttttga    15180 tttattttg agtcaatgca aaaaaccggc aggccccgag ggataatcca taaaacctac    15240
aaaattcaat ttctgaata ttcctaattt agagcgtctc cgaagttgaa gaagttttga    15300 gtatttttg taattttttt tgatttctta cctgtacaca acattgtatt tcttaacaa    15360 actccaaatt tttcaggcaa tcaaaaacgg tcgtctccga gtgattcgag tccctgaacc    15420
```

```
tggacttgtt cacatctatc acccaattca ttgcgatgaa aatatgccaa ctgctcaaaa    15480
ggatatgtgc catggttcaa aagcagcaag tcttgcttca attgatacac ttgtcgagca    15540
gattgcccag tacacatgat agccttgccg gttttccacc tctatcttcc cgttttttct    15600
ttctcaattt tcgaattctt tccgttttta tgaatacggt tgtccctcag ttttcatccg    15660
ggtaattatt gtttctttga tttgttttat ccacttctca cactcacttt tcccccaaaa    15720
ttcctttatt gcatccattt gattaatcac gattattata tattttctat tccccggttg    15780
agttttacca ttttccatca taatttccta acattgccat tttcacaaga agcacacgga    15840
gcttgccccc atttgaagtt caaatttcaa attaattaat tcagttcatg tcaaataata    15900
taatagttca gttaatgacc tattttgaaa cgagtaattg tcccatgctc ccctataaag    15960
ctcagccttt cattgttcaa atgtttattt cacttaaaac attattgatt gttcttcgct    16020
ttaaattcct taattcaatt gttttctttc atattaatat gagatttcca tcaaatcttt    16080
gattgtttct agctttacac aattgtctca ccatcatcat tttgtccatt ctgttgccat    16140
ttctcttccc ccaactacaa caagcatcgg tgttctgtgc ttactcgaaa taaattaatt    16200
gattgcagag tgtagtaatg aacaattgtg gaatcaatac tttacaagtt gtcatgtaag    16260
acatcaattt gacaaaaaag taagtataat ttaaataacc acatgataac gcacacaact    16320
ataaaatata agaatgaatg agaatcttgg tacaatatgg gaggaataac cgaaattaag    16380
atcaattgtt tgggagactc gaagtagaag gcaaagatga atcggatgaa gtgtttgctg    16440
atgttatacc ggctttcttc acattttct gaattgttgt catcatcaga acaccggcac    16500
gaccagtcca aggagcacga caaagtggac atgatgatcc ttccattgaa cctttacggg    16560
ctgcatacca acgacgaaca caactgaaaa tagtcaaatt agggttttcc ttgaattttc    16620
gtaaatgaga ttacgacgtt tttttaaacg taattcagag aaaaatgatg atttagtgag    16680
aacttgggtc cactgaaact agcgattctt ttcagctact ctcaaatggt tttgaatttt    16740
tctgattttt cggagttttt tatcttttaa aattgaggaa aagattaatt taagatctct    16800
gaagatcacc atttaataat ataaaaactc actctgtaca tccaaggaat tgtaggcact    16860
ttttgcatcc ttgtggtttt attggtggat tggaacacat tgtacaatct ccccacgtgg    16920
aatctctgaa atgtttttat ttttatcaag tattctggaa gcttacgggg ttattcatgt    16980
gctgtcgaaa attacaaaaa aaaattttt gtatattttg acggcacatg aataagccca    17040
ttatgaagaa agacttacgg ttcaactagt tttcctccag ctgacactgg ttttgcagct    17100
ggaacgatat attcttcttc atcatgatac aattctagtt catgattgta catgacacga    17160
tcttcgtcga atatcggttg tcttatgtga tttctatcgg catgaactgc tcccttcca    17220 ccaataatca gaacatcatc atcatcactt agatcaataa ctgatgaacc atttgattga    17280
gcttcatcat catcagaatc tgcgtctaca ttctcaggat cactttcatc ttcattattc    17340
aatccagaac ggtaaagtgg atctcttcgt ggattatcag gatatatacg ggaatgaagt    17400
agatcacgta tataatctgc actgatgttg tgttggccac ttccacgata tcttccaggt    17460
gttatcactc taccacggcc tcctggacct cttccgcttc ttgcatatga tcctcttgga    17520
ttaaatgcac gtggcatgtc tcttcttca tgatcagatt cagcctcaga gtctgcatca    17580
gattcagatg atgagattgt aatcgtcgca tttcgttctt cttcttcttc attgtcgctc    17640
tgcgtataat cactgtcatc gtcgtcatct gggaaatagg tttccgccct ggaaattatt    17700
atttttttaa ataattcaat ttagatattg atgtattcta ctaacgttat atcacgtatt    17760
```

| | |
|---|---|
| tcatctccct ggcgtacttg aacacgatct ccttcaaatt gcatttgagg gtctgcaaaa | 17820 |
| aataatcaaa tttgtaagaa tgttatctat atgatagttt tcgaaaatat ttcaaaattt | 17880 |
| tcgtaaaaat actattttt tctgctatta taggctcaaa atatgtccaa ataaacgaac | 17940 |
| aatttctcac taatatttaa tggggattca cagttttgga aaaatattat ttccagctta | 18000 |
| aatctccaat tttgccaact tttccgtgtc gcagaaacag gaaattaatt tttatttaaa | 18060 |
| aatcgtcgta tttggcatat tttttatagc ttaagctaat atgtcaaata cgacaattat | 18120 |
| caaataaaaa ttaatttcct gctactatat ttcgtacgga atttgaatat tcaaaaataa | 18180 |
| tttagctttc ttgcactcac taggattct tgtctggcgt gtcgaacgac gccggttcgg | 18240 |
| actctcggat atttgctgat ttgcacgtgt tcgattcatc gtcgcttcac caccccttgc | 18300 |
| cgatcctctt ccacgtcttg cagacgttgt tcctctggtg cctcgacctc tgactgagct | 18360 |
| ggatgaagat ggtccagcat ctgacgttcc tgcggtgctt cttatccgtg aacgtgaata | 18420 |
| tggacttgct ctttctcgtg ctgcag | 18446 |

<210> SEQ ID NO 28
<211> LENGTH: 3252
<212> TYPE: DNA
<213> ORGANISM: Caenorhabditis elegans

<400> SEQUENCE: 28

| | |
|---|---|
| agctttctgc tcaaagttcc aacacgagga gcggcggtgc ggtgcgattc gcgacgaaaa | 60 |
| tcaatgaatc agagtgccat ctgacgtgca attatatgtc gccacctgct catcttctca | 120 |
| gtgttaatca tcttcatcaa atccacgaga agttcatcac aatcatctca ctacgaccac | 180 |
| caacatcatc agcaacaaca aaacacctga cgaacacacc acactatcca gtgcaaacgt | 240 |
| tcagcagaaa aaacacagaa aataacaaaa ataacagtga gaaccatcat cagtcgattt | 300 |
| tggatcggag gaggagagaa ggcggcggac gaggagacgc agacactctt gctcgacgac | 360 |
| tcatccggta atcgagaaga cacggaagag agtatgcgag tgcggagcac atgcagaatg | 420 |
| ccggtctccc gagccaccgt cacaatccta ctcggaatcc tgtttggttt ctcaatcact | 480 |
| tactatctga cggctctcaa atctctgaca aatccaataa tctgtggccc agaacaacaa | 540 |
| attggcggtt tcgattatct cgatgtgata agtcaacgtg ctgatgctga tgttttcaca | 600 |
| agatcccaaa gtcttccgg tcatcgaagg ggtctgattc ttgtggctat tatgactgct | 660 |
| gcaaaatacg ttgatacacg tgcttataat gtttggaaaa catgggctca acacattccc | 720 |
| ggacgagttt taatatttgt tgccgaagga actgaatcag tgcatgagga tatgccatta | 780 |
| attcgtctga aaggagttga tgatacttat ccaccacaga agaaaagttt cgcaatggta | 840 |
| aaaatggttgg cagagaatat ggctgatgaa tatgattggt tcttgcgagc agacgacgac | 900 |
| ctctacatta gaggagaaga gctcgctttta ttcctaagat ctgtcgattc atccaaagct | 960 |
| catatcatcg gacaggctgg acttggtaac agtgcgaat atggtcttct agctcttgga | 1020 |
| tctaccgata attattgtat gggaggacct ggaattgtta tgagcaggga cacttatta | 1080 |
| aaagtatctc ctcatctcga atcatgcctc caacacatgc tgacttctca cgaggacgtc | 1140 |
| gaactcgggc ggtgtattcg aaaacatgtc ggtgtagctt gcacgtggaa ttatgaaatg | 1200 |
| caaagttgt tccataataa tcaaagtgca atcaaggagt catatgcaaa aaatatgaaa | 1260 |
| gaattgaaag atgcaattac tcttcatccg attaaagatc cagctgtaat gaggaaggtt | 1320 |
| catcttcgaa atcgagaaat taaacttcgt gaagcacgag ctaaacgaag tcttttgagt | 1380 |
| tcggagctca gtactgcaaa agcacagaca ttggtacgaa tgacaccgaa tagaacgaat | 1440 |

-continued

```
gatttgacac catgggaata tattaataac aataaaattc tgttttgtgc ggatcgggtc    1500
aattgtcctc ggcatactgt agatttgagt attcggacgg aaatggccga cactatcaca    1560
cagttattcg acgagttcaa cacaaatgct cgccaaagag gtcgtgttct tcaatttcaa    1620
agtcttcaat atggatacat gcgtgttgaa cctacaaaag gagtcgatta tgttcttgac    1680
atgttacttt ggttcaaaaa gttccgtcca ccaaacagaa caacaatttc cgttcgaaga    1740
cacgcgtatg ttcaacaaac attcggaaaa cttcgaagtc tctctgaagg agtgttccga    1800
tcaaatatga gagcaaactc tacacttatt gaagatccaa cattgcatat gattatgcca    1860
ttaagaggaa gagctgccat atttgcaaga tttgctcaac atttgaagag tatttgtgcg    1920
agaggaggag atgatttagc tgtttcattg acaattgtat tatactcgag tgaagatgaa    1980
atggagaata gagaaacgat tgaaatgctc cgtgcaagct tcatcccagt aacagtaatc    2040
gaaatgggtg atgtttcatt ctcacgtggt gttgctctta tgcgtggagc tgaaactctt    2100
ccagccaatg ctcttctatt ctttactgat gttgatatgc tattcacatg tgatgcattg    2160
aaacgtataa aatcgaatac aattctcaac gcacaaatct acttcccgat cgttttttct    2220
gaattctcac atgagagttg gtctgaaaat gacaagttat tggctgacgc cttccattat    2280
ggacgtggac gtggatattt tagacatttt ggttatggtc tcgcagcgat gtacaaggcg    2340
gatttgatgg atgtcggagg gtttgacaca agatcgaag gatggggaaa ggaagatgtt    2400
gacttgtttg agaaggcaat caaaaacggt cgtctccgag tgattcgagt ccctgaacct    2460
ggacttgttc acatctatca cccaattcat tgcgatgaaa atatgccaac tgctcaaaag    2520
gatatgtgcc atggttcaaa agcagcaagt cttgcttcaa ttgatacact tgtcgagcag    2580
attgcccagt acacatgata gccttgccgg ttttccacct ctatcttccc gtttttttctt    2640 tctcaatttt cgaattcttt ccgtttttat gaatacggtt gtccctcagt tttcatccgg    2700
gtaattattg tttctttgat ttgttttatc cacttctcac actcacttt cccccaaaat    2760 tcctttattg catccatttg attaatcacg attattatat attttctatt ccccggttga    2820
gttttaccat tttccatcat aatttcctaa cattgccatt tcacaagaa gcacacggag    2880 cttgccccca tttgaagttc aaatttcaaa ttaattaatt cagttcatgt caaataatat    2940
aatagttcag ttaatgacct attttgaaac gagtaattgt cccatgctcc cctataaagc    3000
tcagcctttc attgttcaaa tgtttatttc acttaaaaca ttattgattg ttcttcgctt    3060
taaattcctt aattcaattg ttttctttca tattaatatg agatttccat caaatctttg    3120
attgtttcta gctttacaca attgtctcac catcatcatt ttgtccattc tgttgccatt    3180
tctcttcccc caactacaac aagcatcggt gttctgtgct tactcgaaat aaattaattg    3240
attgcagagt gt                                                        3252
```

<210> SEQ ID NO 29
<211> LENGTH: 4545
<212> TYPE: DNA
<213> ORGANISM: Homo sapiens

<400> SEQUENCE: 29

```
ggcgagctaa gccggaggat gtgcagctgc ggcggcggcg ccggctacga agaggacggg      60
gacaggcgcc gtgcgaaccg agcccagcca gccggaggac gcgggcaggg cgggacggga     120
gcccggactc gtctgccgcc gccgtcgtcg ccgtcgtgcc ggccccgcgt ccccgcgcgc     180
gagcgggagg agccgccgcc acctcgcgcc cgagccgccg ctagcgcgcg ccgggcatgg     240
```

```
tccctctta aaggcgcagg ccgcggcggc gggggcgggc gtgcggaaca aagcgccggc    300
gcggggcctg cgggcggctc gggggccgcg atgggcgcg cgggcccgcg gcggcggcg     360 cgctgcccgg gccgggcctc gcggcgctag ggcgggctgg cctccgcggg cggggcagc    420 gggctgaggg cgcgcggagc ctgcggcggc ggcccgcgcg gcggagcggc gcgggcatgg   480
ccgcgcgcgg ccggcgcgcc tggctcagcg tgctgctcgg gctcgtcctg ggcttcgtgc   540
tggcctcgcg gctcgtcctg ccccgggctt ccgagctgaa gcgagcgggc ccacggcgcc   600
gcgccagccc cgagggctgc cggtccgggc aggcggcggc ttcccaggcc ggcggggcgc   660
gcggcgatgc gcgcggggcg cagctctggc cgcccggctc ggacccagat ggcggcccgc   720
gcgacaggaa ctttctcttc gtgggagtca tgaccgccca gaaatacctg cagactcggg   780
ccgtggccgc ctacagaaca tggtccaaga caattcctgg gaaagttcag ttcttctcaa   840
gtgagggttc tgacacatct gtaccaattc cagtagtgcc actacggggt gtggacgact   900
cctacccgcc ccagaagaag tccttcatga tgctcaagta catgcacgac cactacttgg   960
acaagtatga atggtttatg agagcagatg atgacgtgta catcaaagga gaccgtctgg   1020
agaacttcct gaggagtttg aacagcagcg agcccctctt tcttgggcag acaggcctgg   1080
gcaccacgga agaaatggga aaactggccc tggagcctgg tgagaacttc tgcatggggg   1140
ggcctggcgt gatcatgagc cgggaggtgc ttcggagaat ggtgccgcac attggcaagt   1200
gtctccggga gatgtacacc acccatgagg acgtggaggt gggaaggtgt gtccggaggt   1260 ttgcagggg gcagtgtgtc tggtcttatg agatgcagca gcttttttat gagaattacg    1320
agcagaacaa aaaggggtac attagagatc tccataacag taaaattcac caagctatca   1380 cattcaccc caacaaaaac ccaccctacc agtacaggct ccacagctac atgctgagcc   1440
gcaagatatc cgagctccgc catcgcacaa tacagctgca ccgcgaaatt gtcctgatga   1500
gcaaatacag caacacagaa attcataaag gaggacctcca gctgggaatc cctccctcct   1560
tcatgaggtt tcagccccgc cagcgagagg agattctgga atgggagttt ctgactggaa   1620
aatacttgta ttcggcagtt gacgccagcc cccctcgaag aggaatggac tccgcccaga   1680
gggaagcctt ggacgacatt gtcatgcagg tcatggagat gatcaatgcc aacgccaaga   1740
ccagagggcg catcattgac ttcaaagaga tccagtacgg ctaccgccgg gtgaacccca   1800 tgtatgggc tgagtacatc ctggacctgc tgcttctgta caaaaagcac aaagggaaga   1860
aaatgacggt ccctgtgagg aggcacgcgt atttacagca gactttcagc aaaatccagt   1920
ttgtggagca tgaggagctg gatgcacaag agttggccaa gagaatcaat caggaatctg   1980
gatccttgtc ctttctctca aactcccctga agaagctcgt ccccctttcag ctccctgggt   2040 cgaagagtga gcacaaagaa cccaaagata aaaagataaa catactgatt cctttgtctg   2100
ggcgtttcga catgtttgtg agatttatgg gaaactttga gagacgtgt cttatcccca    2160 atcagaacgt caagctcgtg gttctgcttt tcaattctga ctccaaccct gacaaggcca   2220
aacaagttga actgatgaga gattaccgca ttaagtaccc taaagccgac atgcagattt   2280
tgcctgtgtc tggagagttt tcaagagccc tggccctgga agtaggatcc tcccagttta   2340
acaatgaatc tttgctcttc ttctgcgacg tcgacctcgt gtttactaca gaattccttc   2400
agcgatgtcg agcaaataca gttctgggcc aacaaatata ttttccaatc atcttcagcc   2460
agtatgaccc aaagattgtt tatagtggga agttcccag tgacaaccat tttgccttta    2520
ctcagaaaac tggcttctgg agaaactatg ggtttggcat cacgtgtatt tataaggag    2580 atcttgtccg agtgggtggc tttgatgttt ccatccaagg ctgggggctg gaggatgtgg   2640
```

```
accttttcaa caaggttgtc caggcaggtt tgaagacgtt taggagccag gaagtaggag    2700
tagtccacgt ccaccatcct gtcttttgtg atcccaatct tgaccccaaa cagtacaaaa    2760
tgtgcttggg gtccaaagca tcgacctatg ggtccaccca gcagctggct gagatgtggc    2820
tggaaaaaaa tgatccaagt tacagtaaaa gcagcaataa taatggctca gtgaggacag    2880
cctaatgtcc agctttgctg gaaaagacgt ttttaattat ctaatttatt tttcaaaaat    2940
tttttgtatg atcagttttt gaagtccgta tacaaggata tattttacaa gtggttttct    3000
tacataggac tcctttaaga ttgagctttc tgaacaagaa ggtgatcagt gtttgccttt    3060
gaacacatct tcttgctgaa cattatgtag cagacctgct taactttgac ttgaaatgta    3120
cctgatgaac aaaacttttt taaaaaaatg ttttcttttg agaccctttg ctccagtcct    3180
atggcagaaa acgtgaacat tcctgcaaag tattattgta acaaaacact gtaactctgg    3240
taaatgttct gttgtgattg ttaacattcc acagattcta ccttttgtgt tttgtttttt    3300 tttttacaa ttgtttttaaa gccatttcat gttccagttg taagataagg aaatgtgata    3360
atagctgttt catcattgtc ttcaggagag ctttccagag ttgatcattt cctctcatgg    3420
tactctgctc agcatggcca cgtaggtttt ttgtttgttt tgttttgttc ttttttttgag    3480 acggagtctc actctgttac ccaggctgga atgcagtggc gcaatcttgg ctcactttaa    3540
cctccacttc cctggttcaa gcaattcccc tgcctttgcc tcccgagtag ctgggattac    3600
aggcacacac caccacgccc agctagtttt tttgtatttt tagtagagac ggggtttcac    3660
catgcaagcc cagctggcca cgtaggtttt aaagcaaggg gcgtgaagaa ggcacagtga    3720
ggtatgtggc tgttctcgtg gtagttcatt cggcctaaat agacctggca ttaaatttca    3780
agaaggattt ggcattttct cttcttgacc cttctcttta aagggtaaaa tattaatgtt    3840
tagaatgaca aagatgaatt attacaataa atctgatgta cacagactga aacatacaca    3900
catacaccct aatcaaaacg ttggggaaaa atgtatttgg ttttgttcct ttcatcctgt    3960
ctgtgttatg tgggtggaga tggttttcat tctttcatta ctgttttgtt ttatcctttg    4020
tatctgaaat accttttaatt tatttaatat ctgttgttca gagctctgcc atttcttgag    4080
tacctgttag ttagtattat ttatgtgtat cgggagtgtg tttagtctgt tttatttgca    4140
gtaaaccgat ctccaaagat ttccttttgg aaacgctttt tcccctcctt aattttata    4200 ttccttactg ttttactaaa tattaagtgt tctttgacaa ttttggtgct catgtgtttt    4260
ggggacaaaa gtgaaatgaa tctgtcatta taccagaaag ttaaattctc agatcaaatg    4320
tgccttaata aatttgtttt catttagatt tcaaacagtg atagacttgc cattttaata    4380
cacgtcattg gagggctgcg tatttgtaaa tagcctgatg ctcatttgga aaaataaacc    4440
agtgaacaat attttctat tgtacttttc gaaccatttt gtctcattat tcctgtttta    4500
gctgaagaat tgtattacat ttggagagta aaaaacttaa acacg                    4545
```

<210> SEQ ID NO 30
<211> LENGTH: 26
<212> TYPE: DNA
<213> ORGANISM: Artificial Sequence
<220> FEATURE:
<223> OTHER INFORMATION: Primer

<400> SEQUENCE: 30
tctggtacca tgctgagccc cagacg                                          26

<210> SEQ ID NO 31

```
<211> LENGTH: 25
<212> TYPE: DNA
<213> ORGANISM: Artificial Sequence
<220> FEATURE:
<223> OTHER INFORMATION: Primer

<400> SEQUENCE: 31
tctgagctca tcgtcgactc tcaag                                              25

<210> SEQ ID NO 32
<211> LENGTH: 26
<212> TYPE: DNA
<213> ORGANISM: Artificial Sequence
<220> FEATURE:
<223> OTHER INFORMATION: Primer

<400> SEQUENCE: 32
tctgaattca tgctgagccc cagacg                                             26

<210> SEQ ID NO 33
<211> LENGTH: 27
<212> TYPE: DNA
<213> ORGANISM: Artificial Sequence
<220> FEATURE:
<223> OTHER INFORMATION: Primer

<400> SEQUENCE: 33
tctggatcct catcgtcgac tctcaag                                            27

<210> SEQ ID NO 34
<211> LENGTH: 26
<212> TYPE: PRT
<213> ORGANISM: Artificial Sequence
<220> FEATURE:
<223> OTHER INFORMATION: Primer

<400> SEQUENCE: 34

Cys Arg Ser Lys Ser Thr Thr Ile Ser Tyr Lys Pro Leu Pro Met Thr
 1               5                  10                  15

Met Pro Ile Asp Val His Lys Pro Arg Asn
            20                  25

<210> SEQ ID NO 35
<211> LENGTH: 27
<212> TYPE: DNA
<213> ORGANISM: Artificial Sequence
<220> FEATURE:
<223> OTHER INFORMATION: primer

<400> SEQUENCE: 35
tctcccgggg catgctgagc cccagac                                            27

<210> SEQ ID NO 36
<211> LENGTH: 27
<212> TYPE: DNA
<213> ORGANISM: Artificial Sequence
<220> FEATURE:
<223> OTHER INFORMATION: primer

<400> SEQUENCE: 36
tctctcgagt cgtcgactct caagacc                                            27

<210> SEQ ID NO 37
<211> LENGTH: 17
<212> TYPE: DNA
<213> ORGANISM: Artificial Sequence
```

```
<220> FEATURE:
<223> OTHER INFORMATION: primer

<400> SEQUENCE: 37
gatcttggaa agtatgg                                                  17

<210> SEQ ID NO 38
<211> LENGTH: 33
<212> TYPE: DNA
<213> ORGANISM: Artificial Sequence
<220> FEATURE:
<223> OTHER INFORMATION: primer

<400> SEQUENCE: 38
ttgaacattt gcggccgcgt tccttggctt gtg                                33

<210> SEQ ID NO 39
<211> LENGTH: 17
<212> TYPE: DNA
<213> ORGANISM: Artificial Sequence
<220> FEATURE:
<223> OTHER INFORMATION: primer

<400> SEQUENCE: 39
tactacaacc tgcgttg                                                  17

<210> SEQ ID NO 40
<211> LENGTH: 18
<212> TYPE: DNA
<213> ORGANISM: Artificial Sequence
<220> FEATURE:
<223> OTHER INFORMATION: primer

<400> SEQUENCE: 40
gttcgctttt tagtcccg                                                 18

<210> SEQ ID NO 41
<211> LENGTH: 17
<212> TYPE: DNA
<213> ORGANISM: Artificial Sequence
<220> FEATURE:
<223> OTHER INFORMATION: primer

<400> SEQUENCE: 41
gatcttggaa agtatgg                                                  17

<210> SEQ ID NO 42
<211> LENGTH: 18
<212> TYPE: DNA
<213> ORGANISM: Artificial Sequence
<220> FEATURE:
<223> OTHER INFORMATION: primer

<400> SEQUENCE: 42
gttcgctttt tagtcccg                                                 18

<210> SEQ ID NO 43
<211> LENGTH: 27
<212> TYPE: DNA
<213> ORGANISM: Artificial Sequence
<220> FEATURE:
<223> OTHER INFORMATION: primer

<400> SEQUENCE: 43
tctgaattca atgagattct accgaac                                       27
```

<210> SEQ ID NO 44
<211> LENGTH: 27
<212> TYPE: DNA
<213> ORGANISM: Artificial Sequence
<220> FEATURE:
<223> OTHER INFORMATION: primer

<400> SEQUENCE: 44
tctctcgagt tatggaatat tcgatcc                                27

<210> SEQ ID NO 45
<211> LENGTH: 25
<212> TYPE: DNA
<213> ORGANISM: Artificial Sequence
<220> FEATURE:
<223> OTHER INFORMATION: primer

<400> SEQUENCE: 45
tctgaattca attgtggatg ggatg                                  25

<210> SEQ ID NO 46
<211> LENGTH: 27
<212> TYPE: DNA
<213> ORGANISM: Artificial Sequence
<220> FEATURE:
<223> OTHER INFORMATION: primer

<400> SEQUENCE: 46
tctctcgagt tatggaatat tcgatcc                                27

<210> SEQ ID NO 47
<211> LENGTH: 32
<212> TYPE: DNA
<213> ORGANISM: Artificial Sequence
<220> FEATURE:
<223> OTHER INFORMATION: primer

<400> SEQUENCE: 47
tctggtacca ccatggtatt caacgggacg ac                          32

<210> SEQ ID NO 48
<211> LENGTH: 17
<212> TYPE: DNA
<213> ORGANISM: Artificial Sequence
<220> FEATURE:
<223> OTHER INFORMATION: primer

<400> SEQUENCE: 48
ttcctcgtcg gaaatcg                                           17

<210> SEQ ID NO 49
<211> LENGTH: 19
<212> TYPE: DNA
<213> ORGANISM: Artificial Sequence
<220> FEATURE:
<223> OTHER INFORMATION: primer

<400> SEQUENCE: 49
cgattttgag agacttatc                                         19

<210> SEQ ID NO 50
<211> LENGTH: 27
<212> TYPE: DNA
<213> ORGANISM: Artificial Sequence
<220> FEATURE:
<223> OTHER INFORMATION: primer

<400> SEQUENCE: 50
tctgcggccg ctaaatcaag gtctgcg                                27

<210> SEQ ID NO 51
<211> LENGTH: 27
<212> TYPE: DNA
<213> ORGANISM: Artificial Sequence
<220> FEATURE:
<223> OTHER INFORMATION: primer

<400> SEQUENCE: 51
tctggtacca tgactgatca agtcttc                                27

<210> SEQ ID NO 52
<211> LENGTH: 27
<212> TYPE: DNA
<213> ORGANISM: Artificial Sequence
<220> FEATURE:
<223> OTHER INFORMATION: primer

<400> SEQUENCE: 52
tctgatatct taataaccag ctgttcc                                27

<210> SEQ ID NO 53
<211> LENGTH: 20
<212> TYPE: DNA
<213> ORGANISM: Artificial Sequence
<220> FEATURE:
<223> OTHER INFORMATION: primer

<400> SEQUENCE: 53
gacacacacg aatcatcagc                                        20

<210> SEQ ID NO 54
<211> LENGTH: 19
<212> TYPE: DNA
<213> ORGANISM: Artificial Sequence
<220> FEATURE:
<223> OTHER INFORMATION: primer

<400> SEQUENCE: 54
gtacttatcg agtgggatg                                         19

<210> SEQ ID NO 55
<211> LENGTH: 25
<212> TYPE: DNA
<213> ORGANISM: Artificial Sequence
<220> FEATURE:
<223> OTHER INFORMATION: primer

<400> SEQUENCE: 55
tctccatggc tgatcaagtc ttcgg                                  25

<210> SEQ ID NO 56
<211> LENGTH: 27
<212> TYPE: DNA
<213> ORGANISM: Artificial Sequence
<220> FEATURE:
<223> OTHER INFORMATION: primer

<400> SEQUENCE: 56
tctctcgagt taataaccag ctgttcc                                27

<210> SEQ ID NO 57

```
<211> LENGTH: 29
<212> TYPE: DNA
<213> ORGANISM: Artificial Sequence
<220> FEATURE:
<223> OTHER INFORMATION: primer

<400> SEQUENCE: 57
tctcccgggt aatgactgat caagtcttc                                              29

<210> SEQ ID NO 58
<211> LENGTH: 30
<212> TYPE: DNA
<213> ORGANISM: Artificial Sequence
<220> FEATURE:
<223> OTHER INFORMATION: primer

<400> SEQUENCE: 58
tctctcgaga taaccagctg ttccgaatag                                             30

<210> SEQ ID NO 59
<211> LENGTH: 27
<212> TYPE: DNA
<213> ORGANISM: Artificial Sequence
<220> FEATURE:
<223> OTHER INFORMATION: primer

<400> SEQUENCE: 59
tcttctagaa tgactgatca agtcttc                                                27

<210> SEQ ID NO 60
<211> LENGTH: 27
<212> TYPE: DNA
<213> ORGANISM: Artificial Sequence
<220> FEATURE:
<223> OTHER INFORMATION: primer

<400> SEQUENCE: 60
tctgtcgact aataaccag ctgttcc                                                 27

<210> SEQ ID NO 61
<211> LENGTH: 30
<212> TYPE: DNA
<213> ORGANISM: Artificial Sequence
<220> FEATURE:
<223> OTHER INFORMATION: primer

<400> SEQUENCE: 61
tctcccggga taaccagctg ttccgaatag                                             30

<210> SEQ ID NO 62
<211> LENGTH: 18
<212> TYPE: DNA
<213> ORGANISM: Artificial Sequence
<220> FEATURE:
<223> OTHER INFORMATION: primer

<400> SEQUENCE: 62
ccaatatacg aggtgagc                                                          18

<210> SEQ ID NO 63
<211> LENGTH: 19
<212> TYPE: DNA
<213> ORGANISM: Artificial Sequence
<220> FEATURE:
<223> OTHER INFORMATION: primer

<400> SEQUENCE: 63
```

```
aaagttccaa cacgaggag                                                    19

<210> SEQ ID NO 64
<211> LENGTH: 22
<212> TYPE: DNA
<213> ORGANISM: Artificial Sequence
<220> FEATURE:
<223> OTHER INFORMATION: primer

<400> SEQUENCE: 64
gtgtatcaac gtattttgca gc                                                22

<210> SEQ ID NO 65
<211> LENGTH: 21
<212> TYPE: DNA
<213> ORGANISM: Artificial Sequence
<220> FEATURE:
<223> OTHER INFORMATION: primer

<400> SEQUENCE: 65
cctactctga atcctgtttg g                                                 21

<210> SEQ ID NO 66
<211> LENGTH: 22
<212> TYPE: DNA
<213> ORGANISM: Artificial Sequence
<220> FEATURE:
<223> OTHER INFORMATION: primer

<400> SEQUENCE: 66
caacacgcat gtatccatat tg                                                22

<210> SEQ ID NO 67
<211> LENGTH: 19
<212> TYPE: DNA
<213> ORGANISM: Artificial Sequence
<220> FEATURE:
<223> OTHER INFORMATION: primer

<400> SEQUENCE: 67
aaagttccaa cacgaggag                                                    19

<210> SEQ ID NO 68
<211> LENGTH: 18
<212> TYPE: DNA
<213> ORGANISM: Artificial Sequence
<220> FEATURE:
<223> OTHER INFORMATION: primer

<400> SEQUENCE: 68
atcggtagat ccaagagc                                                     18

<210> SEQ ID NO 69
<211> LENGTH: 21
<212> TYPE: DNA
<213> ORGANISM: Artificial Sequence
<220> FEATURE:
<223> OTHER INFORMATION: primer

<400> SEQUENCE: 69
gatgaatagg attggttctt g                                                 21

<210> SEQ ID NO 70
<211> LENGTH: 22
<212> TYPE: DNA
```

-continued

```
<213> ORGANISM: Artificial Sequence
<220> FEATURE:
<223> OTHER INFORMATION: primer

<400> SEQUENCE: 70
caacacgcat gtatccatat tg                                              22

<210> SEQ ID NO 71
<211> LENGTH: 20
<212> TYPE: DNA
<213> ORGANISM: Artificial Sequence
<220> FEATURE:
<223> OTHER INFORMATION: primer

<400> SEQUENCE: 71
cgtccaccaa acagaacaac                                                 20

<210> SEQ ID NO 72
<211> LENGTH: 18
<212> TYPE: DNA
<213> ORGANISM: Artificial Sequence
<220> FEATURE:
<223> OTHER INFORMATION: primer

<400> SEQUENCE: 72
gatgtgaaca agtccagg                                                   18

<210> SEQ ID NO 73
<211> LENGTH: 22
<212> TYPE: DNA
<213> ORGANISM: Artificial Sequence
<220> FEATURE:
<223> OTHER INFORMATION: primer

<400> SEQUENCE: 73
gaaggatgag gaaaggaaga tg                                              22

<210> SEQ ID NO 74
<211> LENGTH: 19
<212> TYPE: DNA
<213> ORGANISM: Artificial Sequence
<220> FEATURE:
<223> OTHER INFORMATION: primer

<400> SEQUENCE: 74
agcatgggac aattactcg                                                  19

<210> SEQ ID NO 75
<211> LENGTH: 18
<212> TYPE: DNA
<213> ORGANISM: Artificial Sequence
<220> FEATURE:
<223> OTHER INFORMATION: primer

<400> SEQUENCE: 75
cactatccag tgcaaacg                                                   18

<210> SEQ ID NO 76
<211> LENGTH: 19
<212> TYPE: DNA
<213> ORGANISM: Artificial Sequence
<220> FEATURE:
<223> OTHER INFORMATION: primer

<400> SEQUENCE: 76
cagctcttcc tcttaatgg                                                  19
```

```
<210> SEQ ID NO 77
<211> LENGTH: 18
<212> TYPE: DNA
<213> ORGANISM: Artificial Sequence
<220> FEATURE:
<223> OTHER INFORMATION: primer

<400> SEQUENCE: 77
ggtaatcgag aagacacg                                                  18

<210> SEQ ID NO 78
<211> LENGTH: 17
<212> TYPE: DNA
<213> ORGANISM: Artificial Sequence
<220> FEATURE:
<223> OTHER INFORMATION: primer

<400> SEQUENCE: 78
gatcggaaca ctccttc                                                   17

<210> SEQ ID NO 79
<211> LENGTH: 31
<212> TYPE: DNA
<213> ORGANISM: Artificial Sequence
<220> FEATURE:
<223> OTHER INFORMATION: primer

<400> SEQUENCE: 79
agaagacacg ggatccagta tgcgagtgcg g                                   31

<210> SEQ ID NO 80
<211> LENGTH: 29
<212> TYPE: DNA
<213> ORGANISM: Artificial Sequence
<220> FEATURE:
<223> OTHER INFORMATION: primer

<400> SEQUENCE: 80
gatagccttg tcgactttcc acctctatc                                      29

<210> SEQ ID NO 81
<211> LENGTH: 30
<212> TYPE: DNA
<213> ORGANISM: Artificial Sequence
<220> FEATURE:
<223> OTHER INFORMATION: primer

<400> SEQUENCE: 81
cacatgatag cggccgcggt tttccacctc                                     30
```

What is claimed is:

1. A method of identifying a compound that modulates a glycosaminoglycan biosynthetic biological activity, said method comprising the steps of:
   (a) providing a first cell comprising a wild-type sqv nucleic acid molecule;
   (b) providing a second cell comprising a sqv-1, sqv-2, sqv-4, sqv-5, or sqv-6 mutant nucleic acid molecule;
   (c) contacting said first cell with a candidate compound;
   (d) contacting said second cell with said candidate compound; and
   (e) detecting, in a protein extract from said first or second cell, an alteration of an enzymatic activity that contributes to the production of a glycosaminoglycan in said first cell when compared to said second cell, wherein said alteration identifies said compound as modulating a glycosaminoglycan biosynthetic biological activity.

2. The method of claim 1, wherein said first and said second cells are mammalian cells.

3. The method of claim 1, wherein said first and said second cells are nematode cells.

4. A method of identifying a compound that modulates a glycosaminoglycan biosynthetic biological activity, said method comprising the steps of:
   (a) providing a first nematode comprising a wild-type sqv nucleic acid molecule;

(b) providing a second nematode comprising a sqv-1, sqv-2, sqv-4, sqv-5, or sqv-6 mutant nucleic acid molecule;
(c) contacting said first nematode with a candidate compound;
(d) contacting said second nematode with said candidate compound; and
(e) detecting, in a protein extract from said first or second nematode, an alteration of an enzymatic activity that contributes to the production of a glycosaminoglycan in said first nematode when compared to said second nematode, wherein said alteration identifies said compound as modulating a glycosaminoglycan biosynthetic biological activity.

5. The method of claim 1, wherein said detecting is an immunological assay.

6. The method of claim 1, wherein said sqv mutant nucleic acid molecule is sqv-5.

7. The method of claim 4, wherein said detecting is an immunological assay.

8. The method of claim 4, wherein said sqv mutant nucleic acid molecule is sqv-5.

\* \* \* \* \*

UNITED STATES PATENT AND TRADEMARK OFFICE
CERTIFICATE OF CORRECTION

PATENT NO. : 7,442,501 B2  
APPLICATION NO. : 10/347470  
DATED : October 28, 2008  
INVENTOR(S) : Horvitz et al.

It is certified that error appears in the above-identified patent and that said Letters Patent is hereby corrected as shown below:

Column 1, lines 13-15: Replace

"This application was supported in part by NIH grant GM24663. The government may have certain rights to this invention"

with

--This invention was made with government support under grant number R37-GM24663 awarded by the NIH. The government has certain rights to this invention--.

Signed and Sealed this
Fourteenth Day of June, 2011

David J. Kappos
*Director of the United States Patent and Trademark Office*